United States Patent
Borzilleri et al.

(10) Patent No.: US 9,783,573 B2
(45) Date of Patent: *Oct. 10, 2017

(54) IAP ANTAGONISTS

(71) Applicant: BRISTOL-MYERS SQUIBB COMPANY, Princeton, NJ (US)

(72) Inventors: Robert M. Borzilleri, New Hope, PA (US); Kyoung S. Kim, North Brunswick, NJ (US); Heidi L. Perez, Ewing, NJ (US); Erik M. Stang, Lawrenceville, NJ (US); David K. Williams, Delran, NJ (US); Liping Zhang, East Windsor, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 46 days.

This patent is subject to a terminal disclaimer.

(21) Appl. No.: 14/428,688

(22) PCT Filed: Sep. 17, 2013

(86) PCT No.: PCT/US2013/060043
§ 371 (c)(1),
(2) Date: Mar. 17, 2015

(87) PCT Pub. No.: WO2014/047024
PCT Pub. Date: Mar. 27, 2014

(65) Prior Publication Data
US 2015/0322111 A1    Nov. 12, 2015

Related U.S. Application Data

(60) Provisional application No. 61/702,384, filed on Sep. 18, 2012.

(51) Int. Cl.
| | |
|---|---|
| C07K 5/08 | (2006.01) |
| C07K 5/083 | (2006.01) |
| A61K 38/06 | (2006.01) |
| A61K 45/06 | (2006.01) |
| C07D 401/14 | (2006.01) |
| C07D 413/14 | (2006.01) |
| C07D 401/06 | (2006.01) |
| C07D 401/10 | (2006.01) |
| C07D 401/12 | (2006.01) |
| C07D 417/14 | (2006.01) |
| C07D 487/04 | (2006.01) |

(52) U.S. Cl.
CPC ......... *C07K 5/0806* (2013.01); *A61K 38/06* (2013.01); *A61K 45/06* (2013.01); *C07D 401/06* (2013.01); *C07D 401/10* (2013.01); *C07D 401/12* (2013.01); *C07D 401/14* (2013.01); *C07D 413/14* (2013.01); *C07D 417/14* (2013.01); *C07D 487/04* (2013.01)

(58) Field of Classification Search
None
See application file for complete search history.

(56) References Cited

U.S. PATENT DOCUMENTS

| | | | |
|---|---|---|---|
| 8,889,712 B2 * | 11/2014 | Borzilleri | A61K 38/08 514/307 |
| 2013/0338081 A1 * | 12/2013 | Borzilleri | A61K 38/08 514/19.3 |

FOREIGN PATENT DOCUMENTS

WO    WO 2009/136290    11/2009

OTHER PUBLICATIONS

Hunter AM ('SMAC-based antagonists of the inhibitors of apoptosis' University of Ottawa thesis 2006, total of 218 pages with last page numbered 165).*

* cited by examiner

*Primary Examiner* — Karlheinz R Skowronek
*Assistant Examiner* — Ronald Niebauer
(74) *Attorney, Agent, or Firm* — Elliott Korsen

(57) ABSTRACT

There are disclosed compounds of formula (I) that modulate the activity of inhibitors of apoptosis (IAPs), pharmaceutical compositions containing said compounds and methods of treating proliferative disorders and disorders of dysregulated apoptosis, such as cancer, utilizing the compounds of the invention.

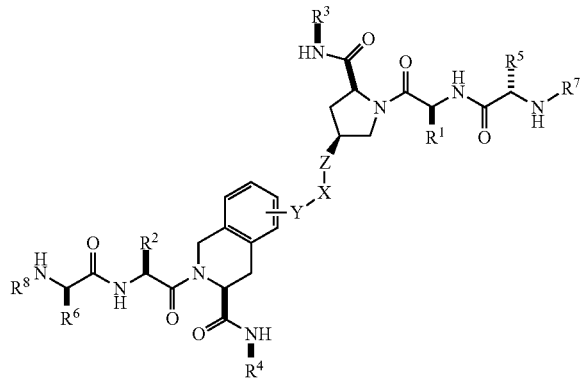

(I)

3 Claims, No Drawings

IAP ANTAGONISTS

FIELD OF THE INVENTION

The invention relates generally to compounds that modulate the activity of inhibitors of apoptosis (IAPs), pharmaceutical compositions containing said compounds and methods of treating proliferative disorders and disorders of dysregulated apoptosis, such as cancer, utilizing the compounds of the invention.

BACKGROUND OF THE INVENTION

Apoptosis or programmed cell death is a genetically and biochemically regulated mechanism that plays an important role in development and homeostasis in invertebrates as well as vertebrates.

Aberrancies in apoptosis that lead to premature cell death have been linked to a variety of developmental disorders. Deficiencies in apoptosis that result in the lack of cell death have been linked to cancer and chronic viral infections.

Caspases are cysteine-containing aspartate specific proteases that play a key role in effecting apoptosis. Once activated from their inactive zymogen form by proteolytic processing, caspases digest vital cell proteins from within the cell. Since caspases are such strong proteases, tight control of this family of proteins is necessary to prevent premature cell death. In addition to proteolytic processing, caspases are also regulated by a family of molecules known as Inhibitors of Apoptosis Proteins (IAP). IAPs are naturally occurring intra-cellular proteins that suppress caspase-dependent apoptosis. SMAC, an intracellular protein also known as DIABLO, functions to modulate the activity of IAPs. In normal healthy cells, SMAC and IAPs function together to maintain healthy cells. However, in certain disease states, e.g., cancers and other proliferative disorders, the activities of IAPs are not adequately modulated and therefore, prevent apoptosis and cause or exacerbate abnormal proliferation and survival.

IAP antagonists, also known as SMAC mimetics, are synthetic molecules that mimic the structure and IAP modulating activity of the four N-terminal amino acids of SMAC (AVPI). When administered to a subject suffering proliferative disorders, the compounds antagonize IAP activities causing an increase in apoptosis among abnormally proliferating cells.

IAPs are found in all organisms ranging from *Drosophila* to human and are known to be overexpressed in many human cancers. IAPs comprise one to three Baculovirus IAP repeat (BIR) domains. The BIR domain is a zinc binding domain of about 70 residues comprising 4 alpha-helices and 3 beta strands, with cysteine and histidine residues that coordinate the zinc ion. The BIR 2 and 3 domains contain a conserved inhibitor of apoptosis binding motif (IBM) capable of binding caspases—and inhibiting their proteolytic activity.

As an example, human X-chromosome linked IAP (XIAP) inhibits the executioner caspases-3, and -7 as well as the Apaf-1-cytochrome C mediated activation of the initiator caspase-9. Caspases-3 and -7 are inhibited by the BIR2 domain of XIAP, while the BIR3 domain of XIAP is responsible for the inhibition of caspase-9 activation. XIAP is expressed ubiquitously in most adult and fetal tissues. Overexpression of XIAP in tumor cells has been demonstrated to confer protection of the tumor cells against a variety of pro-apoptotic stimuli and promotes resistance to chemotherapy. Consistent with this, a strong correlation between XIAP protein levels and survival has been demonstrated for patients with acute myelogenous leukemia.

Other BIR2-3 containing IAP family members, while capable of binding caspases, do not directly inhibit their proteloytic activity. Rather they inhibit apoptosis by affecting signaling activities of key proteins in cell survival pathways. Like XIAP, these IAPs possess a carboxyl-terminal RING finger domain capable of conjugating ubiquitin to specific protein substrates. As an example, cellular IAPs 1 and 2 (cIAP1/2), ubiquitinate RIPK, a signaling intermediate of tumor necrosis death receptor (TNF-DR) activation. Ubiquitinated RIPK is unable to activate caspase-8 in the context of DR activation by TNF family DR ligands. On the contrary, the long ubiquitin chains attached to RIPK provide a scaffold by which cell components of the NFkB cell survival signaling cascade can attach and become activated.

In normal cells undergoing apoptosis, the IAP-mediated inhibition is removed by the mitochondrial protein SMAC (second mitochondrial activator of caspases; also known as DIABLO). SMAC is synthesized as a precursor molecule of 239 amino acids; the N-terminal 55 residues serving as the mitochondria targeting sequence that is removed after import. The mature form of SMAC resides in the intermembrane space of mitochondria. At the time of apoptosis induction, SMAC is released from mitochondria into the cytosol where, together with cytochrome c, it binds to XIAP, and eliminates its' inhibitory effect on caspases. SMAC also binds cIAP1/2 and inhibits their ability to ubiquinate RIPK. SMAC interacts with essentially all IAPs that have been examined to date and thus appears to be a master regulator of apoptosis in mammals.

Down-regulation of XIAP expression by antisense oligonucleotides has been shown to sensitize tumor cells to death induced by a wide range of pro-apoptotic agents, both in vitro and in vivo. SMAC/DIABLO-derived peptides have also been demonstrated to sensitize a number of different tumor induced select cell lines to undergo apoptosis as single agents, while other cell lines require an additional stimulus such as DR agonists or co-treatment with pro-apoptotic drugs. Because IAP inhibition appears to be a viable mechanism for promoting apoptosis and treating diseases and conditions that are sensitive to apoptosis, there is a continuing need to develop compounds that can inhibit IAP.

SUMMARY OF THE INVENTION

There are provided compounds, methods of modulating the activity of IAP, and methods for treating various medical conditions using such compounds.

The present invention also provides processes and intermediates for making the compounds of the present invention or stereoisomers, tautomers or pharmaceutically acceptable salts thereof.

The present invention also provides pharmaceutical compositions comprising a pharmaceutically acceptable carrier and one or more of the compounds of the present invention or stereoisomers, tautomers or pharmaceutically acceptable salts thereof.

The compounds of the invention may be used in the treatment and/or prophylaxis of multiple diseases or disorders associated with IAP inhibition, such as cancer and other maladies.

The compounds of the invention may be used in therapy.

The compounds of the invention may be used for the manufacture of a medicament for the treatment and/or prophylaxis of multiple diseases or disorders associated with IAP inhibition.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, there is provided a compound of Formula (I):

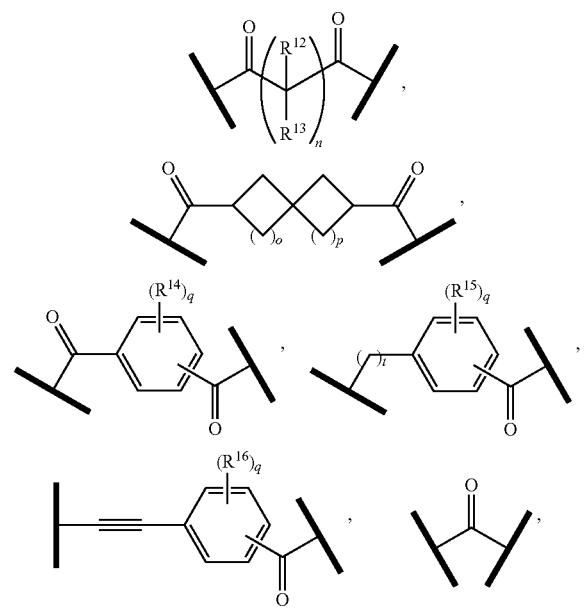

(I)

wherein:

X is absent, —$(CR^{10}R^{11})_m$—, optionally substituted heteroaryl or optionally substituted heterocyclyl,

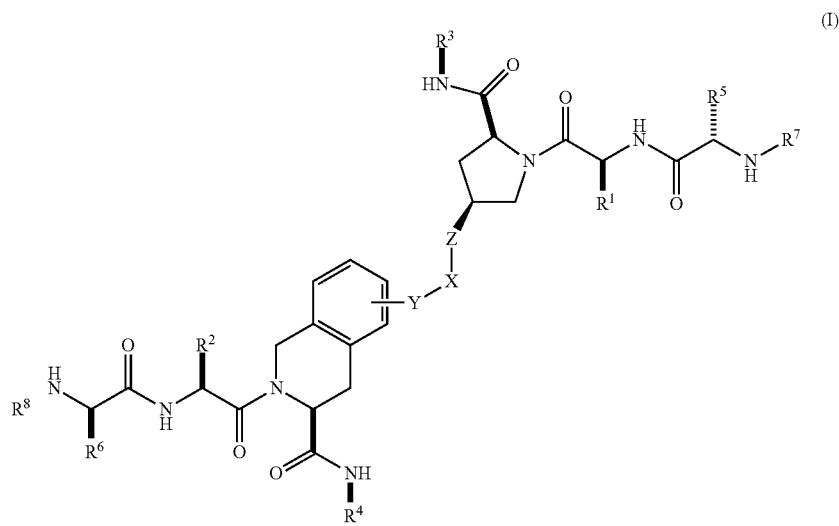

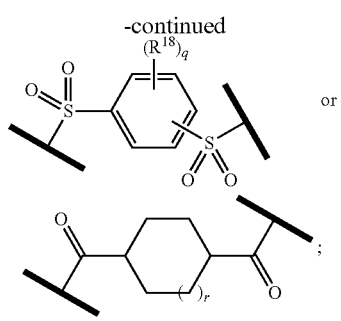

Y and Z are independently C=O, —O—, —$NR^9$—, —CONH—, —NHCO— or may be absent;

$R^1$ and $R^2$ are independently optionally substituted alkyl, optionally substituted cycloalkyl, optionally substituted cycloalkylalkyl, optionally substituted arylalkyl or optionally substituted aryl, or $R^1$ and $R^2$ are independently optionally substituted thioalkyl wherein the substituents attached to the S atom of the thioalkyl are optionally substituted alkyl, optionally substituted branched alkyl, optionally substituted heterocyclyl, —$(CH_2)_vCOR^{20}$, —$CH_2CHR^{21}COR^{22}$ or —$CH_2R^{23}$, wherein:

v=1-3, $R^{20}$ and $R^{22}$ are independently selected from OH, $NR^{24}R^{25}$ or $OR^{26}$, $R^{21}$ is $NR^{24}R^{25}$, $R^{23}$ is optionally substituted aryl or optionally substituted heterocyclyl, where the optional substituents include alkyl and halogen, $R^{24}$ is hydrogen or optionally substituted alkyl, $R^{25}$ is hydrogen, optionally substituted alkyl, optionally substituted branched alkyl, optionally substituted arylalkyl, optionally substituted heterocyclyl, —CH$_2$(OCH$_2$CH$_2$O)$_m$CH$_3$, or a polyamine chain, such as spermine or spermidine, $R^{26}$ is optionally substituted alkyl, and w=1-8, where the optional substituents are OH, halogen or NH$_2$;

$R^3$ and $R^4$ are independently optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

$R^5$, $R^6$, $R^7$ and $R^8$ are independently hydrogen, optionally substituted alkyl or optionally substituted cycloalkyl;

$R^9$ is hydrogen, optionally substituted alkyl, optionally substituted cycloalkyl or CO alkyl;

$R^{10}$ and $R^{11}$ are independently hydrogen, halogen or optionally substituted alkyl;

$R^{12}$ and $R^{13}$ are independently hydrogen, halogen or optionally substituted alkyl, or $R^{12}$ and $R^{13}$ can be taken together to form a carbocyclic ring;

$R^{14}$, $R^{15}$, $R^{16}$, $R^{17}$ and $R^{18}$ are independently hydrogen, halogen, optionally substituted alkyl or OR$^{19}$;

$R^{19}$ is hydrogen, optionally substituted alkyl or optionally substituted cycloalkyl;

m and n are independently 0, 1, 2, 3, or 4;

and p are independently 0, 1, 2 or 3;

q is 0, 1, 2, 3, or 4;

r is 0 or 1;

t is 1, 2, or 3;

and/or a pharmaceutically acceptable salt, tautomer or stereoisomer thereof.

In a second aspect, there is provided a compound of Formula (I) within the scope of the first aspect, wherein:

X is absent, —(CR$^{10}$R$^{11}$)$_m$—, optionally substituted heteroaryl or optionally substituted heterocyclyl,

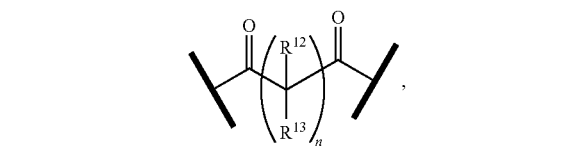,

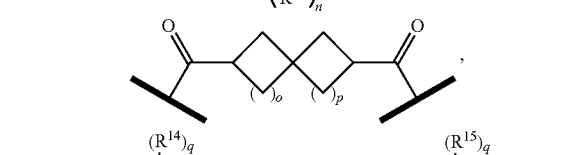,

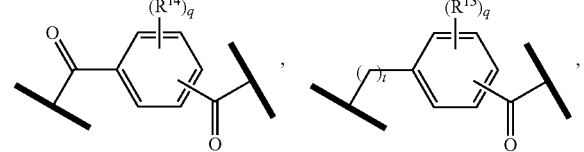,

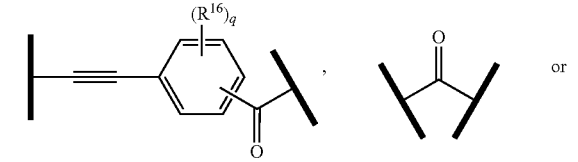 or

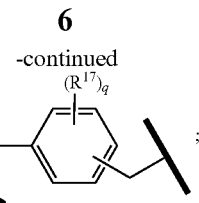;

Y and Z are independently C=O, —O—, —NR$^9$—, —CONH—, —NHCO— or may be absent;

$R^1$ and $R^2$ are independently optionally substituted alkyl, optionally substituted cycloalkyl or optionally substituted thioalkyl;

$R^3$ and $R^4$ are independently optionally substituted alkyl, optionally substituted cycloalkyl, optionally substituted aryl or optionally substituted arylalkyl;

$R^5$ and $R^6$ are independently hydrogen or optionally substituted alkyl;

$R^7$ and $R^8$ are independently hydrogen, optionally substituted alkyl or optionally substituted cycloalkyl;

$R^9$ is hydrogen, optionally substituted alkyl or CO alkyl;

or a pharmaceutically acceptable salt, tautomer or stereoisomer thereof.

In a third aspect, there is provided a compound of Formula (I) within the scope of the first or second aspect, wherein:

X is —(CR$^{10}$R$^{11}$)$_m$—, optionally substituted heteroaryl or optionally substituted heterocyclyl,

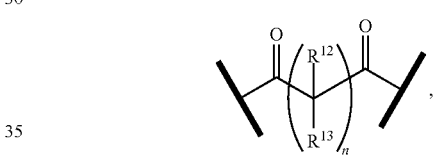,

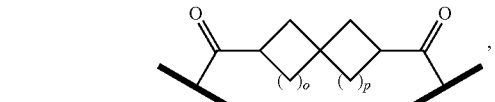,

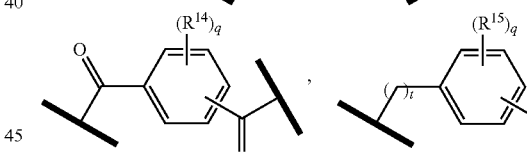,

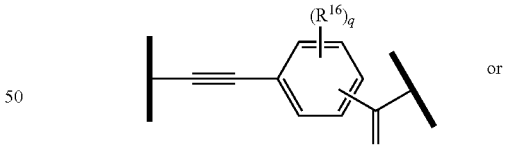 or

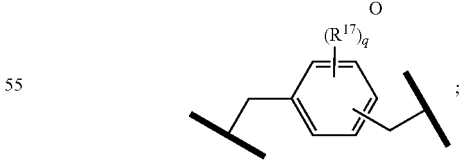;

Y and Z are independently —CONH— or —NHCO—;

$R^1$ and $R^2$ are independently optionally substituted alkyl;

$R^3$ and $R^4$ are independently optionally substituted alkyl, optionally substituted aryl or optionally substituted arylalkyl;

$R^5$ and $R^6$ are independently alkyl;

$R^7$ and $R^8$ are independently optionally substituted alkyl;

$R^9$ is hydrogen;

or a pharmaceutically acceptable salt, tautomer or stereoisomer thereof.

In a fourth aspect, there is provided a compound of Formula (I) within the scope of the first, second or third aspect, wherein:

X is —(CR$^{10}$R$^{11}$)$_m$—, optionally substituted heteroaryl or optionally substituted heterocyclyl, Y and Z are independently —CONH— or —NHCO—;
R$^1$ and R$^2$ are independently alkyl;
R$^3$ and R$^4$ are independently optionally substituted aryl or optionally substituted arylalkyl;
R$^5$ and R$^6$ are independently methyl or ethyl;
R$^7$ and R$^8$ are independently alkyl;
or a pharmaceutically acceptable salt, tautomer or stereoisomer thereof.

In a fifth aspect, there is provided a compound of Formula (I) within the scope of the first, second, third or fourth aspect, wherein:

X is optionally substituted heteroaryl or optionally substituted heterocyclyl wherein the heteroaryl or heterocyclyl is indole, oxazole, thiazole, benzothiazole, pyrrolotriazine, pyridine or isoquinoline.

In a sixth aspect, there is provided a compound of Formula (I) within the scope of the first, second, third, fourth or fifth aspect, wherein:

R$^1$ and R$^2$ are independently t-butyl;
R$^3$ and R$^4$ are independently optionally substituted phenyl or 1,2,3,4-tetrahydronaphthalenyl;
R$^5$ and R$^6$ are independently methyl or ethyl;
R$^7$ and R$^8$ are independently methyl, ethyl or t-butyl;
or a pharmaceutically acceptable salt, tautomer or stereoisomer thereof.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In one embodiment, Y is absent, —CO—, —NH— or —CONH—.

In another embodiment, Y is absent or —CONH—.

In another embodiment, Y is absent.

In another embodiment, Z is absent or —CONH—.

In another embodiment, R$^1$ and R$^2$ are independently t-butyl.

In another embodiment, R$^3$ and R$^4$ are independently 1,2,3,4-tetrahydronaphthalenyl.

In another embodiment, R$^5$, R$^6$, R$^7$ or R$^8$ are independently methyl or ethyl.

In another embodiment, the compounds of the invention have BIR3 IC$_{50}$ values in the FPA assay ≤0.30.

In another embodiment, the compounds of the invention have BIR3 IC$_{50}$ values in the FPA assay ≤0.10.

In another embodiment, the compounds of the invention have BIR3 IC$_{50}$ values in the HTRF assay ≤0.30.

In another embodiment, the compounds of the invention have BIR3 IC$_{50}$ values in the HTRF assay ≤0.03.

In another embodiment, the compounds of the invention have BIR2 IC$_{50}$ values in the AlphaScreen assay ≤2.5.

In another embodiment, the compounds of the invention have BIR2 IC$_{50}$ values in the AlphaScreen assay ≤0.15.

In another embodiment, the compounds of the invention have BIR2-3 IC$_{50}$ values in the HTRF assay ≤0.20.

In another embodiment, the compounds of the invention have BIR2-3 IC$_{50}$ values in the HTRF assay ≤0.008.

II. Other Embodiments of the Invention

In another embodiment, there is provided a composition comprising one or more compounds of the present invention or a stereoisomer, a tautomer, a pharmaceutically acceptable salt, or a solvate thereof.

In another embodiment, there is provided a pharmaceutical composition comprising a pharmaceutically acceptable carrier and at least one of the compounds of the present invention or a stereoisomer, a tautomer, a pharmaceutically acceptable salt, or a solvate thereof.

In another embodiment, there is provided a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, there is provided a process for making a compound of the present invention or a stereoisomer, a tautomer, a pharmaceutically acceptable salt, or a solvate thereof.

In another embodiment, there is provided an intermediate for making a compound of the present invention or a stereoisomer, a tautomer, a pharmaceutically acceptable salt, or a solvate thereof.

In another embodiment, there is provided a method for the treatment and/or prophylaxis of various types of cancer, comprising administering to a patient in need of such treatment and/or prophylaxis a therapeutically effective amount of one or more compounds of the present invention, alone, or, optionally, in combination with another compound of the present invention and/or at least one other type of therapeutic agent.

In another embodiment, there is provided a compound of the present invention for use in therapy.

In another embodiment, there is provided a combined preparation of a compound of the present invention and additional therapeutic agent(s) for simultaneous, separate or sequential use in therapy.

In another embodiment, there is provided a combined preparation of a compound of the present invention and additional therapeutic agent(s) for simultaneous, separate or sequential use in the treatment and/or prophylaxis of multiple diseases or disorders associated with the inhibition of apoptosis.

In another aspect, there is provided a method of treating a patient suffering from or susceptible to a medical condition that is sensitive to apoptosis. A number of medical conditions can be treated. The method comprises administering to the patient a therapeutically effective amount of a composition comprising a compound described herein. For example, the compounds described herein may be used to treat or prevent infections, proliferative diseases (e.g., cancer), and autoimmune diseases.

In another aspect, there is provided a method of inhibiting the activity of an IAP in a cell, thus promoting apoptosis. The method comprises exposing the cell to a compound described herein.

III. Therapeutic Applications

The compounds and pharmaceutical compositions of the present invention are useful in treating or preventing any disease or conditions that are sensitive to apoptosis. These include infections (e.g., skin infections, GI infection, urinary tract infections, genito-urinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the animal. In certain embodiments, the compound or pharmaceutical composition is administered orally. In other embodiments, the compound or pharmaceutical composition is administered parenterally.

In one embodiment, the compounds of this invention can be used for the treatment of any cancer type that fails to undergo apoptosis in a patient. This includes, but is not limited to: solid tumors, including but not limited to carcinomas; sarcomas including Kaposi's sarcoma; erythroblastoma; glioblastoma; meningioma; astrocytoma; melanoma; and myoblastoma. Treatment or prevention of non-solid tumor cancers, such as leukemia, is also contemplated by this invention.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erythematosus or rheumatoid arthritis.

Thus, according to another embodiment, there is provided a method of treating an autoimmune disease by providing to a patient in need thereof a compound or composition of the present invention. Examples of such autoimmune diseases include, but are not limited to, collagen diseases such as rheumatoid arthritis, systemic lupus erythematosus. Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as *pemphigus vulgaris*, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, Malaria and Chagas disease.

Compounds of the invention are useful for sensitizing cells to apoptotic signals. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

IV. Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained release formulation; (3) topical application, for example, as a cream, ointment, or a controlled release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about 99 percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, troches and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

V. Definitions

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans-(or E- and Z—) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$-$C_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or in combination with another radical, means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthyl, 2-naphthyl and tetrahydronaphthyl. The fused aryls may be connected to another group either at a suitable position on the cycloalkyl ring or the aromatic ring. For example:

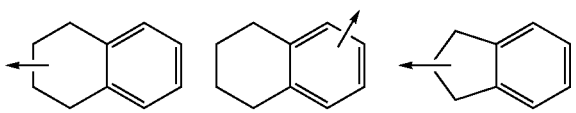

-continued

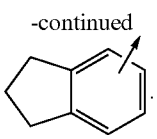

Arrowed lines drawn from the ring system indicate that the bond may be attached to any of the suitable ring atoms.

The term "cycloalkyl" refers to cyclized alkyl groups. $C_{3-6}$ cycloalkyl is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

As used herein, the term "heteroaryl" or "aromatic heterocyclic group" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

As used herein, the term "heterocyclo", "heterocyclic" or "heterocyclyl" is intended to mean a 5-, 6- or 7-membered non-aromatic ring system containing from 1 to 4 heteroatoms selected from O, N or S. Examples of heterocycles include, but are not limited to, pyrrolidinyl, tetrahydrofuranyl, tetrahydropyranyl, piperidyl, pyrrolinyl, piperazinyl, imidazolinyl, morpholinyl, imidazolidinyl, pyrazolidinyl and pyrazolinyl.

The term "counter ion" is used to represent a negatively charged species such as chloride, bromide, hydroxide, acetate, and sulfate or a positively charged species such as sodium ($Na^+$), potassium ($K^+$), ammonium ($R_nNH_m^+$ where n=0-4 and m=0-4) and the like.

As used herein, a "polyamine" is any of a group of aliphatic, straight-chain amines derived biosynthetically from amino acids; polyamines are reviewed in Marton et al., *Ann. Rev. Pharm. Toxicol.*, 35:55-91 (1995). The term "polyamine" is generally meant to include a naturally-occurring polyamine or a polyamine which is naturally produced in eukaryotic cells. Examples of polyamines include putrescine, spermidine, spermine and cadaverine.

The term "electron withdrawing group" (EWG) refers to a substituent which polarizes a bond, drawing electron density towards itself and away from other bonded atoms. Examples of EWG include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O-heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl)$_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, a nucleophile, a hydrazine reducing agent, an activator, a strong base, a hindered amine base and a cyclizing agent. Such amine protecting groups fitting these criteria include those listed in Greene et al., *Protective Groups in Organic Synthesis*, John Wiley & Sons, New York (1991) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);
c) Bundgaard, H., *Adv. Drug Deliv. Rev.*, 8:1-38 (1992);
d) Bundgaard, H. et al., *J. Pharm. Sci.*, 77:285 (1988); and
e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "therapeutically effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

VI. Methods of Preparation

Certain compounds of Formula I may generally be prepared according to the following Schemes 1 to 18. Tautomers and solvates (e.g., hydrates) of the compounds of Formula I are also within the scope of the present invention. Methods of solvation are generally known in the art. Accordingly, the compounds of the instant invention may be in the free or hydrate form, and may be obtained by methods exemplified by the following schemes.

The tetrahydroisoquinoline-based coupling partners 8 can be prepared as shown in Scheme 1. Amide intermediates 3 can be derived from readily available carboxylic acid 1 (European Patent Application No. EP 401676 A1 (1990)) and substituted amines 2 using coupling reagents, such as EDC and HOAt. Following deprotection of the t-butyl carbamate of 3 under acidic conditions (e.g., TFA), the resulting secondary amine can be treated with various N-protected amino acids 4 in the presence of a coupling reagent, such as EDC and HOAt to furnish intermediates 5. Removal of the protecting group (PG) can be achieved under standard conditions dependent on the nature of the PG to liberate the primary amine. Amides 7 can then be obtained by coupling of the intermediate carboxylic acid to N-protected amino acids 6 in the presence of a coupling reagent. Reduction of the nitro group of intermediates 7 under hydrogenation conditions affords the amine coupling partners 8.

Scheme 1

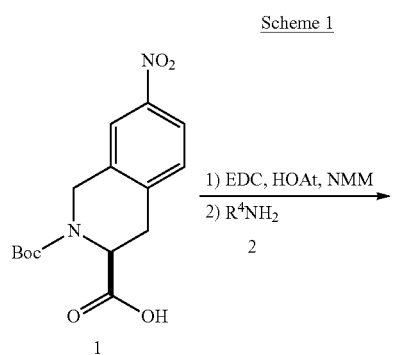

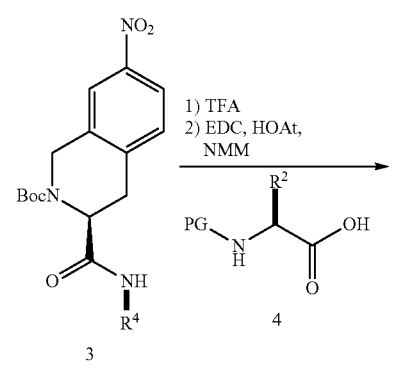

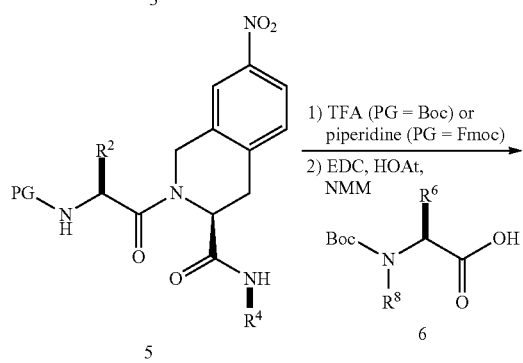

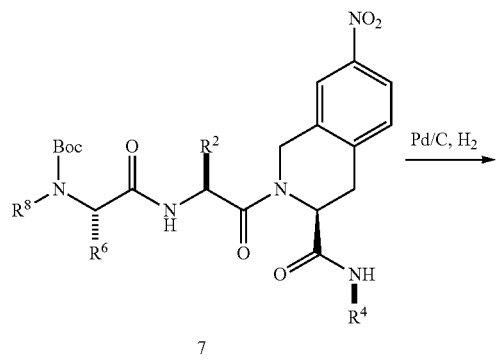

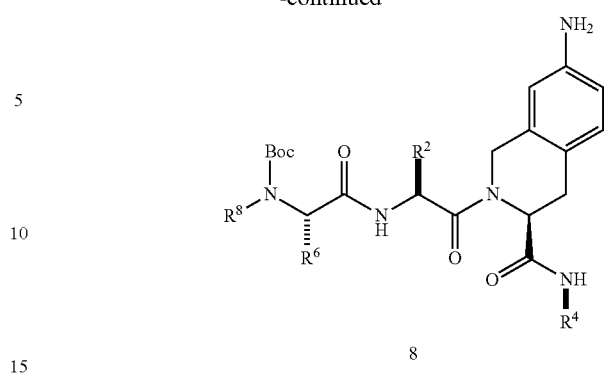

Linear heterodimeric compounds 19 can be prepared by a coupling reaction between carboxylic acids 18 and amines 8 as outlined in Scheme 2. The key coupling partners 18 can be prepared starting with Fmoc-protected aminoproline 9. Compound 9 can be converted to amide intermediates 11 using coupling reagents, such as EDC and HOAt. Conversion of 11 to the elaborated amine intermediates 16 can be accomplished using similar iterative chemistry as described in Scheme 1. The synthesis of acid intermediates 18 can be accomplished utilizing chemistry described in Scheme 1 followed by base-promoted hydrolysis of the ester intermediate. The synthesis of heterodimeric analogs 19 can proceed via a two-step procedure employing carboxylic acids 18 and a coupling reagent followed by removal of the Boc carbamates under acidic conditions.

Scheme 2

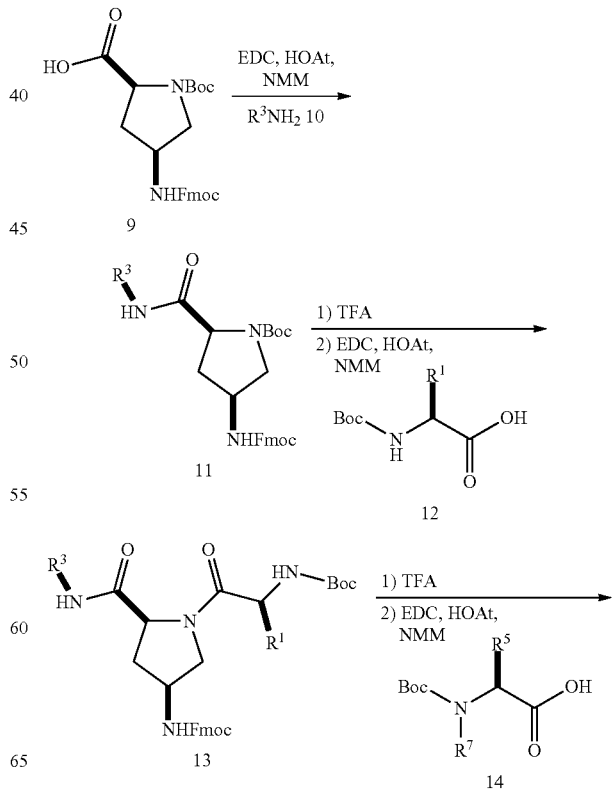

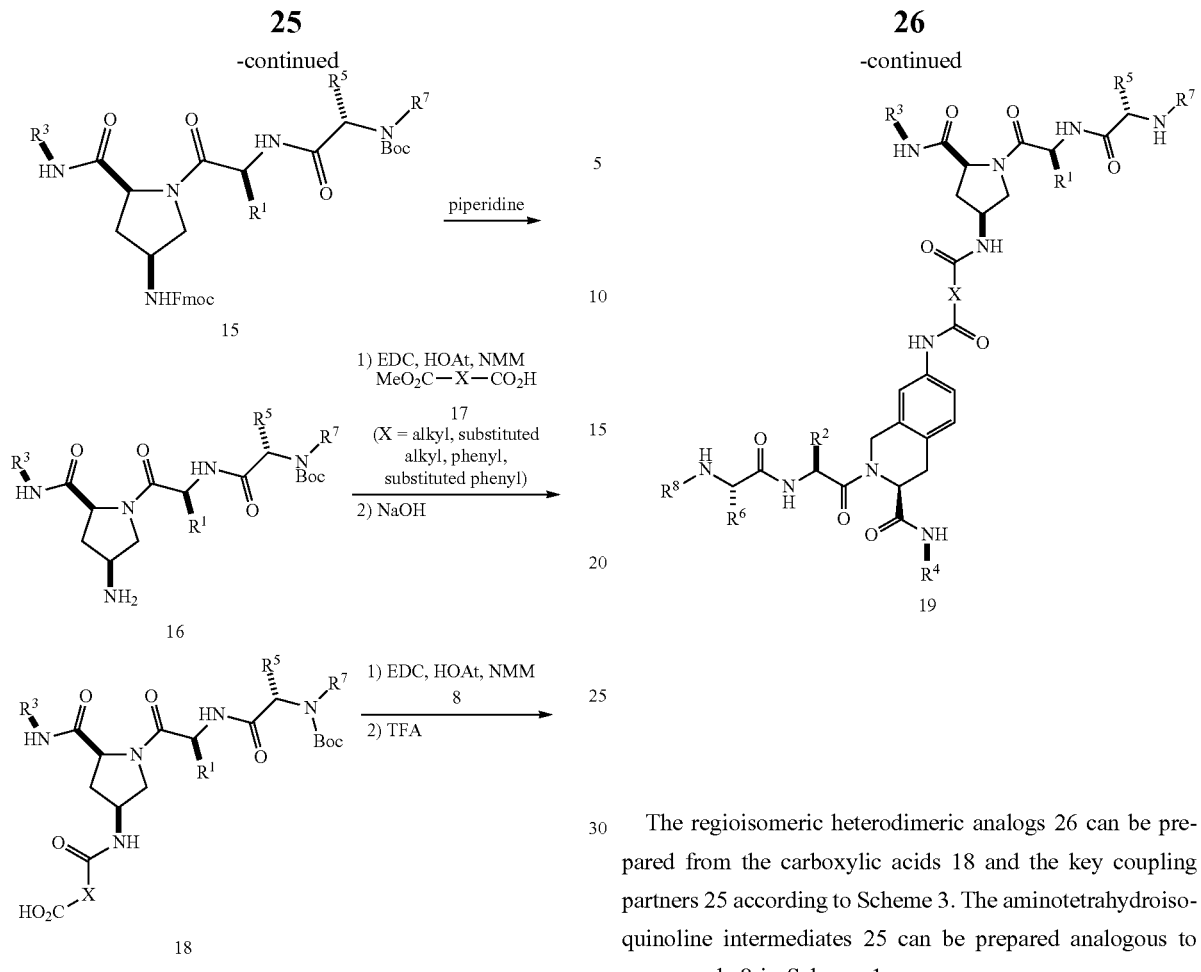
The regioisomeric heterodimeric analogs 26 can be prepared from the carboxylic acids 18 and the key coupling partners 25 according to Scheme 3. The aminotetrahydroisoquinoline intermediates 25 can be prepared analogous to compounds 8 in Scheme 1.
Scheme 3
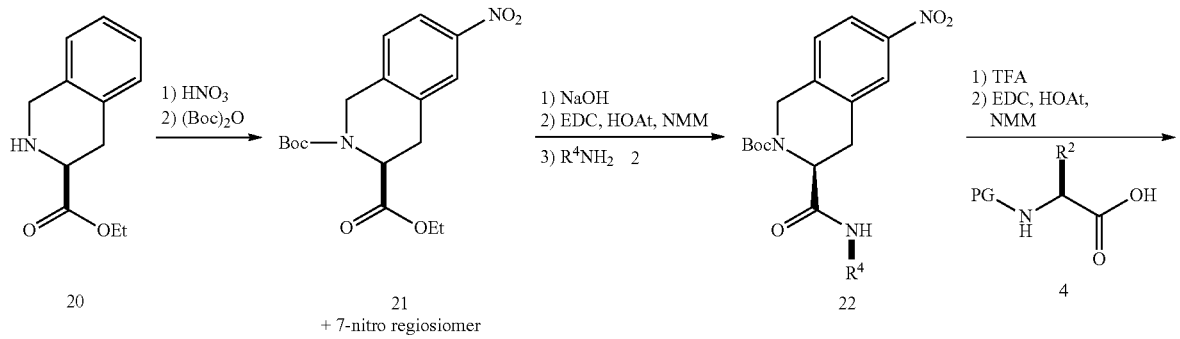
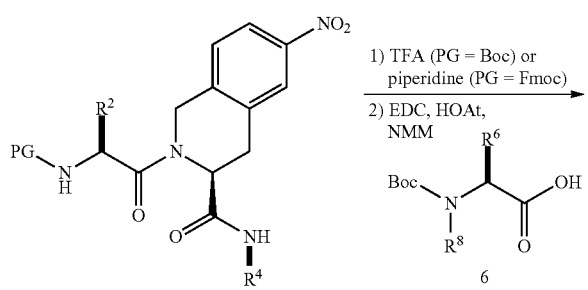

-continued
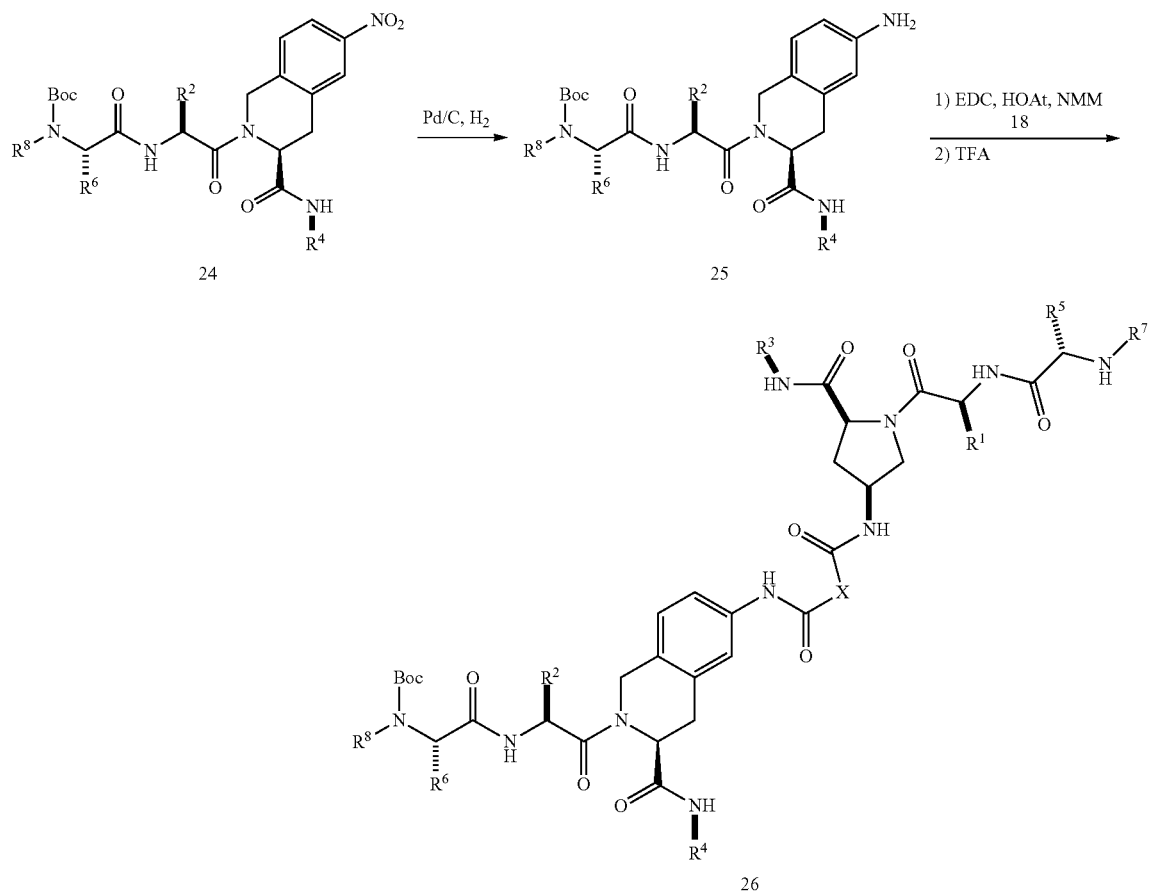
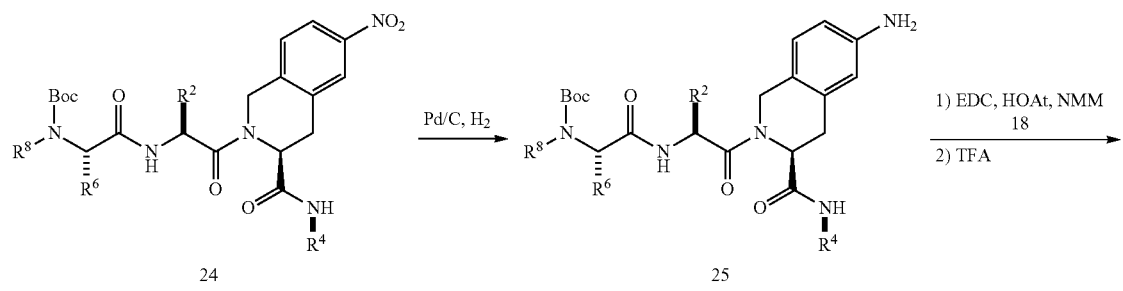

-continued

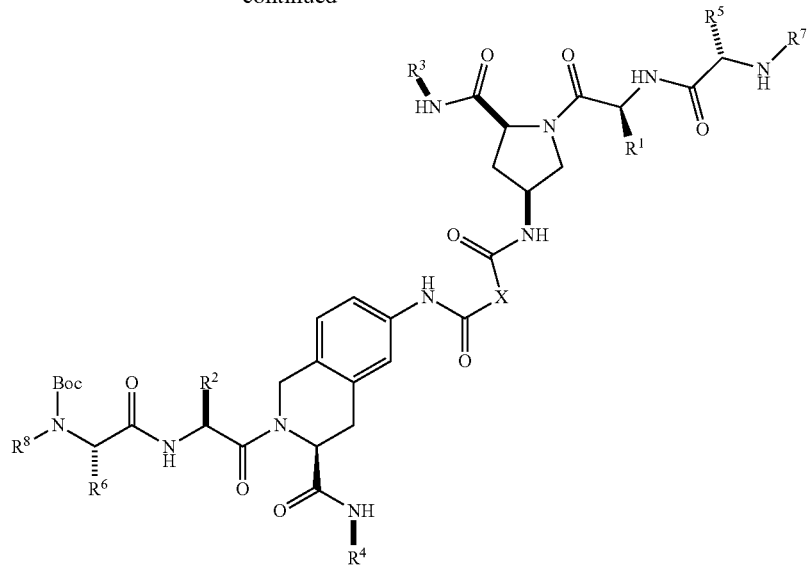

26

Analogs such as 27 and 29 can be readily prepared utilizing the key intermediates 8 and 16 as described in Scheme 4. The ureas 27 can be prepared by treatment of the amino-tetrahydroisoquinolines 8 with triphosgene to form an isocyante intermediate, which can be subsequently quenched with aminopyrrolidines 16. Acid-based cleavage of the t-butyl carbamates affords the desired ureas 27. Analogs 29 can be obtained by reductive amination of intermediates 8 with formyl acids 28 followed by coupling with 16 and subsequent deprotection.

Scheme 4

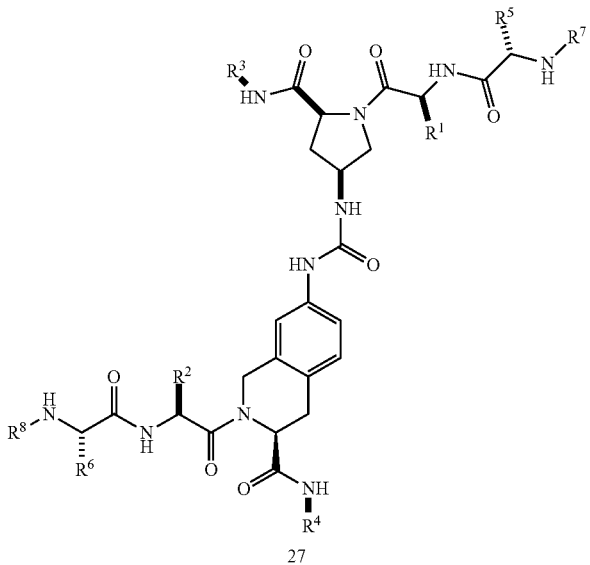

27

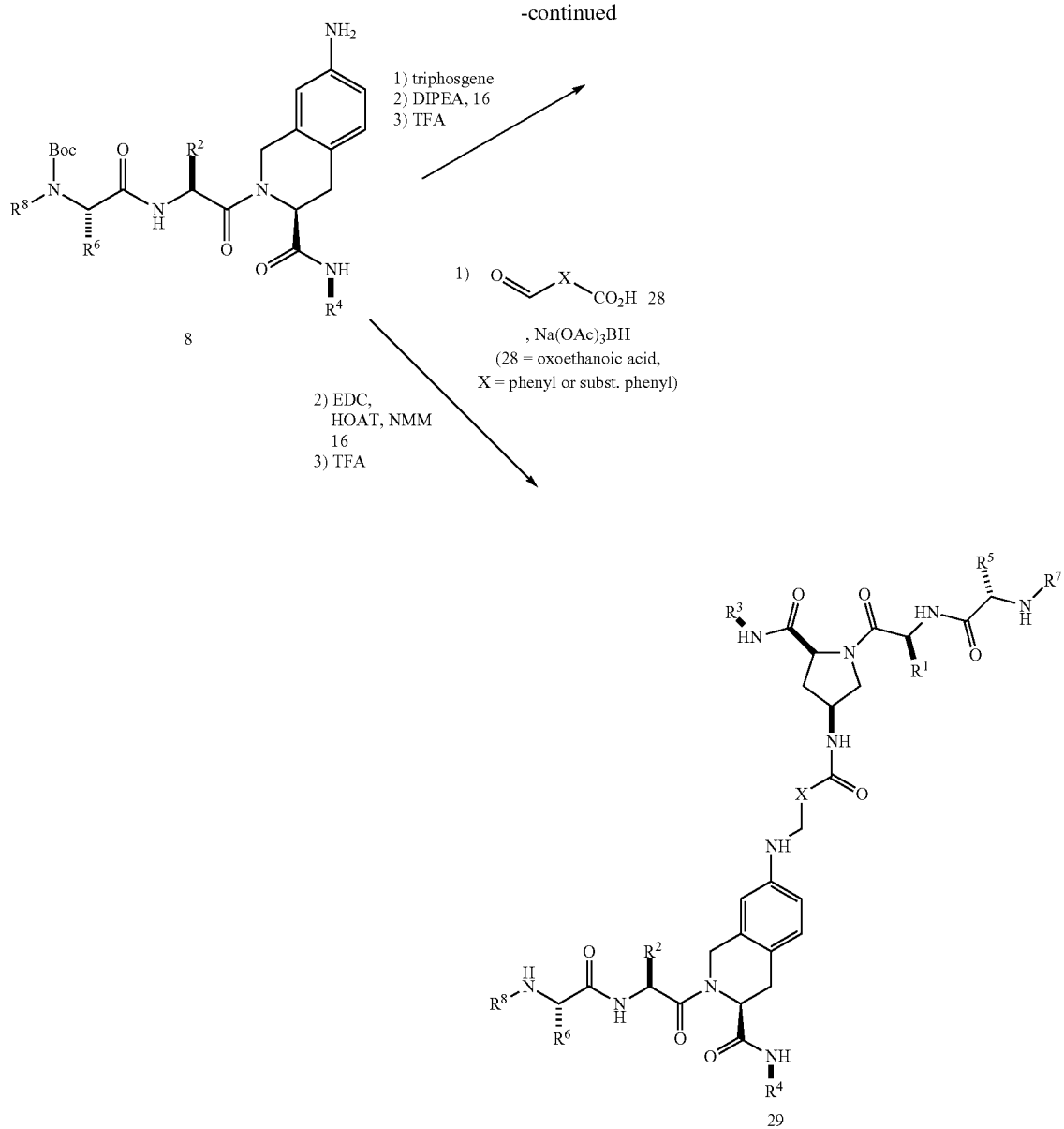

The tetrahydroisoquinoline carboxylic acid coupling partners 36 can be prepared as shown in Scheme 5. Pictet-Spengler cyclization of 3,5-diiodotyrosine 30 with formaldehyde followed by catalytic hydrogenation provides acids 31. N-Boc protection of compound 31 followed by coupling with amines 2 provides the amide intermediates 32. Aryl triflate formation followed by palladium-catalyzed methoxycarbonylation then provides intermediates 33. Following deprotection of the t-butyl carbamate of 33 under acidic conditions (e.g., TFA), the secondary amine can be treated with various N-protected amino acids 4 in the presence of a coupling reagent, such as EDC, to furnish intermediates 34. Primary amine formation can be achieved using conditions dependent on the nature of the PG. Amide formation with acids 6 in the presence of a coupling reagent followed by hydrolysis provides the carboxylic acid coupling partners 36.

Scheme 5

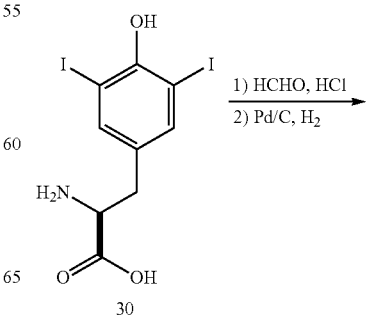

33
-continued

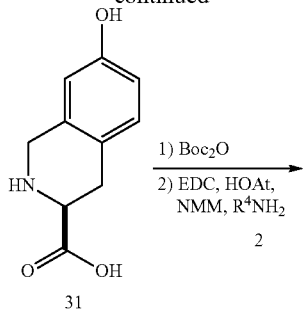
31

1) Boc₂O
2) EDC, HOAt, NMM, R⁴NH₂
2

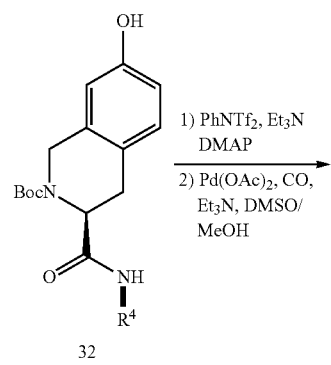
32

1) PhNTf₂, Et₃N DMAP
2) Pd(OAc)₂, CO, Et₃N, DMSO/MeOH

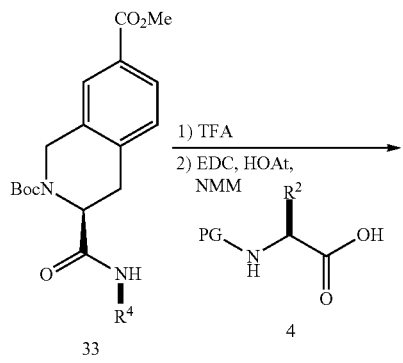
33

1) TFA
2) EDC, HOAt, NMM
4

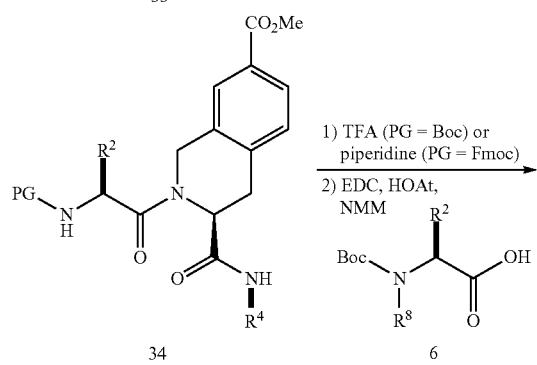
34

1) TFA (PG = Boc) or piperidine (PG = Fmoc)
2) EDC, HOAt, NMM
6

34
-continued

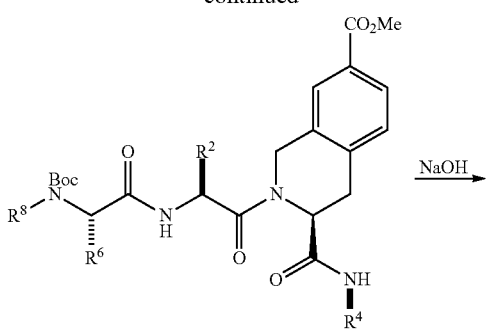
35

NaOH

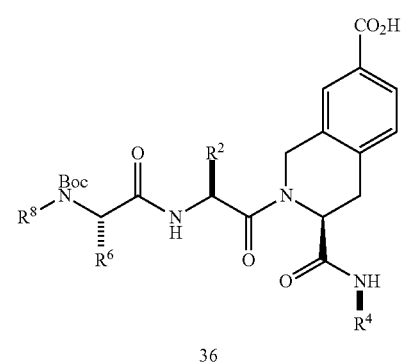
36

Linear heterodimeric compounds 39 can be prepared using the synthetic sequence outlined in Scheme 6. The carboxylic acids 36 can be readily coupled with amino esters 37 in the presence of coupling reagents, such as EDC and DMAP. Subsequent base-promoted hydrolysis of the intermediate methyl ester provides the acids 38. Conversion of compounds 38 to the desired heterodimeric analogs 39 can be carried out as described above.

Scheme 6

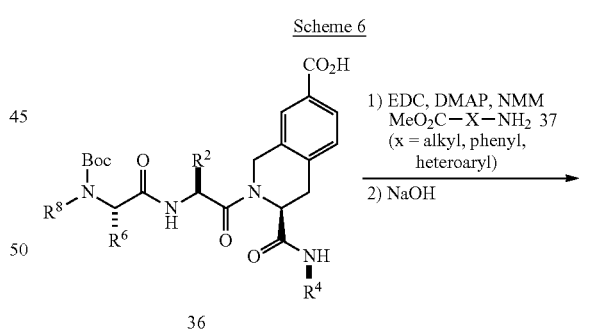
36

1) EDC, DMAP, NMM
MeO₂C—X—NH₂ 37
(x = alkyl, phenyl, heteroaryl)
2) NaOH

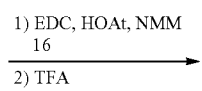

1) EDC, HOAt, NMM
16
2) TFA

38

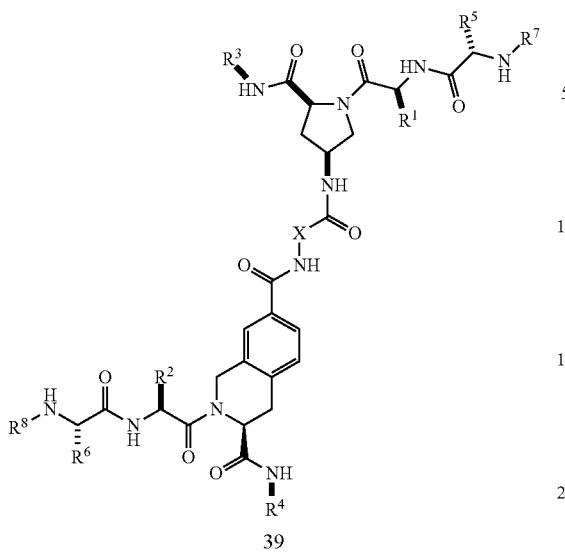

39

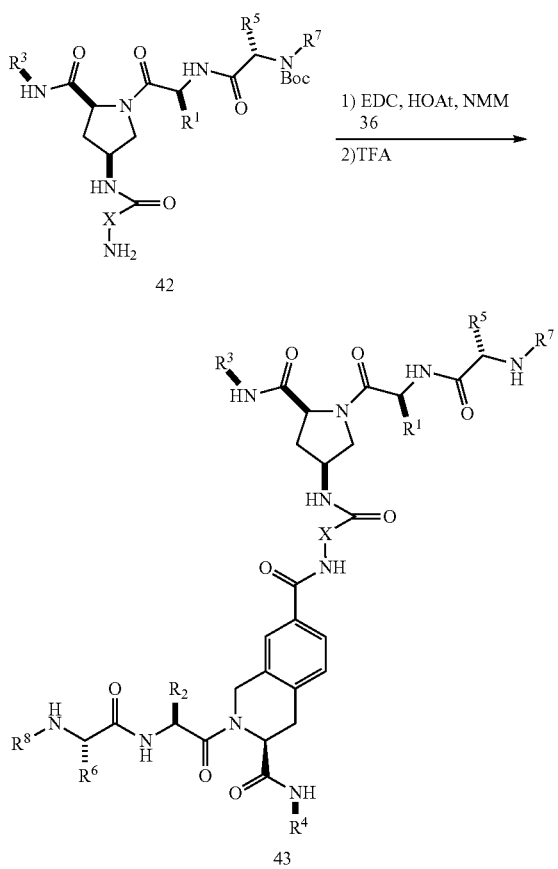

42

43

Alternatively, linear heterodimeric compounds 43 can be prepared using the synthetic sequence outlined in Scheme 7. Aminopyrrolidines 16 can be coupled to carboxylic acids 40 in the presence of coupling reagents, such as EDC and HOAt to afford intermediates 41. Reduction of the nitro group of 41 under hydrogenation conditions with palladium on carbon affords intermediates 42. Compounds 42 can be readily converted to the desired analogs 43 using chemistry described above.

Scheme 7

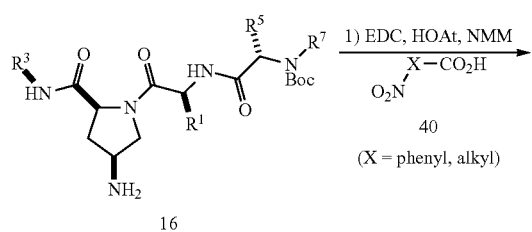

16

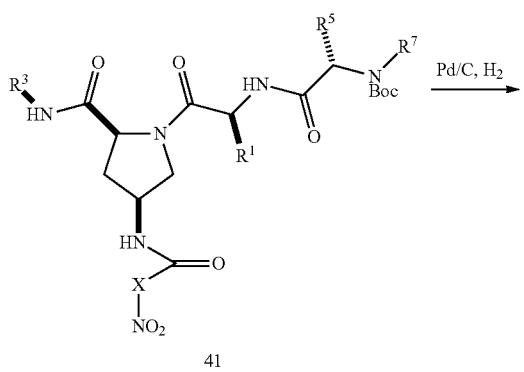

41

Piperidine-based analogs 50 can be prepared as outlined in Scheme 8. Coupling of commercially available (2S,4R)-4-hydroxypiperidine-2-carboxylic acid (44) with amines 2 can provide amides 45. Subsequent benzylation of the alcohol of 45 with methyl 4-((2,2,2-trichloro-1-iminoethoxy)methyl)benzoate (46) and TfOH affords intermediates 47. Coupling of 47 with various N-Boc protected amino acids 4 followed by deprotection led to intermediates 48. Compound 48 can be converted to the desired analogs 50 using chemistry described above.

Scheme 8

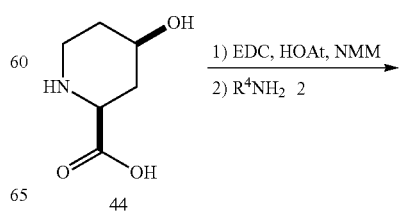

44

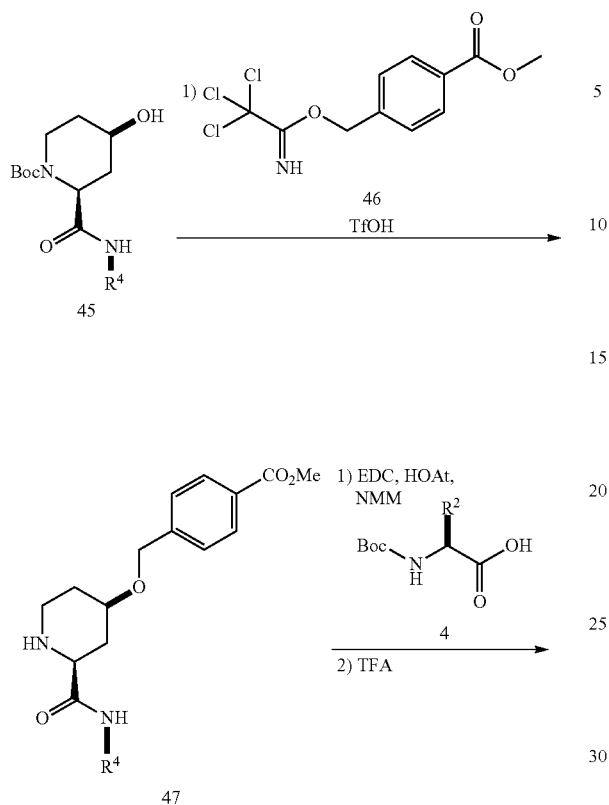
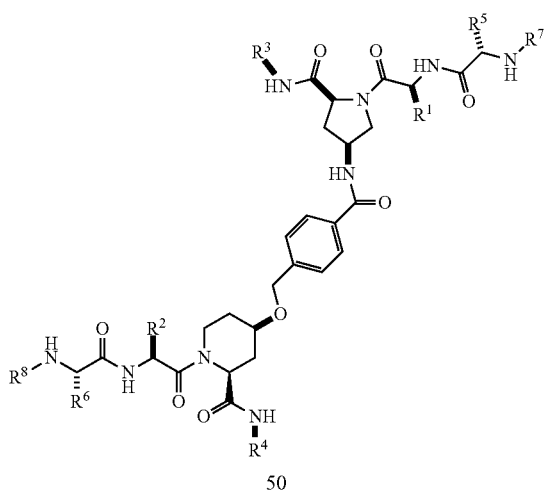
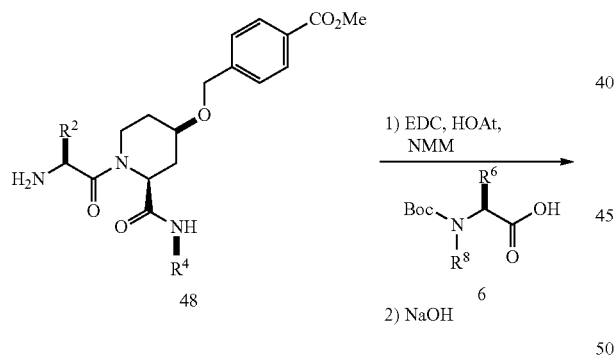
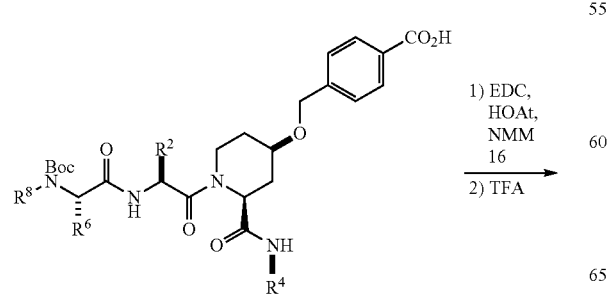
Analogs such as 54 can be prepared according to the synthetic route described in Scheme 9. Reductive amination of 8 with oxoethanoic esters 51 followed by acylation of the resulting intermediate 52 with acetic anhydride gave elaborated intermediates 53. A straightforward 3-step process can then be used to convert compounds 53 to the desired heterodimeric analogs 54.
Scheme 9
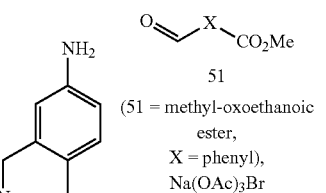

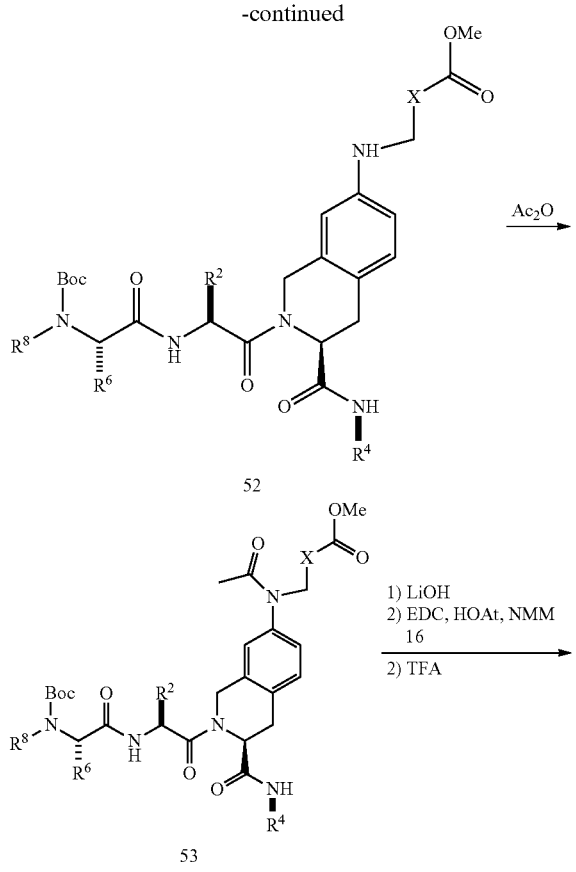
52
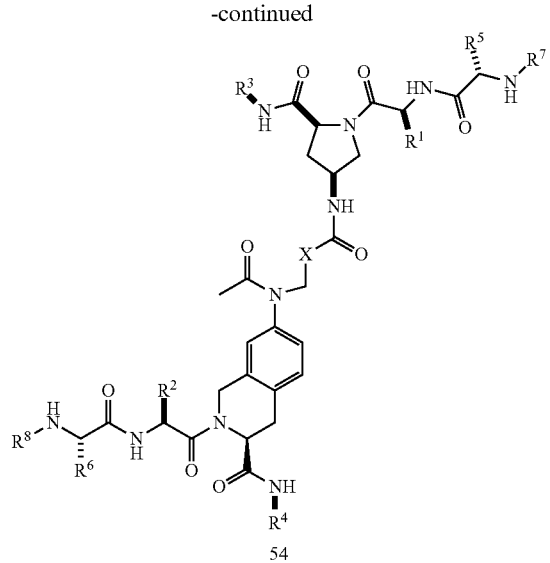
54
53
Heterodimeric analogs 59 can be prepared according to the synthetic route illustrated in Scheme 10. N-Boc-protected 7-hydroxytetrahydroisoquinolines 32 can be treated with methyl 4-(bromomethyl)benzoate (55) followed by acid to afford intermediates 56. Compounds 56 can be converted to the desired analogs 59 using chemistry described above.
Scheme 10
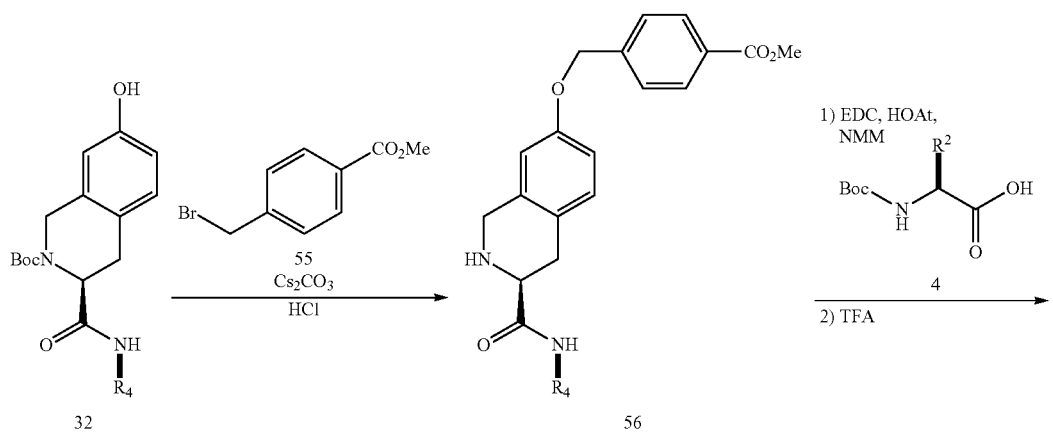

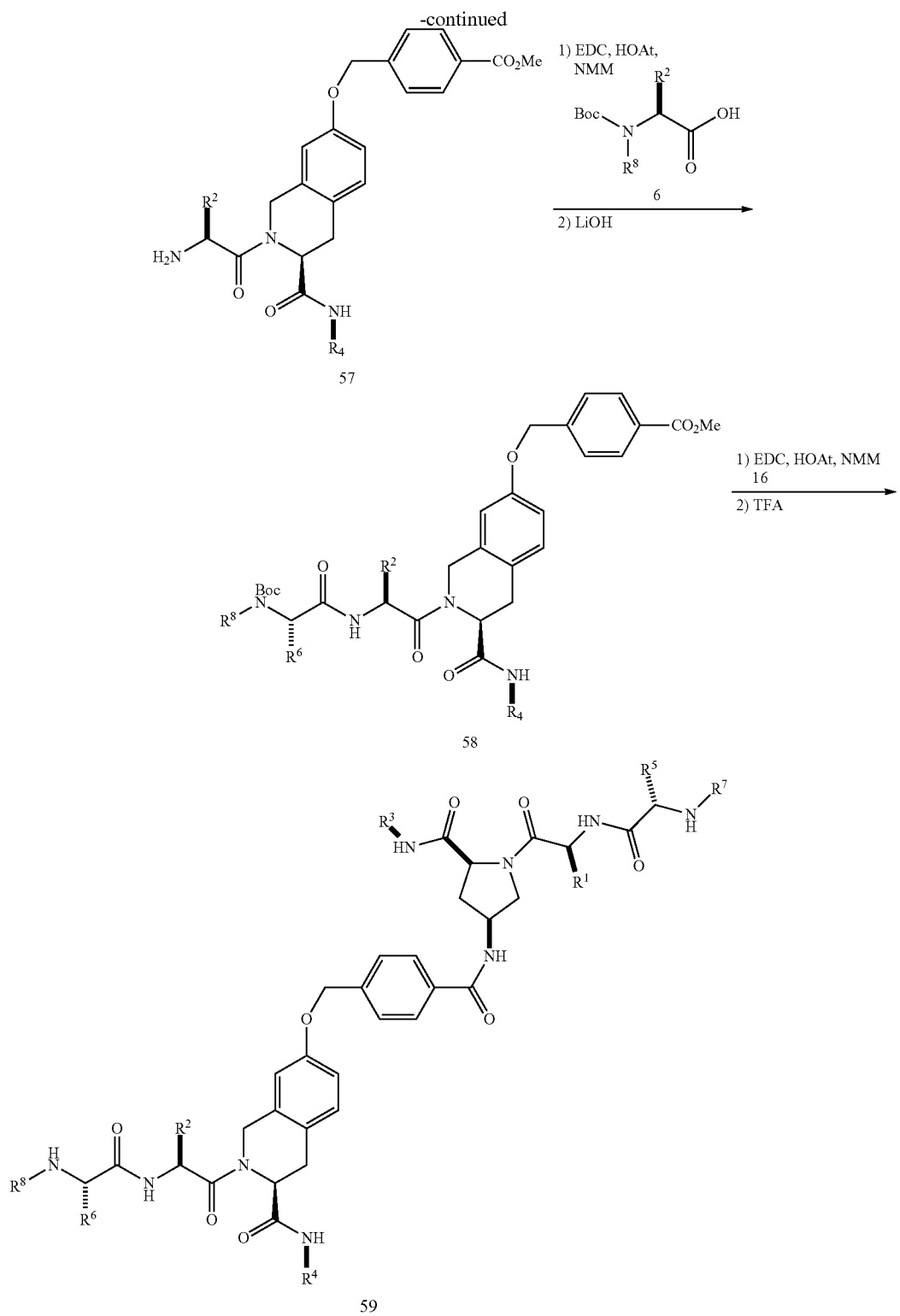

Analogs such as 68 can be prepared using chemistry the outlined in Scheme 11. 7-Hydroxytetrahydroisoquinoline intermediates 61 can be prepared starting from N-Boc-protected phenols 32 utilizing similar methods as described for Scheme 5. Triflates 62, derived from phenols 61 can be coupled with acetylene 65 under Sonogashira conditions to afford intermediate esters 66. Base-promoted hydrolysis of the ester of 66 using lithium hydroxide followed by amide coupling of 16 provided the acetylene derivatives 67. Reduction of the alkyne of 67 followed by global deprotection with TFA affords the desired heterodimeric analogs 68.

Scheme 11
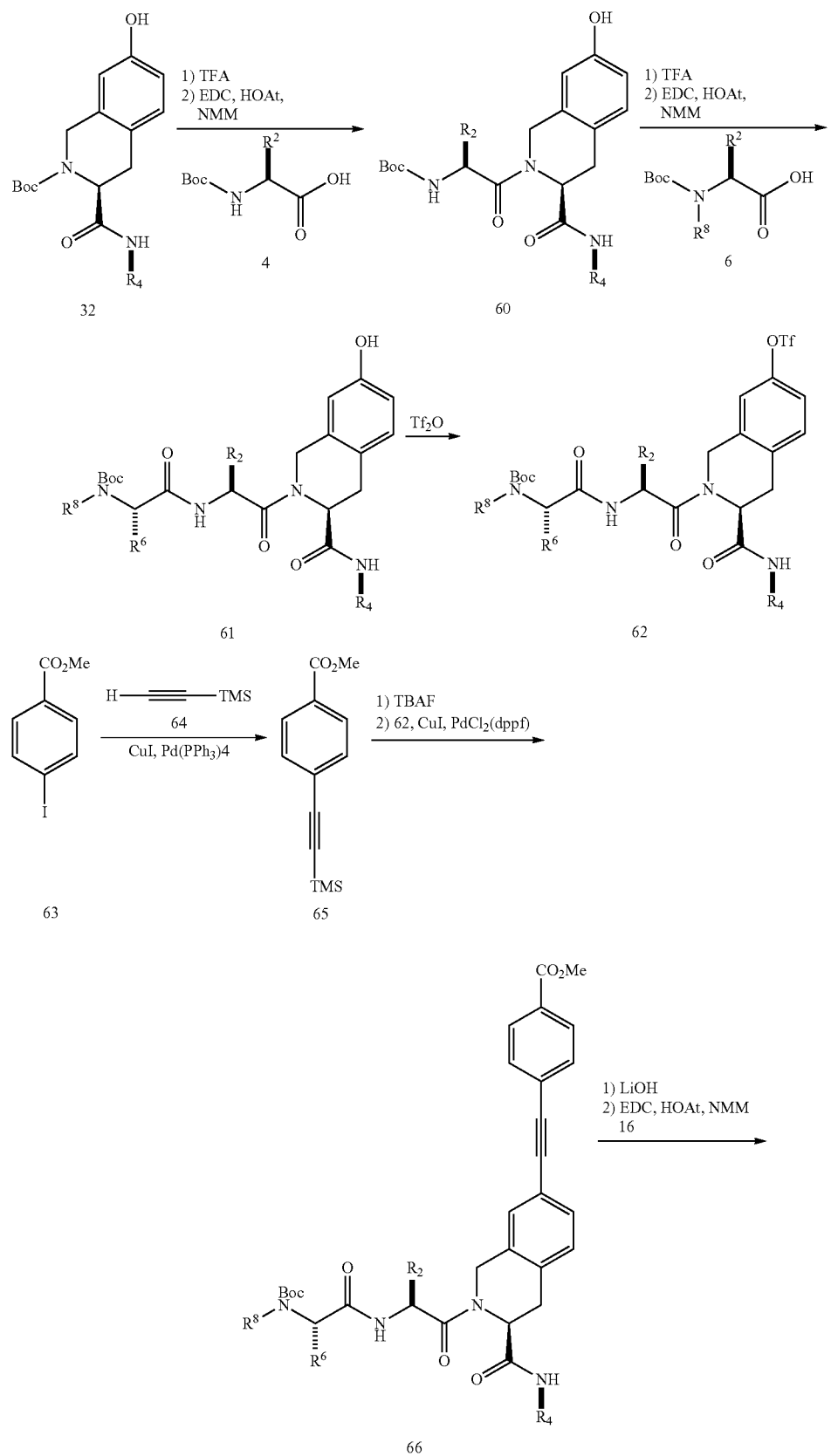

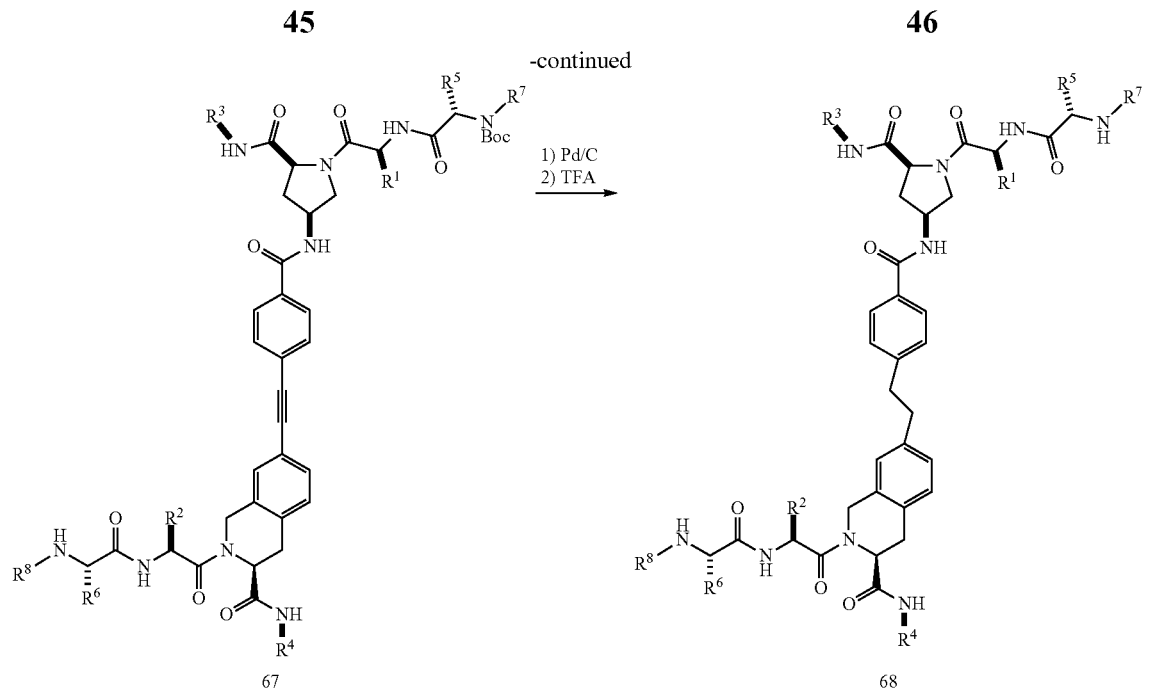

67

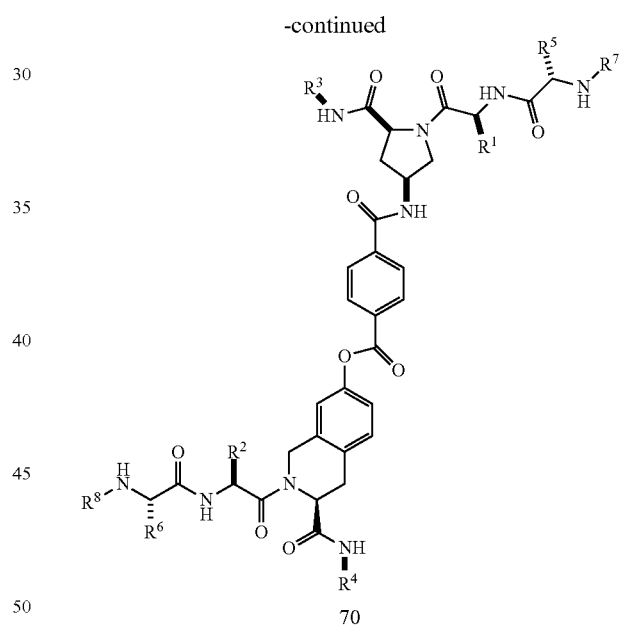

68

Linear heterodimeric compounds 70 can be prepared according to the synthetic sequence outlined in Scheme 12. Treatment of intermediates 61 with terephthaloyl chloride (69) followed by coupling of the requisite acid chlorides with the aminopyrrolidines 16 and global deprotection with TFA affords the heterodimeric analogs 70.

70

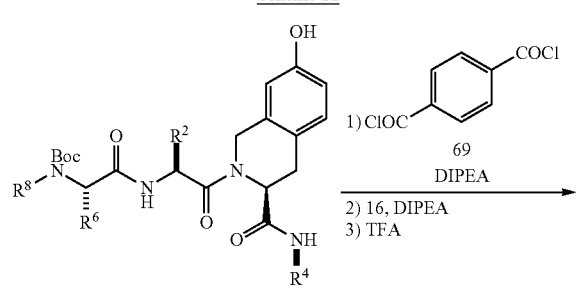

61

Linear heterodimeric compounds 77 can be prepared as outlined in Scheme 13. Commercially available N-Boc-protected pyrrolidine 71 can be treated with methyl 4-(bromomethyl)benzoate (72) to afford ether 73. Compound 73 can be readily converted to peptides 76 using previously described chemistry. The coupling of benzoic acid intermediates 76 with N-Boc-protected 7-amino-tetrahydroisoquinoline intermediates 8 followed by global deprotection with TFA affords the desired heterodimeric analogs 77.

Scheme 13
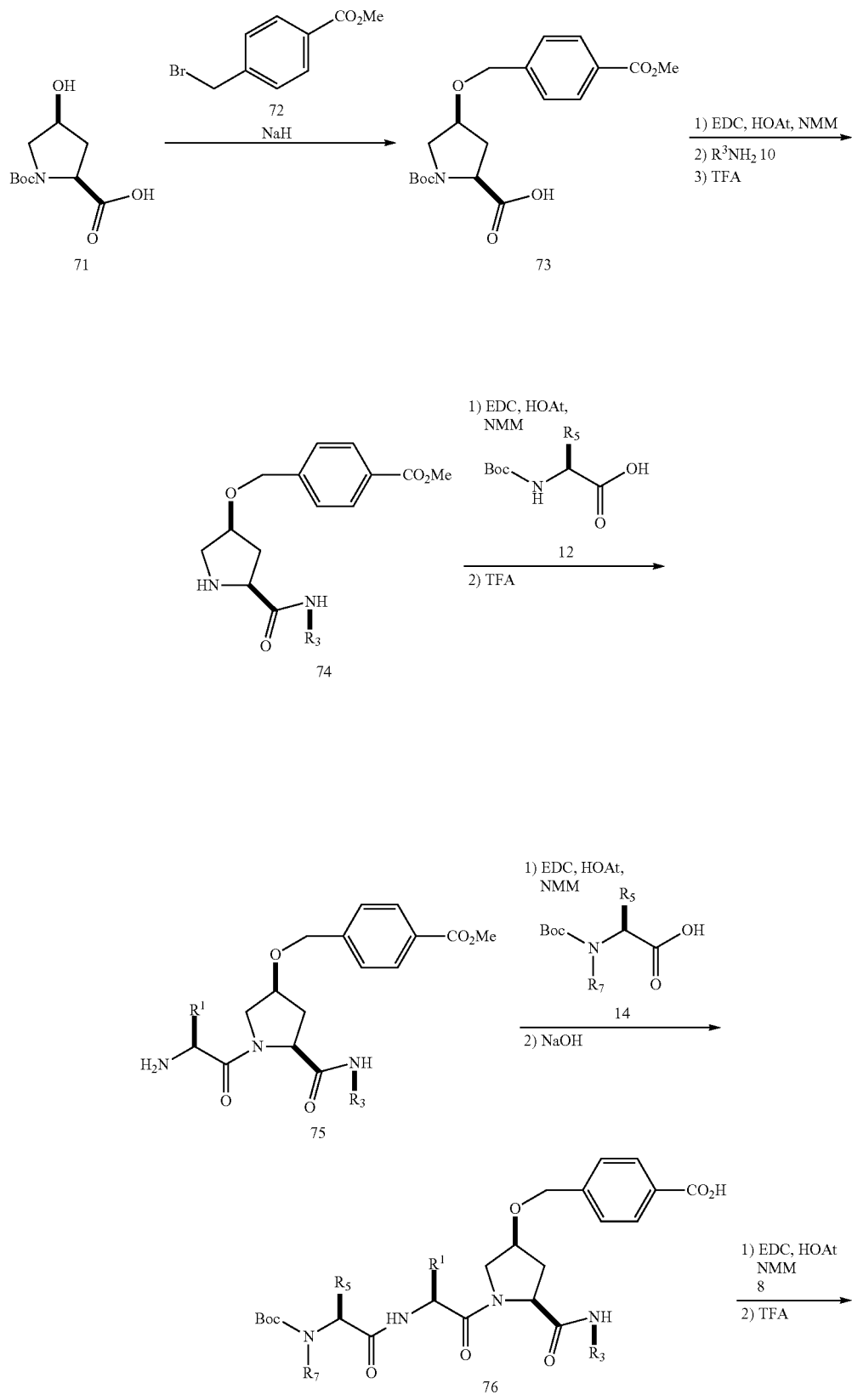

-continued
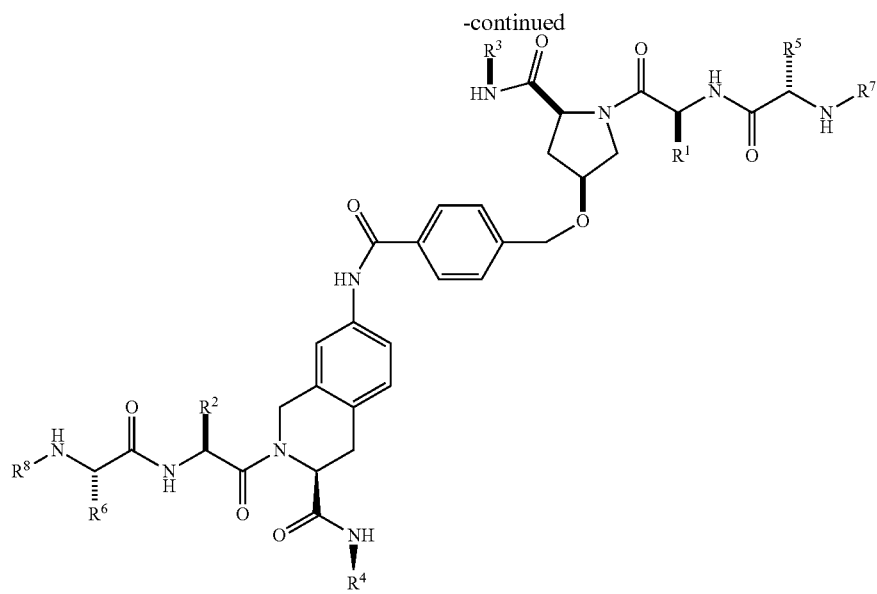
77
The linear heterodimeric analogs 79 can be prepared as illustrated in Scheme 14. The acid chlorides 78, derived from carboxylic acid intermediates 76 can be treated with phenol intermediates 61 and globally deprotected with TFA to afford the desired analogs 79.
Scheme 14
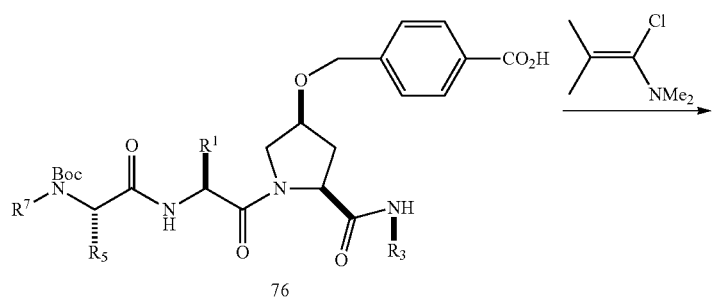
76
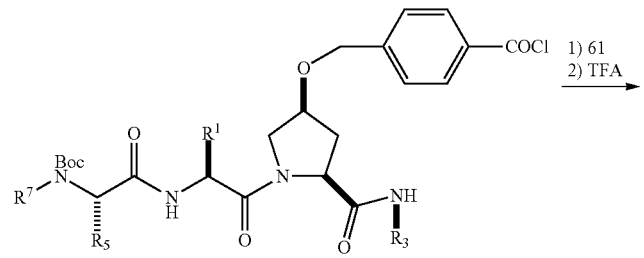
78

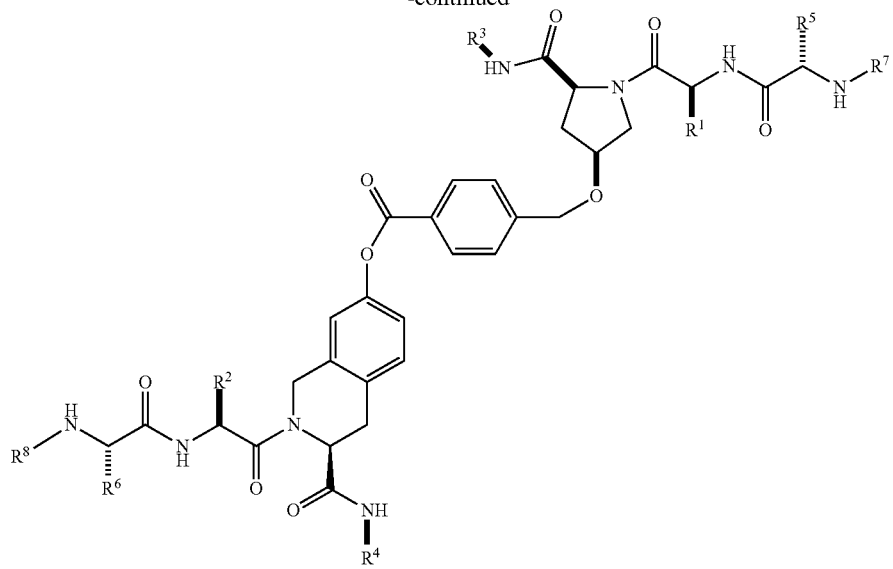

79

The indole containing analogs 84 can be prepared according to the synthetic route outlined in Scheme 15. Treatment of commercially available methyl 1H-indole-5-carboxylate (80) with nitrophenyl carbonate 81 affords the activated intermediate 82, which can be quenched with aminopyrrolidines 16 to afford the urea intermediates 83. Base-promoted hydrolysis of the ester of 83 followed by coupling with anilines 8 and global deprotection with TFA affords the desired analogs 84.

Scheme 15

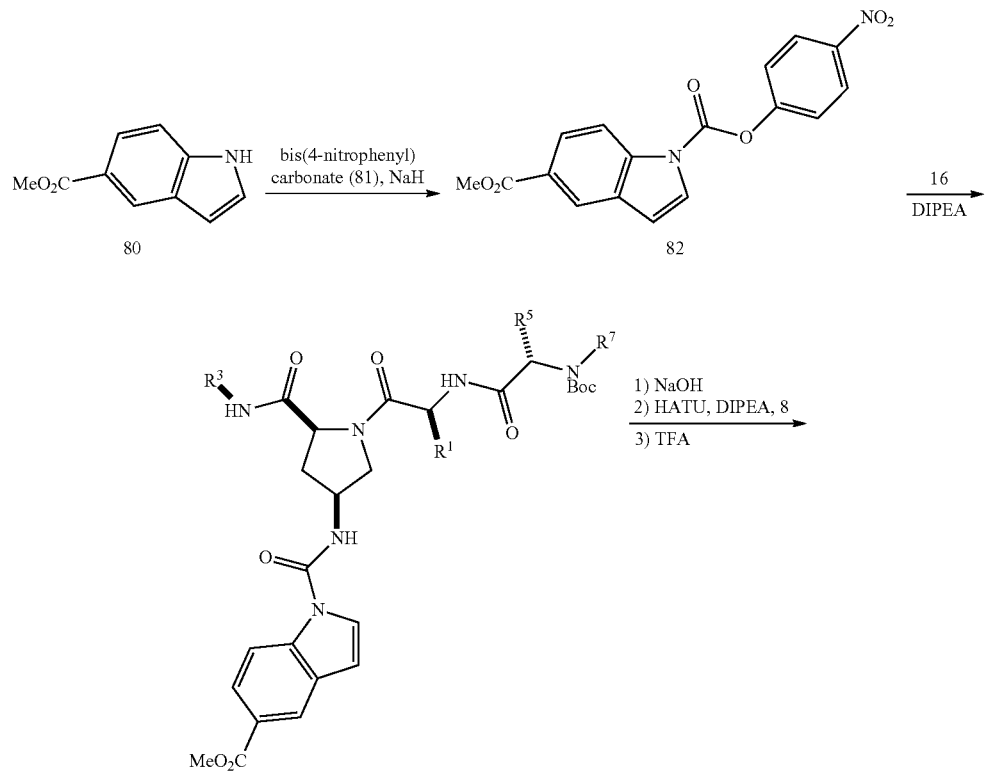

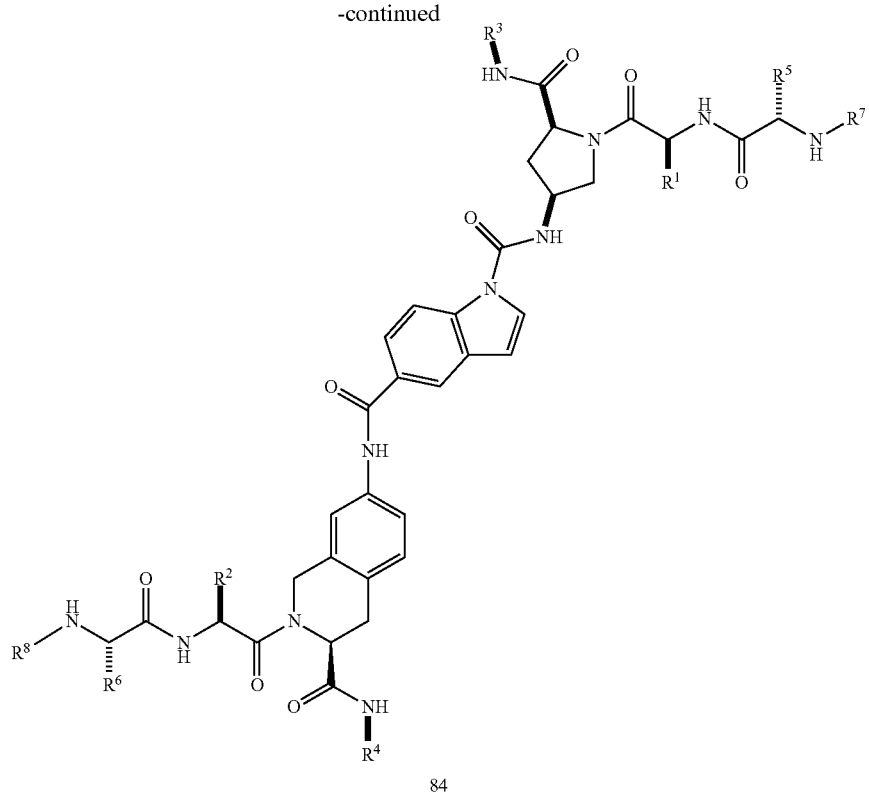

84

Analogs such as 89 can be prepared according to the synthetic route outlined in Scheme 16. Reduction of the nitro group of compound 3 provides anilines 80, which can be coupled with 4-(methoxycarbonyl)benzoic acid (81) in the presence of, for example HATU. Subsequent N-Boc-deprotection of the resulting intermediate 82 with TFA affords the amine intermediates 83. The beta-thiovaline derivative 85, derived from commercially available (R)-2-amino-3-mercapto-3-methylbutanoic acid (84) can be coupled with compound 83 using, for example 4-(4,6-dimethoxy[1,3,5]triazin-2-yl)-4-methyl-morpholinium chloride (DMTMM) to afford intermediate 86. The thiol of 86 can be alkylated with methyl iodide and the N-Boc protecting group of the resulting intermediate can be removed with TFA to furnish amine 87. Compound 87 can be converted to the desired heterodimeric analogs 89 using chemistry described above.

Scheme 16

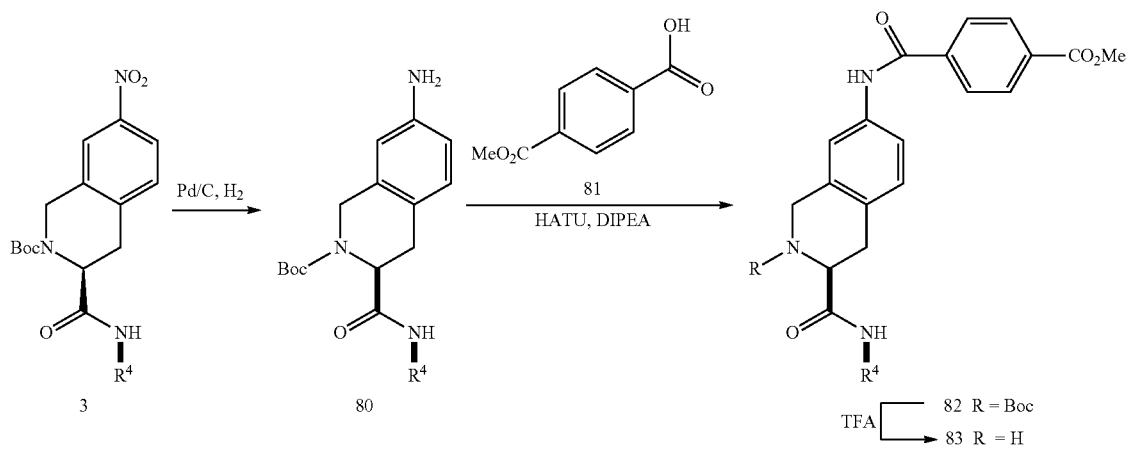

-continued
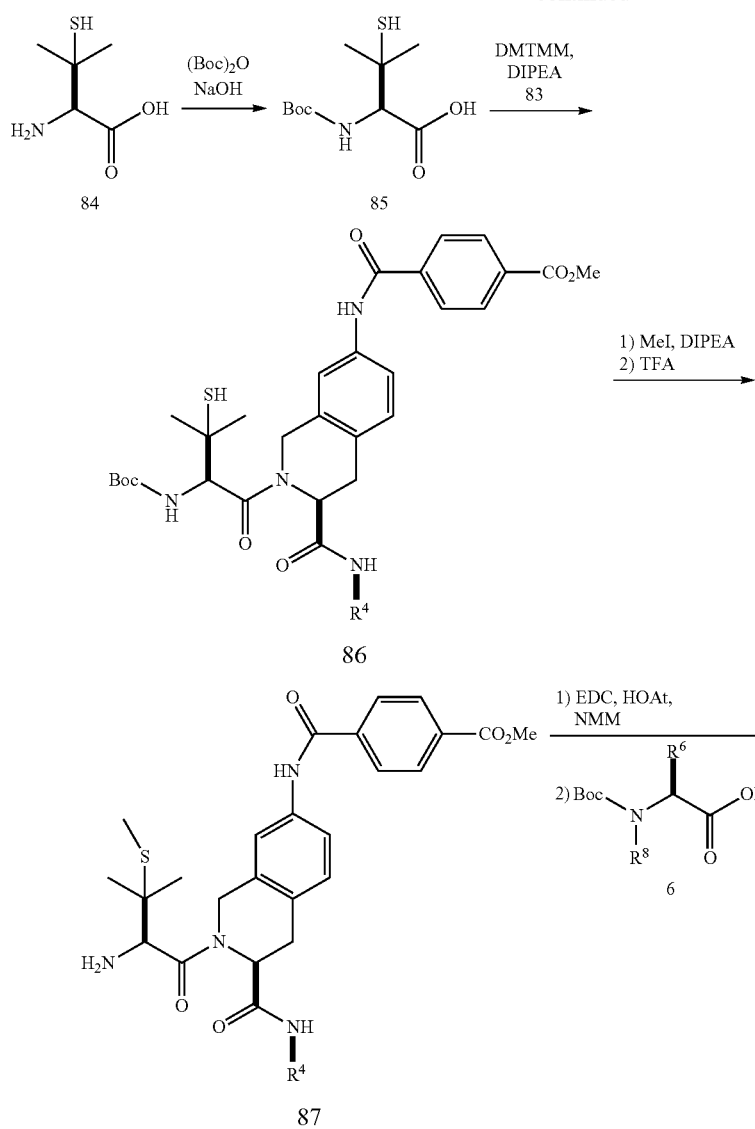
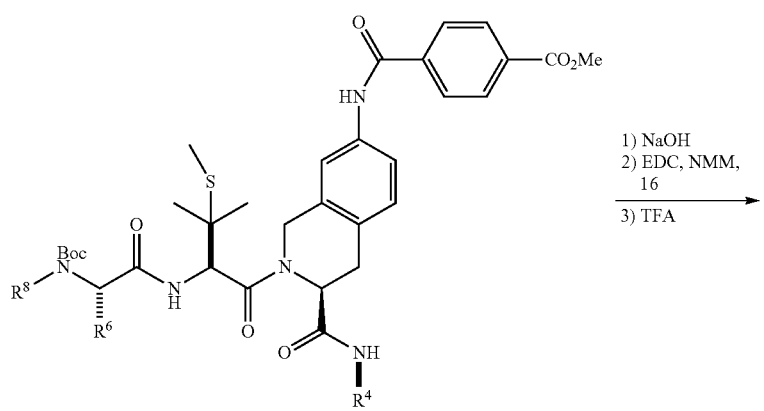

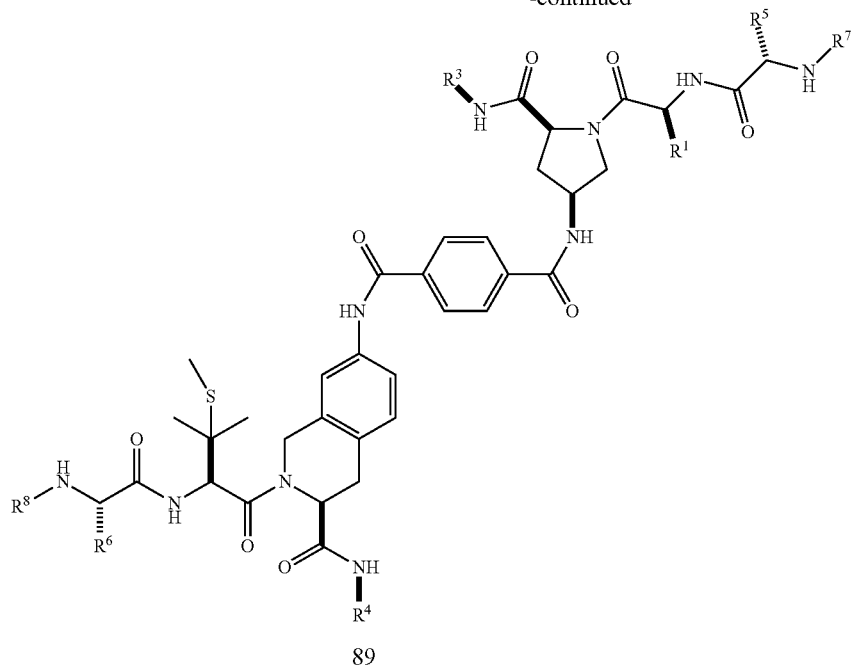

89

Analogs that contain beta-thiovaline, such as 95 can be prepared as outlined in Scheme 17. Alkylation of N-Boc-protected thiol 85 with 2-bromoacetate followed by coupling of the resulting intermediate with amines 90 (derived from compound 3, Scheme 1) in the presence of a coupling reagent, such as HATU affords intermediates 91. Cleavage of the N-Boc-protecting group 91 and subsequent coupling of the requisite amine with carboxylic acids 6 affords the peptides 92. Reduction of the nitro group of compounds 92 with hydrogen in the presence of Pearlman's catalyst (palladium hydroxide) provides anilines 93. Coupling of compound 93 with carboxylic acids 18 affords the N-Boc-protected intermediates 94, which upon treatment with acid affords the desired linear heterodimeric analogs 95.

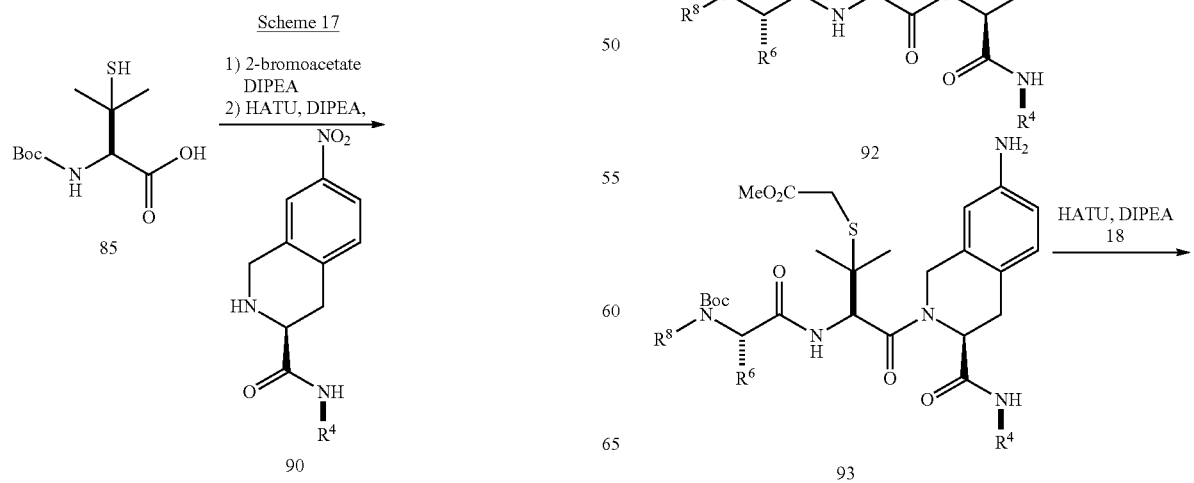

-continued

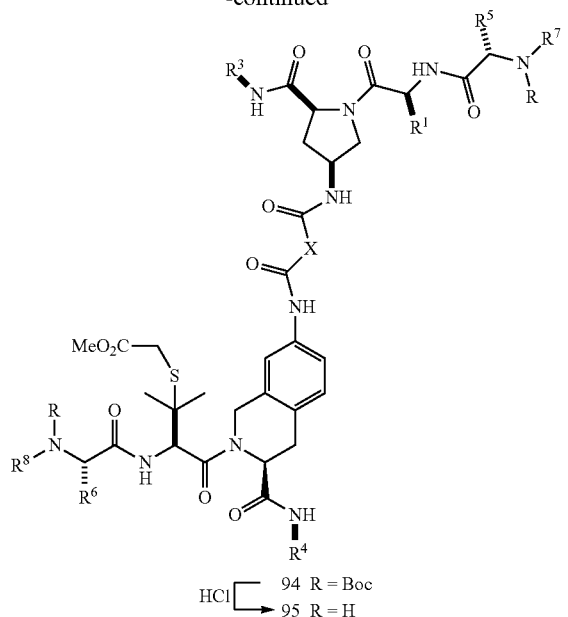

94  R = Boc
95  R = H (X = alkyl, substituted alkyl, phenyl, substituted phenyl)

Amide analogs 98 can be prepared according to the synthetic route outlined in Scheme 18. Hydrolysis of the methyl ester of intermediates 94 using for example, lithium hydroxide provides acids 96. Coupling of compound 96 with various amines 97 (primary, secondary, cyclic, aromatic, etc.) followed by global deprotection with TFA affords the desired heterodimeric analogs 98.

Scheme 18

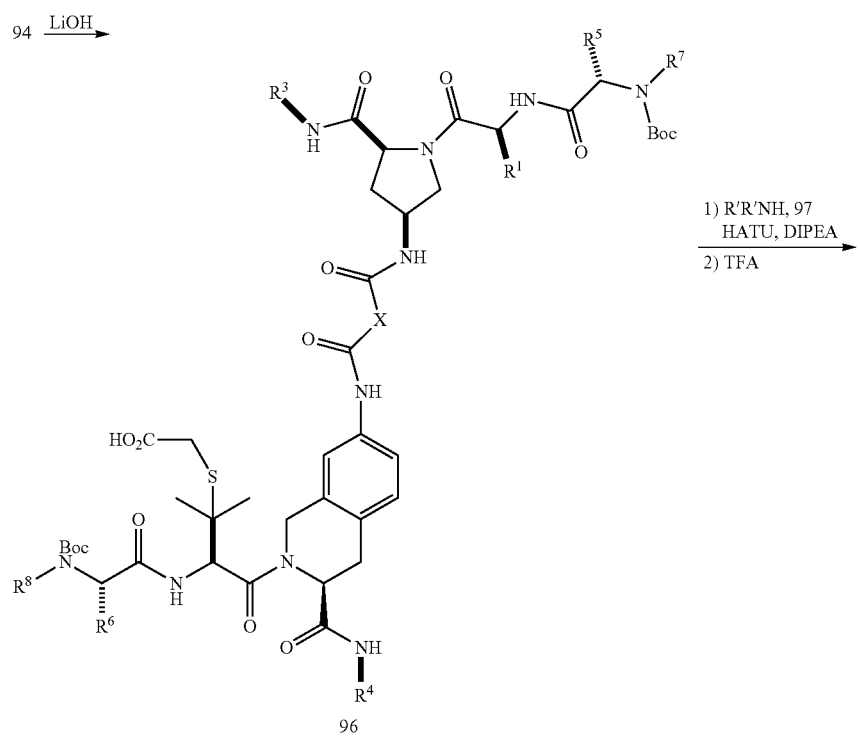

1) R'R'NH, 97
   HATU, DIPEA
2) TFA

96

-continued

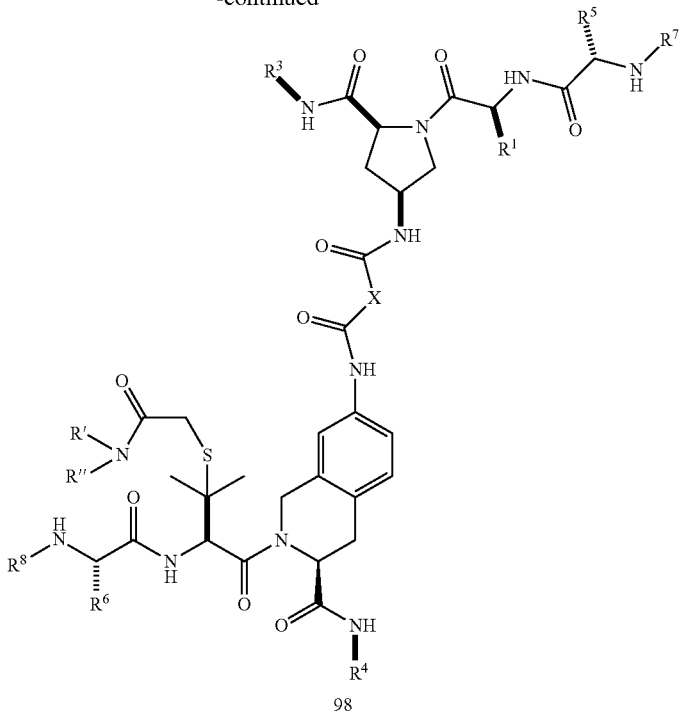

98

(X = alkyl, substituted alkyl, phenyl, substituted phenyl)

EXAMPLES

General Experimental

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using prepacked REDISEP® $R_f$ silica gel columns on a CombiFlash Companion machine.

Preparative Reverse Phase HPLC was performed with a linear gradient elution using $H_2O$/MeOH or $H_2O$/MeCN mixtures buffered with 0.1% trifluoroacetic acid or 10 mM $NH_4OAc$ and detection at 220 nm on one of the following columns: Shimadzu Sunfire S10 30×250 mm (flow rate=40 mL/min), or C18 PHENOMENEX® Luna S5 ODS 21×100 mm (flow rate=20 mL/min), or YMC S5 ODS 20×100 mm (flow rate=20 mL/min) or Waters XBridge C18 19×250 mm (flow rate=20 mL/min). Preparative Supercritical Fluid Chromatography (SFC) was performed using 78% $CO_2$/MeOH buffered with 0.1% diethylamine and detection at 220 nm on a CHIRALPAK® AS-H IDS 25×3 cm column (flow rate=85 mL/min).

All final products were characterized by $^1H$ NMR, RP HPLC and electrospray ionization (ESI) or atmospheric pressure ionization (API) mass spectrometry (MS). $^1H$ NMR spectra were obtained a 500 MHz or a 400 MHz Bruker instrument. Field strengths are expressed in units of δ (parts per million, ppm) relative to the solvent peaks, and peak multiplicities are designated as follows: s, singlet; d, doublet; dd, doublet of doublets; t, triplet; q, quartet; sxt, sextet; br s, broad singlet; m, multiplet.

ABBREVIATIONS

| | |
|---|---|
| Ac | acetyl |
| AcOH | acetic acid |
| $Ac_2O$ | acetic anhydride |
| ADDP | 1,1'-(azodicarbonyl)dipiperidine |
| aq. | aqueous |
| Bn | benzyl |
| Boc | t-butyl carbamate |
| $Boc_2O$ | di-t-butyl dicarbonate |
| Bu | butyl |
| $Bu_4NI$ | tetrabutylammonium iodide |
| CDI | 1,1'-carbonyldiimidazole |
| conc. | concentrated |
| DBU | 1,8-diazabicyclo[5.4.0]undec-7-ene |
| DCE | dichloroethane |
| DCM | dichloromethane |
| DDQ | 2,3-dichloro-5,6-dicyano-1,4-benzoquinone |
| DIAD | diisopropyl azodicarboxylate |
| DIEA | diisopropylethylamine |
| DMAP | 4-N,N-dimethylaminopyridine |
| DMF | dimethyl formamide |
| DMSO | dimethyl sulfoxide |
| EDC | 1-(dimethylaminopropyl)-3-ethylcarbodiimide hydrochloride |
| Et | ethyl |
| EtOAc | ethyl acetate |
| EtOH | ethanol |
| $Et_2O$ | diethyl ether |
| $Et_3N$ | triethyl amine |
| h | hour(s) |
| HATU | O-(7-azabenzotriazol-1-yl)-N,N,N'N'-tetramethyluronium hexafluorophosphate |

| | |
|---|---|
| HNBu$_2$ | dibutyl amine |
| H$_2$NNHBn | 1-benzylhydrazine |
| HOAt | 1-hydroxy-7-azabenzotriazole |
| HPLC | high pressure liquid chromatography |
| i-PrOH | isopropanol |
| i-Pr$_2$EtN | di(isopropyl)ethylamine |
| KOAc | potassium acetate |
| min | minute(s) |
| m-CPBA | m-chloro-3-chloroperbenzoic acid |
| Me | methyl |
| MeCN | acetonitrile |
| MeOH | methanol |
| Me$_2$NH | dimethyl amine |
| MTBE | methyl tert-butyl ether |
| Na(OAc)$_3$BH | sodium triacetoxyborohydride |
| NaSEt | sodium ethanethiolate |
| NBS | N-bromosuccinimide |
| n-BuLi | n-butyl lithium |
| NCS | N-chlorosuccinimide |
| NMM | N-methylmorpholine |
| NMP | n-methylpyrrolidinone |
| NMR | nuclear magnetic resonance |
| OTBDPS | tert-butyldiphenylsilyloxy |
| OTf | trifluoromethylsulfonyloxy |
| Pd/C | palladium on carbon |
| Pd(dppf)$_2$Cl$_2$ | [1,1'-bis(diphenylphosphino)ferrocene]dichloropalladium(II) |
| Pd(OAc)$_2$ | palladium acetate |
| Pd(PPh$_3$)$_4$ | tetrakis(triphenylphosphine)palladium |
| Pd$_2$(dba)$_3$ | tris(dibenzylideneacetone)dipalladium(0) |
| Ph | phenyl |
| PhI(OAc)$_2$ | phenyl iodoacetate |
| PhMe | toluene |
| Ph$_2$TfN | 1,1,1-trifluoro-N-phenyl-N-(trifluoromethyl)sulfonyl methanesulfonamide |
| PPh$_3$ | triphenyl phosphorus |
| sat. | saturated |
| SEM | (trimethylsilyl)ethoxy)methyl |
| SEM-Cl | (trimethylsilyl)ethoxy)methyl chloride |
| TBAF | tetrabutylammonium fluoride |
| TBAI | tetrabutylammonium iodide |
| TBSO | tert-butyldimethylsilyloxy |
| t-Bu | tertiary butyl |
| t-BuOH | tertiary butanol |
| t-BuOK | potassium tertiary-butoxide |
| tert-BuOH | tertiary butanol |
| TFA | trifluoroacetic acid |
| Tf$_2$O | trifluoromethylsulfonic anhydride |
| THF | tetrahydrofuran |
| TMS | trimethylsilyl |
| THP | tetrahydro-2H-pyran-2-yl |
| TMS-OTf | trimethylsilyl triflate |
| TsO | p-toluenesulfonyl |

Example 1

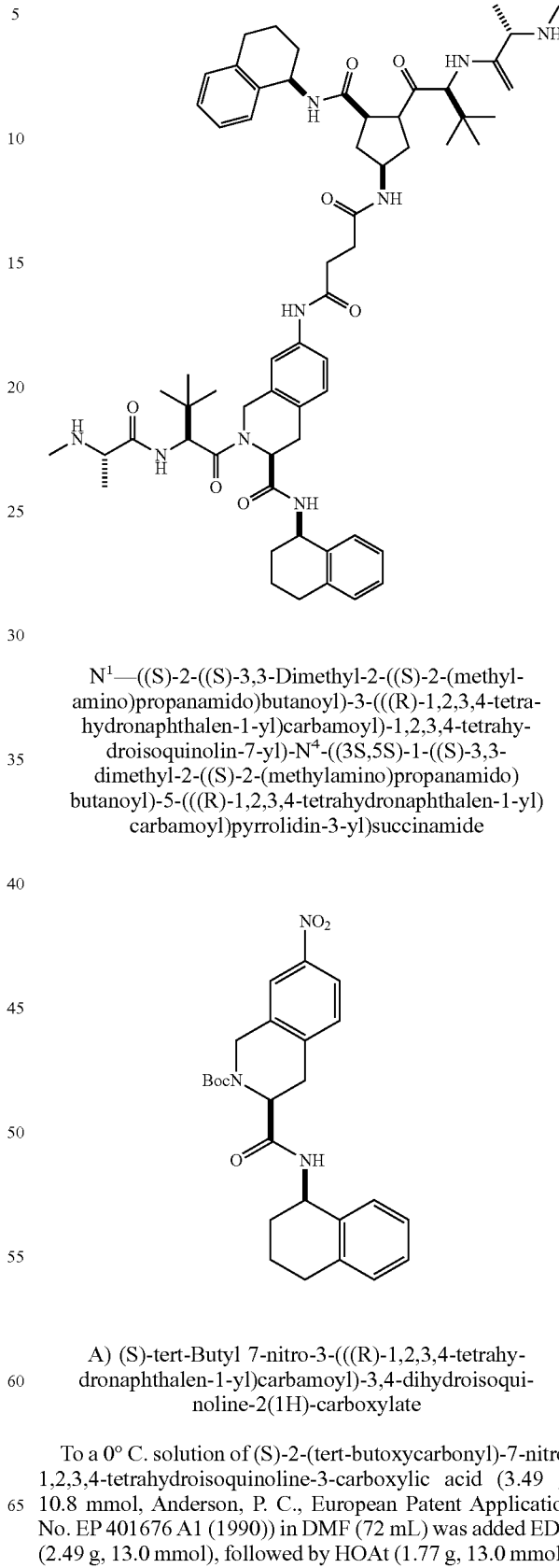

N$^1$—((S)-2-((S)-3,3-Dimethyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)-N$^4$-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)succinamide A) (S)-tert-Butyl 7-nitro-3-(((R)-1,2,3,4-tetrahydronaphthalen-1-yl)carbamoyl)-3,4-dihydroisoquinoline-2(1H)-carboxylate To a 0° C. solution of (S)-2-(tert-butoxycarbonyl)-7-nitro-1,2,3,4-tetrahydroisoquinoline-3-carboxylic acid (3.49 g, 10.8 mmol, Anderson, P. C., European Patent Application No. EP 401676 A1 (1990)) in DMF (72 mL) was added EDC (2.49 g, 13.0 mmol), followed by HOAt (1.77 g, 13.0 mmol).

After 10 min, (R)-1,2,3,4-tetrahydronaphthalen-1-amine (ALFA AESAR®, 1.59 mL, 10.8 mmol) and NMM (3.57 mL, 32.5 mmol) were added, and the resulting reaction mixture was stirred warming to room temperature overnight. The reaction mixture was then diluted with EtOAc and sat. NaHCO₃. The aqueous layer was extracted with EtOAc (3×), and the combined organic extracts were washed with 1N HCl, water, 10% aq. LiCl solution and sat. NaCl. The extracts were dried over Na₂SO₄, filtered through a pad of silica gel and concentrated in vacuo to provide the title compound (4.27 g, 87%) as a yellow solid. MS(ESI⁺) m/z 452.3 (M+H)⁺.

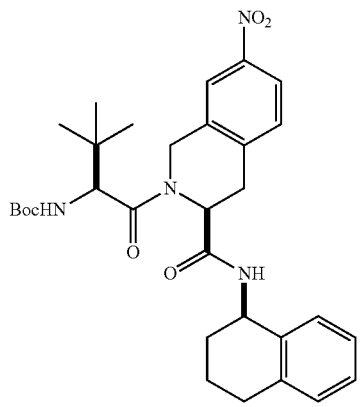

C) tert-Butyl ((S)-3,3-dimethyl-1-((S)-7-nitro-3-(((R)-1,2,3,4-tetrahydronaphthalen-1-yl)carbamoyl)-3,4-dihydroisoquinolin-2(1H)-yl)-1-oxobutan-2-yl)carbamate Following a procedure analogous to that for the synthesis of Compound A of Example 1, (S)-7-nitro-N—((R)-1,2,3,4-tetrahydronaphthalen-1-yl)-1,2,3,4-tetrahydroisoquinoline-3-carboxamide (1.69 g, 4.81 mmol) and (S)-2-((tert-butoxycarbonyl)amino)-3,3-dimethylbutanoic acid (1.22 g, 5.29 mmol) were converted to the title compound (2.65 g, 98%). MS(ESI) m/z 565.3 (M+H)⁺.

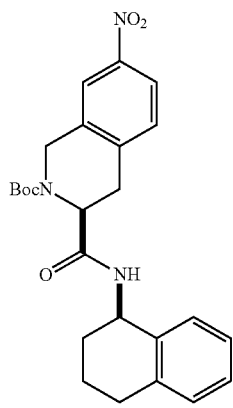

B) (S)-7-Nitro-N—((R)-1,2,3,4-tetrahydronaphthalen-1-yl)-1,2,3,4-tetrahydroisoquinoline-3-carboxamide To a solution of (S)-tert-butyl 7-nitro-3-(((R)-1,2,3,4-tetrahydronaphthalen-1-yl)carbamoyl)-3,4-dihydroisoquinoline-2(1H)-carboxylate (4.45 g, 9.86 mmol) in CH₂Cl₂ (49 mL) was added TFA (11.4 mL, 148 mmol). The resulting solution was stirred at room temperature for 1 h and then quenched carefully with sat. aq. NaHCO₃ solution until bubbling ceased. The aqueous layer was extracted with CH₂Cl₂ (3×), and the combined organic extracts were washed with sat. aq. NaHCO₃ solution, water and brine. The extracts were dried over Na₂SO₄, filtered and concentrated in vacuo to give 3.38 g of the title compound as a pale yellow solid. ¹H NMR (CDCl₃, mixture of amide rotamers) δ 8.05 (d, J=6.6 Hz, 1H), 7.97-7.88 (m, 1H), 7.53-7.32 (m, 2H), 7.22-6.94 (m, 4H), 5.25-5.03 (m, 1H), 4.18-3.94 (m, 2H), 3.83-3.65 (m, 1H), 3.35 (dd, J=16.7, 5.1 Hz, 1H), 3.09 (dd, J=17.1, 9.1 Hz, 1H), 2.90-2.70 (m, 2H), 2.18-1.96 (m, 1H), 1.93-1.44 (m, 3H); MS(ESI⁺) m/z 352.2 (M+H)⁺.

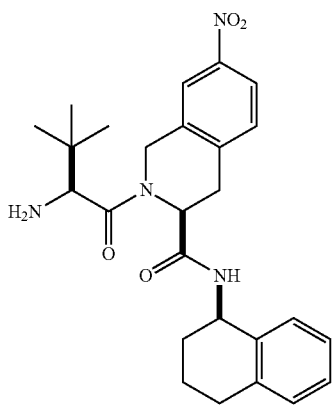

D) (S)-2-((S)-2-Amino-3,3-dimethylbutanoyl)-7-nitro-N—((R)-1,2,3,4-tetrahydronaphthalen-1-yl)-1,2,3,4-tetrahydroisoquinoline-3-carboxamide Following a procedure analogous to that for the synthesis of Compound B of Example 1, tert-butyl ((S)-3,3-dimethyl-1-((S)-7-nitro-3-(((R)-1,2,3,4-tetrahydronaphthalen-1-yl)carbamoyl)-3,4-dihydroisoquinolin-2(1H)-yl)-1-oxobutan-2-yl)carbamate (2.65 g, 4.69 mmol) was converted to the title compound (2.17 g, 100%). MS(ESI⁺) m/z 465.3 (M+H)⁺.

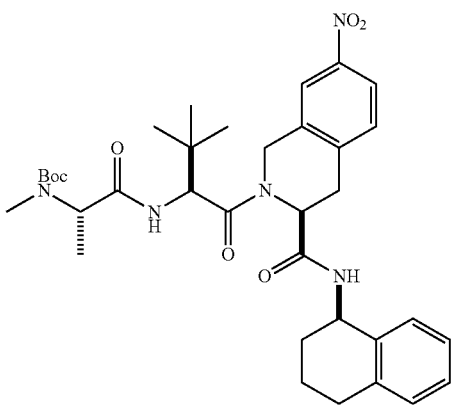

E) tert-Butyl ((S)-1-(((S)-3,3-dimethyl-1-((S)-7-nitro-3-(((R)-1,2,3,4-tetrahydronaphthalen-1-yl)carbamoyl)-3,4-dihydroisoquinolin-2(1H)-yl)-1-oxobutan-2-yl)amino)-1-oxopropan-2-yl)(methyl)carbamate Following a procedure analogous to that for the synthesis of Compound A of Example 1, (S)-2-((S)-2-amino-3,3-dimethylbutanoyl)-7-nitro-N—((R)-1,2,3,4-tetrahydronaphthalen-1-yl)-1,2,3,4-tetrahydroisoquinoline-3-carboxamide (2.17 g, 4.67 mmol) and (S)-2-((tert-butoxycarbonyl)(methyl)amino)propanoic acid (Advanced ChemTech, 0.95 g, 4.67 mmol) were converted to the title compound (2.93 g, 97%). MS(ESI⁺) m/z 650.5 (M+H)⁺.

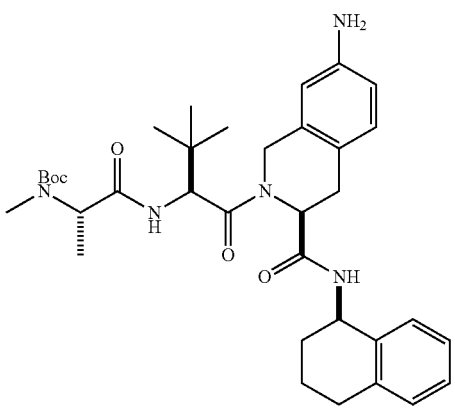

F) tert-Butyl ((S)-1-(((S)-1-((S)-7-amino-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate To a pressure flask containing Pd/C (240 mg, 0.23 mmol) was added a solution of tert-butyl ((S)-1-(((S)-3,3-dimethyl-1-((S)-7-nitro-3-(((R)-1,2,3,4-tetrahydronaphthalen-1-yl)carbamoyl)-3,4-dihydroisoquinolin-2(1H)-yl)-1-oxobutan-2-yl)amino)-1-oxopropan-2-yl)(methyl)carbamate (1.46 g, 2.25 mmol) in MeOH (11.2 mL). The resulting reaction mixture was stirred under H₂ at 15 psi for 3 h and then filtered through a pad of CELITE® rinsing with EtOAc. The filtrate was concentrated in vacuo and redissolved in CH₂Cl₂. The solution was filtered through a 0.45 μM PTFE filter and concentrated in vacuo to give the title compound (1.28 g, 92%) as a yellow solid. MS(ESI⁺) m/z 620.4 (M+H)⁺.

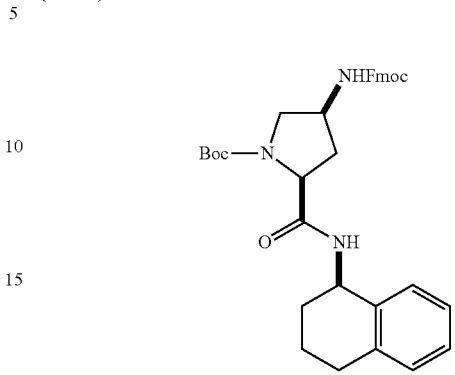

G) (2S,4S)-tert-Butyl 4-((((9H-fluoren-9-yl)methoxy)carbonyl)amino)-2-(((R)-1,2,3,4-tetrahydronaphthalen-1-yl)carbamoyl)pyrrolidine-1-carboxylate To a solution of (2S,4S)-Boc-4-(Fmoc-amino)-proline (Chem-Impex, 6.00 g, 13.3 mmol) in DMF (20 mL) at 0° C. were added EDC (3.05 g, 15.9 mmol), HOAt (2.17 g, 15.9 mmol) and NMM (4.38 mL, 39.8 mmol). The reaction mixture was stirred at ice bath temperature for 20 min then treated with a solution of (R)-1,2,3,4-tetrahydronaphthalen-1-amine (ALFA AESAR®, 2.15 g, 14.6 mmol) in DMF (2 mL). The reaction mixture was stirred at rt for 1 h and cold water (100 mL) was added to the reaction mixture. The solid that formed was collected by filtration and washed with cold water (100 mL). The solid was dissolved in CH₂Cl₂ (200 mL) and the organic solution was washed with 5% aq. citric acid solution and brine, dried over MgSO₄, and filtered. The filtrate was concentrated in vacuo. The residue was dissolved in CH₂Cl₂ and purified by flash column chromatography (gradient elution from 10 to 30% EtOAc in CH₂Cl₂) provided the title compound (6.70 g, 87%) as a light tan solid. ¹H NMR (400 MHz, CDCl₃) δ 7.79 (d, J=7.5 Hz, 2H), 7.67 (d, J=7.3 Hz, 2H), 7.42 (td, J=7.2, 4.0 Hz, 2H), 7.37-7.03 (m, 6H), 5.22 (br. s., 1H), 4.57-4.23 (m, 5H), 3.68-3.49 (m, 2H), 2.91-2.74 (m, 2H), 2.52 (d, J=13.4 Hz, 1H), 2.35-2.21 (m, 1H), 2.14 (d, J=5.1 Hz, 1H), 1.97-1.80 (m, 3H), 1.44 (s, 9H); MS(ESI⁺) m/z 582.2 (M+H)⁺.

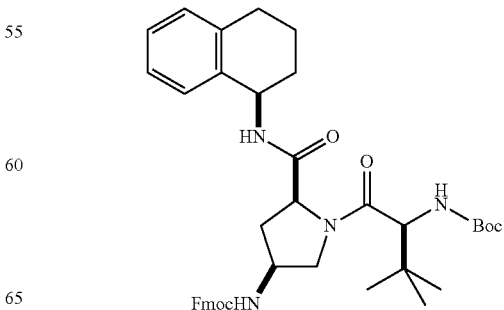

H) tert-Butyl ((S)-3,3-dimethyl-1-((2S,4S)-4-(((9H-fluoren-9-yl)methoxy)carbonyl)amino)-2-(((R)-1,2,3,4-tetrahydronaphthalen-1-yl)carbamoyl)pyrrolidin-1-yl)-1-oxobutan-2-yl)carbamate To a solution of (2S,4S)-tert-butyl 4-((((9H-fluoren-9-yl)methoxy)carbonyl)amino)-2-(((R)-1,2,3,4-tetrahydronaphthalen-1-yl)carbamoyl)pyrrolidine-1-carboxylate (6.70 g, 11.5 mmol) in CH$_2$Cl$_2$ (50 mL) at rt was added TFA (15 mL) dropwise. The reaction mixture was stirred at rt for 2 h, and then concentrated in vacuo. The residue was dissolved in CH$_2$Cl$_2$ (200 mL) and washed with aq. K$_2$HPO$_4$ solution (50 mL). The organic layer was dried over MgSO$_4$, filtered and concentrated in vacuo to give crude (9H-fluoren-9-yl)methyl ((3S,5S)-5-(((R)-1,2,3,4-tetrahydronaphthalen-1-yl)carbamoyl)pyrrolidin-3-yl)carbamate (5.54 g, 100%), which was used directly in the next step.

To a solution of (S)-2-((tert-butoxycarbonyl)amino)-3,3-dimethylbutanoic acid (3.19 g, 13.8 mmol) in DMF (20 mL) at 0° C. were added EDC (3.31 g, 17.3 mmol), HOAt (2.35 g, 17.3 mmol) and NMM (3.80 mL, 34.5 mmol). The reaction mixture was stirred at ice bath temperature for 20 min, then treated with a suspension of (9H-fluoren-9-yl)methyl ((3S,5S)-5-(((R)-1,2,3,4-tetrahydronaphthalen-1-yl)carbamoyl)pyrrolidin-3-yl)carbamate (5.54 g, 11.5 mmol) in DMF (5 mL). The reaction mixture was stirred at rt for 1 h and cold water (200 mL) was added to the reaction mixture. The solid that formed was collected by filtration and washed with of cold water (100 mL). The solid was dissolved in CH$_2$Cl$_2$ (200 mL). The organic solution was washed with aq. NaHCO$_3$ solution, 5% aq. citric acid solution and brine, dried over MgSO$_4$ and filtered. The filtrate was concentrated in vacuo. The residue was dissolved in CH$_2$Cl$_2$ and purified using flash column chromatography (gradient elution from 10 to 30% EtOAc in CH$_2$Cl$_2$) provided the title compound (7.10 g, 89%) as a light tan solid. MS(ESI$^+$) m/z 695.5 (M+H)$^+$.

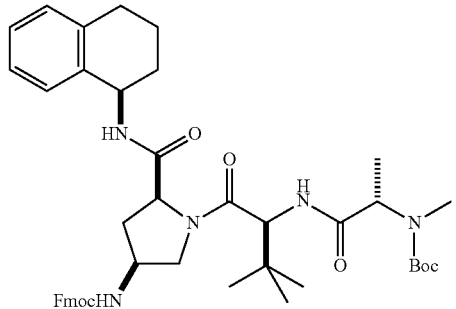

I) tert-Butyl ((S)-1-(((S)-1-((2S,4S)-4-((((9H-fluoren-9-yl)methoxy)carbonyl)amino)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate To a solution of tert-butyl ((S)-3,3-dimethyl-1-((2S,4S)-4-(((9H-fluoren-9-yl)methoxy)carbonyl)amino)-2-(((R)-1,2,3,4-tetrahydronaphthalen-1-yl)carbamoyl)pyrrolidin-1-yl)-1-oxobutan-2-yl)carbamate (7.10 g, 10.2 mmol) in CH$_2$Cl$_2$ (50 mL) at rt was added TFA (15 mL) dropwise. The reaction mixture was stirred at rt for 2 h, and then concentrated in vacuo. The residue was dissolved in CH$_2$Cl$_2$ (200 mL) and washed with aq. K$_2$HPO$_4$ solution (50 mL). The organic layer was dried over MgSO$_4$, filtered and concentrated in vacuo to give crude (9H-fluoren-9-yl)methyl ((3S,5S)-5-(((R)-1,2,3,4-tetrahydronaphthalen-1-yl)carbamoyl)pyrrolidin-3-yl)carbamate (6.08 g, 100%), which was used directly in the next step.

To a solution of (S)-2-((tert-butoxycarbonyl)(methyl)amino)propanoic acid (Chem-Impex, 2.49 g, 12.3 mmol) in DMF (20 mL) at 0° C. were added EDC (2.94 g, 15.3 mmol), HOAt (2.09 g, 15.3 mmol) and NMM (2.81 mL, 25.6 mmol). The reaction mixture was stirred at ice bath temperature for 20 min, and then treated with a solution of (9H-fluoren-9-yl)methyl ((3S,5S)-5-(((R)-1,2,3,4-tetrahydronaphthalen-1-yl)carbamoyl)pyrrolidin-3-yl)carbamate (6.45 g, 10.2 mmol) in DMF (5 mL). The reaction mixture was stirred at rt for 2 h and then cold water (200 mL) was added to the reaction mixture. The solid that formed was collected by filtration and washed with cold water (100 mL). The solid was dissolved in CH$_2$Cl$_2$ (200 mL). The organic solution was washed with aq. NaHCO$_3$ solution, 5% aq. citric acid solution and brine, dried over MgSO$_4$, and filtered. The filtrate was concentrated in vacuo. The residue was dissolved in CH$_2$Cl$_2$ and purified by flash column chromatography (gradient elution from 10 to 40% EtOAc in CH$_2$Cl$_2$) provided the title compound (6.14 g, 77%) as a light tan solid. MS(ESI$^+$) m/z 780.5 (M+H)$^+$.

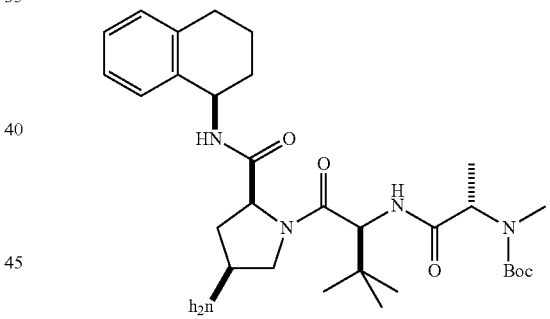

J) tert-Butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate To a solution of tert-butyl ((S)-1-(((S)-1-((2S,4S)-4-((((9H-fluoren-9-yl)methoxy)carbonyl)amino)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (6.14 g, 7.87 mmol) in CH$_2$Cl$_2$ (40 mL) was added piperidine (4.67 mL, 47.2 mmol) dropwise. The reaction mixture was stirred at rt for 2 h and concentrated in vacuo. The residue was washed with methanol and the resulting solid was removed by filtration. The filtrate was concentrated in vacuo and purified by flash column chromatography (gradient elution from 0 to 10% MeOH/CH$_2$Cl$_2$) to give the title compound (3.48 g, 79%) as a light tan solid. MS(ESI$^+$) m/z 558.4 (M+H)$^+$.

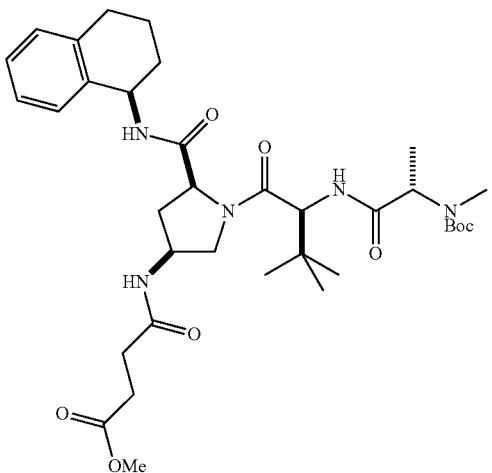

K) Methyl 4-(((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)amino)-4-oxobutanoate Following a procedure analogous to that for the synthesis of Compound A of Example 1, tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (75 mg, 0.13 mmol) and 4-methoxy-4-oxobutanoic acid (18 mg, 0.13 mmol) were converted to the title compound (90 mg, 100%). MS(ESI+) m/z 672.6 (M+H)+.

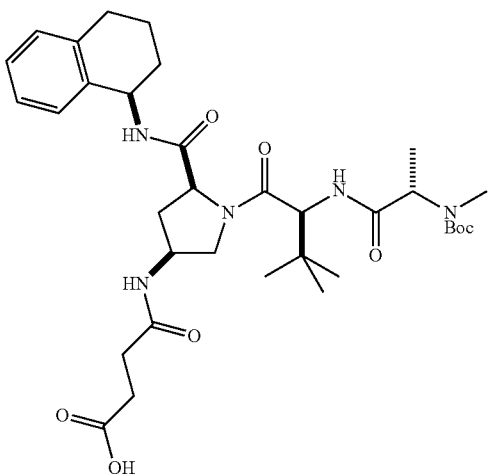

L) 4-(((3S,5S)-1-((S)-2-((S)-2-((tert-Butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)amino)-4-oxobutanoic acid To a solution of methyl 4-(((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)amino)-4-oxobutanoate (90 mg, 0.13 mmol) in THF (1.28 mL) and MeOH (0.64 mL) was added 3N NaOH (670 µl, 2.00 mmol). The resulting reaction mixture was stirred at room temperature for 2 h and then poured into EtOAc and 1N HCl. The aqueous layer was extracted with EtOAc (3 x). The combined organics were dried over Na$_2$SO$_4$, filtered and concentrated in vacuo and lyophilized to give the title compound (81 mg, 92%) as white solid. MS(ESI+) m/z 658.6 (M+H)+.

M) $N^1$—((S)-2-((S)-3,3-Dimethyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)-$N^4$-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)succinamide To a solution of 4-(((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)amino)-4-oxobutanoic acid (43 mg, 0.065 mmol) and tert-butyl ((S)-1-(((S)-1-((S)-7-amino-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (41 mg, 0.065 mmol) in DMF (1.10 mL) was added HATU (32 mg, 0.085 mmol) followed by i-Pr$_2$EtN (34 µl, 0.20 mmol). The resulting reaction mixture was stirred at room temperature overnight and then poured into a sep funnel containing EtOAc and sat. aq. NaHCO$_3$ solution. The aqueous layer was extracted with EtOAc (3×), and the combined organic extracts were washed with water, 1N HCl and brine. The extracts were dried over Na$_2$SO$_4$ and filtered through a pad of silica gel washing with 10% MeOH/CH$_2$Cl$_2$. The filtrate was concentrated in vacuo and redissolved in CH$_2$Cl$_2$ (1.6 mL). TFA (50 µL, 0.64 mmol) was added, and the resulting reaction mixture was stirred at room temperature for 1 h and then concentrated in vacuo. Purification using preparative HPLC provided the title compound (17 mg, 49%) as a white solid after lyophilization. MS(ESI+) m/z 1059.7 (M+H)+.

Example 2

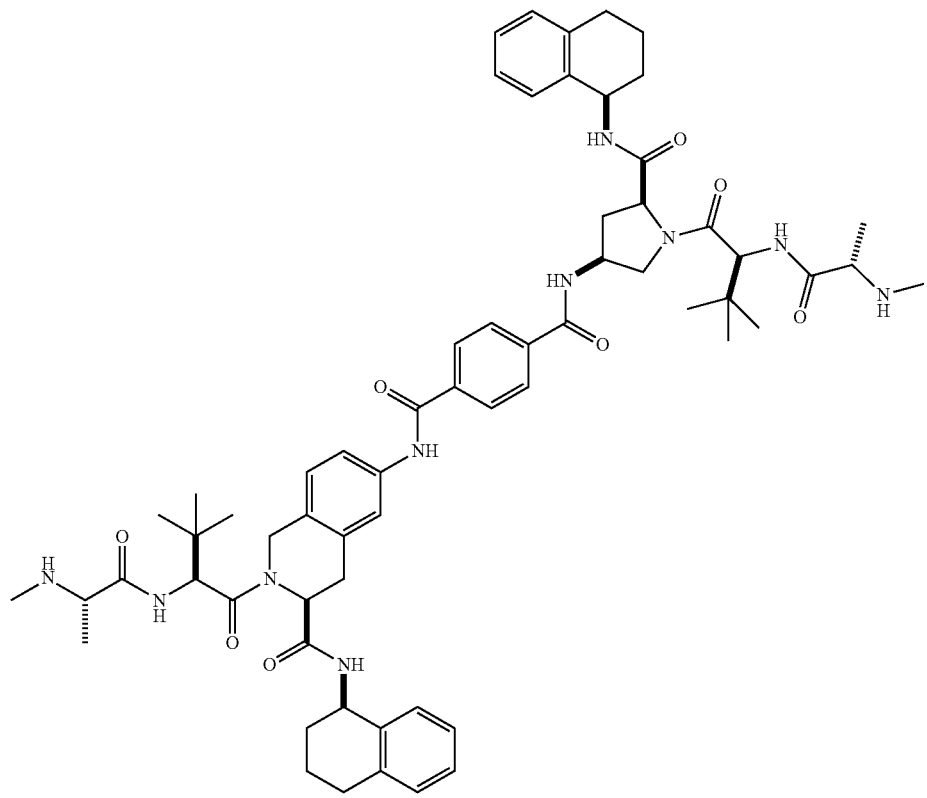

N¹—((S)-2-((S)-3,3-Dimethyl-2-((S)-2-(methyl-amino)propanamido)butanoyl)-3-(((R)-1,2,3,4-tetra-hydronaphthalen-1-yl)carbamoyl)-1,2,3,4-tetrahydroisoquinolin-6-yl)-N⁴-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)terephthalamide

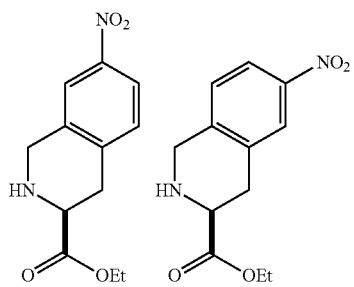

A) (S)-Ethyl 7-nitro-1,2,3,4-tetrahydroisoquinoline-3-carboxylate (S)-Ethyl 6-nitro-1,2,3,4-tetrahydroisoquinoline-3-carboxylate To a −10° C. solution of H₂SO₄ (180 mL, 3.4 mol) was added (S)-ethyl 1,2,3,4-tetrahydroisoquinoline-3-carboxylate, HCl (AK Scientific, 50 g, 207 mmol) slowly. (fuming) HNO₃ (39 mL, 873 mmol) was then added dropwise. The resulting reaction mixture was stirred at −10° C. for 15 min and then poured onto ice. The mixture was basified with NaHCO₃ and filtered through CELITE® washing with EtOAc. The filtrate was extracted with EtOAc (3×), and the combined organic extracts were washed with sat. aq. NaCl, dried over Na₂SO₄, filtered and concentrated in vacuo. The crude solid was purified using flash column chromatography to give the 7-nitro isomer as the major product (27 g, 52%) and the 6-nitro isomer as mixture (22 g, ~42%) which was used in the subsequent step without further purification. MS(ESI⁺) m/z 251.0 (M+H)⁺ for both.

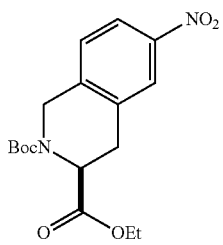 [SMILES: CCOC(=O)[C@@H]1Cc2cc([N+](=O)[O-])ccc2CN1C(=O)OC(C)(C)C]

B) (S)-2-tert-Butyl 3-ethyl 6-nitro-3,4-dihydroisoquinoline-2,3(1H)-dicarboxylate To a solution of (S)-ethyl 6-nitro-1,2,3,4-tetrahydroisoquinoline-3-carboxylate (22 g, 88 mmol) in dioxane (270 mL) and water (270 mL) was added i-Pr₂NH (23 mL, 162 mmol) followed by Boc₂O (28 g, 129 mmol). The resulting reaction mixture was stirred at room temperature for 1 h and then diluted with water. A 10% citric acid solution was added to adjust the solution to pH 4. The aqueous layer was extracted with EtOAc (3×), and the combined organics were washed with sat. NaCl, dried over $Na_2SO_4$, filtered and concentrated in vacuo. The crude oil was purified using prep SFC to give the title compound (14.5 g, 47%) as a brown oil. MS($ESI^+$) m/z 251.2 (M+H-Boc)$^+$.

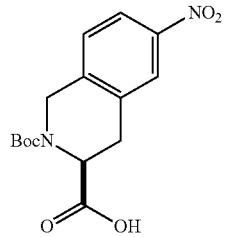 [SMILES: CC(C)(C)OC(=O)N1Cc2ccc([N+](=O)[O-])cc2C[C@H]1C(=O)O]

C) (S)-2-(tert-Butoxycarbonyl)-6-nitro-1,2,3,4-tetrahydroisoquinoline-3-carboxylic acid To a solution of (S)-2-tert-butyl 3-ethyl 6-nitro-3,4-dihydroisoquinoline-2,3(1H)-dicarboxylate (1.15 g, 3.28 mmol) from procedure B in THF (10 mL) and EtOH (10 mL) was added 2 M lithium hydroxide (3.28 mL, 3.28 mmol). The reaction mixture was stirred at rt for 4 h. At 0° C. the reaction mixture was neutralized to pH 3-4 with 1 N HCl and extracted with DCM, 3×. The combined organic extracts were dried and concentrated in vacuo to give the title compound (1.06 g, 100%). MS($ESI^+$) m/z 223.0 (M+H-Boc)$^+$.

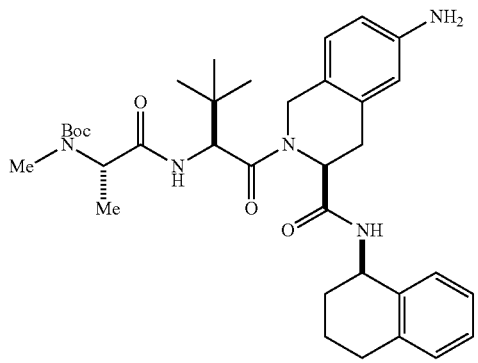

D) tert-Butyl ((S)-1-(((S)-1-((S)-6-amino-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate Following procedures analogous to those described for the preparation of Compounds A-F of Example 1, (S)-2-(tert-butoxycarbonyl)-6-nitro-1,2,3,4-tetrahydroisoquinoline-3-carboxylic acid (750 mg, 2.33 mmol) was converted to the title compound (773 mg, 38% over 6 steps). MS($ESI^+$) m/z 223.0 (M+H-Boc)$^+$.

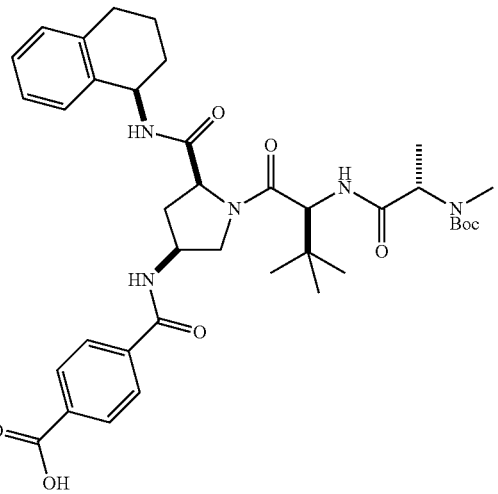

E) 4-(((3S,5S)-1-((S)-2-((S)-2-((tert-Butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)carbamoyl)benzoic acid Following procedures analogous to those described for the preparation of Compounds G and H of Example 1, tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound J in Example 1, 279 mg, 0.50 mmol) and 4-(methoxycarbonyl)benzoic acid (95 mg, 0.52 mmol) were converted to the title compound following ester hydrolysis of the precursor analogous to that of procedure C Example 2, (270 mg, 77% over 2 steps). MS($ESI^+$) m/z 706.5 (M+H)$^+$.

F) $N^1$—((S)-2-((S)-3,3-Dimethyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-6-yl)-$N^4$-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)terephthalamide Following a procedure analogous to that for the synthesis of Compound M of Example 1, 4-(((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)carbamoyl)benzoic acid (71 mg, 0.10 mmol) and tert-butyl ((S)-1-(((S)-1-((S)-6-amino-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (62 mg, 0.10 mmol) were converted to the title compound (31 mg, 26%). MS($ESI^+$) m/z 1107.4 (M+H)$^+$.

Examples 3 to 10

The following Examples were prepared according to the procedures described for the synthesis of Example 1.

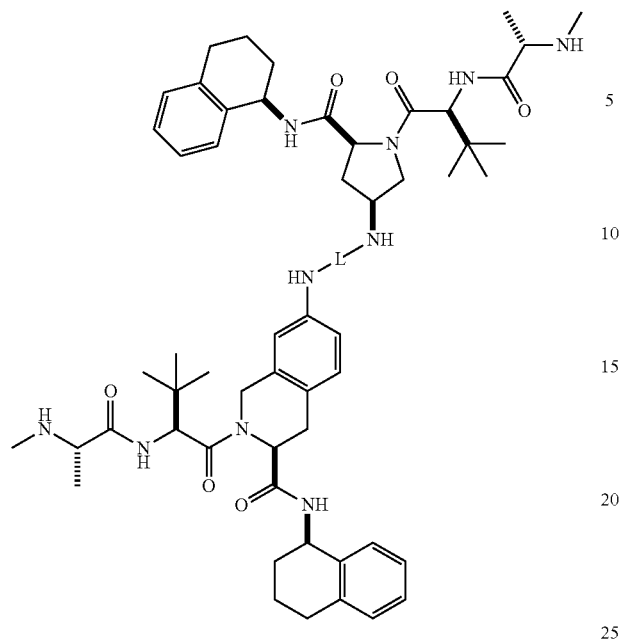

| Ex. No. | L | Name | LCMS (M + H) |
|---|---|---|---|
| 3 | (glutaryl linker) | N$^1$-((S)-2-((S)-3,3-Dimethyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)-N$^5$-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)glutaramide | 1074.1 |
| 4 | (cyclopropane-1,1-dicarbonyl linker) | N-((S)-2-((S)-3,3-Dimethyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)-N-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)cyclopropane-1,1-dicarboxamide | 1071.7 |
| 5 | (cyclobutane-1,1-dicarbonyl linker) | N-((S)-2-((S)-3,3-Dimethyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)-N-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)cyclobutane-1,1-dicarboxamide | 1086.0 |
| 6 | (oxalyl linker) | N$^1$-((S)-2-((S)-3,3-Dimethyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)-N$^2$-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)oxalamide | 1032.0 |

-continued

| Ex. No. | L | Name | LCMS (M + H) |
|---|---|---|---|
| 7 | | $N^2$-((S)-2-((S)-3,3-Dimethyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)-$N^6$-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)spiro[3.3]heptane-2,6-dicarboxamide | 1125.7 |
| 8 | | (S)-2-((S)-3,3-Dimethyl-2-((S)-2-(methylamino)propanamido)butanoyl)-7-(3-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)phenyl)propanamido)-N-((R)-1,2,3,4-tetrahydronaphthalen-1-yl)-1,2,3,4-tetrahydroisoquinoline-3-carboxamide | 1136.2 |
| 9 | | (S)-2-((S)-3,3-Dimethyl-2-((S)-2-(methylamino)propanamido)butanoyl)-7-(4-(3-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)amino)-3-oxopropyl)benzamido)-N-((R)-1,2,3,4-tetrahydronaphthalen-1-yl)-1,2,3,4-tetrahydroisoquinoline-3-carboxamide | 1135.9 |
| 10 | | $N^1$-((S)-2-((S)-3,3-Dimethyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)-$N^4$-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)terephthalamide | 1108.5 |

Examples 11 to 15

The following Examples were prepared according to the procedures described for the synthesis of Example 1 incorporating various modifications of $R^3$ and $R^4$ amines.

| Ex. No. | Structure | Name | LCMS (M + H) |
|---|---|---|---|
| 11 | 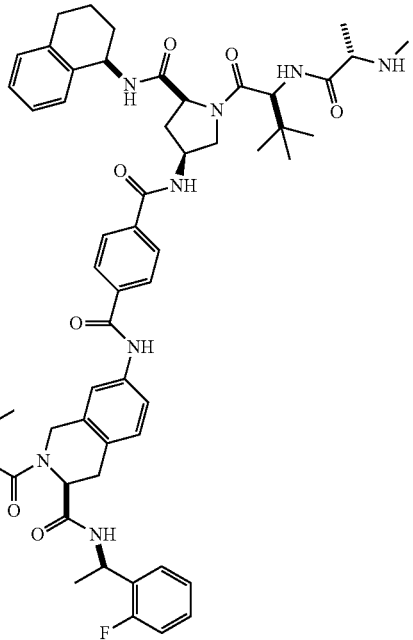 | N¹-((S)-2-((S)-3,3-Dimethyl-2-((S)-2-(methylamino)propanamido)butanoyl)-3-(((R)-1-(2-fluorophenyl)ethyl)carbamoyl)-1,2,3,4-tetrahydroisoquinolin-7-yl)-N⁴-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)terephthalamide | 1099.7 |
| 12 | 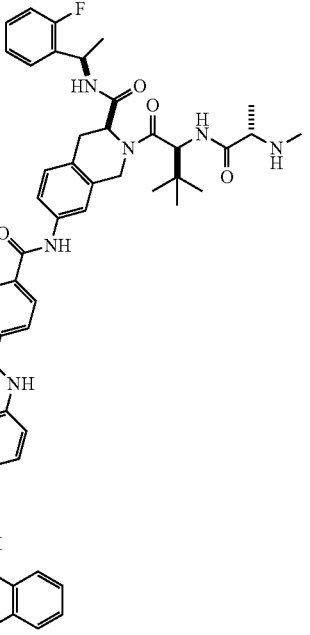 | N¹,N⁴-bis((S)-2-((S)-3,3-Dimethyl-2-((S)-2-(methylamino)propanamido)butanoyl)-3-(((R)-1-(2-fluorophenyl)ethyl)carbamoyl)-1,2,3,4-tetrahydroisoquinolin-7-yl)terephthalamide | 1153.7 |

| Ex. No. | Structure | Name | LCMS (M + H) |
|---|---|---|---|
| 13 | 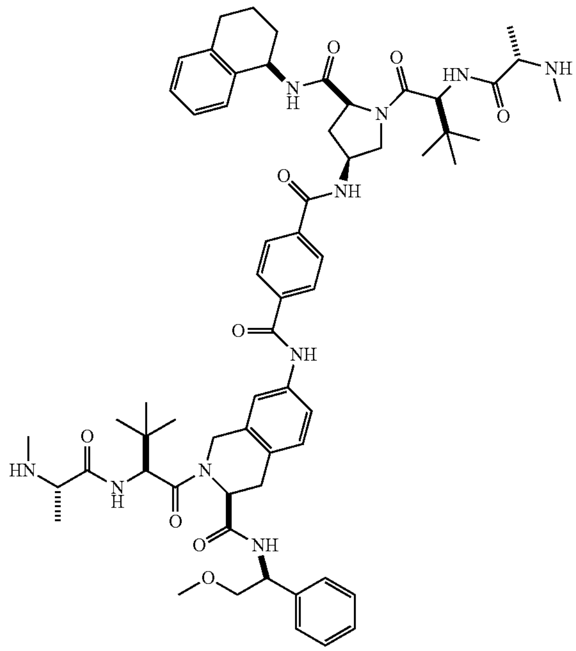 | N¹-((S)-2-((S)-3,3-Dimethyl-2-((S)-2-(methylamino)propanamido)butanoyl)-3-(((R)-2-methoxy-1-phenylethyl)carbamoyl)-1,2,3,4-tetrahydroisoquinolin-7-yl)-N⁴-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)terephthalamide | 1112.6 |
| 14 | 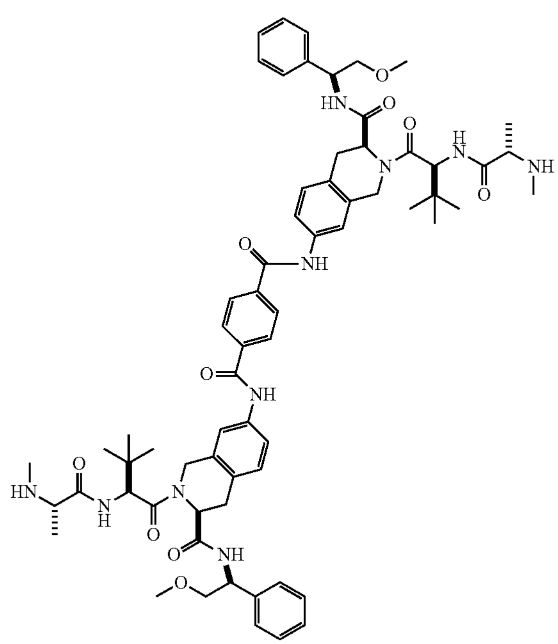 | N¹,N⁴-bis((S)-2-((S)-3,3-Dimethyl-2-((S)-2-(methylamino)propanamido)butanoyl)-3-(((R)-2-methoxy-1-phenylethyl)carbamoyl)-1,2,3,4-tetrahydroisoquinolin-7-yl)terephthalamide | 1178.6 |

| Ex. No. | Structure | Name | LCMS (M + H) |
|---|---|---|---|
| 15 | 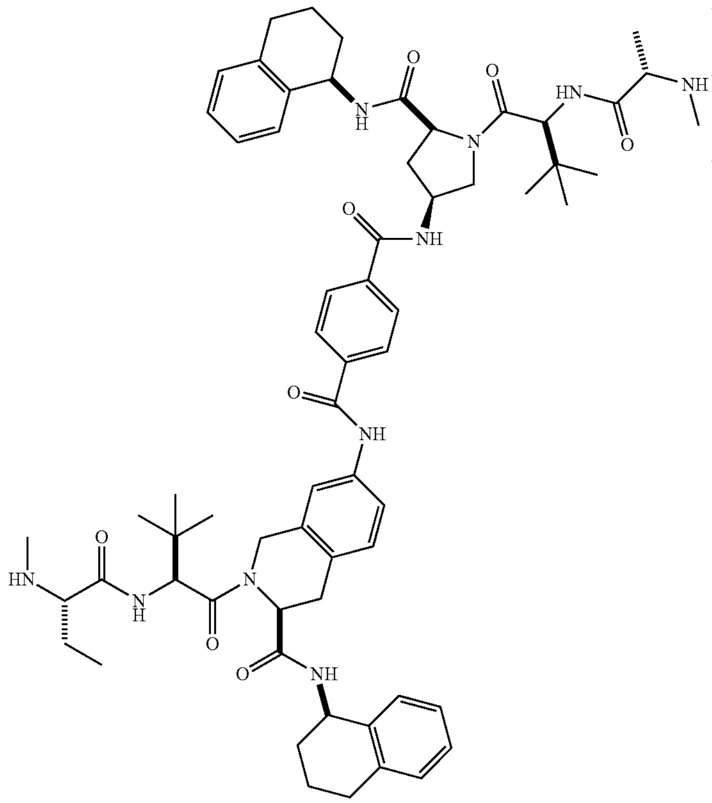 | $N^1$-((S)-2-((S)-3,3-Dimethyl-2-((S)-2-(methylamino)butanamido)butanoyl)-3-(((R)-1,2,3,4-tetrahydronaphthalen-1-yl)carbamoyl)-1,2,3,4-tetrahydroisoquinolin-7-yl)-$N^4$-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)terephthalamide | 1122.8 |
Example 16
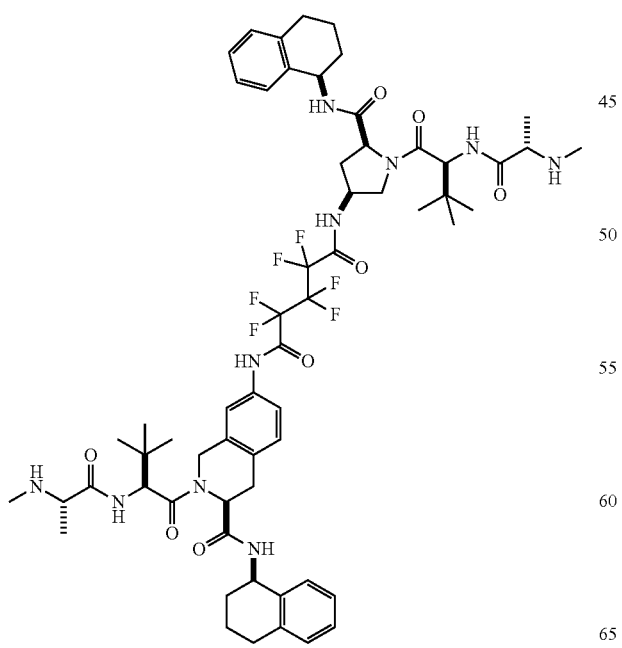

N[1]—((S)-2-((S)-3,3-Dimethyl-2-((S)-2-(methyl-amino)propanamido)butanoyl)-3-(((R)-1,2,3,4-tetra-hydronaphthalen-1-yl)carbamoyl)-1,2,3,4-tetrahy-droisoquinolin-7-yl)-N5-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-2,2,3,3,4,4-hexafluoropentanediamide

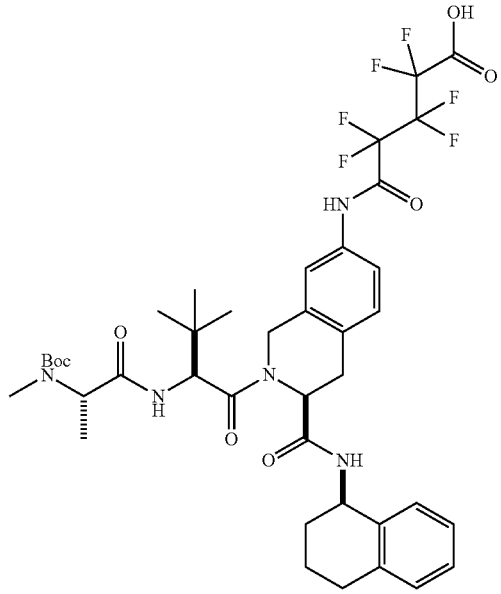

A) 5-(((S)-2-((S)-2-((S)-2-((tert-Butoxycarbonyl)(methylamino)propanamido)-3,3-dimethylbutanoyl)-3-(((R)-1,2,3,4-tetrahydronaphthalen-1-yl)carbam-oyl)-1,2,3,4-tetrahydroisoquinolin-7-yl)amino)-2,2,3,3,4,4-hexafluoro-5-oxopentanoic acid A solution of tert-butyl ((S)-1-(((S)-1-((S)-7-amino-3-(((R)-1,2,3,4-tetrahydronaphthalen-1-yl)carbamoyl)-3,4-di-hydroisoquinolin-2(1H)-yl)-3,3-dimethyl-1-oxobutan-2-yl)amino)-1-oxopropan-2-yl)(methyl)carbamate (Compound F of Example 1, 85 mg, 0.14 mmol) and Et$_3$N (80 μL, 0.58 mmol) in CH$_2$Cl$_2$ (1.4 mL) was cooled to 0° C. Methyl 5-chloro-2,2,3,3,4,4-hexafluoro-5-oxopentanoate (157 mg, 0.58 mmol, Rice, D. E., U.S. Pat. No. 3,461,155 A (1965)) in CH$_2$Cl$_2$ (1.4 mL) was added dropwise via syringe, and the resulting reaction mixture was stirred warming to room temperature over 2 h. Additional methyl 5-chloro-2,2,3,3,4,4-hexafluoro-5-oxopentanoate (157 mg, 0.58 mmol) was added and stirring was continued for 1 h. The reaction mixture was then concentrated in vacuo and triturated with hexanes. The residue was redissolved in PhMe (1.0 mL) and Et$_3$N (13 μl, 0.091 mmol) was added. The resulting reaction mixture was heated at 80° C. overnight, then concentrated in vacuo and purified using preparative HPLC to give the title compound (65 mg, 55%) as a pale yellow oil. MS(ESI$^+$) m/z 842.5 (M+H)$^+$.

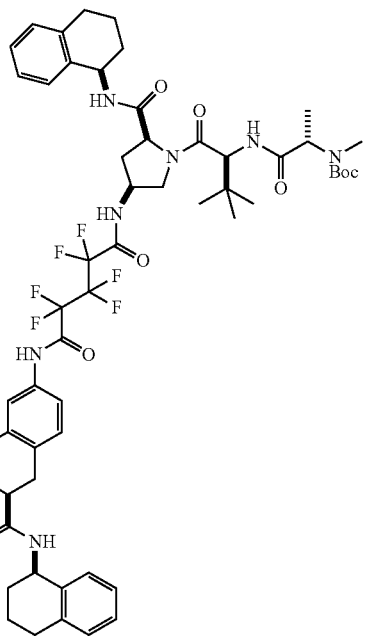

B) N[1]—((S)-2-((S)-3,3-Dimethyl-2-((S)-2-((tert-butoxycarbonyl)(methylamino)propanamido)bu-tanoyl)-3-(((R)-1,2,3,4-tetrahydronaphthalen-1-yl)carbamoyl)-1,2,3,4-tetrahydroisoquinolin-7-yl)-N5-((3S,5S)-1-((S)-3,3-dimethyl-2-((S)-2-((tert-butoxycarbonyl)(methylamino)propanamido)butanoyl)-5-(((R)-1,2,3,4-tetrahydronaphthalen-1-yl)carbamoyl)pyrrolidin-3-yl)-2,2,3,3,4,4-hexafluoropentanediamide To a solution of 5-(((S)-2-((S)-2-((S)-2-((tert-butoxycar-bonyl)(methylamino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)amino)-2,2,3,3,4,4-hexafluoro-5-oxopentanoic acid (65 mg, 0.077 mmol) in CH$_2$Cl$_2$ (1.0 mL) was added 1-chloro-N,N,2-trimethylpro-penylamine (31 μL, 0.23 mmol) via syringe. The resulting reaction mixture was stirred at room temperature for 20 min. tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound J of Example 1, 43 mg, 0.077 mmol) was added, and the reaction mixture was stirred at room temperature for 30 min. i-Pr$_2$EtN (27 μL, 0.15 mmol) was added, and the reaction mixture was allowed to stir at room temperature overnight, then concen-trated in vacuo and purified using preparative HPLC to give the title compound (21 mg, 20%) as a colorless oil. MS(ESI$^+$) m/z 1382.2 (M+H)$^+$.

C) N[1]—((S)-2-((S)-3,3-Dimethyl-2-((S)-2-(methyl-amino)propanamido)butanoyl)-3-(((R)-1,2,3,4-tetra-hydronaphthalen-1-yl)carbamoyl)-1,2,3,4-tetrahy-droisoquinolin-7-yl)-N5-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-2,2,3,3,4,4-hexafluoropentanediamide To a solution of N[1]—((S)-2-((S)-3,3-dimethyl-2-((S)-2-((tert-butoxycarbonyl)(methylamino)propanamido)butanoyl)-3-(((R)-1,2,3,4-tetrahydronaphthalen-1-yl)carbamoyl)-1,2,3,4-tetrahydroisoquinolin-7-yl)-N⁵-((3S,5S)-1-((S)-3,3-dimethyl-2-((S)-2-((tert-butoxycarbonyl)(methylamino)propanamido)butanoyl)-5-(((R)-1,2,3,4-tetrahydronaphthalen-1-yl)carbamoyl)pyrrolidin-3-yl)-2,2,3,3,4,4-hexafluoropentanediamide (21 mg, 0.015 mmol) in CH₂Cl₂ (1.0 mL) was added TFA (47 µL, 0.61 mmol). The resulting solution was stirred at room temperature for 1 h. Additional TFA (100 µL, 1.29 mmol) was added and stirring was continued at room temperature for 1 h. The reaction mixture was then concentrated in vacuo and purified using preparative HPLC to give the title compound (7 mg, 36%) as a white solid after lyophilization. MS(ESI⁺) m/z 1181.6 (M+H)⁺.

Example 17

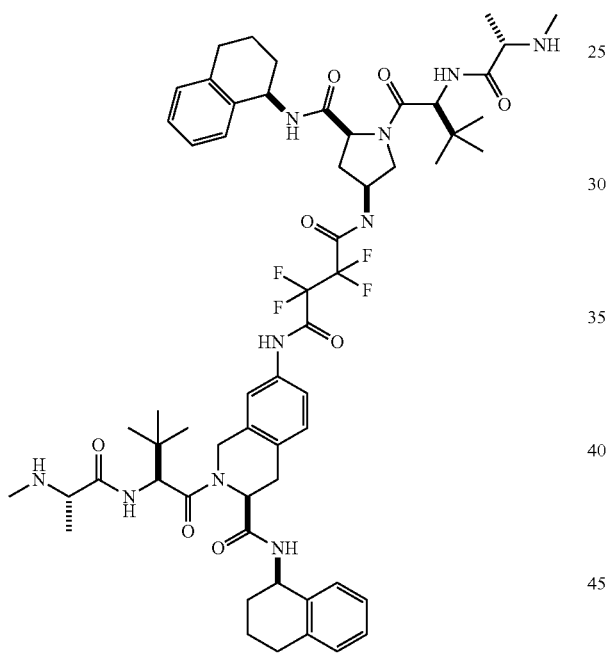

N¹—((S)-2-((S)-3,3-Dimethyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)-N⁴-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-2,2,3,3-tetrafluorosuccinamide Following a procedure analogous to that for the synthesis of Example 16, tert-butyl ((S)-1-(((S)-1-((S)-7-amino-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (Compound F of Example 1, 85 mg, 0.14 mmol) was converted to the title compound (5 mg, 3%). MS(ESI⁺) m/z 1131.5 (M+H)⁺.

Example 18

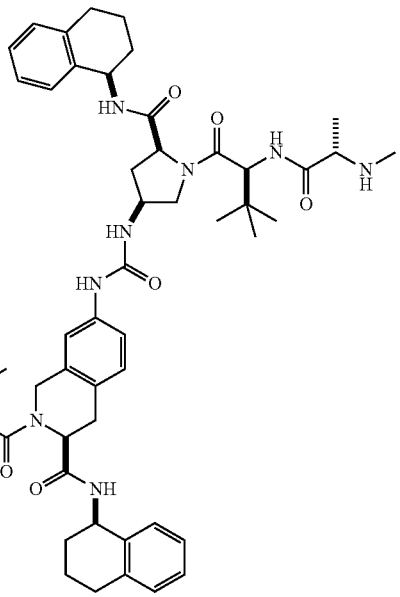

(S)-2-((S)-3,3-Dimethyl-2-((S)-2-(methylamino)propanamido)butanoyl)-7-(3-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)ureido)-N—((R)-1,2,3,4-tetrahydronaphthalen-1-yl)-1,2,3,4-tetrahydroisoquinoline-3-carboxamide To a 0° C. solution of triphosgene (10 mg, 0.032 mmol) in CH₂Cl₂ (0.5 mL) was added a solution of tert-butyl ((S)-1-(((S)-1-(((S)-7-amino-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (Compound F of Example 1, 50 mg, 0.081 mmol) and i-Pr₂EtN (21 µl, 0.12 mmol) in CH₂Cl₂ (0.5 mL). The resulting reaction mixture was stirred at 0° C. for 2 h. A solution of tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate, TFA (Compound J of Example 1, 54 mg, 0.081 mmol) and i-Pr₂EtN (21 µl, 0.12 mmol) in CH₂Cl₂ (0.5 mL) was added and stirring was continued at room temperature for 30 min. TFA (110 µl, 1.45 mmol) was then added. The reaction mixture was stirred at room temperature overnight, then concentrated in vacuo and purified using preparative HPLC to give the title compound (27 mg, 32%) as a white solid after lyophilization. MS(ESI⁺) m/z 1003.7 (M+H)⁺.

Example 19

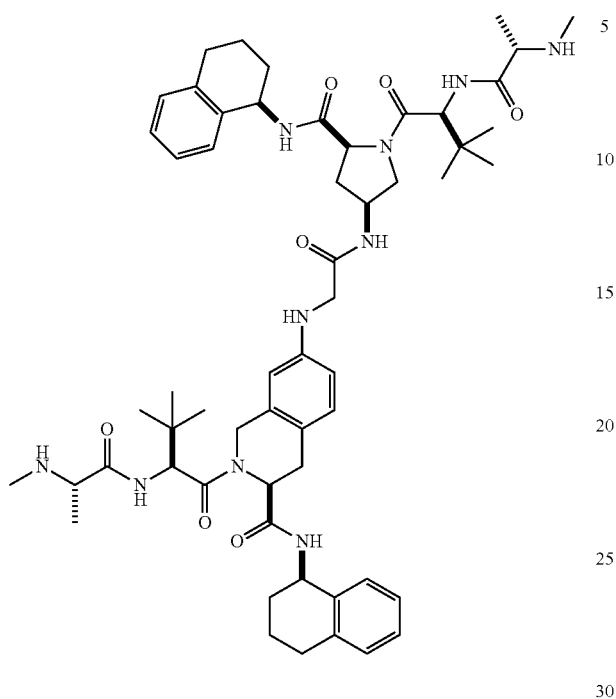

(S)-2-((S)-3,3-Dimethyl-2-((S)-2-(methylamino)
propanamido)butanoyl)-7-((2-(((3S,5S)-1-((S)-3,3-
dimethyl-2-((S)-2-(methylamino)propanamido)bu-
tanoyl)-5-(((R)-1,2,3,4-tetrahydronaphthalen-1-yl)
carbamoyl)pyrrolidin-3-yl)amino)-2-oxoethyl)
amino)-N—((R)-1,2,3,4-tetrahydronaphthalen-1-yl)-
1,2,3,4-tetrahydroisoquinoline-3-carboxamide To a solution of tert-butyl ((S)-1-(((S)-1-((S)-7-amino-3-
(((R)-1,2,3,4-tetrahydronaphthalen-1-yl)carbamoyl)-3,4-di-
hydroisoquinolin-2(1H)-yl)-3,3-dimethyl-1-oxobutan-2-yl)
amino)-1-oxopropan-2-yl)(methyl)carbamate (Compound F
of Example 1, 30 mg, 0.048 mmol) in DCE (1.0 mL) was
added 2-oxoacetic acid, $H_2O$ (5 mg, 0.053 mmol). After 10
min, Na(OAc)$_3$BH (18 mg, 0.087 mmol) was added. The
resulting reaction mixture was stirred at room temperature
for 3 h and then poured into a separatory funnel containing
1N HCl and EtOAc. The aqueous layer was extracted with
EtOAc (3 x), and the combined organics were washed with
sat. NaCl, dried over $Na_2SO_4$, filtered and concentrated in
vacuo. The residue was dissolved in DMF (1.0 mL). EDC
(11 mg, 0.058 mmol) and HOAt (8 mg, 0.058 mmol) were
added. After 5 min, tert-butyl ((S)-1-(((S)-1-((2S,4S)-4-
amino-2-(((R)-1,2,3,4-tetrahydronaphthalen-1-yl)carbam-
oyl)pyrrolidin-1-yl)-3,3-dimethyl-1-oxobutan-2-yl)amino)-
1-oxopropan-2-yl)(methyl)carbamate (Compound J of
Example 1, 27 mg, 0.048 mmol) and NMM (16 µL, 0.14
mmol) were added. The resulting reaction mixture was
stirred at room temperature for 2 h and then poured into a
separatory funnel containing EtOAc and sat. aq. NaHCO$_3$.
The aqueous layer was extracted with EtOAc (3×). The
combined organic extracts were washed with 1N HCl and
sat. NaCl, dried over Na$_2$SO$_4$, filtered and concentrated in
vacuo. The crude oil was dissolved in CH$_2$Cl$_2$ (1.0 mL) and
TFA (142 µL, 1.84 mmol) was added. The resulting solution
was stirred at room temperature for 30 min, then concen-
trated in vacuo and purified using preparative HPLC to give
the title compound (12 mg, 26%) as a white solid after
lyophilization. MS(ESI$^+$) m/z 1018.6 (M+H)$^+$.

Example 20

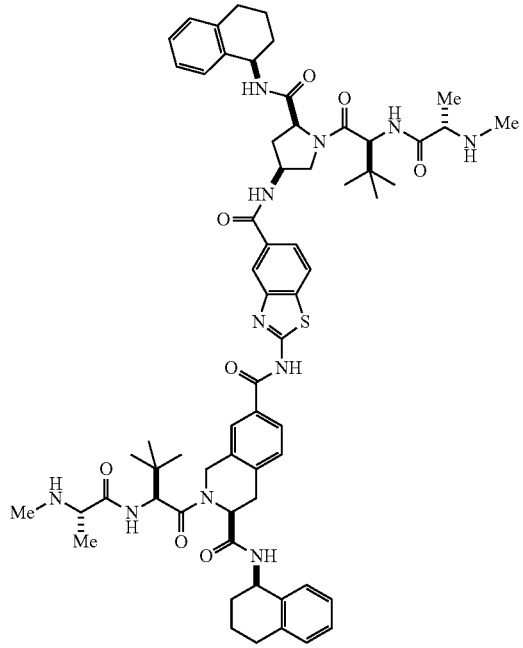

(S)-2-((S)-3,3-Dimethyl-2-((S)-2-(methylamino)
propanamido)butanoyl)-N$^7$-(5-(((3S,5S)-1-((S)-3,3-
dimethyl-2-((S)-2-(methylamino)propanamido)bu-
tanoyl)-5-(((R)-1,2,3,4-tetrahydronaphthalen-1-yl)
carbamoyl)pyrrolidin-3-yl)carbamoyl)benzo[d]
thiazol-2-yl)-N$^3$—((R)-1,2,3,4-
tetrahydronaphthalen-1-yl)-1,2,3,4-
tetrahydroisoquinoline-3,7-dicarboxamide

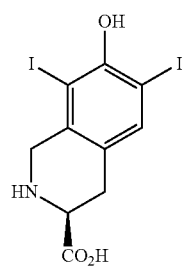 [SMILES: O=C(O)[C@@H]1Cc2cc(I)c(O)c(I)c2CN1]

A) (S)-7-Hydroxy-6,8-diiodo-1,2,3,4-tetrahydroiso-
quinoline-3-carboxylic acid

A thick-walled reaction flask with screw top was charged
sequentially with (S)-2-amino-3-(4-hydroxy-3,5-diiodophe-
nyl)propanoic acid (5.0 g, 11.6 mmol), 1,2-dimethoxyethane
(5.0 mL, 2.31 M), formaldehyde (37% wt. in H$_2$O, 4.5 mL,
60.4 mmol), and conc. HCl (60.2 mL, 1981 mmol). The
resulting tan slurry was sealed with screw top and heated to 72° C. slowly over 0.5 h then maintained at 72° C. for 12 h. The resulting brown reaction slurry was then cooled to 0° C., filtered while cold, and washed with small amounts of 1,2-dimethoxyethane to give the title compound (2.42 g, 5.45 mmol, 47%) as a white solid. $^1$H NMR (400 MHz, DMSO-$d_6$) δ 9.93 (br. s., 1H), 9.69 (br. s., 1H), 7.75 (s, 1H), 4.34 (d, J=7.7 Hz, 1H), 4.21-3.94 (m, 2H), 3.93-3.47 (m, 1H), 3.33-3.16 (m, 1H), 3.15-2.97 (m, 1H); MS(ESI$^+$) m/z 445.9 (M+H)$^+$.

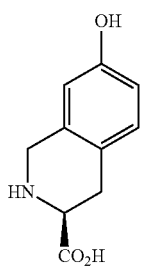

B) (S)-7-Hydroxy-1,2,3,4-tetrahydroisoquinoline-3-carboxylic acid (S)-7-Hydroxy-6,8-diiodo-1,2,3,4-tetrahydroisoquinoline-3-carboxylic acid (2.0 g, 4.49 mmol) and palladium on carbon (5%, 0.478 g, 0.225 mmol) were suspended in H$_2$O (24.4 mL) and Et$_3$N (2.07 mL, 14.8 mmol). Ethanol (73.3 mL) purged with H$_2$ was then syringed into the reaction and the reaction flask was topped with a balloon of H$_2$. The reaction mixture was stirred for 4 h, filtered through CELITE®, washing with MeOH, and concentrated in vacuo to give crude (S)-7-hydroxy-1,2,3,4-tetrahydroisoquinoline-3-carboxylic acid, which was used directly in the next step. MS(ESI$^+$) m/z 193.1 (M+H)$^+$.

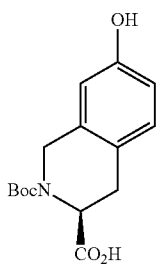 [SMILES: CC(C)(C)OC(=O)N1Cc2cc(O)ccc2C[C@H]1C(=O)O]

C) (S)-2-(tert-Butoxycarbonyl)-7-hydroxy-1,2,3,4-tetrahydroisoquinoline-3-carboxylic acid To a solution of crude L-7-hydroxy-1,2,3,4-tetrahydroisoquinoline-3-carboxylic acid (0.868 g, 4.49 mmol) and sodium bicarbonate (0.755 g, 8.99 mmol) in
THF (26.1 mL) and H$_2$O (26.1 mL) was added di-t-butyldicarbonate (1135 mL, 4.94 mmol). After 12 h, the reaction was concentrated in vacuo to remove volatiles, and acidified to pH=4 with 1M HCl. The resulting cloudy yellow solution was then partitioned in DCM, and the layers were separated. The aq. layer was extracted with DCM (3×) and the combined organic layers were dried over MgSO$_4$, filtered, and concentrated in vacuo to give crude (S)-2-(tert-butoxycarbonyl)-7-hydroxy-1,2,3,4-tetrahydroisoquinoline-3-carboxylic acid which was used directly in the next step. MS(ESI$^1$) m/z 294.3 (M+H)$^+$.

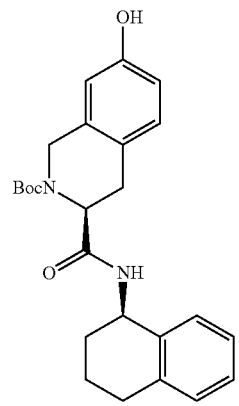 [SMILES: CC(C)(C)OC(=O)N1Cc2cc(O)ccc2C[C@H]1C(=O)N[C@@H]1CCCc2ccccc21]

D) Ethyl 4-fluoro-3-(1,2,3,4-tetrahydroisoquinoline-2-carbonyl)benzoate

To a 0° C. solution of (S)-2-(tert-butoxycarbonyl)-7-hydroxy-1,2,3,4-tetrahydroisoquinoline-3-carboxylic acid (1.318 g, 4.49 mmol) in DMF (30.0 mL) was added EDC (1.03 g, 5.39 mmol) followed by 3H-[1,2,3]-triazolo[4,5-b]pyridin-3-ol (0.734 g, 5.39 mmol). After 10 min, (R)-1,2,3,4-tetrahydronaphthalen-1-amine (0.660 mL, 4.49 mmol) and N-methylmorpholine (1.48 mL, 13.5 mmol) were added and the resulting reaction mixture was allowed to warm to room temperature slowly. After 4 h, the reaction mixture was partitioned in EtOAc and H$_2$O and the layers were separated. The aq. layer was extracted with EtOAc (3×) and the combined organic extracts were washed with H$_2$O, 1N HCl, 10% LiCl and sat. NaCl, dried over MgSO$_4$, filtered and concentrated in vacuo. The crude material was then purified by flash chromatography (linear gradient 0-70% EtOAc/hexanes) to afford the title compound (1.25 g, 2.96 mmol, 66% over 3 steps) as a light yellow foam. $^1$H NMR (400 MHz, CDCl$_3$) δ 7.18-6.86 (m, 4H), 6.84-6.67 (m, 1H), 6.58-6.39 (m, 1H), 6.04-5.74 (m, 2H), 4.94 (d, J=5.7 Hz, 1H), 4.78-4.61 (m, 1H), 4.56-4.41 (m, 1H), 4.20 (d, J=15.6 Hz, 1H), 3.34 (d, J=13.4 Hz, 1H), 3.02 (d, J=12.1 Hz, 1H), 2.81-2.60 (m, 2H), 1.87-1.68 (m, 2H), 1.67-1.54 (m, 2H), 1.53-1.37 (m, 9H); MS(ESI$^+$) m/z 423.2 (M+H)$^+$.

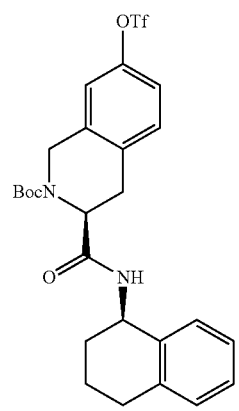 [SMILES: CC(C)(C)OC(=O)N1Cc2cc(OS(=O)(=O)C(F)(F)F)ccc2C[C@H]1C(=O)N[C@@H]1CCCc2ccccc21]

E) (S)-tert-Butyl 3-(((R)-1,2,3,4-tetrahydronaphthalen-1-yl)carbamoyl)-7-(((trifluoromethyl)sulfonyl)oxy)-3,4-dihydroisoquinoline-2(1H)-carboxylate To a solution of (S)-tert-butyl 7-hydroxy-3-(((R)-1,2,3,4-tetrahydronaphthalen-1-yl)carbamoyl)-3,4-dihydroisoquinoline-2(1H)-carboxylate (1.25 g, 2.96 mmol) in DCM (29.6 mL) under N₂, was added Et₃N (1.24 mL, 8.89 mmol) and DMAP (0.036 g, 0.296 mmol). The solution was cooled to 0° C., and 1,1,1-trifluoro-N-phenyl-N-((trifluoromethyl)sulfonyl)methanesulfonamide (1.27 g, 3.55 mmol) was then added in one portion. After stirring at 0° C. for 15 min, the reaction was let warm to room temperature and continued to stir. After stirring for 1 h, the reaction was concentrated in vacuo and purified by flash chromatography (linear gradient 0-70% EtOAc/hexanes) to afford the title compound (S)-tert-butyl 3-(((R)-1,2,3,4-tetrahydronaphthalen-1-yl)carbamoyl)-7-(((trifluoromethyl)sulfonyl)oxy)-3,4-dihydroisoquinoline-2(1H)-carboxylate (1.39 g, 2.50 mmol, 84%) as a white foam. MS(ESI⁺) m/z 555.4 (M+H)⁺.

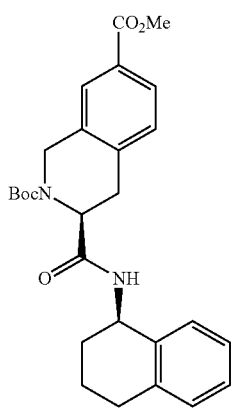 [SMILES: COC(=O)c1ccc2c(c1)CN(C(=O)OC(C)(C)C)[C@H](C(=O)N[C@@H]1CCCc3ccccc31)C2]

F) (S)-2-tert-Butyl 7-methyl 3-(((R)-1,2,3,4-tetrahydronaphthalen-1-yl)carbamoyl)-3,4-dihydroisoquinoline-2,7(1H)-dicarboxylate A 20 mL scintillation vial with septum top under N₂ was charged sequentially with (S)-tert-butyl 3-(((R)-1,2,3,4-tetrahydronaphthalen-1-yl)carbamoyl)-7-(((trifluoromethyl)sulfonyl)oxy)-3,4-dihydroisoquinoline-2(1H)-carboxylate (1.39 g, 2.50 mmol), Pd(OAc)₂ (0.028 g, 0.125 mmol), and 1,3-bis(diphenylphosphino)propane (0.052 g, 0.125 mmol). DMSO (3.75 mL), MeOH (2.501 mL), and Et₃N (0.767 mL, 5.50 mmol) were then added and the reaction was stirred for 5 min. A CO balloon was then used to purge the reaction vial, turning the solution black. The reaction was then topped with the CO balloon and heated to 70° C. for 12 h. The reaction was then filtered through an ACRODISC® and partitioned in EtOAc and sat. aq. NH₄Cl. The layers were separated and the aq. layer was extracted with EtOAc (2×). The combined organic layers were washed with sat. NaCl (2×), dried over MgSO₄, filtered and concentrated in vacuo. The crude material was then purified by flash chromatography (linear gradient 0-50% EtOAc/hexanes) to afford the title compound (1.06 g, 2.28 mmol, 91%) as a light yellow solid. MS(ESI⁺) m/z 465.2 (M+H)⁺.

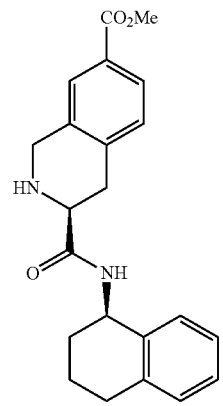 [SMILES: COC(=O)c1ccc2c(c1)CN[C@H](C(=O)N[C@@H]1CCCc3ccccc31)C2]

G) (S)-Methyl 3-(((R)-1,2,3,4-tetrahydronaphthalen-1-yl)carbamoyl)-1,2,3,4-tetrahydroisoquinoline-7-carboxylate To a solution of (S)-2-tert-butyl 7-methyl 3-(((R)-1,2,3,4-tetrahydronaphthalen-1-yl)carbamoyl)-3,4-dihydroisoquinoline-2,7(1H)-dicarboxylate (1.06 g, 2.28 mmol) in DCM (22.8 mL) was added TFA (5.71 mL). After 1 h, the reaction was quenched with sat. NaHCO₃ and the layers were separated. The aq. layer was extracted with EtOAc (3×) and the combined organic extracts were washed with sat. NaCl, dried over MgSO₄, filtered and concentrated in vacuo. The material was then lyophilized overnight to give (S)-methyl 3-(((R)-1,2,3,4-tetrahydronaphthalen-1-yl)carbamoyl)-1,2,3,4-tetrahydroisoquinoline-7-carboxylate (0.80 g, 2.2 mmol, 96%) as a light yellow solid. ¹H NMR (400 MHz, DMSO-d₆) δ 8.39 (d, J=8.6 Hz, 1H), 7.85-7.67 (m, 2H), 7.34 (d, J=7.9 Hz, 1H), 7.24-7.02 (m, 4H), 5.12-4.93 (m, 1H), 4.23-3.97 (m, 2H), 3.86 (s, 3H), 3.73 (dd, J=10.0, 4.7 Hz, 1H), 3.33 (br. s., 1H), 3.18-3.05 (m, 1H), 3.03-2.88 (m, 1H), 2.86-2.63 (m, 2H), 2.02-1.83 (m, 2H), 1.81-1.64 (m, 2H); MS(ESI⁺) m/z 365.1 (M+H)⁺.

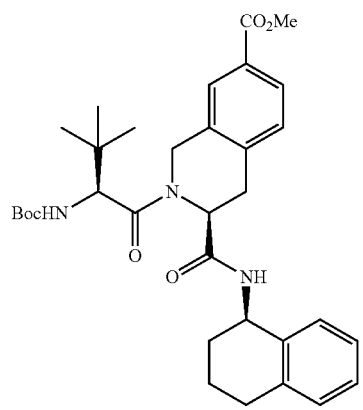 [SMILES: COC(=O)c1ccc2c(c1)CN(C(=O)[C@@H](NC(=O)OC(C)(C)C)C(C)(C)C)[C@H](C(=O)N[C@@H]1CCCc3ccccc31)C2]

H) (S)-Methyl 2-((S)-2-((tert-butoxycarbonyl)amino)-3,3-dimethylbutanoyl)-3-(((R)-1,2,3,4-tetrahydronaphthalen-1-yl)carbamoyl)-1,2,3,4-tetrahydroisoquinoline-7-carboxylate To a 0° C. solution of (S)-2-((tert-butoxycarbonyl)amino)-3,3-dimethylbutanoic acid (473 mg, 2.05 mmol) and (S)-methyl 3-(((R)-1,2,3,4-tetrahydronaphthalen-1-yl)carbamoyl)-1,2,3,4-tetrahydroisoquinoline-7-carboxylate (745 mg, 2.05 mmol) in DCM (12.4 mL) was added EDC (471 mg, 2.454 mmol), 3H-[1,2,3]-triazolo[4,5-b]pyridin-3-ol (334 mg, 2.45 mmol), and N-methylmorpholine (675 µL, 6.14 mmol). The reaction mixture was allowed to warm to room temperature overnight and was quenched with EtOAc and sat. aq. NaHCO$_3$. The layers were separated and the aq. layer was extracted with EtOAc (3×). The combined organic extracts were washed with 1N HCl (2×), sat. NaCl (1×), dried over MgSO$_4$, filtered and concentrated in vacuo to give crude (S)-methyl 2-((S)-2-((tert-butoxycarbonyl)amino)-3,3-dimethylbutanoyl)-3-(((R)-1,2,3,4-tetrahydronaphthalen-1-yl)carbamoyl)-1,2,3,4-tetrahydroisoquinoline-7-carboxylate (1.18 g, 2.05 mmol, 100%) as a light yellow foam, which was used without further purification. MS(ESI$^+$) m/z 578.2 (M+H)$^+$.

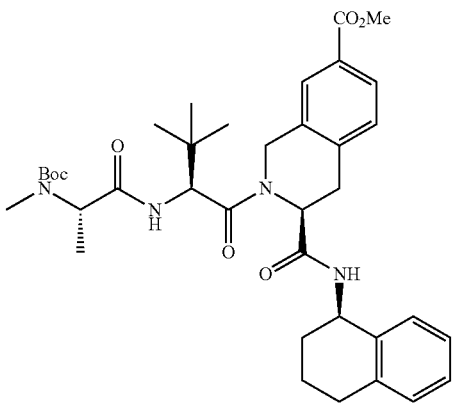

J) (S)-Methyl 2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxylate To a 0° C. solution of (S)-methyl 2-((S)-2-amino-3,3-dimethylbutanoyl)-3-(((R)-1,2,3,4-tetrahydronaphthalen-1-yl)carbamoyl)-1,2,3,4-tetrahydroisoquinoline-7-carboxylate (965 mg, 2.02 mmol) and (S)-2-((tert-butoxycarbonyl)(methyl)amino)propanoic acid (411 mg, 2.02 mmol) in DMF (20.2 mL) was added EDC (465 mg, 2.43 mmol), followed by 3H-[1,2,3]-triazolo[4,5-b]pyridin-3-ol (330 mg, 2.43 mmol). N-methylmorpholine (667 µl, 6.07 mmol) was then added and the resulting reaction mixture was stirred at 0° C. for 30 min, and then warmed to room temperature. After 4 h, the reaction mixture was partitioned in EtOAc and sat. aq. NaHCO$_3$, the layers were separated and the aq. layer was extracted with EtOAc (3×). The combined organic extracts were washed with 1N HCl (2×) and 10% LiCl, dried over MgSO$_4$, filtered, and concentrated in vacuo to give (S)-methyl 2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxylate (1.34 g, 2.02 mmol, 100%) as a light yellow foam, which was used without further purification. MS(ESI$^+$) m/z 663.3 (M+H)$^+$.

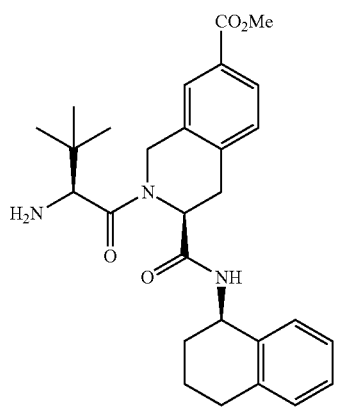 [SMILES: COC(=O)c1ccc2c(c1)CN(C(=O)[C@@H](N)C(C)(C)C)[C@H](C(=O)N[C@@H]1CCCc3ccccc31)C2]

I) (S)-Methyl 2-((S)-2-amino-3,3-dimethylbutanoyl)-3-(((R)-1,2,3,4-tetrahydronaphthalen-1-yl)carbamoyl)-1,2,3,4-tetrahydroisoquinoline-7-carboxylate A solution of (S)-methyl 2-((S)-2-((tert-butoxycarbonyl)amino)-3,3-dimethylbutanoyl)-3-(((R)-1,2,3,4-tetrahydronaphthalen-1-yl)carbamoyl)-1,2,3,4-tetrahydroisoquinoline-7-carboxylate (1.21 g, 2.10 mmol) in DCM (13.97 mL) was charged with TFA (3.49 mL) at room temperature. After 40 min, the reaction was quenched with sat. aq. NaHCO$_3$ and extracted with EtOAc (3×). The combined extracts were washed with brine, dried over MgSO$_4$, filtered and concentrated in vacuo to afford (S)-methyl 2-((S)-2-amino-3,3-dimethylbutanoyl)-3-(((R)-1,2,3,4-tetrahydronaphthalen-1-yl)carbamoyl)-1,2,3,4-tetrahydroisoquinoline-7-carboxylate (0.97 g, 2.0 mmol, 97%) as a light yellow foam, which was used without further purification. MS(ESI$^+$) m/z 478.2 (M+H)$^+$.

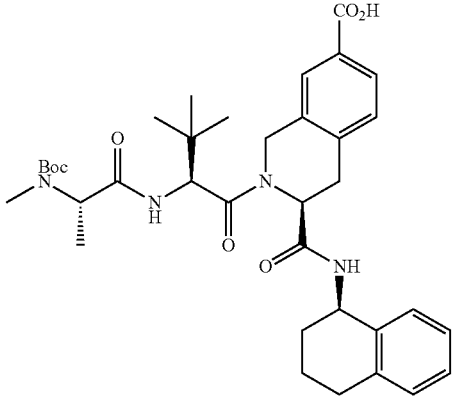 [SMILES: C[C@@H](C(=O)N[C@H](C(=O)N1Cc2cc(C(=O)O)ccc2C[C@H]1C(=O)N[C@@H]1CCCc2ccccc21)C(C)(C)C)N(C)C(=O)OC(C)(C)C]

K) (S)-2-((S)-2-((S)-2-((tert-Butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxylic acid To a solution of (S)-methyl 2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxylate (1.34 g, 2.02 mmol) in THF (13.5 mL) and MeOH (6.74 mL) was added aq. NaOH (3 N, 3.37 mL, 10.1 mmol). After 3 h, the reaction mixture was poured into EtOAc and 1N HCl and the layers were separated. The aq. layer was extracted with EtOAc (3 x) and the combined organic extracts were dried over MgSO$_4$, filtered and concentrated in vacuo to afford (S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxylic acid (1.25 g, 1.93 mmol, 95%) as a light yellow foam, which was used without further purification. MS(ESI$^+$) m/z 649.3 (M+H)$^+$.

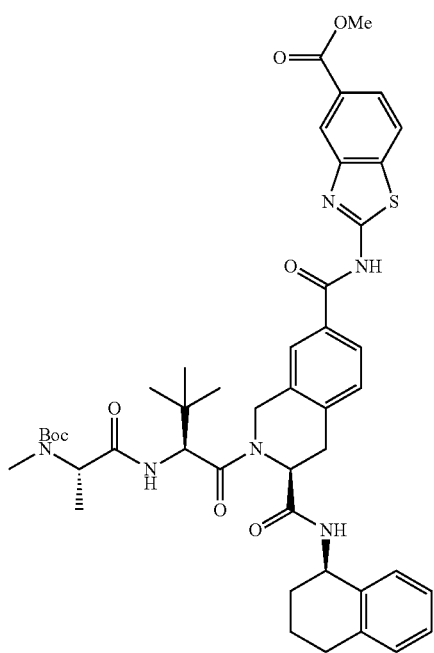 [SMILES: COC(=O)c1ccc2sc(NC(=O)c3ccc4c(c3)CN(C(=O)[C@@H](NC(=O)[C@H](C)N(C)C(=O)OC(C)(C)C)C(C)(C)C)[C@H](C(=O)N[C@@H]3CCCc5ccccc53)C4)nc2c1]

L) Methyl 2-((S)-2-((S)-2-((S)-2-((tert-butoxycarbonyl)(methyl)amino) propanamido)-3,3-dimethylbutanoyl)-3-(((R)-1,2,3,4-tetrahydronaphthalen-1-yl)carbamoyl)-1,2,3,4-tetrahydroisoquinoline-7-carboxamido)benzo[d]thiazole-5-carboxylate A 2 dram vial was charged sequentially with (S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxylic acid (33 mg, 0.051 mmol), methyl 2-aminobenzo[d]thiazole-5-carboxylate (21.2 mg, 0.102 mmol), DMAP (6.21 mg, 0.051 mmol), DCM (1927 µl), and DMF (385 µl). After stirring for 5 min to dissolve the solids, EDC (19.5 mg, 0.102 mmol) was added and the reaction was stirred overnight at room temperature. The reaction was quenched with 1M HCl, and extracted EtOAc (2×). The combined organic extracts were washed with 1M HCl and 10% LiCl, dried over MgSO$_4$, filtered and concentrated in vacuo to afford methyl 2-((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxamido)benzo[d]thiazole-5-carboxylate (40 mg, 0.048 mmol, 94%) as a light yellow oil, which was used without further purification. MS(ESI$^+$) m/z 839.3 (M+H)$^+$.

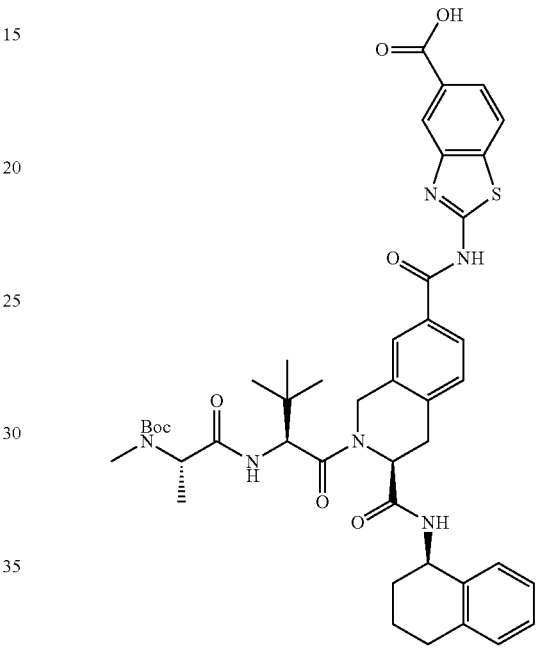

M) 2-((S)-2-((S)-2-((S)-2-((tert-Butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxamido)benzo[d]thiazole-5-carboxylic acid To a solution of methyl 2-((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxamido)benzo[d]thiazole-5-carboxylate (40 mg, 0.048 mmol) in THF (318 µl) and MeOH (159 µl) was added aq. NaOH (3 N, 318 µl, 0.954 mmol). After stirring overnight, the reaction mixture was poured into EtOAc and 1N HCl and the layers were separated. The aq. layer was extracted with EtOAc (3×) and the combined organic extracts were dried over MgSO$_4$, filtered and concentrated in vacuo to give 2-((S)-2-((S)-2-(((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxamido)benzo[d]thiazole-5-carboxylic acid (36 mg, 0.044 mmol, 91%) as a white film, which was used without further purification. MS(ESI$^+$) m/z 825.2 (M+H)$^+$.

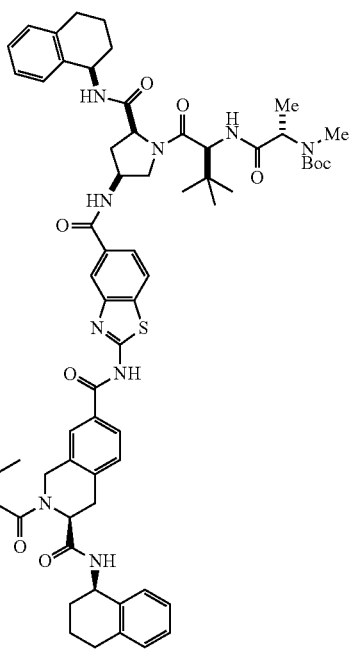

N) (S)-2-((S)-3,3-Dimethyl-2-((S)-2-((tert-butoxycarbonyl)(methylamino)propanamido)butanoyl)-N⁷-(5-(((3S,5S)-1-((S)-3,3-dimethyl-2-((S)-2-((tert-butoxycarbonyl)(methylamino)propanamido)butanoyl)-5-(((R)-1,2,3,4-tetrahydronaphthalen-1-yl)carbamoyl)pyrrolidin-3-yl)carbamoyl)benzo[d]thiazol-2-yl)-N³—((R)-1,2,3,4-tetrahydronaphthalen-1-yl)-1,2,3,4-tetrahydroisoquinoline-3,7-dicarboxamide To a solution of 2-((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxamido)benzo[d]thiazole-5-carboxylic acid (36 mg, 0.044 mmol) in DMF (967 µl) was added EDC (10.01 mg, 0.052 mmol) followed by 3H-[1,2,3]-triazolo[4,5-b]pyridin-3-ol (7.1 mg, 0.052 mmol). After 5 min, tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound J of Example 1, 25.5 mg, 0.046 mmol) and N-methylmorpholine (14.4 µl, 0.131 mmol) were added and the resulting reaction mixture was stirred at room temperature overnight. The reaction mixture was partitioned in EtOAc and sat. aq. NaHCO₃ and the layers were separated. The aq. layer was extracted with EtOAc (3×) and the combined organic extracts were washed with 1N HCl and sat. NaCl, dried over MgSO₄, filtered and concentrated in vacuo to give the title compound (57.4 mg, 0.042 mmol, 97%) as a light yellow film, which was used without further purification. MS(ESI⁺) m/z 1365.3 (M+H)⁺.

O) (S)-2-((S)-3,3-Dimethyl-2-((S)-2-(methylamino)propanamido)butanoyl)-N⁷-(5-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzo[d]thiazol-2-yl)-N³-((R)-1,2,3,4-tetrahydronaphthalen-1-yl)-1,2,3,4-tetrahydroisoquinoline-3,7-dicarboxamide Compound (S)-2-((S)-3,3-dimethyl-2-((S)-2-((tert-butoxycarbonyl)(methylamino)propanamido)butanoyl)-N⁷-(5-(((3S,5S)-1-((S)-3,3-dimethyl-2-((S)-2-((tert-butoxycarbonyl)(methylamino)propanamido)butanoyl)-5-(((R)-1,2,3,4-tetrahydronaphthalen-1-yl)carbamoyl)pyrrolidin-3-yl)carbamoyl)benzo[d]thiazol-2-yl)-N³—((R)-1,2,3,4-tetrahydronaphthalen-1-yl)-1,2,3,4-tetrahydroisoquinoline-3,7-dicarboxamide (57 mg, 0.042 mmol) was dissolved in a solution of 20% TFA/DCM (1052 µl) at room temperature. After 1 h, the solution was concentrated in vacuo and the crude material was purified via preparative LC/MS to give the title compound (8.4 mg, 17%). MS(ESI⁺) m/z 1165.2 (M+H)⁺.

Examples 21 to 26

The following Examples were prepared using (S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxylic acid (Compound K of Example 20) and tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound J of Example 1) according to the procedure for the synthesis of Example 1 and 20.

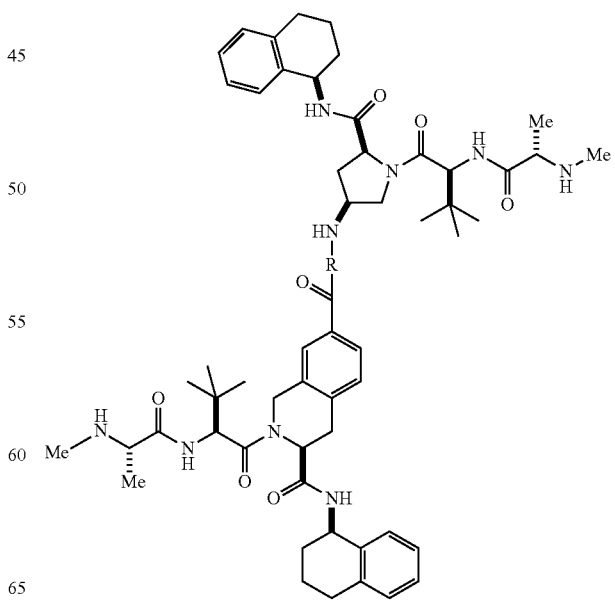

| Ex. No. | R | Name | LCMS (M + H) |
|---|---|---|---|
| 21 | 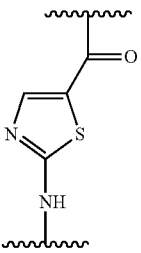 [SMILES: *Nc1ncc(C(*)=O)s1] | (S)-2-((S)-3,3-Dimethyl-2-((S)-2-(methylamino)propanamido)butanoyl)-N$^7$-(5-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)thiazol-2-yl)-N$^3$-((R)-1,2,3,4-tetrahydronaphthalen-1-yl)-1,2,3,4-tetrahydroisoquinoline-3,7-dicarboxamide | 1115.0 |
| 22 | 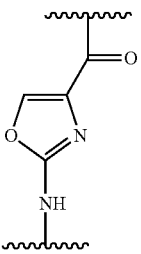 [SMILES: *Nc1nc(C(*)=O)co1] | (S)-2-((S)-3,3-Dimethyl-2-((S)-2-(methylamino)propanamido)butanoyl)-N$^7$-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)oxazol-2-yl)-N$^3$-((R)-1,2,3,4-tetrahydronaphthalen-1-yl)-1,2,3,4-tetrahydroisoquinoline-3,7-dicarboxamide | 1098.6 |
| 23 | 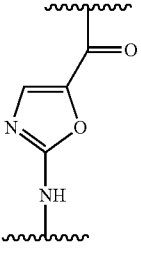 [SMILES: *Nc1ncc(C(*)=O)o1] | (S)-2-((S)-3,3-Dimethyl-2-((S)-2-(methylamino)propanamido)butanoyl)-N$^7$-(5-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)oxazol-2-yl)-N$^3$-((R)-1,2,3,4-tetrahydronaphthalen-1-yl)-1,2,3,4-tetrahydroisoquinoline-3,7-dicarboxamide | 1098.2 |

-continued

| Ex. No. | R | Name | LCMS (M + H) |
|---|---|---|---|
| 24 | (indole structure with carbonyl at 2-position and NH at 6-position) | (S)-2-((S)-3,3-Dimethyl-2-((S)-2-(methylamino)propanamido)butanoyl)-N⁷-(2-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)-1H-indol-6-yl)-N³-((R)-1,2,3,4-tetrahydronaphthalen-1-yl)-1,2,3,4-tetrahydroisoquinoline-3,7-dicarboxamide | 1147.1 |
| 25 | (pyridine structure with carbonyl and CH2NH) | (S)-2-((S)-3,3-Dimethyl-2-((S)-2-(methylamino)propanamido)butanoyl)-N⁷-((5-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)pyridin-2-yl)methyl)-N³-((R)-1,2,3,4-tetrahydronaphthalen-1-yl)-1,2,3,4-tetrahydroisoquinoline-3,7-dicarboxamide | 1121.64 |
| 26 | (pyrrolotriazine structure with carbonyl, methyl and NH) | (S)-2-((S)-3,3-Dimethyl-2-((S)-2-(methylamino)propanamido)butanoyl)-N⁷-(6-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)-5-methylpyrrolo[2,1-f][1,2,4]triazin-4-yl)-N³-((R)-1,2,3,4-tetrahydronaphthalen-1-yl)-1,2,3,4-tetrahydroisoquinoline-3,7-dicarboxamide | 1161.65 |

Example 27

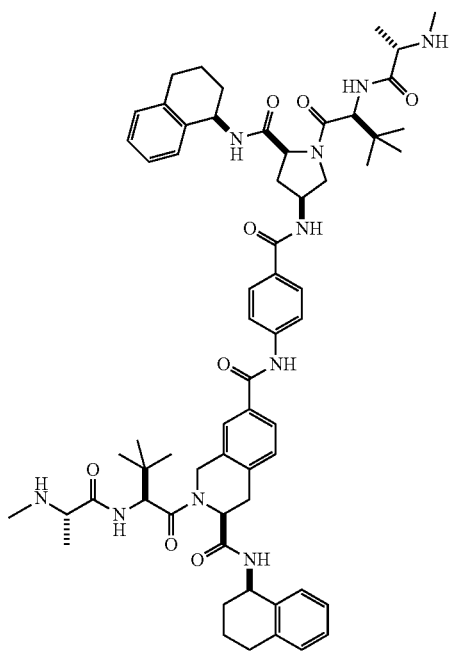

(S)-2-((S)-3,3-Dimethyl-2-((S)-2-(methylamino)
propanamido)butanoyl)-N[7]-(4-(((3S,5S)-1-((S)-3,3-
dimethyl-2-((S)-2-(methylamino)propanamido)bu-
tanoyl)-5-(((R)-1,2,3,4-tetrahydronaphthalen-1-yl)
carbamoyl)pyrrolidin-3-yl)carbamoyl)phenyl)-N[3]—
((R)-1,2,3,4-tetrahydronaphthalen-1-yl)-1,2,3,4-
tetrahydroisoquinoline-3,7-dicarboxamide

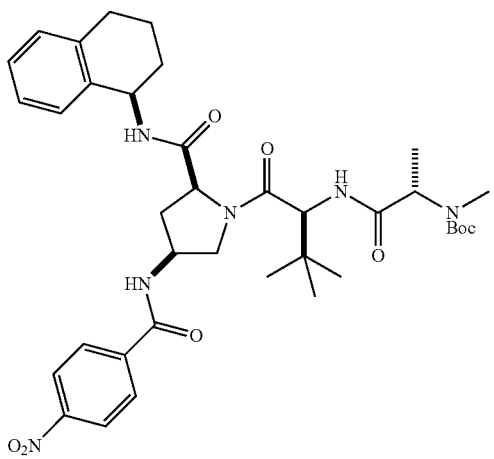

A) tert-Butyl ((S)-1-(((S)-3,3-dimethyl-1-((2S,4S)-
4-(4-nitrobenzamido)-2-(((R)-1,2,3,4-tetrahy-
dronaphthalen-1-yl)carbamoyl)pyrrolidin-1-yl)-1-
oxobutan-2-yl)amino)-1-oxopropan-2-yl)(methyl)
carbamate Following a procedure analogous to that for the synthesis of Compound E of Example 2, tert-butyl ((S)-1-(((S)-1-((2S, 4S)-4-amino-2-(((R)-1,2,3,4-tetrahydronaphthalen-1-yl)carbamoyl)pyrrolidin-1-yl)-3,3-dimethyl-1-oxobutan-2-yl) amino)-1-oxopropan-2-yl)(methyl)carbamate (Compound J of Example 1, 45 mg, 0.081 mmol) and 4-nitrobenzoic acid (15 mg, 0.089 mmol) were converted to the title compound (57 mg, 100%). MS(ESI) m/z 707.5 (M+H)+.

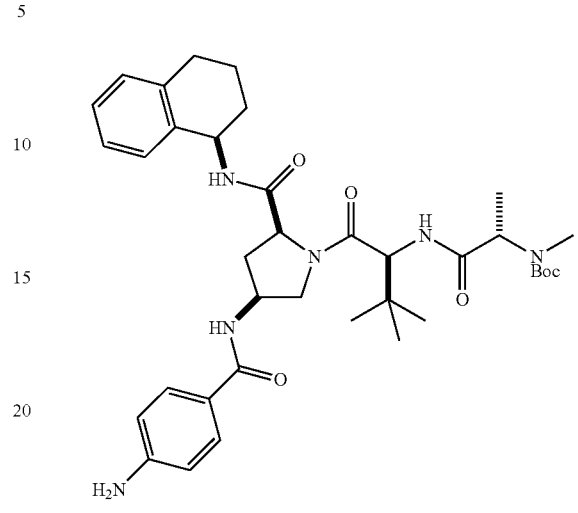

B) tert-Butyl ((S)-1-(((S)-1-((2S,4S)-4-(4-aminoben-
zamido)-2-(((R)-1,2,3,4-tetrahydronaphthalen-1-yl)
carbamoyl)pyrrolidin-1-yl)-3,3-dimethyl-1-oxobu-
tan-2-yl)amino)-1-oxopropan-2-yl)(methyl)
carbamate Following a procedure analogous to that for the synthesis of Compound F of Example 1, tert-butyl ((S)-1-(((S)-3,3-dimethyl-1-((2S,4S)-4-(4-nitrobenzamido)-2-(((R)-1,2,3,4-tetrahydronaphthalen-1-yl)carbamoyl)pyrrolidin-1-yl)-1-oxobutan-2-yl)amino)-1-oxopropan-2-yl)(methyl)carbamate (57 mg, 0.081 mmol) was converted to the title compound (45 mg, 83%). MS(ESI+) m/z 678.2 (M+H)+.

C) (S)-2-((S)-3,3-Dimethyl-2-((S)-2-(methylamino)
propanamido)butanoyl)-N[7]-(4-(((3S,5S)-1-((S)-3,3-
dimethyl-2-((S)-2-(methylamino)propanamido)bu-
tanoyl)-5-(((R)-1,2,3,4-tetrahydronaphthalen-1-yl)
carbamoyl)pyrrolidin-3-yl)carbamoyl)phenyl)-N[3]—
((R)-1,2,3,4-tetrahydronaphthalen-1-yl)-1,2,3,4-
tetrahydroisoquinoline-3,7-dicarboxamide Following procedures analogous to those for the preparation of Compound M of Example 1, tert-butyl ((S)-1-(((S)-1-((2S,4S)-4-(4-aminobenzamido)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl) (methyl)carbamate (45 mg, 0.068 mmol) and (S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxylic acid (Compound K of Example 1, 37 mg, 0.057 mmol) were converted to the title compound (4 mg, 10% over 2 steps). MS(ESI+) m/z 1107.6 (M+H)+.

Examples 28 and 29

The following Examples were prepared according to the procedures described for the synthesis of Example 20.

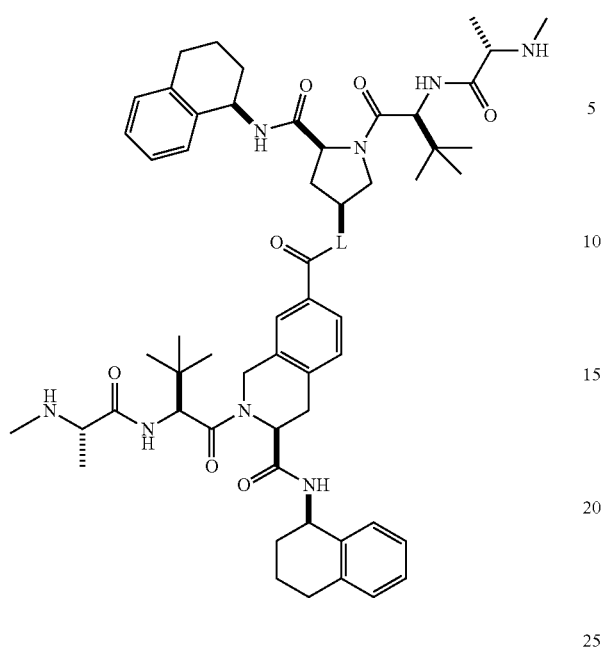

| Ex. No. | L | Name | LCMS (M + H) |
|---|---|---|---|
| 28 | | (S)-2-((S)-3,3-Dimethyl-2-((S)-2-(methylamino)propanamido)butanoyl)-N7-(1-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)cyclopropyl)-N3((R)-1,2,3,4-tetrahydronaphthalen-1-yl)-1,2,3,4-tetrahydroisoquinoline-3,7-dicarboxamide | 1072.2 |
| 29 | | (S)-2-((S)-3,3-Dimethyl-2-((S)-2-(methylamino)propanamido)butanoyl)-N7-(1-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)amino)-2-methyl-1-oxopropan-2-yl)-N3-((R)-1,2,3,4-tetrahydronaphthalen-1-yl)-1,2,3,4-tetrahydroisoquinoline-3,7-dicarboxamide | 1074.2 |

Example 30

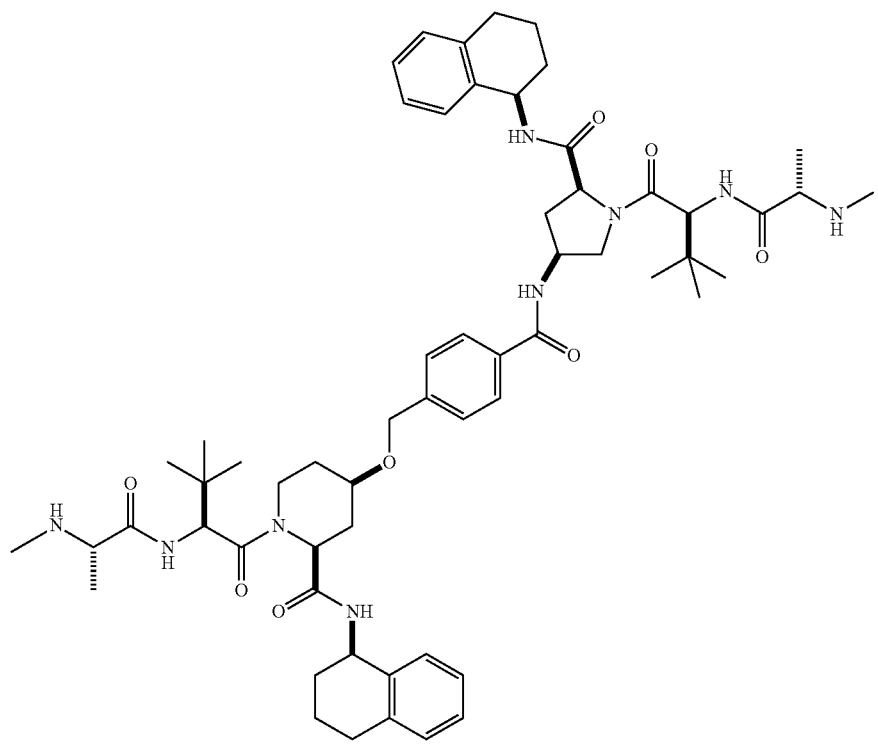

(2S,4R)-1-((S)-3,3-Dimethyl-2-((S)-2-(methyl-amino)propanamido)butanoyl)-4-((4-(((3S,5S)-1-((S)-3,3-dimethyl-2-((S)-2-(methylamino)propana-mido)butanoyl)-5-(((R)-1,2,3,4-tetrahydronaphthalen-1-yl)carbamoyl)pyrrolidin-3-yl)carbamoyl)benzyl)oxy)-N—((R)-1,2,3,4-tetrahydronaphthalen-1-yl)piperidine-2-carboxamide

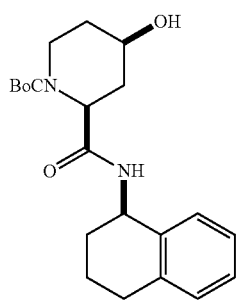

A) (2S,4R)-tert-Butyl 4-hydroxy-2-(((R)-1,2,3,4-tetrahydronaphthalen-1-yl)carbamoyl)piperidine-1-carboxylate To a solution of (2S,4R)-1-(tert-butoxycarbonyl)-4-hydroxypiperidine-2-carboxylic acid (Chem-Impex, 482 mg, 1.97 mmol) and EDC (414 mg, 2.16 mmol) in DMF (7.9 mL) was added HOBt (331 mg, 2.16 mmol). The resulting reaction mixture was stirred at room temperature for 10 min and then cooled to 0° C. (R)-1,2,3,4-tetrahydronaphthalen-1-amine (ALFA AESAR®, 290 µL, 1.96 mmol) was added followed by i-Pr$_2$EtN (690 µL, 3.93 mmol). The reaction mixture was stirred warming to room temperature over 2 h and then at room temperature for 5 d. The mixture was then poured into EtOAc and sat. NaHCO$_3$. The aqueous layer was extracted with EtOAc (3×). The combined organics were washed with 1N HCl, sat. NaHCO$_3$ and sat. NaCl and then dried over Na$_2$SO$_4$. Filtration and concentration in vacuo gave the title compound (510 mg, 69%) as a pale yellow solid. MS(ESI$^+$) m/z 375.2 (M+H)$^+$.

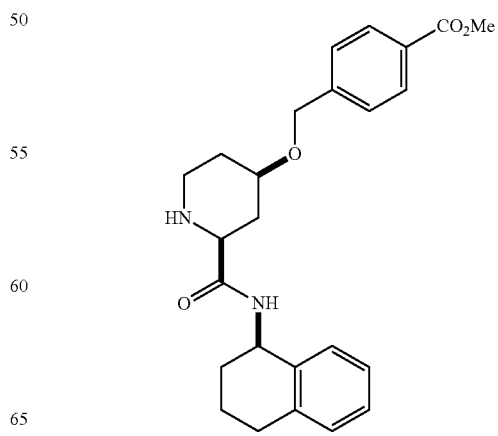

B) Methyl 4-((((2S,4R)-2-(((R)-1,2,3,4-tetrahydronaphthalen-1-yl)carbamoyl)piperidin-4-yl)oxy)methyl)benzoate To a 0° C. solution of (2S,4R)-tert-butyl 4-hydroxy-2-(((R)-1,2,3,4-tetrahydronaphthalen-1-yl)carbamoyl)piperidine-1-carboxylate (200 mg, 0.53 mmol) and methyl 4-((2,2,2-trichloro-1-iminoethoxy)methyl)benzoate (249 mg, 0.80 mmol, Santella, J. B. et al., PCT International Application No., WO 2009/015166 A1 (2009)) in CH$_2$Cl$_2$ (1.2 mL) and cyclohexane (2.4 mL) was added TfOH (24 µL, 0.27 mmol) via syringe. The resulting reaction mixture was stirred at 50° C. for 3 h. Additional TfOH (24 µL, 0.27 mmol) was then added, and the reaction mixture was stirred at 50° C. for 12 h. Additional TfOH (24 µL, 0.27 mmol) was added, and the reaction mixture was stirred at 50° C. for 2 h and then concentrated in vacuo. The crude oil was purified using flash column chromatography (gradient from 0% to 40% EtOAc/hexanes, then isocratic at 10% (NH$_3$/MeOH)/CH$_2$Cl$_2$) to give the title compound (65 mg, 28%) as a colorless oil. MS(ESI$^+$) m/z 423.4 (M+H)$^+$.

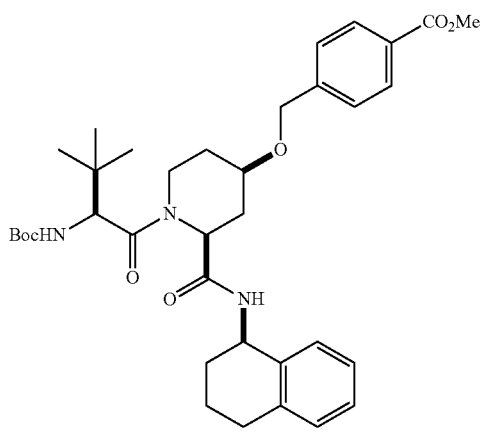

C) Methyl 4-((((2S,4R)-1-((S)-2-((tert-butoxycarbonyl)amino)-3,3-dimethylbutanoyl)-2-(((R)-1,2,3,4-tetrahydronaphthalen-1-yl)carbamoyl)piperidin-4-yl)oxy)methyl)benzoate Following a procedure analogous to that for the synthesis of Compound C of Example 1, methyl 4-((((2S,4R)-2-(((R)-1,2,3,4-tetrahydronaphthalen-1-yl)carbamoyl)piperidin-4-yl)oxy)methyl)benzoate (69 mg, 0.16 mmol) and (S)-2-((tert-butoxycarbonyl)amino)-3,3-dimethylbutanoic acid (38 mg, 0.16 mmol) were converted to the title compound (63 mg, 61%). MS(ESI$^+$) m/z 636.4 (M+H)$^+$.

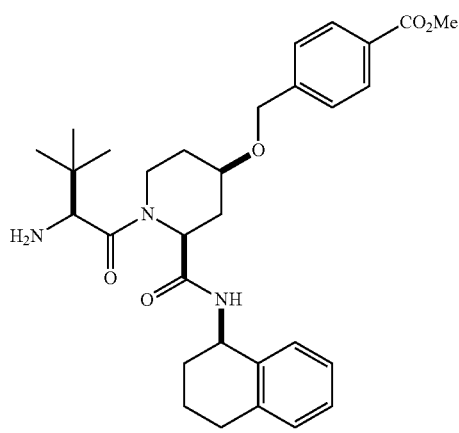

D) Methyl 4-((((2S,4R)-1-((S)-2-amino-3,3-dimethylbutanoyl)-2-(((R)-1,2,3,4-tetrahydronaphthalen-1-yl)carbamoyl)piperidin-4-yl)oxy)methyl)benzoate, HCl To a solution of methyl 4-((((2S,4R)-1-((S)-2-((tert-butoxycarbonyl)amino)-3,3-dimethylbutanoyl)-2-(((R)-1,2,3,4-tetrahydronaphthalen-1-yl)carbamoyl)piperidin-4-yl)oxy)methyl)benzoate (63 mg, 0.10 mmol) in CH$_2$Cl$_2$ (1.0 mL) was added HCl (495 µL, 1.98 mmol, 4N in dioxane). The resulting reaction mixture was stirred at room temperature for 1 h. Additional HCl (200 µL, 0.80 mmol, 4N in dioxane) was added, and the reaction mixture was stirred at room temperature for 30 min and then concentrated in vacuo to give the title compound (56 mg, 99%) as a colorless oil. MS(ESI$^+$) m/z 536.4 (M+H)$^+$.

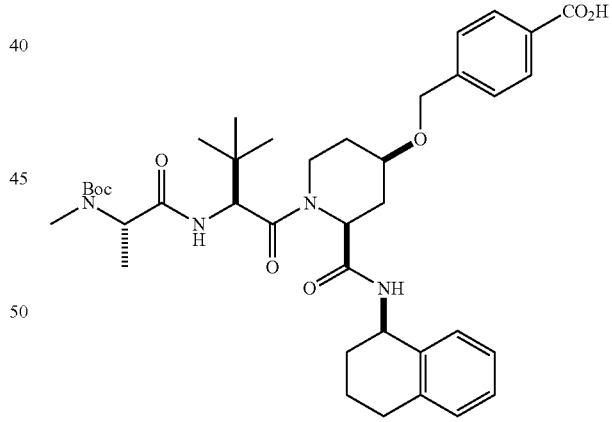

E) 4-((((2S,4R)-1-((S)-2-((S)-2-((tert-butoxycarbonyl)(methyl)amino)propanamido)-3,3-dimethylbutanoyl)-2-(((R)-1,2,3,4-tetrahydronaphthalen-1-yl)carbamoyl)piperidin-4-yl)oxy)methyl)benzoic acid Following a procedure analogous to that for the synthesis of Compound C of Example 1, methyl 4-((((2S,4R)-1-((S)-2-amino-3,3-dimethylbutanoyl)-2-(((R)-1,2,3,4-tetrahydronaphthalen-1-yl)carbamoyl)piperidin-4-yl)oxy)methyl)benzoate, HCl (56 mg, 0.098 mmol) and (S)-2-((tert-butoxycarbonyl)(methyl)amino)propanoic acid (Advanced ChemTech, 20 mg, 0.098 mmol) were reacted to give a crude oil which was dissolved in in THF (660 μL) and MeOH (330 μL). To the solution was added 3N NaOH (490 μL, 1.48 mmol). After stirring at room temperature for 1 h, the mixture was poured into EtOAc and 1N HCl. The aqueous layer was extracted with EtOAc (3×). The combined organics were dried over Na$_2$SO$_4$, filtered and concentrated in vacuo to give the title compound (70 mg, 100% over 2 steps) as a colorless oil. MS(ESI$^+$) m/z 707.5 (M+H)$^+$.

F) (2S,4R)-1-((S)-3,3-Dimethyl-2-((S)-2-(methylamino)propanamido)butanoyl)-4-((4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)oxy)-N—((R)-1,2,3,4-tetrahydronaphthalen-1-yl)piperidine-2-carboxamide Following a procedure analogous to that for the synthesis of Compound A of Example 1, 4-(((((2S,4R)-1-((S)-2-((S)-2-((tert-butoxycarbonyl)(methyl)amino)propanamido)-3,3-dimethylbutanoyl)-2-(((R)-1,2,3,4-tetrahydronaphthalen-1-yl)carbamoyl)piperidin-4-yl)oxy)methyl)benzoic acid (70 mg, 0.098 mmol) and tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound J of Example 1, 55 mg, 0.099 mmol) were reacted to give a crude oil which was dissolved in CH$_2$Cl$_2$ (1.0 mL). TFA (62 μL, 0.80 mmol) was added, and the resulting reaction mixture was stirred at room temperature for 30 min, then concentrated in vacuo and purified using prep HPLC to give the title compound (10 mg, 10% over 2 steps) as a white solid after lyophilization. MS(ESI$^+$) m/z 1047.5 (M+H)$^+$.

Example 31

(S)-2-((S)-3,3-Dimethyl-2-((S)-2-(methylamino)propanamido)butanoyl)-7-((4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)amino)-N—((R)-1,2,3,4-tetrahydronaphthalen-1-yl)-1,2,3,4-tetrahydroisoquinoline-3-carboxamide

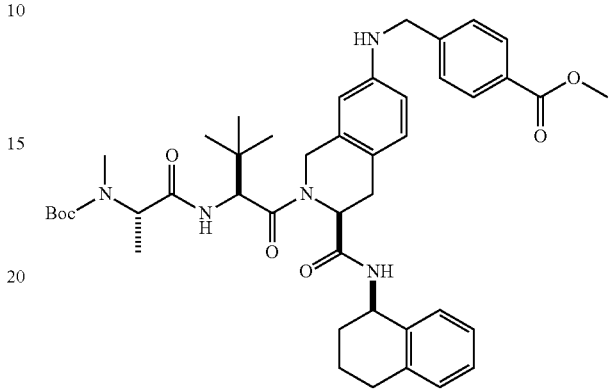

A) Methyl 4-(((((S)-2-((S)-2-((S)-2-((tert-butoxycarbonyl)(methyl)amino) propanamido)-3,3-dimethylbutanoyl)-3-(((R)-1,2,3,4-tetrahydronaphthalen-1-yl)carbamoyl)-1,2,3,4-tetrahydroisoquinolin-7-yl)amino)methyl)benzoate To a solution of tert-butyl ((S)-1-(((S)-1-((S)-7-amino-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (Compound F of Example 1) (116 mg, 0.187 mmol) in DCM (2 mL) and 2-propanol (1.0 mL) was added methyl 4-formylbenzoate (36.8 mg, 0.224 mmol, Aldrich). The resulting reaction mixture was stirred at room temperature for 0.5 h. Sodium triacetoxyborohydride (79 mg, 0.374 mmol, Aldrich) was added and stirring was continued for 2 h. The reaction mixture was diluted with EtOAc and filtered through a pad of CELITE®, rinsing with EtOAc. The filtrate was washed with 1.0 N NaOH and brine and dried over Na$_2$SO$_4$, and

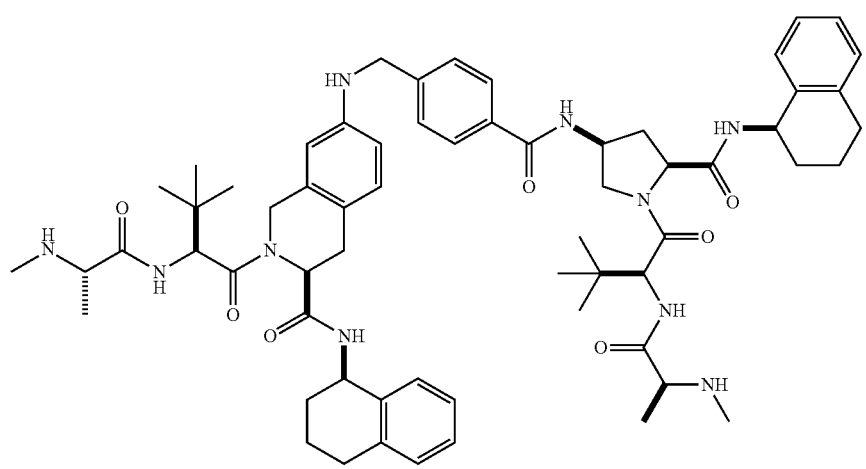

concentrated in vacuo. Purification by flash chromatography (gradient from 10% to 30% EtOAc in CH₂Cl₂) provided the title compound (100 mg, 87%) as a light yellow solid. MS(ESI⁺) m/z 768.5 (M+H)⁺.

B) (S)-2-((S)-3,3-Dimethyl-2-((S)-2-(methylamino) propanamido)butanoyl)-7-((4-(((3S,5S)-1-((S)-3,3-dimethyl-2-((S)-2-(methylamino)propanamido)butanoyl)-5-(((R)-1,2,3,4-tetrahydronaphthalen-1-yl) carbamoyl)pyrrolidin-3-yl)carbamoyl)benzyl) amino)-N—((R)-1,2,3,4-tetrahydronaphthalen-1-yl)-1,2,3,4-tetrahydroisoquinoline-3-carboxamide To a solution of the compound from procedure A (37 mg, 0.048 mmol) in THF (1.0 mL) and MeOH (1.0 mL) was added 1 M lithium hydroxide (0.384 mL, 0.384 mmol). The reaction mixture was stirred at rt for 4 h. At 0° C. the reaction mixture was neutralized to pH 3-4 with 1 N HCl and extracted with DCM, 3×. The combined organic extracts were dried and concentrated in vacuo. The resulting crude oil (35 mg, 0.046 mmol) was dissolved in DMF (1.0 mL). HATU (26.5 mg, 0.070 mmol) and DIPEA (12.00 mg, 0.093 mmol) were added and the reaction mixture was stirred at rt for 20 min. A solution of tert-butyl ((S)-1-((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound J of Example 1, 25.9 mg, 0.046 mmol) in 0.5 mL of DMF was added and the mixture was then stirred at rt for 2 h. The reaction mixture was concentrated in vacuo and purified by preparative HPLC to give the title compound as a white solid (45 mg, 75%). MS(ESI⁺) m/z 1294.7 (M+H)⁺. To a solution of the above compound (45 mg, 0.035 mmol) in DCM (2.0 mL) at rt was added TFA (1.0 mL). The reaction mixture was stirred at rt for 1 h and concentrated in vacuo to give the title compound as an off-white solid (35 mg, 90%). MS(ESI⁺) m/z 1094.6 (M+H)⁺.

Example 32

(S)-2-((S)-3,3-Dimethyl-2-((S)-2-(methylamino) propanamido)butanoyl)-7-(N-(4-(((3S,5S)-1-((S)-3,3-dimethyl-2-((S)-2-(methylamino)propanamido) butanoyl)-5-(((R)-1,2,3,4-tetrahydronaphthalen-1-yl) carbamoyl)pyrrolidin-3-yl)carbamoyl)benzyl) acetamido)-N—((R)-1,2,3,4-tetrahydronaphthalen-1-yl)-1,2,3,4-tetrahydroisoquinoline-3-carboxamide

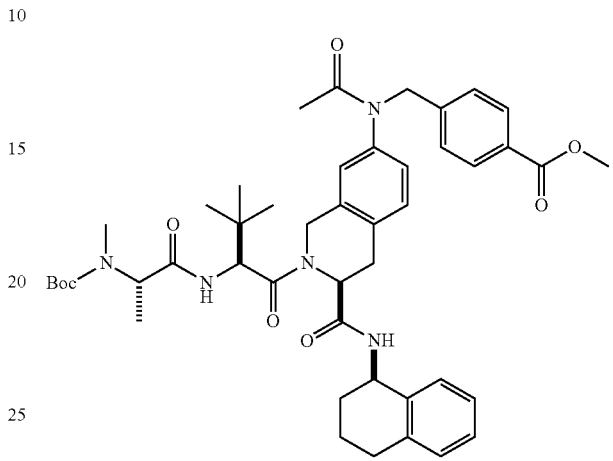

A) Methyl 4-((N—((S)-2-((S)-2-((S)-2-((tert-butoxycarbonyl)(methyl)amino) propanamido)-3,3-dimethylbutanoyl)-3-(((R)-1,2,3,4-tetrahydronaphthalen-1-yl)carbamoyl)-1,2,3,4-tetrahydroisoquinolin-7-yl)acetamido)methyl) benzoate To a solution of methyl 4-(((((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)amino)methyl)

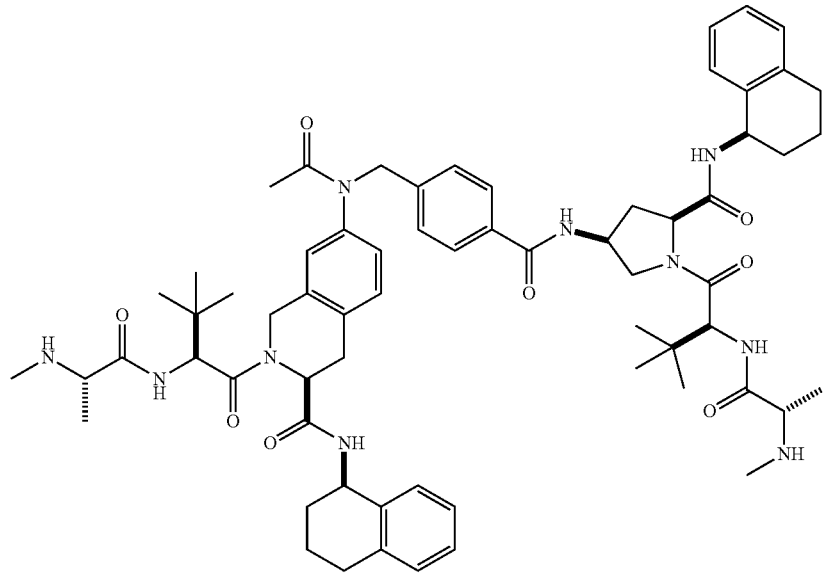

benzoate (0.046 g, 0.06 mmol), Compound A of Example 31, in DCM (2.0 mL) were added acetic anhydride (0.031 g, 0.30 mmol, Aldrich) and TEA (0.042 mL, 0.30 mmol). The reaction mixture was stirred at rt for 4 h and concentrated in vacuo to give the title compound (46 mg, 94%). MS(ESI) m/z 810.5 (M+H)+.

B) (S)-2-((S)-3,3-Dimethyl-2-((S)-2-(methylamino) propanamido)butanoyl)-7-(N-(4-(((3S,5S)-1-((S)-3, 3-dimethyl-2-((S)-2-(methylamino)propanamido) butanoyl)-5-(((R)-1,2,3,4-tetrahydronaphthalen-1-yl) carbamoyl)pyrrolidin-3-yl)carbamoyl)benzyl) acetamido)-N—((R)-1,2,3,4-tetrahydronaphthalen-1-yl)-1,2,3,4-tetrahydroisoquinoline-3-carboxamide The title compound was prepared according to the procedure for the synthesis of Compound B in Example 31. MS(ESI+) m/z 1136.0 (M+H)+.

Example 33

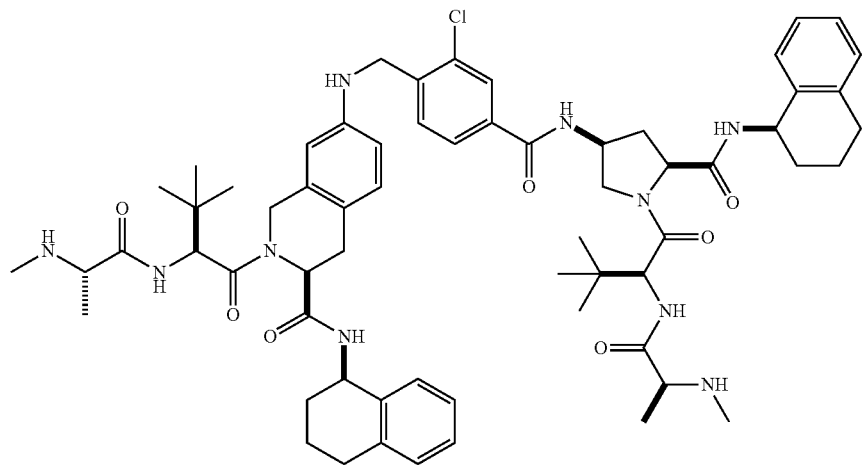

(S)-7-((2-Chloro-4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl) pyrrolidin-3-yl)carbamoyl)benzyl)amino)-2-((S)-3,3-dimethyl-2-((S)-2-(methylamino)propanamido) butanoyl)-N—((R)-1,2,3,4-tetrahydronaphthalen-1-yl)-1,2,3,4-tetrahydroisoquinoline-3-carboxamide The title compound was prepared following procedures analogous to those for the synthesis of Compound B in Example 31. MS(ESI+) m/z 1127.9 (M+H)+.

Examples 34 to 37

The following Examples were prepared according to the procedure for the synthesis of Example 1 and Example 2.

| Ex. No. | Structure | Name | LCMS (M + H) |
|---|---|---|---|
| 34 | 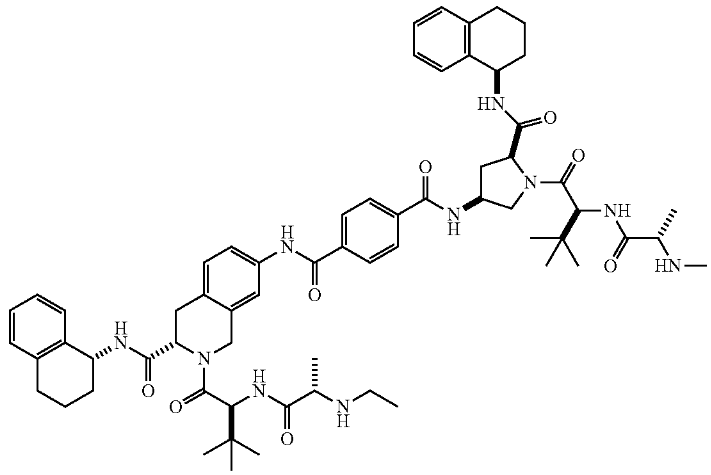 | N¹-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N⁴-((S)-2-((S)-2-((S)-2-(ethylamino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)terephthalamide | 1122.5 |
| 35 | 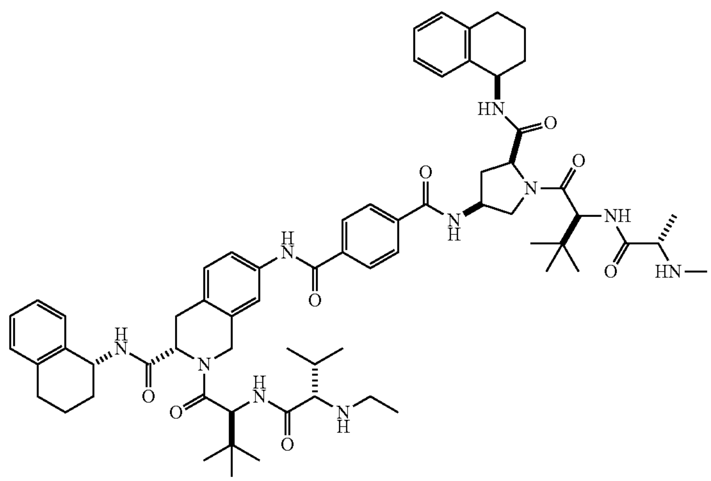 | N¹-(3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N⁴-((S)-2-((S)-3,3-dimethyl-2-((S)-3-methyl-2-(methylamino)butanamido)butanoyl)-3-(((R)-1,2,3,4-tetrahydronaphthalen-1-yl)carbamoyl)-1,2,3,4-tetrahydroisoquinolin-7-yl)terephthalamide | 1136.0 |
| 36 | 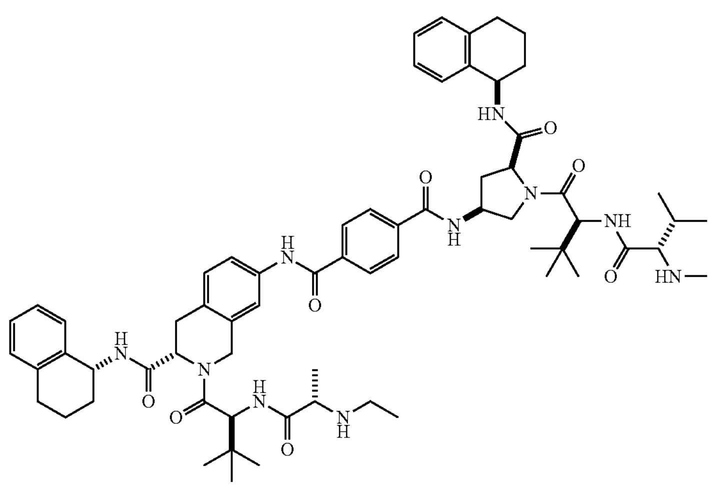 | N¹-((S)-2-((S)-3,3-dimethyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)-N⁴-((3S,5S)-1-((S)-3,3-dimethyl-2-((S)-3-methyl-2-(methylamino)butanamido)butanoyl)-5-(((R)-1,2,3,4-tetrahydronaphthalen-1-yl)carbamoyl)pyrrolidin-3-yl)terephthalamide | 1136.6 |

| Ex. No. | Structure | Name | LCMS (M + H) |
|---|---|---|---|
| 37 | 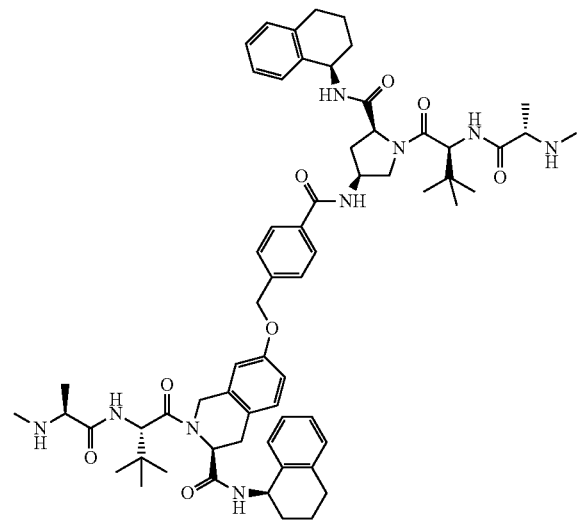 | (2S,3R)-N¹-((3S,5S)-5-((S)-3,3-dimethyl-2-((S)-2-(methylamino)propanamido)butanoyl)-1-(((R)-1,2,3,4-tetrahydronaphthalen-1-yl)carbamoyl)pyrrolidin-3-yl)-N⁴-((S)-2-((S)-3,3-dimethyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)-2,3-bis(3,3,3-trifluoropropyl)succinamide | 1251.7 |

Example 38

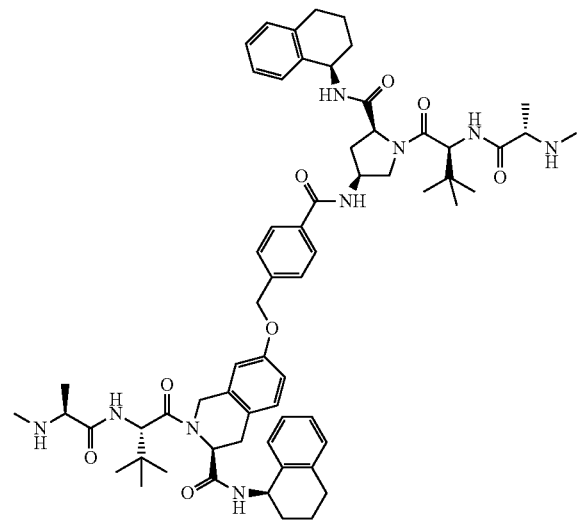

(S)-2-((S)-3,3-Dimethyl-2-((S)-2-(methylamino)propanamido)butanoyl)-7-((4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)oxy)-N—((R)-1,2,3,4-tetrahydronaphthalen-1-yl)-1,2,3,4-tetrahydroisoquinoline-3-carboxamide A) (S)-tert-Butyl 7-hydroxy-3-(((R)-1,2,3,4-tetrahydronaphthalen-1-yl)carbamoyl)-3,4-dihydroisoquinoline-2(1H)-carboxylate To a solution of (S)-2-(tert-butoxycarbonyl)-7-hydroxy-1,2,3,4-tetrahydroisoquinoline-3-carboxylic acid (3.50 g, 11.93 mmol) in DMF (30 mL) were added EDC (2.97 g, 15.5 mmol) and 3H-[1,2,3]-triazolo[4,5-b]pyridin-3-ol (1.62 g, 11.9 mmol) at ice bath temperature, followed by addition of (R)-1,2,3,4-tetrahydronaphthalen-1-amine (2.02 g, 13.7 mmol) and 4-methylmorpholine (2.6 mL, 23.9 mmol). The resulting reaction mixture was stirred at rt for 1 h. The reaction mixture was diluted with ethyl acetate and brine. The organic layer was separated, washed with 1 N HCl solution, brine successively and dried over MgSO₄. The filtrate was concentrated in vacuo and the residue was purified by flash chromatography (30% EtOAc/DCM) to afford the title compound as a white solid (3.5 g, 70%). ¹H NMR (CDCl₃) δ 7.16-7.06 (m, 1H), 7.01 (d, J=7.5 Hz, 2H), 6.82-6.39 (m, 2.5H), 5.89 (d, J=16.1 Hz, 1.5H), 5.02-4.86 (m, 1H), 4.78-4.40 (m, 2H), 3.32 (dd, J=15.0, 2.2 Hz, 1H), 3.00 (d, J=10.3 Hz, 1H), 2.82-2.63 (m, 2H), 2.06-2.03 (m, 1H), 1.86-1.71 (m, 2H), 1.67-1.54 (m, 2H), 1.49 (s, 9H); MS(ESI⁺) m/z 423.0 (M+H)⁺.

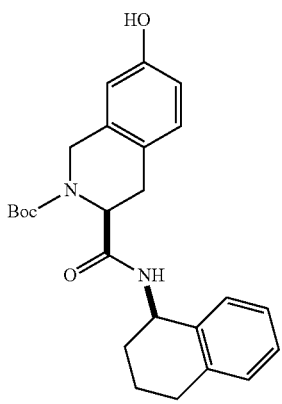

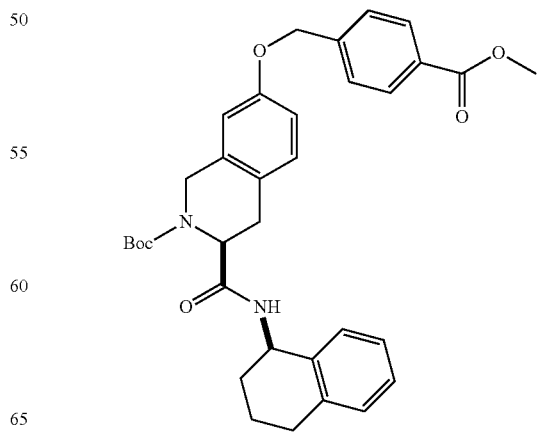

B) (S)-tert-Butyl 7-((4-(methoxycarbonyl)benzyl)oxy)-3-(((R)-1,2,3,4-tetrahydronaphthalen-1-yl)carbamoyl)-3,4-dihydroisoquinoline-2(1H)-carboxylate To a solution of (S)-tert-butyl 7-hydroxy-3-(((R)-1,2,3,4-tetrahydronaphthalen-1-yl)carbamoyl)-3,4-dihydroisoquinoline-2(1H)-carboxylate (2.60 g, 6.15 mmol) in DMF (30 mL) was added $Cs_2CO_3$ (5.01 g, 15.4 mmol) at rt under nitrogen, followed by addition of methyl-4-(bromomethyl-benzoate) (1.90 g, 8.31 mmol). The resulting heterogeneous mixture was stirred at rt under nitrogen. After 1.5 hours, the reaction was quenched with water then extracted with EtOAc (×2). The combined organic extracts were washed with brine, dried over $MgSO_4$, filtered. The filtrate was concentrated in vacuo to afford an amber oil. The residue was purified by flash chromatography (15% EtOAc/DCM) to afford the title compound as a white solid (3.3 g, 94%). $^1H$ NMR ($CDCl_3$) δ 8.08 (d, J=8.4 Hz, 2H), 7.52 (d, J=8.4 Hz, 2H), 7.24 (d, J=8.4 Hz, 1H), 7.11-6.69 (m, 5H), 5.86 (br. s., 1H), 5.18-5.03 (m, 2H), 5.00-4.24 (m, 4H), 3.94 (s, 3H), 3.38 (d, J=14.7 Hz, 1H), 3.07 (d, J=8.8 Hz, 1H), 2.81-2.63 (m, 2H), 2.06-1.98 (m, 1H), 1.86-1.70 (m, 2H), 1.60-1.52 (m, 1H), 1.48 (s, 9H); MS(ESI$^+$) m/z 571.5 (M+H)$^+$.

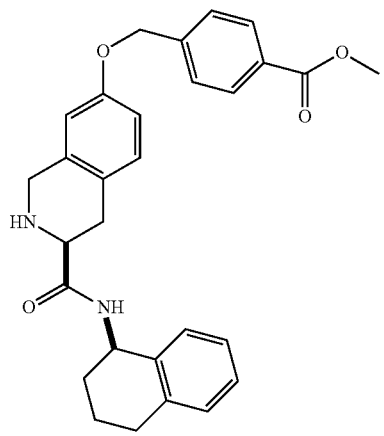

C) Methyl 4-(((((S)-3-(((R)-1,2,3,4-tetrahydronaphthalen-1-yl)carbamoyl)-1,2,3,4-tetrahydroisoquinolin-7-yl)oxy)methyl)benzoate.HCl To a solution of (S)-tert-butyl 7-((4-(methoxycarbonyl)benzyl)oxy)-3-(((R)-1,2,3,4-tetrahydronaphthalen-1-yl)carbamoyl)-3,4-dihydroisoquinoline-2(1H)-carboxylate (3.30 g, 5.78 mmol) in DCM (15 mL) was added HCl (4 N solution in dioxane) (28.9 mL, 116 mmol). The reaction mixture was stirred at rt for 3 h and concentrated in vacuo to give the title compound HCl salt as a white solid (2.9 g, 99%). $^1H$ NMR (DMSO-$d_6$) δ 9.88-9.28 (m, 1H), 8.94 (d, J=8.6 Hz, 1H), 7.98 (d, J=8.4 Hz, 2H), 7.57 (d, J=8.4 Hz, 2H), 7.35-7.08 (m, 5H), 6.96-6.92 (m, 2H), 5.20 (s, 2H), 5.05 (d, J=6.6 Hz, 1H), 4.53-3.99 (m, 3H), 3.86 (s, 3H), 3.24 (dd, J=16.5, 4.6 Hz, 1H), 2.93 (dd, J=16.5, 12.3 Hz, 1H), 2.82-2.67 (m, 2H), 2.04-1.59 (m, 4H); MS(ESI$^+$) m/z 471.0 (M+H)$^+$.

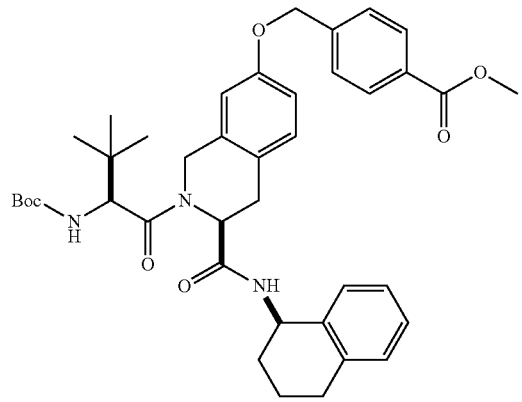

D) Methyl 4-(((((S)-2-((S)-2-((tert-butoxycarbonyl)amino)-3,3-dimethylbutanoyl)-3-(((R)-1,2,3,4-tetrahydronaphthalen-1-yl)carbamoyl)-1,2,3,4-tetrahydroisoquinolin-7-yl)oxy)methyl)benzoate To a solution of (S)-2-((tert-butoxycarbonyl)amino)-3,3-dimethylbutanoic acid (1.72 g, 7.44 mmol) in DMF (35 mL) were added EDC (1.65 g, 8.58 mmol) and 3H-[1,2,3]-triazolo[4,5-b]pyridin-3-ol (0.78 g, 5.72 mmol) at ice bath temperature. After 5 min, methyl 4-(((((S)-3-(((R)-1,2,3,4-tetrahydronaphthalen-1-yl)carbamoyl)-1,2,3,4-tetrahydroisoquinolin-7-yl)oxy)methyl)benzoate HCl (2.90 g, 5.72 mmol) and 4-methylmorpholine (2.36 mL, 22.9 mmol) were added at ice bath temperature. The resulting reaction mixture was stirred at rt for 5 h. The reaction mixture was diluted with ethyl acetate and brine. The organic layer was separated and washed with saturated $NaHCO_3$ solution, 1 N HCl solution successively. The organic layer was separated and dried over $MgSO_4$. The filtrate was concentrated in vacuo to give light brown oil. The residue was purified by flash chromatography (15% EtOAc/DCM) to afford the title compound as a white solid (3.0 g, 77%). $^1H$ NMR ($CDCl_3$) δ 8.07 (d, J=8.1 Hz, 2H), 7.51 (dd, J=8.4, 2.9 Hz, 2H), 7.23-7.08 (m, 2H), 7.07-6.68 (m, 4H), 6.56-6.13 (m, 1H), 5.19-4.94 (m, 5H), 4.69-4.30 (m, 2H), 3.94 (s, 3H), 3.65-3.35 (m, 1H), 3.06-2.94 (m, 1H), 2.81-2.62 (m, 2H), 1.99-1.84 (m, 1H), 1.81-1.66 (m, 2H), 1.56 (s, 2H), 1.47-1.35 (m, 5H), 1.23 (s, 3H), 1.10 (s, 3H), 1.05 (s, 3H), 0.96 (s, 3H); MS(ESI$^+$) m/z 684.1 (M+H)$^+$.

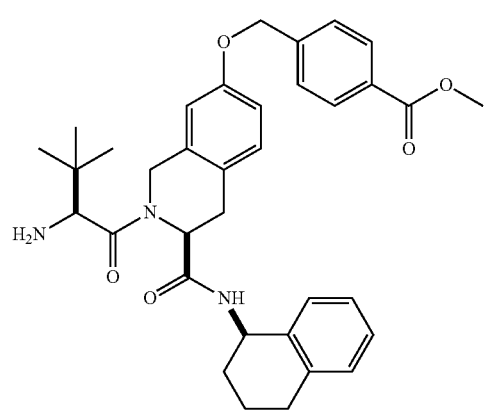

E) Methyl 4-((((S)-2-((S)-2-amino-3,3-dimethylbutanoyl)-3-(((R)-1,2,3,4-tetrahydronaphthalen-1-yl)carbamoyl)-1,2,3,4-tetrahydroisoquinolin-7-yl)oxy)methyl)benzoate.HCl To a solution of methyl 4-((((S)-2-((S)-2-((tert-butoxycarbonyl)amino)-3,3-dimethylbutanoyl)-3-(((R)-1,2,3,4-tetrahydronaphthalen-1-yl)carbamoyl)-1,2,3,4-tetrahydroisoquinolin-7-yl)oxy)methyl)benzoate (3.02 g, 4.42 mmol) in DCM (20 mL) was added HCl (4 M solution in dioxane) (22.1 mL, 88.0 mmol). The reaction mixture was stirred at rt for 2 h and concentrated in vacuo to give the title compound HCl salt as a white solid (2.75 g, 99%). $^1$H NMR (DMSO-d$_6$) δ 9.16 (br. s., 1H), 8.43 (d, J=8.6 Hz, 1H), 8.07-7.92 (m, 4H), 7.59 (d, J=8.4 Hz, 2H), 7.32-6.77 (m, 6H), 5.20 (s, 2H), 5.08 (d, J=15.0 Hz, 1H), 4.98-4.80 (m, 1H), 4.52-4.39 (m, 2H), 3.86 (s, 3H), 3.15-3.05 (m, 1H), 2.99-2.88 (m, 1H), 2.81-2.64 (m, 2H), 1.94-1.79 (m, 2H), 1.76-1.55 (m, 2H), 1.14 (s, 7H), 1.06-0.89 (m, 3H); MS(ESI$^+$) m/z 584.0 (M+H)$^+$.

solution, brine successively. The organic layer was separated, and dried over MgSO$_4$. The filtrate was concentrated in vacuo and the residue was purified by flash chromatography (20% EtOAc/DCM) to afford the title compound as a white solid (1.6 g, 77%). $^1$H NMR (CDCl$_3$) δ 8.07 (d, J=8.4 Hz, 2H), 7.52 (dd, J=8.4, 1.5 Hz, 2H), 7.21-6.96 (m, 3H), 6.95-6.66 (m, 3H), 6.44-6.10 (m, 1H), 5.11 (d, J=6.2 Hz, 3H), 5.05-4.89 (m, 2H), 4.75-4.30 (m, 2H), 3.94 (s, 3H), 3.65-3.33 (m, 1H), 3.06-2.98 (m, 1H), 2.78-2.64 (m, 5H), 2.04-1.84 (m, 1.5H), 1.80-1.66 (m, 2.5H), 1.53-1.42 (m, 10H), 1.33-1.23 (m, 3H), 1.04-0.89 (m, 9H); MS(ESI$^+$) m/z 769.7 (M+H)$^+$.

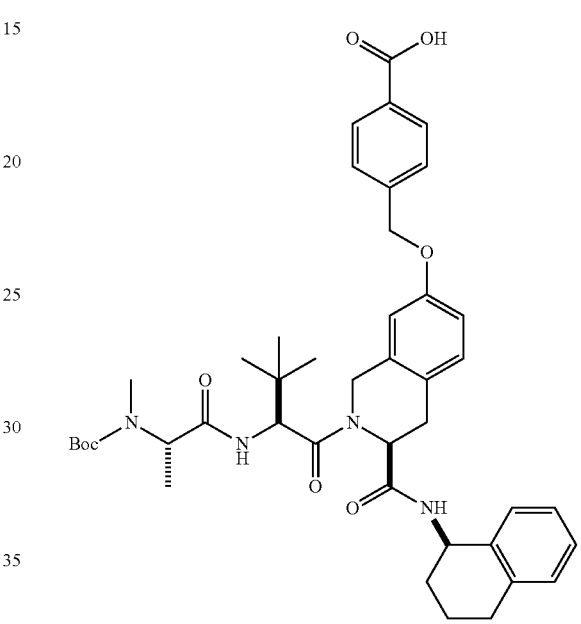

G) 4-((((S)-2-((S)-2-((S)-2-((tert-Butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)oxy)methyl)benzoic acid To a solution of methyl 4-((((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)oxy)methyl)benzoate (1.58 g, 2.06 mmol) in THF (6.00 mL) and MeOH (6.00 mL) was added a solution of NaOH (0.33 g, 8.22 mmol) in water (6.00 mL). The reaction mixture was stirred at rt for 3.5 h. The reaction mixture was acidified with 1 N HCl solution to adjust its pH to 1 and the residue was extracted with ethyl acetate. The organic layer was separated, washed with brine, and dried over MgSO$_4$. The filtrate was concentrated in vacuo to give the title compound as a white solid (1.43 g, 92%). $^1$H NMR (DMSO-d$_6$) δ 8.16 (d, J=8.8 Hz, 1H), 7.96 (d, J=8.1 Hz, 2H), 7.65-7.45 (m, 2H), 7.21-6.78 (m, 6H), 5.18 (s, 2H), 5.04-4.49 (m, 6H), 3.06-2.86 (m, 2H), 2.78-2.60 (m, 5H), 1.88-1.49 (m, 4H), 1.40 (br. s., 9H), 1.23-1.07 (m, 4H), 1.05-0.89 (m, 8H); MS(ESI$^+$) m/z 755.7 (M+H)$^+$.

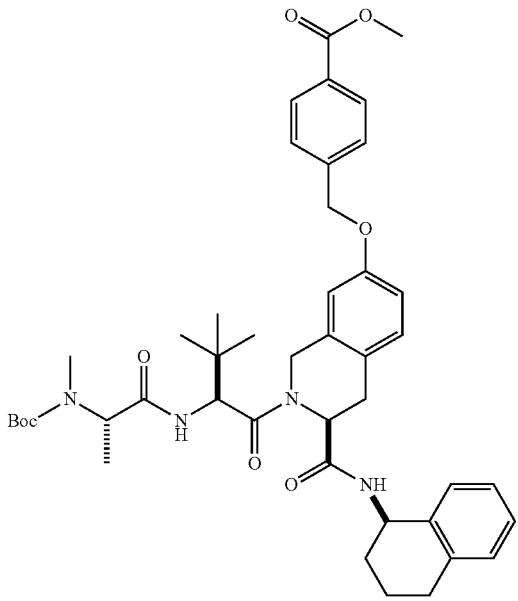

F) Methyl 4-((((S)-2-((S)-2-((S)-2-((tert-butoxycarbonyl)(methyl)amino) propanamido)-3,3-dimethylbutanoyl)-3-(((R)-1,2,3,4-tetrahydronaphthalen-1-yl)carbamoyl)-1,2,3,4-tetrahydroisoquinolin-7-yl)oxy)methyl)benzoate To a solution of (S)-2-((tert-butoxycarbonyl)(methyl)amino)propanoic acid (0.68 g, 3.35 mmol) in DMF (18 mL) were added EDC (0.74 g, 3.87 mmol) and 3H-[1,2,3]-triazolo[4,5-b]pyridin-3-ol (0.35 g, 2.58 mmol) at ice bath temperature. After the reaction mixture was stirred for 5 min, methyl 4-((((S)-2-((S)-2-amino-3,3-dimethylbutanoyl)-3-(((R)-1,2,3,4-tetrahydronaphthalen-1-yl)carbamoyl)-1,2,3,4-tetrahydroisoquinolin-7-yl)oxy)methyl)benzoate, HCl (1.60 g, 2.58 mmol) and 4-methylmorpholine (1.42 mL, 12.9 mmol) were added at ice bath temperature. The reaction mixture was warmed to rt by removing the ice bath and stirred at rt for 1.5 h. The reaction mixture was diluted with saturated NaHCO$_3$ solution and ethyl acetate. The organic layer was combined, washed with brine, 1N HCl H) (S)-2-((S)-3,3-Dimethyl-2-((S)-2-(methylamino)propanamido)butanoyl)-7-((4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)oxy)-N—((R)-1,2,3,4-tetrahydronaphthalen-1-yl)-1,2,3,4-tetrahydroisoquinoline-3-carboxamide To a solution of 4-((((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)oxy)methyl)benzoic acid (0.60 g, 0.80 mmol) in DMF (7 mL) was added EDC (0.23 g, 1.19 mmol) and 3H-[1,2,3]-triazolo[4,5-b]pyridin-3-ol (0.11 g, 0.80 mmol) at ice bath temperature. The reaction mixture was stirred for 5 min, followed by addition of tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound J of Example 1, 0.49 g, 0.87 mmol) and DIPEA (0.35 mL, 1.99 mmol). The reaction mixture was stirred at rt for 4 h. The reaction mixture was diluted with ethyl acetate and brine. The organic layer was separated and washed with saturated NaHCO₃ solution, brine, 1 N HCl solution successively and dried over MgSO₄. The filtrate was concentrated in vacuo and the residue was purified by flash chromatography (65% EtOAc/DCM) to afford a white solid (0.7 g, 68%). To a solution of the obtained solid (0.53 g, 0.41 mmol) in DCM (8.00 mL) was added TFA (5.50 mL, 71.40 mmol). The reaction mixture was stirred at rt for 1 h. The reaction mixture was concentrated in vacuo and the residue was basified with saturated NaHCO₃ solution and the resulting mixture was extracted with ethyl acetate twice. The combined organic layer was dried over MgSO₄. The filtrate was concentrated in vacuo and the residue was dissolved in DCM and 4.0 M HCl in dioxane (0.41 mL, 1.64 mmol). The mixture was stirred for 3 min and concentrated in vacuo. The residue was lyophilized to give the title compound 2HCl salt as a white solid (0.42 g, 86%). $^1$H NMR (CD$_3$OD) δ 8.65-8.54 (m, 1H), 8.42 (t, J=7.8 Hz, 1H), 8.10-7.99 (m, 1H), 7.94-7.85 (m, 2H), 7.58 (d, J=8.4 Hz, 2H), 7.40 (d, J=7.7 Hz, 1H), 7.25-6.81 (m, 10H), 5.20-4.86 (m, 6H), 4.79-4.50 (m, 5H), 4.19-3.60 (m, 5H), 3.08 (d, J=6.8 Hz, 2H), 2.93-2.70 (m, 4H), 2.70-2.60 (m, 6H), 2.17-1.56 (m, 9H), 1.50-1.35 (m, 6H), 1.21-0.98 (m, 18H); MS(ESI$^+$) m/z 1094.8 (M+H)$^+$.

Examples 39 to 43

The following Examples were prepared according to the procedures used in the synthesis of Example 38 incorporating various alkyl modifications at R$^6$ and R$^8$.

| Ex. No. | Structure | Name | LCMS (M + H) |
|---|---|---|---|
| 39 | 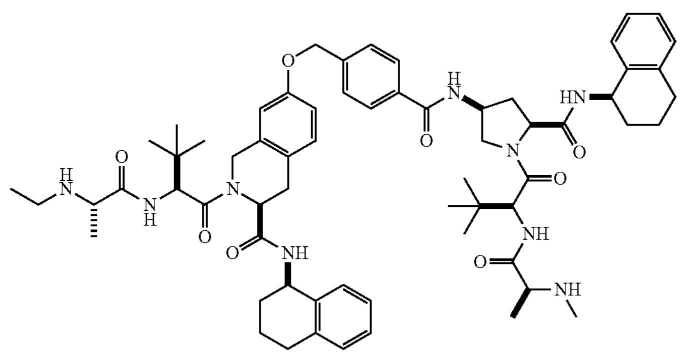 | ((S)-7-((4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)oxy)-2-((S)-2-((S)-2-(ethylamino)propanamido)-3,3-dimethylbutanoyl)-N-((R)-1,2,3,4-tetrahydronaphthalen-1-yl)-1,2,3,4-tetrahydroisoquinoline-3-carboxamide | 1109.4 |
| 40 | 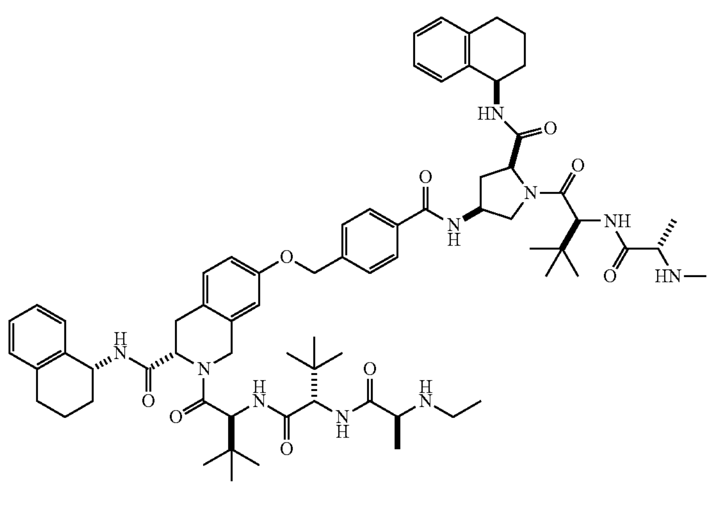 | (S)-7-((4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)oxy)-2-((S)-2-((S)-2-((S)-2-(ethylamino)propanamido)-3,3-dimethylbutanamido)-3,3-dimethylbutanoyl)-N-((R)-1,2,3,4-tetrahydronaphthalen-1-yl)-1,2,3,4-tetrahydroisoquinoline-3-carboxamide | 1222.6 |

| Ex. No. | Structure | Name | LCMS (M + H) |
|---|---|---|---|
| 41 | 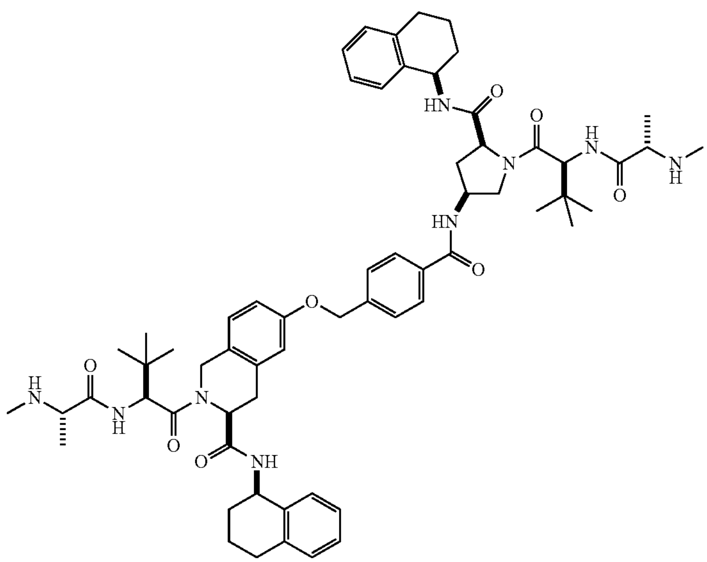 | (S)-2-((S)-3,3-Dimethyl-2-((S)-2-(methylamino)propanamido)butanoyl)-6-((4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)oxy)-N-((R)-1,2,3,4-tetrahydronaphthalen-1-yl)-1,2,3,4-tetrahydroisoquinoline-3-carboxamide | 1095.9 |
| 42 | 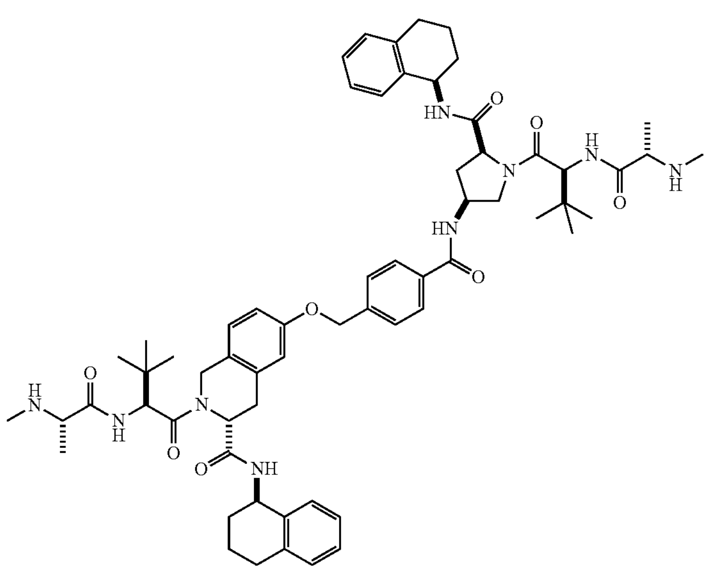 | (R)-2-((S)-3,3-Dimethyl-2-((S)-2-(methylamino)propanamido)butanoyl)-6-((4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)oxy)-N-((R)-1,2,3,4-tetrahydronaphthalen-1-yl)-1,2,3,4-tetrahydroisoquinoline-3-carboxamide | 1096.0 |

| Ex. No. | Structure | Name | LCMS (M + H) |
|---|---|---|---|
| 43 | 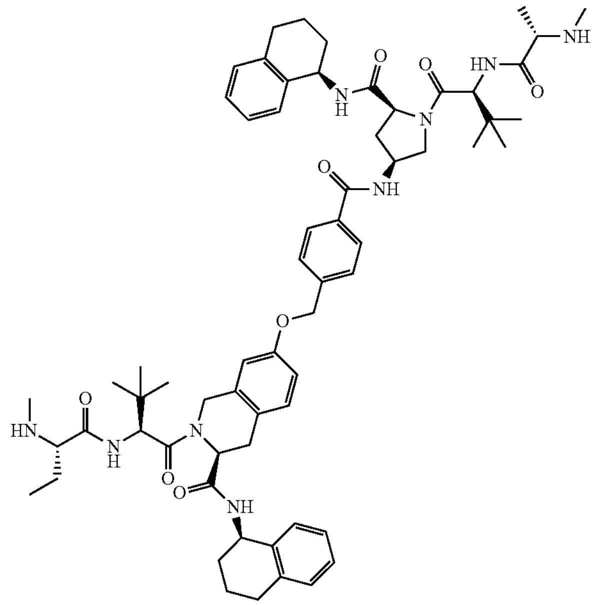 | S)-2-((S)-3,3-Dimethyl-2-((S)-2-(methylamino)butanamido)butanoyl)-7-((4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)oxy)-N-((R)-1,2,3,4-tetrahydronaphthalen-1-yl)-1,2,3,4-tetrahydroisoquinoline-3-carboxamide | 1108.6 |

Example 44

(S)-2-((S)-3,3-Dimethyl-2-((S)-2-(methylamino)propanamido)butanoyl)-7-((4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)phenyl)ethynyl)-N—((R)-1,2,3,4-tetrahydronaphthalen-1-yl)-1,2,3,4-tetrahydroisoquinoline-3-carboxamide A) tert-Butyl ((S)-1-(((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate To a solution of 4-(((((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)oxy)methyl)benzoic acid (0.64 g, 0.85 mmol, Compound E in Example 38) in MeOH (10 mL) was added Pd—C (0.27 g, 0.25 mmol). The reaction mixture was evacuated and then filled hydrogen. The process was repeated twice. The reaction mixture was then hydrogenated under hydrogen balloon over night. The reaction mixture was filtered through a CELITE® pad and the pad was rinsed with MeOH. The filtrate was concentrated in vacuo. The residue was diluted with saturated NaHCO$_3$ solution and the resulting mixture was extracted with ethyl acetate. The organic layer was separated and dried over MgSO$_4$. The filtrate was concentrated in vacuo to give the title compound as a white solid (0.50 g, 92%). $^1$H NMR (CDCl$_3$) δ 7.19-6.82 (m, 4.5H), 6.71 (td, J=8.5, 2.4 Hz, 1H), 6.57 (d, J=2.2 Hz, 0.5H), 6.44 (s, 0.5H), 6.19 (d, J=8.6 Hz, 0.5H), 5.18-4.91 (m, 2.5H), 4.87-4.66 (m, 1.5H), 4.54-4.29 (m, 1H), 3.63-3.46 (m, 0.5H), 3.27 (dd, J=15.4, 5.7 Hz, 0.5H), 3.00-2.87 (m, 1H), 2.82-2.69 (m, 4H), 2.69 (d, J=9.2 Hz, 1H), 2.03-1.84 (m, 1H), 1.81-1.55 (m, 4H), 1.49 (d, J=10.1 Hz, 9H), 1.34-1.23 (m, 1.5H), 1.12 (d, J=7.0 Hz, 1.5H), 1.06-0.87 (m, 9H); MS(ESI$^+$) m/z 621.5 (M+H)$^+$.

mixture was concentrated in vacuo and the residue was purified by preparative HPLC. Fractions containing the product were combined, concentrated, and lyophilized to give the title compound as a white solid (128 mg, 62%). $^1$H NMR (DMSO-d$_6$) δ 8.44-8.18 (m, 1H), 7.56-7.23 (m, 3H), 7.17-6.94 (m, 3H), 5.11-4.91 (m, 2H), 4.89-4.68 (m, 3H), 4.63-4.24 (m, 2H), 3.41 (d, J=15.8 Hz, 0.5H), 3.22-2.93 (m, 1.5H), 2.78-2.66 (m, 4H), 1.92-1.49 (m, 4H), 1.40 (br. s., 9H), 1.18-1.03 (m, 3H), 1.03-0.91 (m, 9H); MS(ESI$^+$) m/z 753.6 (M+H)$^+$.

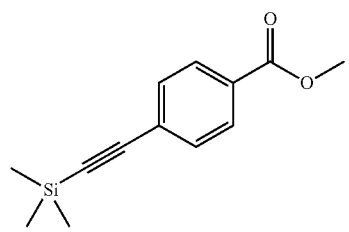

C) Methyl 4-((trimethylsilyl)ethynyl)benzoate

To a solution of methyl 4-iodobenzoate (1.5 g, 5.72 mmol) and trimethylsilylacetylene (1.58 mL, 11.5 mmol, Aldrich) in toluene (12 mL) were added Pd(PPh$_3$)$_4$ (0.66 g, 0.57 mmol), CuI (0.16 g, 0.86 mmol), and TEA (6.4 mL, 45.80 mmol). The resulting reaction mixture was purged with nitrogen for 3 min and stirred at rt for 3 h. The reaction mixture was diluted with ethyl acetate and aq. NH$_4$Cl solution. The organic layer was separated, washed with brine, and dried over MgSO$_4$. The filtrate was concentrated in vacuo and the residue was purified by flash column chromatography (10% EtOAc/hexane) to afford the title compound as a white solid (1.35 g, 96%). $^1$H NMR (CDCl$_3$) δ 7.98 (d, J=8.6 Hz, 2H), 7.53 (d, J=8.6 Hz, 2H), 3.92 (s, 3H), 0.27 (s, 9H); MS(ESI$^+$) m/z 233.1 (M+H)$^+$.

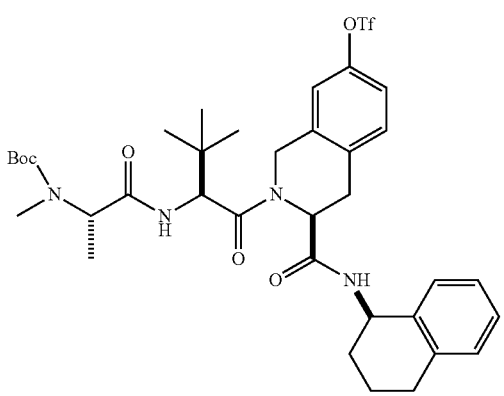

B) (S)-2-((S)-2-((S)-2-((tert-Butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl trifluoromethanesulfonate To a solution of tert-butyl ((S)-1-(((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (170 mg, 0.27 mmol) in DCM (3 mL) was added Tf$_2$O (0.070 mL, 0.41 mmol) and pyridine (0.067 mL, 0.82 mmol) at 0° C. The reaction mixture was stirred at 0° C. for 40 min. The reaction mixture turned to a brown solution. The reaction D) Methyl 4-ethynylbenzoate

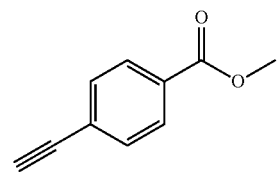

To a solution of methyl 4-((trimethylsilyl)ethynyl)benzoate (1.35 g, 5.35 mmol) in THF (10 mL) was added TBAF (1 M solution in THF) (10.7 mL, 10.7 mmol). The reaction mixture was turned into brown solution after addition of TBAF and stirred at rt for 3 h. The reaction mixture was concentrated in vacuo and the residue was purified by flash column chromatography (5% EtOAc/hexane) to afford the title compound as a white solid (0.65 g, 76%). $^1$H NMR (CDCl$_3$) δ 8.00 (d, J=8.6 Hz, 2H), 7.56 (d, J=8.6 Hz, 2H), 3.93 (s, 3H), 3.23 (s, 1H).

(((R)-1,2,3,4-tetrahydronaphthalen-1-yl)carbamoyl)-1,2,3,4-tetrahydroisoquinolin-7-yl trifluoromethanesulfonate (127 mg, 0.17 mmol) and methyl 4-ethynylbenzoate (40.5 mg, 0.25 mmol) in DMF (3 mL) were added CuI (6.4 mg, 0.034 mmol) and PdCl$_2$(dppf) (24.7 mg, 0.034 mmol, Combiphos). The reaction mixture was purged with nitrogen stream for 2 min, followed by addition of TEA (0.19 mL, 1.35 mmol). The resulting reaction mixture was heated at 85° C. for 3.5 h. The reaction mixture was diluted with ethyl acetate and saturated aq. NaHCO$_3$ solution. The organic layer was separated and washed with brine, aq. NH$_4$Cl solution. The organic layer was separated and dried over MgSO$_4$. The filtrate was concentrated in vacuo. The residue was purified by preparative HPLC. Fractions containing the product were combined, concentrated, and lyophilized to give the title compound as a white solid (72 mg, 56%). $^1$H NMR (CD$_3$OD) δ 8.03 (d, J=8.6 Hz, 2H), 7.67-7.58 (m, 2H), 7.56-7.36 (m, 2.5H), 7.33-7.21 (m, 1.5H), 7.15-6.94 (m, 3H), 5.36 (br. s., 0.5H), 5.17-4.87 (m, 2.5H), 4.77-4.49 (m, 3H), 3.93 (s, 3H), 3.26-3.10 (m, 2H), 2.86 (s, 2H), 2.83-2.67 (m, 3H), 2.03-1.60 (m, 4H), 1.53-1.38 (m, 9H), 1.34-1.16 (m, 3H), 1.15-0.94 (m, 9H); MS(ESI$^+$) m/z 763.4 (M+H)$^+$.

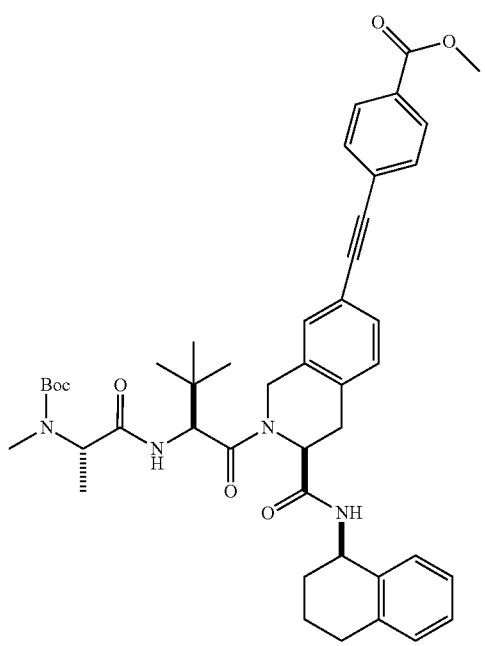

E) Methyl 4-(((S)-2-((S)-2-((S)-2-((tert-butoxycarbonyl)(methyl)amino) propanamido)-3,3-dimethylbutanoyl)-3-(((R)-1,2,3,4-tetrahydronaphthalen-1-yl)carbamoyl)-1,2,3,4-tetrahydroisoquinolin-7-yl)ethynyl)benzoate To a solution of (S)-2-((S)-2-((S)-2-((tert-butoxycarbonyl)(methyl)amino)propanamido)-3,3-dimethylbutanoyl)-3-

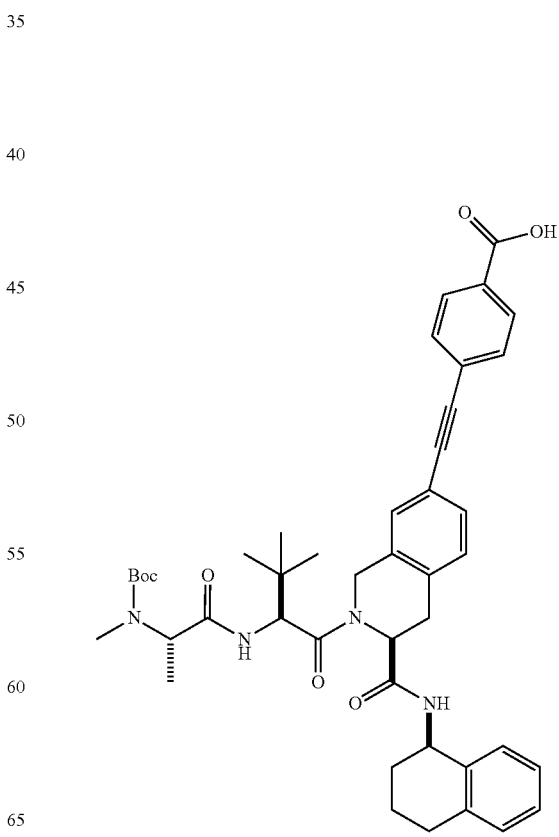

F) 4-(((S)-2-((S)-2-((S)-2-((tert-Butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)ethynyl)benzoic acid To a solution of methyl 4-(((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)ethynyl)benzoate (85 mg, 0.11 mmol) in MeOH (1 mL) and THF (1 mL) was added a solution of lithium hydroxide, $H_2O$ (18.7 mg, 0.45 mmol) in water (1 mL). The reaction mixture was stirred at rt for 2 h. To the reaction mixture was added more lithium hydroxide-$H_2O$ (18.7 mg, 0.45 mmol) solution in water (1 mL) and the resulting mixture was stirred at rt overnight. The reaction mixture was acidified with 1 N HCl solution to adjust its pH to 1 and the residue was extracted with ethyl acetate. The organic layer was combined, dried over $MgSO_4$. The filtrate was concentrated in vacuo to give the title compound as a white solid (80 mg, 91%). MS(ESI$^+$) m/z 749.7 (M+H)$^+$.

G) (S)-2-((S)-3,3-Dimethyl-2-((S)-2-(methylamino)propanamido)butanoyl)-7-((4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)phenyl)ethynyl)-N—((R)-1,2,3,4-tetrahydronaphthalen-1-yl)-1,2,3,4-tetrahydroisoquinoline-3-carboxamide To a solution of 4-(((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)ethynyl)benzoic acid (80 mg, 0.11 mmol) in DMF (1 mL) and DMSO (1 mL) was added HATU (52.8 mg, 0.14 mmol), followed by addition of tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound J of Example 1, 71.5 mg, 0.13 mmol) and DIPEA (0.06 mL, 0.32 mmol). The reaction mixture was stirred at rt for 2 h. The reaction mixture was diluted with ethyl acetate and brine. The organic layer was separated and washed with saturated NaHCO$_3$ solution, brine. The combined organic layer (×2) was dried over $MgSO_4$. The filtrate was concentrated in vacuo and the residue was purified by flash chromatography (65% EtOAc/DCM) to afford the title compound as a white solid (100 mg, 73%). MS(ESI$^+$) m/z 1289.9 (M+H)$^+$. The resulting solid (35 mg, 0.03 mmol) was then dissolved in DCM (1 mL) was added HCl (4.0 M solution in dioxane) (0.4 mL, 1.63 mmol). The reaction mixture was stirred at rt for 2 h. The reaction mixture was concentrated in vacuo and the residue was purified by preparative HPLC. Fractions containing the product were combined, concentrated, and lyophilized to give the title compound 2TFA salt as a white solid (28 mg, 77%). MS(ESI$^+$) m/z 1089.6 (M+H)$^+$.

Example 45

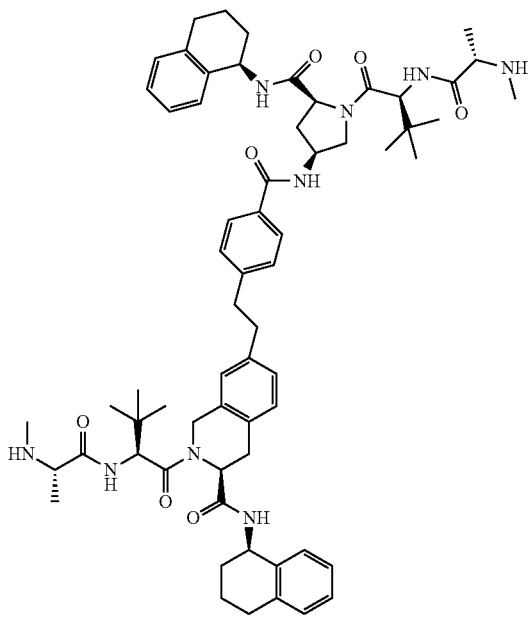 [SMILES: CN[C@@H](C)C(=O)N[C@H](C(=O)N1Cc2cc(CCc3ccc(C(=O)N[C@H]4C[C@@H](C(=O)N[C@@H]5CCCc6ccccc65)N(C(=O)[C@@H](NC(=O)[C@H](C)NC)C(C)(C)C)C4)cc3)ccc2C[C@H]1C(=O)N[C@@H]1CCCc2ccccc21)C(C)(C)C]

(S)-2-((S)-3,3-Dimethyl-2-((S)-2-(methylamino)
propanamido)butanoyl)-7-(4-(((3S,5S)-1-((S)-3,3-
dimethyl-2-((S)-2-(methylamino)propanamido)bu-
tanoyl)-5-(((R)-1,2,3,4-tetrahydronaphthalen-1-yl)
carbamoyl)pyrrolidin-3-yl)carbamoyl)phenethyl)-
N—((R)-1,2,3,4-tetrahydronaphthalen-1-yl)-1,2,3,4-
tetrahydroisoquinoline-3-carboxamide

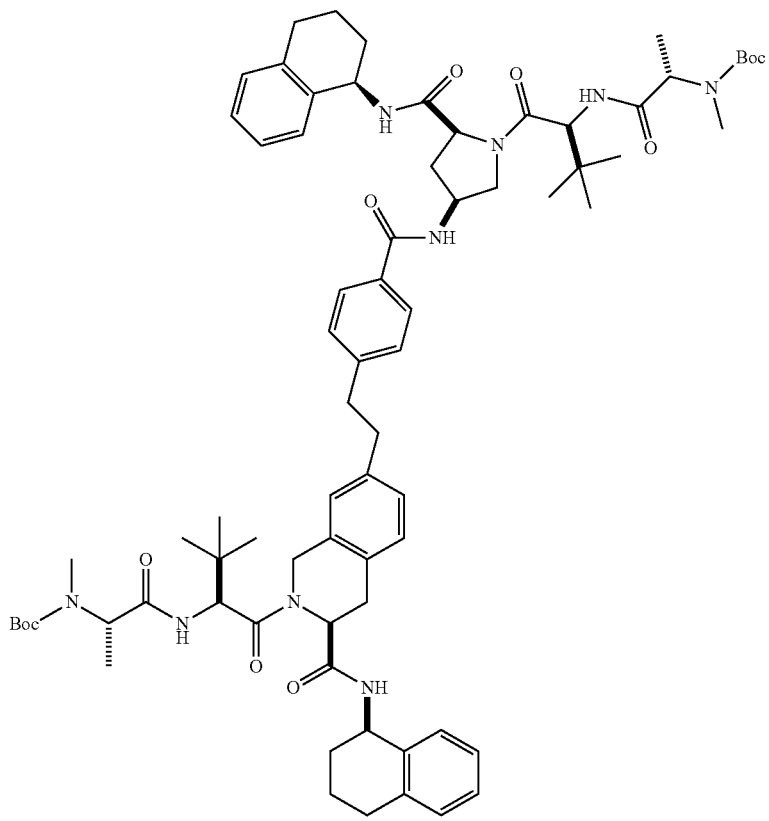

A) To a solution of bis-Boc protected (S)-2-((S)-3,3-dimethyl-2-((S)-2-(methylamino)propanamido)butanoyl)-7-((4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)phenyl)ethynyl)-N—((R)-1,2,3,4-tetrahydronaphthalen-1-yl)-1,2,3,4-tetrahydroisoquinoline-3-carboxamide (65 mg, 0.050 mmol, Compound G in Example 44) in MeOH (3 mL) was added Pd—C (54 mg, 0.050 mmol) under nitrogen. The reaction mixture was evacuated, then purged with hydrogen and stirred at rt under hydrogen balloon over night. The reaction mixture was filtered through a CELITE® pad. The filtrate was concentrated in vacuo to give the title compound as a white solid (55 mg, 84%). MS(ESI$^+$) m/z 1293.1 (M+H)$^+$.

B) (S)-2-((S)-3,3-Dimethyl-2-((S)-2-(methylamino)
propanamido)butanoyl)-7-(4-(((3S,5S)-1-((S)-3,3-
dimethyl-2-((S)-2-(methylamino)propanamido)bu-
tanoyl)-5-(((R)-1,2,3,4-tetrahydronaphthalen-1-yl)
carbamoyl)pyrrolidin-3-yl)carbamoyl)phenethyl)-
N—((R)-1,2,3,4-tetrahydronaphthalen-1-yl)-1,2,3,4-
tetrahydroisoquinoline-3-carboxamide To a solution of the above product (55 mg, 0.043 mmol) in DCM (2 mL) was added HCl (4.0 M solution in dioxane) (1.1 mL, 4.25 mmol). The reaction mixture was stirred at rt for 1 h. The reaction mixture was concentrated in vacuo and the residue was purified by preparative HPLC. Fractions containing the product were combined, concentrated, and lyophilized to give the title compound 2TFA salt as a white solid (37 mg, 65%). MS(ESI$^+$) m/z 1093.8 (M+H)$^+$.

143
Example 46
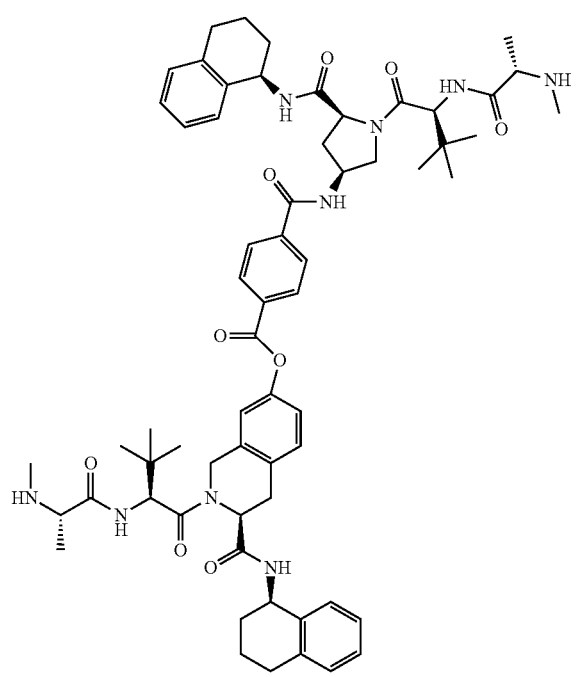 [SMILES: CN[C@@H](C)C(=O)N[C@H](C(=O)N1Cc2cc(OC(=O)c3ccc(C(=O)N[C@H]4C[C@@H](C(=O)N[C@@H]5CCCc6ccccc65)N(C(=O)[C@@H](NC(=O)[C@H](C)NC)C(C)(C)C)C4)cc3)ccc2C[C@H]1C(=O)N[C@@H]1CCCc2ccccc21)C(C)(C)C]
144
(S)-2-((S)-3,3-Dimethyl-2-((S)-2-(methylamino)
propanamido)butanoyl)-3-(((R)-1,2,3,4-tetrahy-
dronaphthalen-1-yl)carbamoyl)-1,2,3,4-tetrahy-
droisoquinolin-7-yl 4-(((3S,5S)-1-((S)-3,3-dimethyl-
2-((S)-2-(methylamino)propanamido)butanoyl)-5-
(((R)-1,2,3,4-tetrahydronaphthalen-1-yl)carbamoyl)
pyrrolidin-3-yl)carbamoyl)benzoate
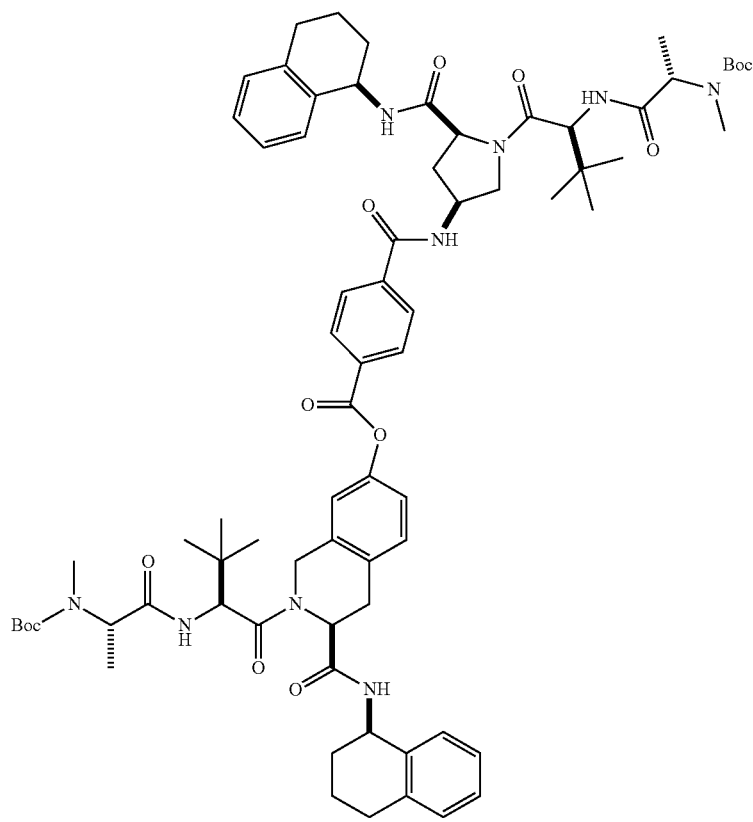

A) (S)-2-((S)-2-((S)-2-((tert-Butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl 4-(((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)carbamoyl)benzoate To a solution of tert-butyl ((S)-1-(((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (60 mg, 0.097 mmol, Compound A in Example 44) and terephthaloyl dichloride (23.6 mg, 0.12 mmol) in DCM (2 mL) was added DIEA (0.05 mL, 0.29 mmol). The reaction mixture was stirred at rt under nitrogen stream for 15 min. To the reaction mixture was added tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound J of Example 1, 59 mg, 0.11 mmol) and DIEA (0.05 mL, 0.29 mmol). The reaction mixture was stirred at rt for another 10 min. The reaction mixture was concentrated in vacuo and the residue was purified by preparative HPLC. Fractions containing the product were combined, concentrated, and lyophilized to give the title compound as a white solid (62 mg, 48%). MS(ESI$^+$) m/z 1308.8 (M+H)$^+$.

B) (S)-2-((S)-3,3-Dimethyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl 4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzoate To a solution of (S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl 4-(((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)carbamoyl)benzoate (58 mg, 0.044 mmol) in DCM (2 mL) was added TFA (0.5 mL, 6.49 mmol). The reaction mixture was stirred at rt for 40 min and was concentrated in vacuo. The residue was lyophilized to give the title compound 2TFA salt as a white solid (56 mg, 93%). MS(ESI$^+$) m/z 1108.7 (M+H)$^+$.

Example 47

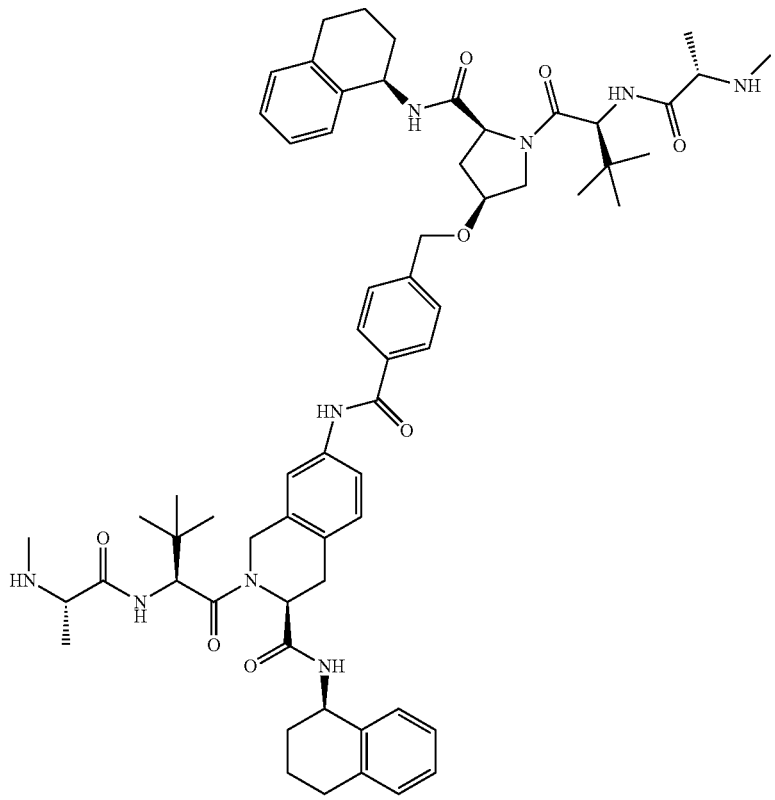 [SMILES: CN[C@@H](C)C(=O)N[C@H](C(=O)N1Cc2cc(NC(=O)c3ccc(CO[C@H]4C[C@@H](C(=O)N[C@@H]5CCCc6ccccc65)N(C(=O)[C@@H](NC(=O)[C@H](C)NC)C(C)(C)C)C4)cc3)ccc2C[C@H]1C(=O)N[C@@H]1CCCc2ccccc21)C(C)(C)C]

(S)-2-((S)-3,3-Dimethyl-2-((S)-2-(methylamino)
propanamido)butanoyl)-7-(4-(((((3S,5S)-1-((S)-3,3-
dimethyl-2-((S)-2-(methylamino)propanamido)bu-
tanoyl)-5-(((R)-1,2,3,4-tetrahydronaphthalen-1-yl)
carbamoyl)pyrrolidin-3-yl)oxy)methyl)benzamido)-
N—((R)-1,2,3,4-tetrahydronaphthalen-1-yl)-1,2,3,4-
tetrahydroisoquinoline-3-carboxamide

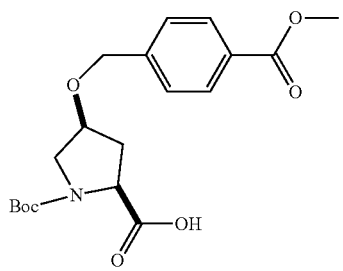

A) (2S,4S)-1-(tert-Butoxycarbonyl)-4-((4-(methoxy-
carbonyl)benzyl)oxy)pyrrolidine-2-carboxylic acid NaH (0.97 g, 24.22 mmol) was suspended in DMF (15 mL) under nitrogen at ice bath temperature. A solution of (2S,4S)-1-(tert-butoxycarbonyl)-4-hydroxypyrrolidine-2-carboxylic acid (2.00 g, 8.65 mmol) in DMF (20 mL) was added dropwise. The reaction mixture was stirred at 0° C. for 10 min, followed by addition of a solution of methyl 4-(bromomethyl)benzoate (2.28 g, 9.95 mmol) in DMF (5 mL). The reaction mixture was stirred at 0° C. for 1 h. The reaction mixture was quenched with water and the resulting mixture was transferred to a separatory funnel along with ethyl acetate and 1N HCl solution. The combined organic layer was washed with brine, and dried over MgSO$_4$. The filtrate was concentrated in vacuo. The residue was purified by purified by flash chromatography (20% EtOAc/DCM) to afford the title compound as a white solid (1.2 g, 37%). $^1$H NMR (CDCl$_3$) δ 7.99 (d, J=8.1 Hz, 2H), 7.36 (d, J=3.5 Hz, 2H), 4.78-4.26 (m, 3H), 4.19-4.11 (m, 1H), 3.90 (s, 3H), 3.71-3.46 (m, 2H), 2.84-2.39 (m, 1H), 2.23-2.04 (m, 1H), 1.48 (br. s., 9H); MS(ESI$^+$) m/z 324.0 (M-55)$^+$.

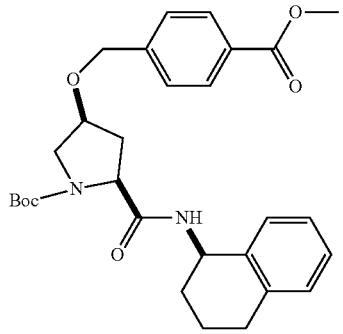

B) (2S,4S)-tert-Butyl 4-((4-(methoxycarbonyl)ben-
zyl)oxy)-2-(((R)-1,2,3,4-tetrahydronaphthalen-1-yl)
carbamoyl)pyrrolidine-1-carboxylate To a solution of (2S,4S)-1-(tert-butoxycarbonyl)-4-((4-(methoxycarbonyl)benzyl)oxy)pyrrolidine-2-carboxylic acid (1.2 g, 3.16 mmol) in DMF (10 mL) was added EDC (0.91 g, 4.74 mmol) and 3H-[1,2,3]-triazolo[4,5-b]pyridin-3-ol (0.431 g, 3.16 mmol). The reaction mixture was stirred at rt for 5 min, followed by addition of a solution of (R)-1,2,3,4-tetrahydronaphthalen-1-amine (0.54 g, 3.64 mmol) in DMF (5 mL) and 4-methylmorpholine (0.70 mL, 6.33 mmol). The reaction mixture was stirred at rt for 1 h. The reaction mixture was diluted with ethyl acetate and brine. The organic layer was separated and washed with saturated aq. NaHCO$_3$ solution, brine, 1 N HCl solution successively and dried over MgSO$_4$. The filtrate was concentrated in vacuo. The residue was purified by purified by flash chromatography (20% EtOAc/DCM) to afford the title compound as a white solid (1.31 g, 81%). $^1$H NMR (CDCl$_3$) δ 7.99 (d, J=8.4 Hz, 2H), 7.33 (d, J=6.8 Hz, 2H), 7.13-6.94 (m, 3H), 6.85-6.80 (m, 1H), 5.21-5.01 (m, 1H), 4.49-4.33 (m, 2H), 4.11 (d, J=3.1 Hz, 1H), 3.93 (s, 3H), 3.70-3.41 (m, 2H), 2.74 (d, J=3.3 Hz, 2H), 2.05 (s, 2H), 1.90-1.68 (m, 3H), 1.58 (s, 1H), 1.45 (s, 10H); MS(ESI$^+$) m/z 509.5 (M+H)$^+$.

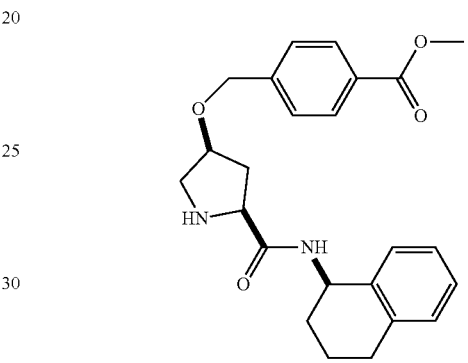

C) Methyl 4-(((((3S,5S)-5-(((R)-1,2,3,4-tetrahy-
dronaphthalen-1-yl)carbamoyl)pyrrolidin-3-yl)oxy)
methyl)benzoate To a solution of (2S,4S)-tert-butyl 4-((4-(methoxycarbo-nyl)benzyl)oxy)-2-(((R)-1,2,3,4-tetrahydronaphthalen-1-yl)carbamoyl)pyrrolidine-1-carboxylate (1.31 g, 2.58 mmol) in DCM (10 mL) was added HCl (4.0 M solution in dioxane) (12.9 mL, 51.50 mmol). The reaction mixture was stirred at rt for 1.5 h. and concentrated in vacuo to give the title compound HCl salt as a white solid (1.15 g, 100%). $^1$H NMR (DMSO-d$_6$) δ 8.83 (d, J=8.4 Hz, 1H), 8.74 (d, J=8.6 Hz, 1H), 7.95 (d, J=8.4 Hz, 2H), 7.46 (d, J=8.4 Hz, 2H), 7.26-7.00 (m, 3H), 5.05-4.88 (m, 1H), 4.56 (q, J=12.8 Hz, 2H), 4.31 (br. s., 2H), 3.86 (s, 3H), 3.55-3.46 (m, 1.5H), 2.81-2.61 (m, 2.5H), 2.48-2.21 (m, 2H), 1.84-1.53 (m, 4H); MS(ESI$^+$) m/z 409.4 (M+H)$^+$.

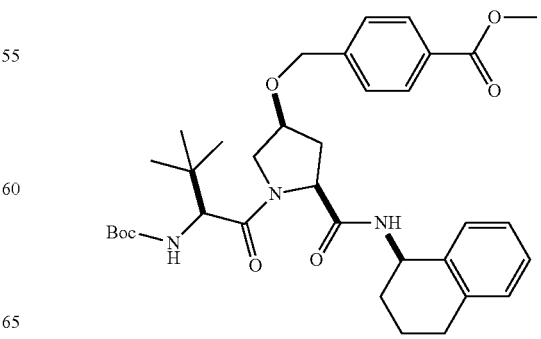

D) Methyl 4-(((((3S,5S)-1-((S)-2-((tert-butoxycarbonyl)amino)-3,3-dimethylbutanoyl)-5-(((R)-1,2,3,4-tetrahydronaphthalen-1-yl)carbamoyl)pyrrolidin-3-yl)oxy)methyl)benzoate To a solution of (S)-2-((tert-butoxycarbonyl)amino)-3,3-dimethylbutanoic acid (0.72 g, 3.1 mmol) in DMF (6 mL) were added EDC (0.74 g, 3.9 mmol) and 3H-[1,2,3]-triazolo[4,5-b]pyridin-3-ol (0.35 g, 2.6 mmol). After stirring for 5 min, a solution of methyl 4-(((((3S,5S)-5-(((R)-1,2,3,4-tetrahydronaphthalen-1-yl)carbamoyl)pyrrolidin-3-yl)oxy)methyl)benzoate, HCl (1.15 g, 2.58 mmol) in DMF (10 mL) and 4-methylmorpholine (1.14 mL, 10.3 mmol) were added. The resulting reaction mixture was stirred at rt for 1 h. The reaction mixture was diluted with brine and ethyl acetate. The organic layer was separated and washed with saturated aq. NaHCO$_3$ solution, 1 N HCl solution successively. The organic layer was dried over MgSO$_4$ and the filtrate was concentrated in vacuo. The residue was purified by purified by flash chromatography (20% EtOAc/DCM) to afford the title compound as a white solid (1.41 g, 88%). $^1$H NMR (CDCl$_3$) δ 8.00 (d, J=8.4 Hz, 2H), 7.39 (d, J=8.4 Hz, 2H), 7.13-6.82 (m, 4H), 5.21-4.95 (m, 2H), 4.77-4.63 (m, 2H), 4.44 (d, J=12.1 Hz, 1H), 4.28-4.11 (m, 2H), 3.91 (s, 3H), 3.70 (d, J=10.8 Hz, 1H), 2.71 (t, J=5.7 Hz, 2H), 2.14-1.72 (m, 5H), 1.41 (s, 9H), 1.10-0.92 (m, 1H), 0.78 (s, 9H); MS(ESI$^+$) m/z 622.6 (M+H)$^+$.

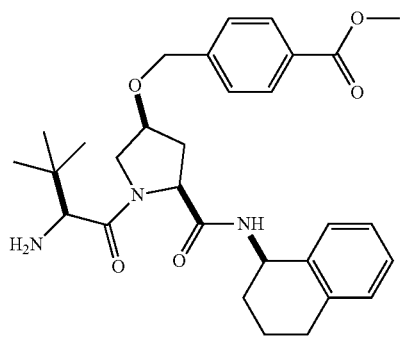

E) Methyl 4-(((((3S,5S)-1-((S)-2-amino-3,3-dimethylbutanoyl)-5-(((R)-1,2,3,4-tetrahydronaphthalen-1-yl)carbamoyl)pyrrolidin-3-yl)oxy)methyl)benzoate To a solution of methyl 4-(((((3S,5S)-1-((S)-2-((tert-butoxycarbonyl)amino)-3,3-dimethylbutanoyl)-5-(((R)-1,2,3,4-tetrahydronaphthalen-1-yl)carbamoyl)pyrrolidin-3-yl)oxy)methyl)benzoate (1.40 g, 2.25 mmol) in DCM (8 mL) was added HCl (4.0 M solution in dioxane) (8.4 mL, 34 mmol). The reaction mixture was stirred at rt for 1.5 h. and was concentrated in vacuo to give the title compound HCl salt as a white solid (1.26 g, 100%). $^1$H NMR (DMSO-d$_6$) δ 8.31-8.17 (m, 1H), 7.94 (d, J=8.1 Hz, 2H), 7.48 (d, J=8.1 Hz, 1.5H), 7.25 (d, J=7.5 Hz, 0.5H), 7.14-7.01 (m, 3H), 4.99-4.85 (m, 1H), 4.63 (s, 2H), 4.41 (t, J=8.0 Hz, 1H), 4.33-4.09 (m, 2H), 3.93 (d, J=5.5 Hz, 1H), 3.85 (s, 3H), 3.42 (dd, J=10.3, 6.8 Hz, 1H), 2.77-2.64 (m, 3H), 1.95-1.56 (m, 5H), 1.06 (s, 9H); MS(ESI$^+$) m/z 522.5 (M+H)$^+$.

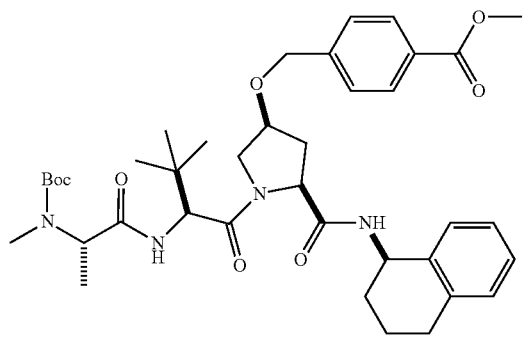

F) Methyl 4-(((((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)oxy)methyl)benzoate To a solution of (S)-2-((tert-butoxycarbonyl)(methyl)amino)propanoic acid (0.53 g, 2.60 mmol) in DMF (8 mL) were added EDC (0.65 g, 3.4 mmol) and 3H-[1,2,3]-triazolo[4,5-b]pyridin-3-ol (0.31 g, 2.3 mmol). After 5 min, a solution of methyl 4-(((((3S,5S)-1-((S)-2-amino-3,3-dimethylbutanoyl)-5-(((R)-1,2,3,4-tetrahydronaphthalen-1-yl)carbamoyl)pyrrolidin-3-yl)oxy)methyl)benzoate, HCl (1.26 g, 2.26 mmol) in DMF (8 mL) and 4-methylmorpholine (1.1 mL, 10.2 mmol) were added. The resulting reaction mixture was stirred at rt for 1 h. The reaction mixture was diluted with brine and ethyl acetate. The organic was separated and washed with saturated aq. NaHCO$_3$ solution, 1 N HCl solution successively. The organic layer was dried over MgSO$_4$ and the filtrate was concentrated in vacuo. The residue was purified by flash chromatography (40% EtOAc/DCM) to afford the title compound as a white solid (1.35 g, 85%). $^1$H NMR (CDCl$_3$) δ 8.01 (d, J=8.4 Hz, 2H), 7.39 (d, J=8.4 Hz, 2H), 7.13-6.82 (m, 4H), 5.12-4.96 (m, 1H), 4.81-4.62 (m, 3H), 4.53-4.35 (m, 2H), 4.22 (dt, J=4.6, 2.2 Hz, 1H), 4.00 (dd, J=10.9, 4.7 Hz, 1H), 3.91 (s, 3H), 3.71 (d, J=11.0 Hz, 1H), 2.81-2.63 (m, 5H), 2.13-1.74 (m, 6H), 1.48 (s, 9H), 1.33-1.28 (m, 3H), 0.77 (s, 9H); MS(ESI$^+$) m/z 707.5 (M+H)$^+$.

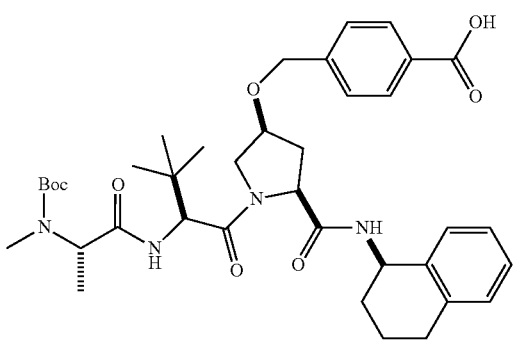

G) 4-(((((3S,5S)-1-((S)-2-((S)-2-((tert-Butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)oxy)methyl)benzoic acid To a solution of methyl 4-(((((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)oxy)methyl)benzoate (1.35 g, 1.91 mmol) in THF (5 mL) and MeOH (3 mL) was added a solution of NaOH (0.31 g, 7.64 mmol) in water (6 mL). The reaction mixture was stirred at rt for 4 h. The reaction mixture was acidified with 1 N HCl solution and the resulting mixture was extracted with ethyl acetate. The organic layer was separated, washed with brine, and dried over MgSO$_4$. The filtrate was concentrated in vacuo to give the title compound as a white solid (1.30 g, 98%). $^1$H NMR (DMSO-d$_6$) δ 8.01 (d, J=8.6 Hz, 0.5H), 7.91 (d, J=8.4 Hz, 1.5H), 7.43 (d, J=8.4 Hz, 2H), 7.24 (d, J=7.7 Hz, 1H), 7.15-6.98 (m, 3H), 4.98-4.83 (m, 1H), 4.60 (s, 2H), 4.47 (d, J=9.0 Hz, 1H), 4.34 (t, J=7.7 Hz, 1H), 4.21 (t, J=6.2 Hz, 1H), 4.12-4.05 (m, 1H), 3.86-3.71 (m, 1H), 3.54 (dd, J=10.2, 6.1 Hz, 1H), 2.81-2.65 (m, 5H), 2.45-2.36 (m, 1H), 2.02-1.92 (m, 1H), 1.86-1.56 (m, 4H), 1.40 (br. s., 9H), 1.26-1.15 (m, 3H), 1.03-0.86 (m, 9H); MS(ESI$^+$) m/z 693.6 (M+H)$^+$.

H) (S)-2-((S)-3,3-Dimethyl-2-((S)-2-(methylamino)propanamido)butanoyl)-7-(4-(((((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)oxy)methyl)benzamido)-N—((R)-1,2,3,4-tetrahydronaphthalen-1-yl)-1,2,3,4-tetrahydroisoquinoline-3-carboxamide To a solution of 4-(((((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)oxy)methyl)benzoic acid (27 mg, 0.039 mmol) in DMF (1 mL) was added HATU (16 mg, 0.043 mmol), tert-butyl ((S)-1-(((S)-1-((S)-7-amino-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate, TFA (26 mg, 0.035 mmol) and DIEA (0.04 mL, 0.22 mmol). The reaction mixture was stirred at rt for 3 h. The reaction mixture was concentrated in vacuo and the residue was purified by preparative HPLC. Fractions containing the product were combined, concentrated, and lyophilized to give white solid. To a solution of the obtained product (11 mg, 8.50 μmol) in DCM (1 mL) was added TFA (0.4 mL, 5.19 mmol). The reaction mixture was stirred at rt for 1 h. The reaction mixture was concentrated in vacuo and lyophilized to give the title compound 2TFA salt as a white solid (11 mg, 23%). MS(ESI$^+$) m/z 1094.7 (M+H)$^+$.

Example 48

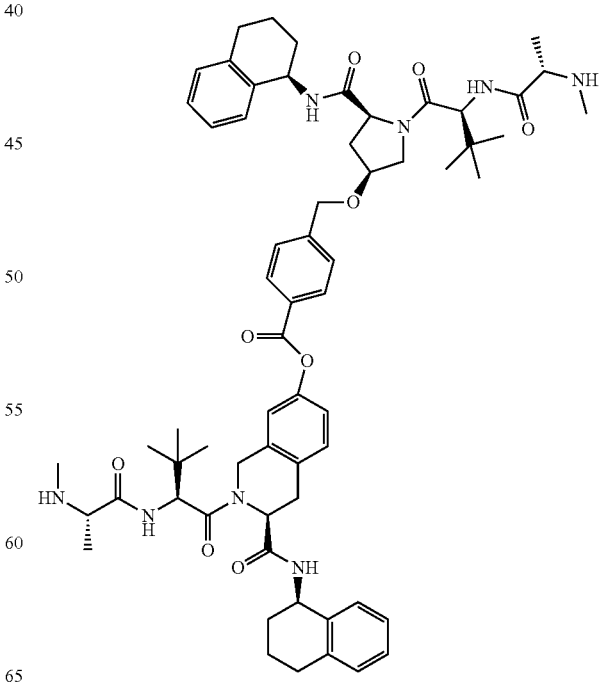

(S)-2-((S)-3,3-Dimethyl-2-((S)-2-(methylamino) propanamido)butanoyl)-3-(((R)-1,2,3,4-tetrahydronaphthalen-1-yl)carbamoyl)-1,2,3,4-tetrahydroisoquinolin-7-yl 4-((((3S,5S)-1-((S)-3,3-dimethyl-2-((S)-2-(methylamino)propanamido) butanoyl)-5-(((R)-1,2,3,4-tetrahydronaphthalen-1-yl) carbamoyl)pyrrolidin-3-yl)oxy)methyl)benzoate

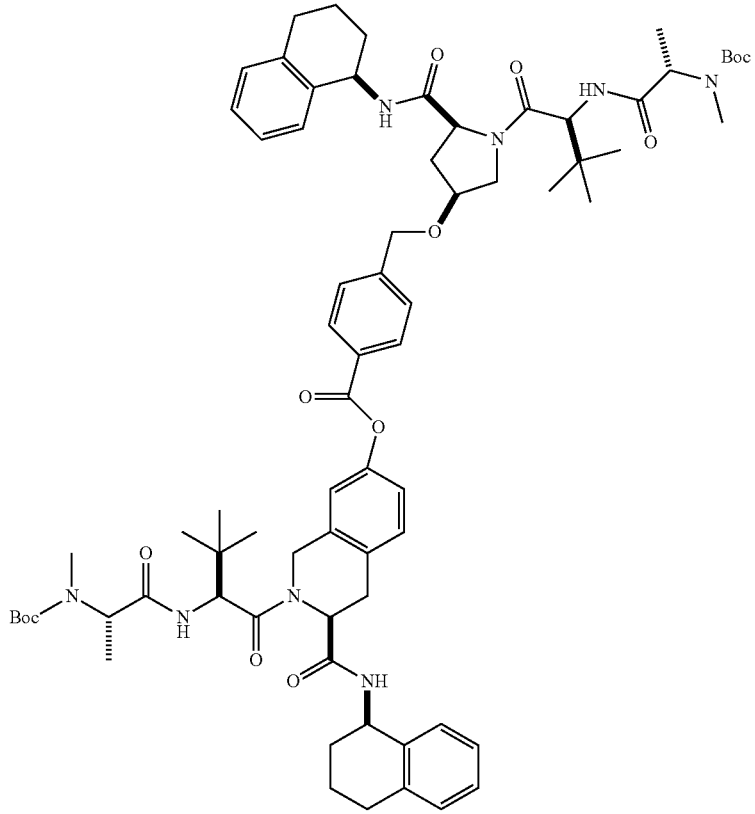

A) (S)-2-((S)-2-((S)-2-((tert-Butoxycarbonyl) (methyl)amino)propanamido)-3,3-dimethylbutanoyl)-3-(((R)-1,2,3,4-tetrahydronaphthalen-1-yl) carbamoyl)-1,2,3,4-tetrahydroisoquinolin-7-yl 4-((((3S,5S)-1-((S)-2-((S)-2-((tert-butoxycarbonyl) (methyl)amino)propanamido)-3,3-dimethylbutanoyl)-5-(((R)-1,2,3,4-tetrahydronaphthalen-1-yl) carbamoyl)pyrrolidin-3-yl)oxy)methyl)benzoate To a solution of 4-((((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)oxy)methyl)benzoic acid (51 mg, 0.074 mmol, Compound G in Example 47) in DCM (1.5 mL) was added 1-chloro-N,N,2-trimethylpropenylamine (0.014 mL, 0.11 mmol), followed by addition of DIEA (0.068 mL, 0.39 mmol) and tert-butyl ((S)-1-(((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl) carbamate (40 mg, 0.064 mmol, Compound A in Example 44). The reaction mixture was stirred at rt for 45 min. and concentrated in vacuo. The residue was purified by preparative HPLC. Fractions containing the product were combined, concentrated, and lyophilized to give the title compound as a white solid (18 mg, 21%). MS(ESI$^+$) m/z 1318.1 (M+23)$^+$.

B) (S)-2-((S)-3,3-Dimethyl-2-((S)-2-(methylamino) propanamido)butanoyl)-3-(((R)-1,2,3,4-tetrahydronaphthalen-1-yl)carbamoyl)-1,2,3,4-tetrahydroisoquinolin-7-yl 4-((((3S,5S)-1-((S)-3,3-dimethyl-2-((S)-2-(methylamino)propanamido) butanoyl)-5-(((R)-1,2,3,4-tetrahydronaphthalen-1-yl) carbamoyl)pyrrolidin-3-yl)oxy)methyl)benzoate To a solution of (S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl 4-((((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)oxy)methyl)benzoate (25 mg, 0.019 mmol) in DCM (2 mL) was added TFA (0.40 mL, 5.19 mmol). The reaction mixture was stirred at rt for 40 min and was concentrated in vacuo. The residue was lyophilized to give the title compound 2TFA salt as a white solid (24 mg, 92%). MS(ESI$^+$) m/z 1095.7 (M+H)$^+$.

Example 49

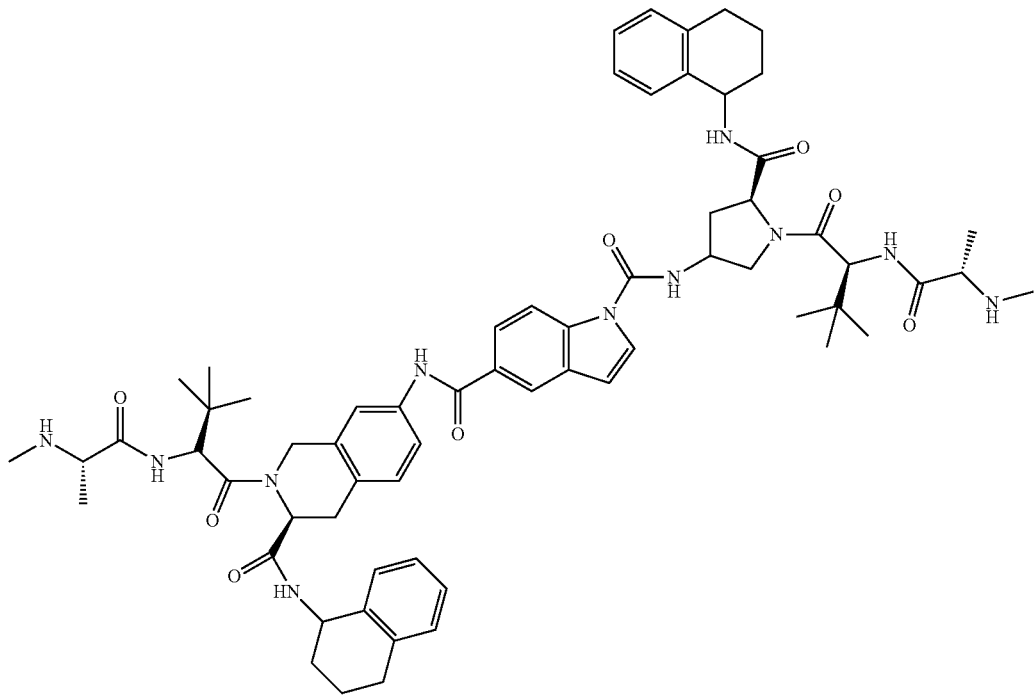

$N^5$—((S)-2-((S)-3,3-Dimethyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)-$N^1$-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-1H-indole-1,5-dicarboxamide

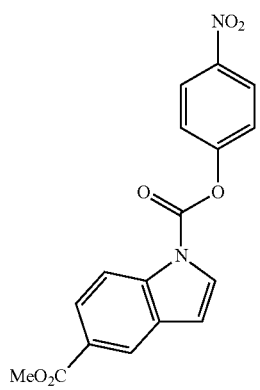 [SMILES: COC(=O)c1ccc2c(ccn2C(=O)Oc2ccc([N+](=O)[O-])cc2)c1]

A) 5-Methyl 1-(4-nitrophenyl) 1H-indole-1,5-dicarboxylate

A solution of methyl 1H-indole-5-carboxylate (1.0 g, 5.71 mmol) and bis(4-nitrophenyl) carbonate (1.70 g, 5.71 mmol) in THF (20 mL) was cooled to −78° C. During the cooling a solid started to precipitate and an additional THF (10 mL) was added. NaH (60%, 0.25 g, 6.25 mmol) was added and the reaction mixture was warmed to 0° C. with stirring. The mixture was again cooled to −45° C. Additional bis(4-nitrophenyl) carbonate (0.6 g, 1.97 mmol) and NaH (60%, 0.2 g, 5.0 mmol) and THF (10 mL) were added to the reaction mixture at 0° C., which was warmed to rt and then stirred for 30 minutes. To the reaction mixture was added HOAc (2 mL), followed by MeOH (5 mL), mostly concentrated in vacuo and the residue was mixed with $CH_2Cl_2$ (30 mL) and water (15 mL), stirred for 10 minutes, precipitated solid was filtered, washed with a small amount of $CH_2Cl_2$ and dried to obtain the 1st crop of the desired product. The filtrate solution was mixed with 0.5 mL of 28% $NH_4OH$ solution, stirred for 10 minutes, organic layer was separated, mixed with EtOAc (20 mL), dried over MgSO4 and concentrated in vacuo to obtain the 2nd crop of product solid. Both crops of the solid was combined and dried to obtain the title compound (1.45 g, 4.26 mmol, 74.6% yield) as a white solid. MS(ESI$^+$) m/z 341.2 (M+H)$^+$.

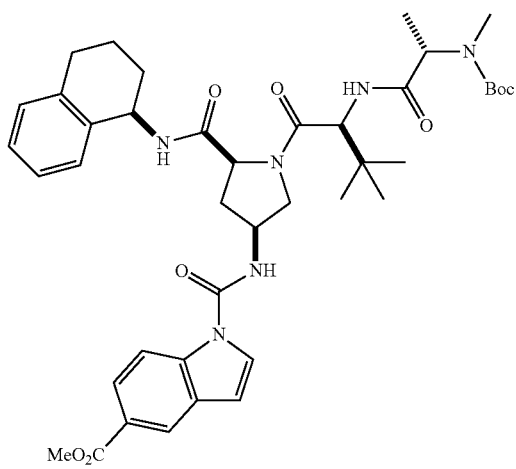
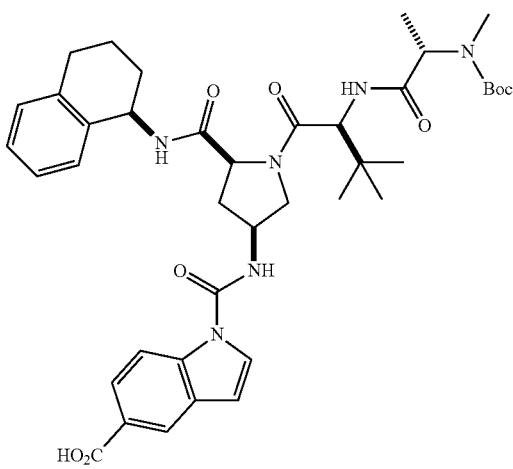

B) Methyl 1-(((3S,5S)-1-((S)-2-((S)-2-((tert-butoxy-carbonyl)(methyl)amino)propanamido)-3,3-dimethylbutanoyl)-5-(((R)-1,2,3,4-tetrahydronaphthalen-1-yl)carbamoyl)pyrrolidin-3-yl)carbamoyl)-1H-indole-5-carboxylate To a mixture of 5-methyl 1-(4-nitrophenyl) 1H-indole-1,5-dicarboxylate (101 mg, 0.296 mmol) and tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl) carbamate (Compound J of Example 1, 150 mg, 0.269 mmol), in DMF (6 mL) at rt was added Hunig's base (200 uL) and the mixture was stirred for 3 h. To the reaction mixture were added EtOAc (50 mL) and water (20 mL), EtOAc layer was separated, washed successively with 1N HCl, 1N NaOH and water (20 mL) and concentrated in vacuo to obtain the crude coupling product mixture (220 mg) which was used directly for the next step of hydrolysis. $^1$H NMR (CD$_3$OD) δ 8.62 (d, J=8.8 Hz, 1H), 8.31 (d, J=8.8 Hz, 1H), 8.25 (d, J=1.3 Hz, 1H), 7.92 (dd, J=8.8, 1.8 Hz, 1H), 7.74 (d, J=3.7 Hz, 1H), 7.44-7.37 (m, 2H), 7.14-7.02 (m, 3H), 6.73 (d, J=3.7 Hz, 1H), 5.15-5.09 (m, 1H), 4.71-4.53 (m, 4H), 4.10 (dd, J=10.8, 5.1 Hz, 1H), 3.97 (dd, J=10.6, 3.1 Hz, 1H), 3.90 (s, 3H), 3.33-3.29 (m, 1H), 2.87 (s, 3H), 2.86-2.82 (m, 2H), 2.80-2.55 (m, 3H), 2.13 (dt, J=13.5, 3.6 Hz, 1H), 1.47 (s, 9H), 1.31 (d, J=7.0 Hz, 3H), 1.03-0.97 (m, 9H); MS(ESI$^+$) m/z 759.6 (M+H)$^+$.

C) 1-(((3S,5S)-1-((S)-2-((S)-2-((tert-Butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)carbamoyl)-1H-indole-5-carboxylic acid A mixture of the crude coupling methyl 1-(((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)carbamoyl)-1H-indole-5-carboxylate (220 mg) obtained above, LiOH.H$_2$O (440 mg), water (4 mL) and MeOH (15 mL) was sonicated for a few minutes and it was stirred at rt for 5 h. Most of the MeOH was removed in vacuo and the residue was mixed with EtOAc (60 mL), TFA (2.5 mL) and H$_2$O (25 mL), EtOAc layer was separated, washed with H$_2$O and mostly concentrated in vacuo. The residue was purified by preparative HPLC to provide the title compound (100 mg, 0.13 mmol, 50% overall yield) as a white solid. $^1$H NMR (CD$_3$OD) δ 8.66 (d, J=8.8 Hz, 1H), 8.34 (d, J=8.8 Hz, 1H), 8.30 (d, J=8.8 Hz, 1H), 7.96 (dd, J=8.8, 1.8 Hz, 1H), 7.75 (d, J=3.7 Hz, 1H), 7.44-7.37 (m, 2H), 7.15-7.03 (m, 3H), 6.79-6.76 (m, 1H), 5.17-5.09 (m, 1H), 4.72-4.53 (m, 4H), 4.15-4.08 (m, 1H), 4.01-3.95 (m, 1H), 3.35 (s, 1H), 3.31-3.33 (m, 1H), 2.85 (s, 3H), 2.83-2.75 (m, 2H), 2.67-2.58 (m, 1H), 2.18-2.10 (m, 1H), 1.96-1.90 (m, 1H), 1.83-1.75 (m, 2H), 1.48 (s, 9H), 1.33 (d, J=7.0 Hz, 3H), 1.02 (s, 9H); MS(ESI$^+$) m/z 745.5 (M+H)$^+$.

D) N$^5$—((S)-2-((S)-3,3-Dimethyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)-N$^1$-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-1H-indole-1,5-dicarboxamide To a solution of 1-(((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)carbamoyl)-1H-indole-5-carboxylic acid (100 mg, 0.134 mmol) in DMF (1.5 mL) at rt was added HATU (56.2 mg, 0.15 mmol) followed by tert-butyl ((S)-1-(((S)-1-((S)-7-amino-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (Compound F in Example 1) (83 mg, 0.13 mmol) and Hunig's base (150 uL). The reaction mixture was stirred at rt for 6 h and direct purification by preparative HPLC provided the coupling product. This coupling product was dissolved in CH$_2$Cl$_2$ (10 mL) and TFA (1 mL). After 1.5 h at rt, it was concentrated in vacuo and the residue was mixed with EtOAc and aq NaHCO$_3$, EtOAc layer was separated, washed with water, dried over MgSO$_4$ and here was added 3 mL of 4N HCl in dioxane and concentrated in vacuo, mixed with water and lyophilized to obtain the title compound 2 HCl salt (35 mg, 0.027 mmol, 20% yield) as a white solid. MS(ESI$^+$) m/z 1147.9 (M+H)$^+$.

Examples 50 to 54

The following Examples were prepared according to the procedure for the synthesis of Examples 47 to 49 described above incorporating various R$^4$ amines.

| Ex. No. | Structure | Name | LCMS (M + H) |
|---|---|---|---|
| 50 | 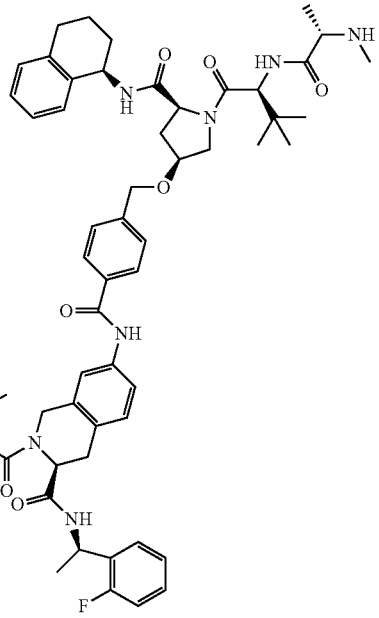 | (S)-2-((S)-3,3-Dimethyl-2-((S)-2-(methylamino)propanamido)butanoyl)-7-(4-((((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)oxy)methyl)benzamido)-N-((R)-1-(2-fluorophenyl)ethyl)-1,2,3,4-tetrahydroisoquinoline-3-carboxamide | 1086.5 |
| 51 | 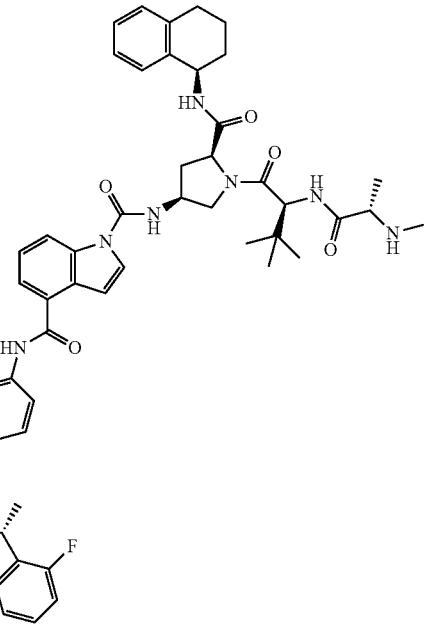 | N$^4$-((S)-2-((S)-3,3-Dimethyl-2-((S)-2-(methylamino)propanamido)butanoyl)-3-(((R)-1-(2-fluorophenyl)ethyl)carbamoyl)-1,2,3,4-tetrahydroisoquinolin-7-yl)-N$^1$-(3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-1H-indole-1,4-dicarboxamide | 1138.9 |

| Ex. No. | Structure | Name | LCMS (M + H) |
|---|---|---|---|
| 52 | 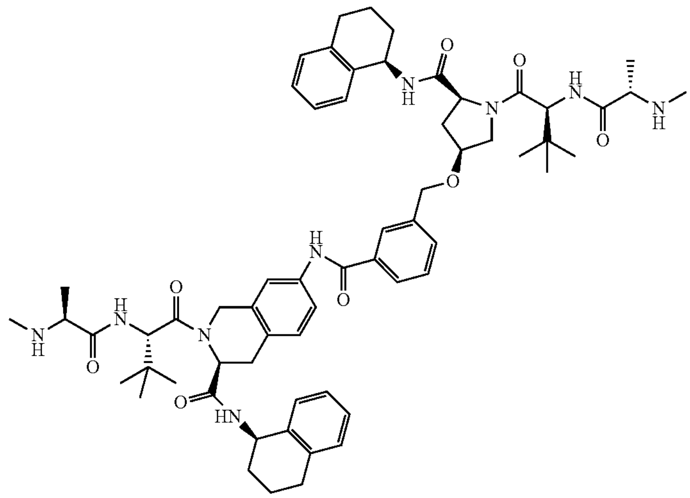 | (S)-2-((S)-3,3-Dimethyl-2-((S)-2-(methylamino)propanamido)butanoyl)-7-(3-((((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)oxy)methyl)benzamido)-N-((R)-1,2,3,4-tetrahydronaphthalen-1-yl)-1,2,3,4-tetrahydroisoquinoline-3-carboxamide | 1094.8 |
| 53 | 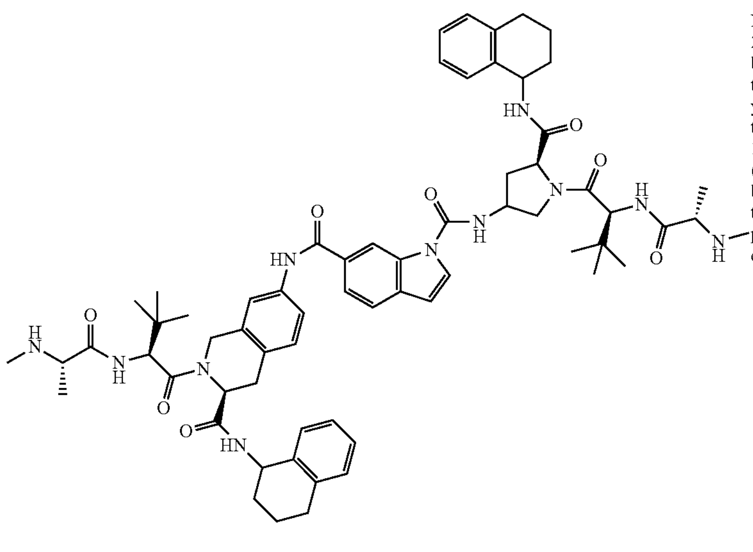 | N⁶-((3S)-2-((S)-3,3-Dimethyl-2-((S)-2-(methylamino)propanamido)butanoyl)-3-((1,2,3,4-tetrahydronaphthalen-1-yl)carbamoyl)-1,2,3,4-tetrahydroisoquinolin-7-yl)-N¹-((5S)-1-((S)-3,3-dimethyl-2-((S)-2-(methylamino)propanamido)butanoyl)-5-((1,2,3,4-tetrahydronaphthalen-1-yl)carbamoyl)pyrrolidin-3-yl)-1H-indole-1,6-dicarboxamide | 1146.8 |

| Ex. No. | Structure | Name | LCMS (M + H) |
|---|---|---|---|
| 54 | 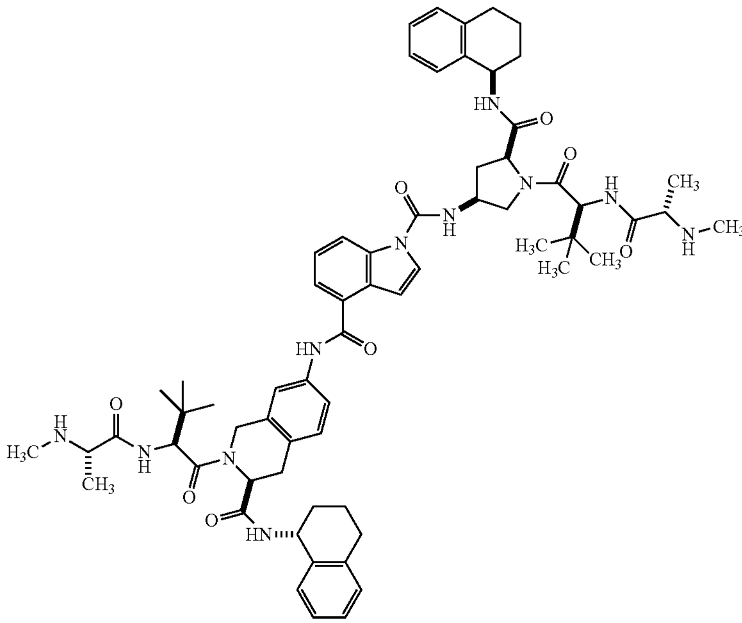 | N⁴-((S)-2-((S)-3,3-Dimethyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)-N¹-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-1H-indole-1,4-dicarboxamide | 1146.9 |

Example 55

N¹-((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-N⁴—((S)-2-((R)-3-methyl-2-((S)-2-(methylamino)propanamido)-3-(methylthio)butanoyl)-3-(((R)-1,2,3,4-tetrahydronaphthalen-1-yl)carbamoyl)-1,2,3,4-tetrahydroisoquinolin-7-yl)terephthalamide A) (S)-tert-Butyl 7-nitro-3-(((R)-1,2,3,4-tetrahydronaphthalen-1-yl)carbamoyl)-3,4-dihydroisoquinoline-2(1H)-carboxylate To a solution of (S)-2-(tert-butoxycarbonyl)-7-nitro-1,2,3,4-tetrahydroisoquinoline-3-carboxylic acid (1.0 g, 3.1 mmol) in DMF (12 mL) was added EDC (0.89 g, 4.65 mmol) at 0° C. The reaction mixture was stirred at 0° C. for 10 min, and treated with HOAt (0.42 g, 3.1 mmol) and a solution of (R)-1,2,3,4-tetrahydronaphthalen-1-amine (0.50 g, 3.4 mmol) in DMF (2 mL) and DIEA (1.1 mL, 6.21 mmol) at 0° C. The resulting reaction mixture was stirred at rt for 1.5 h. The reaction mixture was diluted with ethyl acetate and brine. The organic layer was separated, washed with saturated aq. NaHCO$_3$ solution. The organic layer was separated and dried over MgSO$_4$. The filtrate was concentrated in vacuo. The residue was purified by flash chromatography (25% EtOAc/DCM) to afford the title compound as a light yellow solid (1.15 g, 82%). $^1$H NMR (CDCl$_3$) δ 8.20 (br. s., 1H), 8.00 (d, J=2.2 Hz, 1H), 7.49 (d, J=8.1 Hz, 1H), 7.14-6.97 (m, 3H), 5.93 (br. s., 1H), 4.97 (br. s., 1H), 4.83-4.40 (m, 2H), 3.57 (dd, J=15.6, 2.9 Hz, 1H), 3.15 (br. s., 1H), 2.73 (d, J=7.5 Hz, 2H), 2.13-1.94 (m, 2H), 1.85-1.71 (m, 1H), 1.64 (br. s., 1H), 1.48 (s, 9H); MS(ESI$^+$) m/z 452.1 (M+H)$^+$.

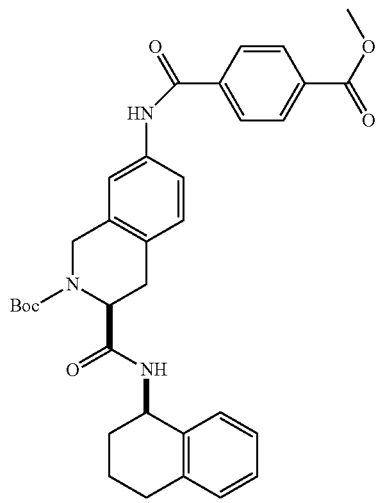

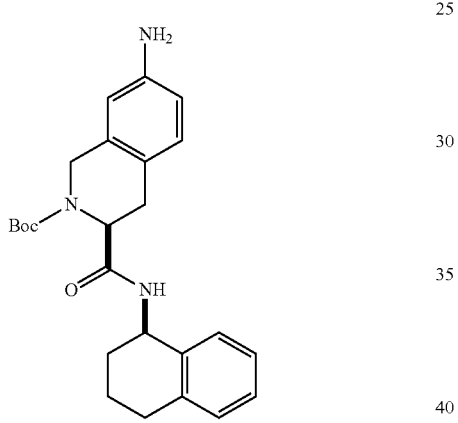

B) (S)-tert-Butyl 7-amino-3-(((R)-1,2,3,4-tetrahydronaphthalen-1-yl)carbamoyl)-3,4-dihydroisoquinoline-2(1H)-carboxylate To a solution of (S)-tert-butyl 7-nitro-3-(((R)-1,2,3,4-tetrahydronaphthalen-1-yl)carbamoyl)-3,4-dihydroisoquinoline-2(1H)-carboxylate (1.15 g, 2.55 mmol) in MeOH (15 mL) was added Pd—C (0.45 g, 0.64 mmol). The reaction mixture was evacuated and then filled with hydrogen balloon. The reaction mixture was hydrogenated for 2 h. The reaction mixture was filtered through a pad of CELITE®. The filtrate was concentrated in vacuo to give white solid as the title compound (1.0 g, 93%). $^1$H NMR (CDCl$_3$) δ 8.03 (s, 0.5H), 7.14-6.92 (m, 4H), 6.66 (d, J=7.7 Hz, 1H), 6.47 (s, 1H), 5.98-5.79 (m, 1.5H), 4.96 (br. s., 1H), 4.72-4.19 (m, 3H), 3.68 (br. s., 2H), 3.38-3.28 (m, 1H), 2.78-2.61 (m, 2H), 2.14-1.98 (m, 1H), 1.88-1.71 (m, 2H), 1.62-1.52 (m, 2H), 1.48 (s, 9H); MS(ESI$^+$) m/z 422.3 (M+H)$^+$.

C) (S)-tert-Butyl 7-(4-(methoxycarbonyl)benzamido)-3-(((R)-1,2,3,4-tetrahydronaphthalen-1-yl)carbamoyl)-3,4-dihydroisoquinoline-2(1H)-carboxylate To a solution of 4-(methoxycarbonyl)benzoic acid (0.49 g, 2.7 mmol) in DMF (5 mL) was added HATU (1.31 g, 3.44 mmol). The reaction mixture was stirred at rt for 10 min, followed by addition of a solution of (S)-tert-butyl 7-amino-3-(((R)-1,2,3,4-tetrahydronaphthalen-1-yl)carbamoyl)-3,4-dihydroisoquinoline-2(1H)-carboxylate (1.0 g, 2.37 mmol) in DMF (5 mL) and DIEA (0.8 mL, 4.74 mmol) at ice bath temperature. The resulting reaction mixture was stirred at rt for 1 h. The reaction mixture was diluted with ethyl acetate and brine. The organic layer was separated and washed with saturated NaHCO$_3$ solution, and dried over MgSO$_4$. The filtrate was concentrated in vacuo. The residue was purified by flash chromatography (35% EtOAc/DCM) to afford the title compound as a white solid (1.2 g, 87%). $^1$H NMR (CDCl$_3$) δ 8.29-8.13 (m, 2H), 8.02-7.86 (m, 3H), 7.75-7.29 (m, 3H), 7.14-6.77 (m, 3H), 6.29-5.68 (m, 1H), 5.10-4.27 (m, 4H), 4.04-3.92 (m, 3H), 3.42 (d, J=15.2 Hz, 1H), 2.76-2.60 (m, 2H), 2.11-1.94 (m, 1H), 1.85-1.73 (m, 2H), 1.48 (s, 9H), 1.13 (d, J=6.8 Hz, 1H); MS(ESI$^+$) m/z 584.4 (M+H)$^+$.

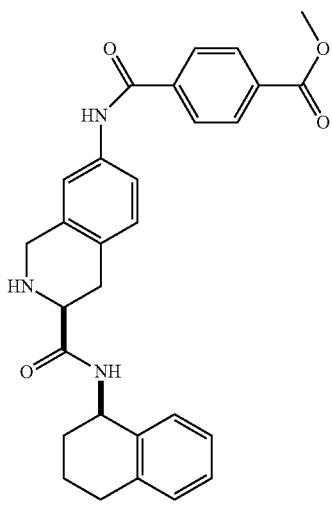

D) Methyl 4-(((S)-3-(((R)-1,2,3,4-tetrahydronaphthalen-1-yl)carbamoyl)-1,2,3,4-tetrahydroisoquinolin-7-yl)carbamoyl)benzoate To a solution of (S)-tert-butyl 7-(4-(methoxycarbonyl)benzamido)-3-(((R)-1,2,3,4-tetrahydronaphthalen-1-yl)carbamoyl)-3,4-dihydroisoquinoline-2(1H)-carboxylate (1.18 g, 2.02 mmol) in DCE (7 mL) was added TFA (2 mL, 26.0 mmol). The reaction mixture was stirred at rt for 1.5 h. The reaction mixture was concentrated in vacuo and to the residue was added saturated aq. NaHCO$_3$ solution to adjust its pH to 8. The resulting mixture was extracted with ethyl acetate. The organic layer was separated, washed with brine, and dried over MgSO$_4$. The filtrate was concentrated in vacuo to give the title compound as a light yellow solid (0.92 g, 94%). $^1$H NMR (DMSO-d$_6$) δ 10.32 (s, 1H), 8.17-8.01 (m, 5H), 7.58-7.41 (m, 2H), 7.23-7.03 (m, 5H), 4.99 (d, J=5.9 Hz, 1H), 3.95-3.80 (m, 5H), 3.48 (dd, J=9.5, 4.8 Hz, 1H), 2.97-2.59 (m, 5H), 1.95-1.65 (m, 4H); MS(ESI$^+$) m/z 484.4 (M+H)$^+$.

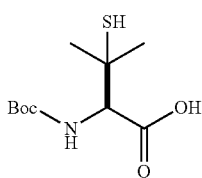 [SMILES: CC(C)(C)OC(=O)N[C@H](C(=O)O)C(C)(C)S]

E) (R)-2-((tert-Butoxycarbonyl)amino)-3-mercapto-3-methylbutanoic acid

To a suspension of (R)-2-amino-3-mercapto-3-methylbutanoic acid (8.0 g, 54 mmol) in 1,4-dioxane (90 mL) was added a solution of NaOH (4.72 g, 118 mmol) in water (45 mL). The solution turned clear. The reaction mixture was then cooled with an ice bath and di-t-butyldicarbonate (14.0 g, 64.3 mmol) was added dropwise. The reaction mixture was then stirred at rt for 20 h. After 2 h, a precipitate formed. The reaction mixture was extracted with ethyl acetate. The aqueous layer was acidified with 2N HCl solution to pH of 1. The resulting mixture was extracted with ethyl acetate (3×). The organic layer was separated and dried over MgSO$_4$. The filtrate was concentrated in vacuo to give viscous solid, which was dried under vacuum to give the title compound as a white solid (11.8 g, 88%). $^1$H NMR (DMSO-d$_6$) δ 6.90 (d, J=9.2 Hz, 1H), 4.07 (d, J=9.2 Hz, 1H), 3.57 (s, 1H), 3.00 (br. s., 1H), 1.40 (s, 15H); MS(ESI$^+$) m/z 194.1 (M-56) (M+H)$^+$.

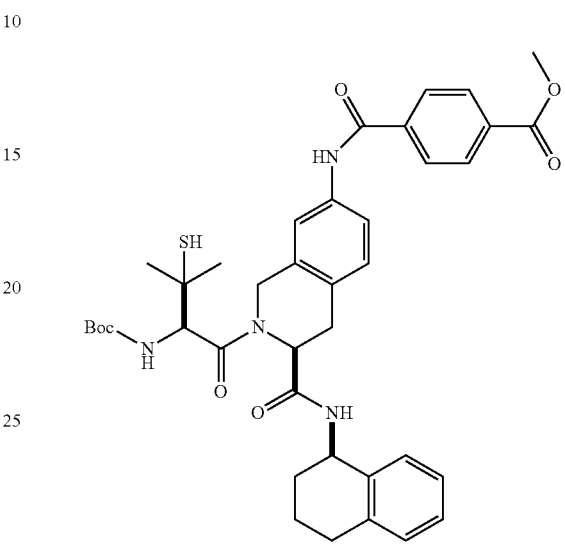

F) Methyl 4-(((S)-2-((R)-2-((tert-butoxycarbonyl)amino)-3-mercapto-3-methylbutanoyl)-3-(((R)-1,2,3,4-tetrahydronaphthalen-1-yl)carbamoyl)-1,2,3,4-tetrahydroisoquinolin-7-yl)carbamoyl)benzoate To a solution of (R)-2-((tert-butoxycarbonyl)amino)-3-mercapto-3-methylbutanoic acid (17 mg, 0.066 mmol) in DMF (0.5 mL) was added DMTMM (18 mg, 0.066 mmol). The reaction mixture was stirred at rt for 15 min, followed by addition of methyl 4-(((S)-3-(((R)-1,2,3,4-tetrahydronaphthalen-1-yl)carbamoyl)-1,2,3,4-tetrahydroisoquinolin-7-yl)carbamoyl)benzoate (20 mg, 0.041 mmol) and DIEA (0.02 mL, 0.12 mmol). The reaction mixture was stirred at rt for 8 days. The reaction mixture was purified by preparative HPLC. Fractions containing the product were combined, concentrated, and lyophilized to give the title compound as a white solid (18 mg, 61%). $^1$H NMR (DMSO-d$_6$) δ 10.50-10.36 (m, 1H), 8.15-7.99 (m, 4H), 7.92-7.73 (m, 1H), 7.68-7.49 (m, 1H), 7.30-7.15 (m, 1H), 7.12-6.83 (m, 4H), 6.60 (d, J=7.3 Hz, 1H), 5.16-4.66 (m, 4H), 3.90 (s, 3H), 3.19-2.94 (m, 2H), 2.66 (br. s., 2H), 1.88-1.51 (m, 4H), 1.49-1.21 (m, 16H); MS(ESI$^+$) m/z 715.5 (M+H)$^+$.

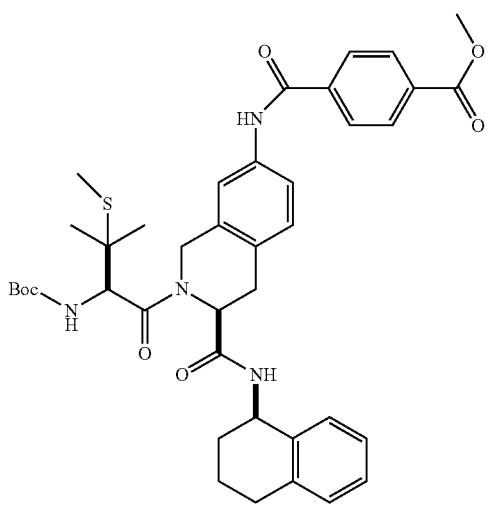

G) Methyl 4-(((S)-2-((R)-2-((tert-butoxycarbonyl)amino)-3-methyl-3-(methylthio)butanoyl)-3-(((R)-1,2,3,4-tetrahydronaphthalen-1-yl)carbamoyl)-1,2,3,4-tetrahydroisoquinolin-7-yl)carbamoyl)benzoate To a solution of methyl 4-(((S)-2-((R)-2-((tert-butoxycarbonyl)amino)-3-mercapto-3-methylbutanoyl)-3-(((R)-1,2,3,4-tetrahydronaphthalen-1-yl)carbamoyl)-1,2,3,4-tetrahydroisoquinolin-7-yl)carbamoyl)benzoate (60 mg, 0.084 mmol) in DCM (2 mL) was added iodomethane (0.11 mL, 1.7 mmol) and DIEA (0.03 mL, 0.17 mmol). The reaction mixture was stirred at rt for 30 min. and concentrated in vacuo to give the title compound as a white solid (61 mg, 98%). MS(ESI$^+$) m/z 729.5 (M+H)$^+$.

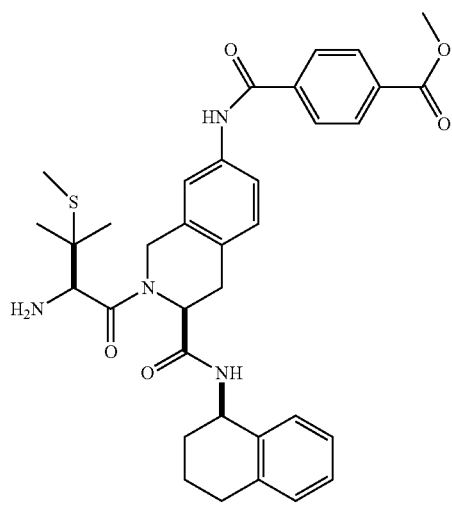

H) Methyl 4-(((S)-2-((R)-2-amino-3-methyl-3-(methylthio)butanoyl)-3-(((R)-1,2,3,4-tetrahydronaphthalen-1-yl)carbamoyl)-1,2,3,4-tetrahydroisoquinolin-7-yl)carbamoyl)benzoate To a solution of methyl 4-(((S)-2-((R)-2-((tert-butoxycarbonyl)amino)-3-methyl-3-(methylthio)butanoyl)-3-(((R)-1,2,3,4-tetrahydronaphthalen-1-yl)carbamoyl)-1,2,3,4-tetrahydroisoquinolin-7-yl)carbamoyl)benzoate (60 mg, 0.082 mmol) in DCM (2 mL) was added TFA (0.5 mL, 5.8 mmol). The reaction mixture was stirred at rt for 1 h. The reaction mixture was concentrated in vacuo to give the title compound TFA salt as a brown solid (60 mg, 98%) without purification. MS(ESI$^+$) m/z 629.4 (M+H)$^+$.

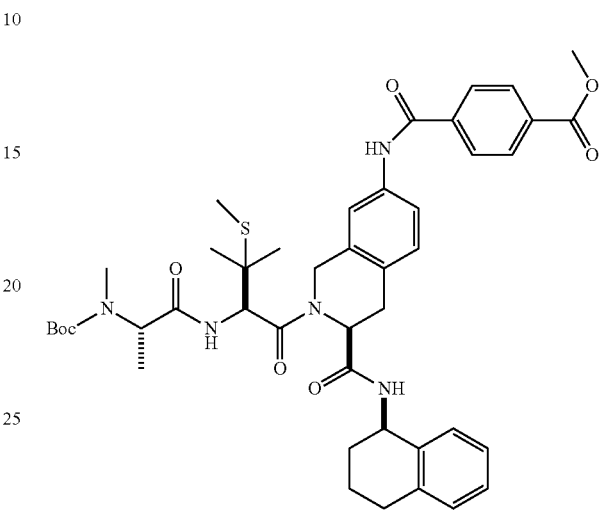

I) Methyl 4-(((S)-2-((R)-2-((S)-2-((tert-butoxycarbonyl)(methyl)amino)propanamido)-3-methyl-3-(methylthio)butanoyl)-3-(((R)-1,2,3,4-tetrahydronaphthalen-1-yl)carbamoyl)-1,2,3,4-tetrahydroisoquinolin-7-yl)carbamoyl)benzoate To a solution of (S)-2-((tert-butoxycarbonyl)(methyl)amino)propanoic acid (21 mg, 0.11 mmol) in DMF (1 mL) were added EDC (23 mg, 0.12 mmol) and HOAt (11 mg, 0.081 mmol). The reaction mixture was stirred at rt for 5 min, followed by addition of a solution of methyl 4-(((S)-2-((R)-2-((S)-2-((tert-butoxycarbonyl)(methyl)amino)propanamido)-3-methyl-3-(methylthio)butanoyl)-3-(((R)-1,2,3,4-tetrahydronaphthalen-1-yl)carbamoyl)-1,2,3,4-tetrahydroisoquinolin-7-yl)carbamoyl)benzoate in DMF (2.5 mL) and DIEA (0.06 mL, 0.32 mmol). The resulting mixture was stirred at rt for 1 h. The reaction mixture was diluted with ethyl acetate and brine. The organic layer was separated and washed with saturated NaHCO$_3$ solution, brine successively. The organic layer was separated and dried over MgSO$_4$. The filtrate was concentrated in vacuo and the crude product was used in the next step without further purification. MS(ESI$^+$) m/z 814.5 (M+H)$^+$.

171

J) 4-(((S)-2-(R-2-((S)-2-((tert-Butoxycarbonyl)(methyl)amino)propanamido)-3-methyl-3-(methylthio)butanoyl)-3-((R-1,2,3,4-tetrahydronaphthalen-1-yl)carbamoyl)-1,2,3,4-tetrahydroisoquinolin-7-yl)carbamoyl)benzoic acid

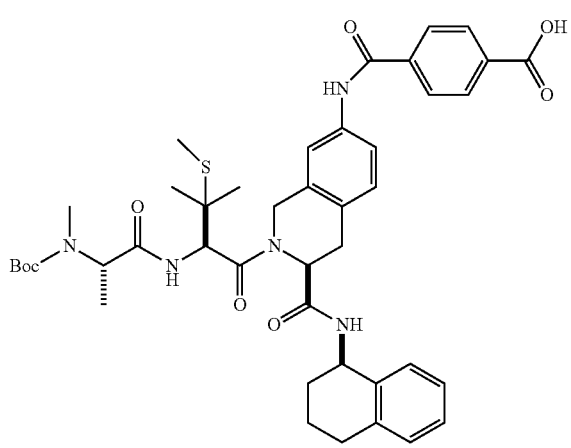

To a solution of the crude methyl 4-(((S)-2-(R-2-((S)-2-((tert-butoxycarbonyl)(methyl)amino)propanamido)-3-methyl-3-(methylthio)butanoyl)-3-((R-1,2,3,4-tetrahydronaphthalen-1-yl)carbamoyl)-1,2,3,4-tetrahydroisoquinolin-7-yl)carbamoyl)benzoate (60 mg, 0.074 mmol) in THF (1 mL) and MeOH (1 mL) was added 2 M LiOH solution (0.6 mL, 1.1 mmol). The reaction mixture was stirred at rt for 2 h and treated with 1N HCl solution until the pH of the solution was 1. The resulting mixture was extracted with ethyl acetate. The organic layer was separated and washed with saturated aq. $NaHCO_3$ solution and brine successively. The organic layer was separated and dried over $MgSO_4$. The filtrate was concentrated in vacuo to give the title compound as a light brown solid without purification. MS(ESI$^+$) m/z 800.5 (M+H)$^+$.

172

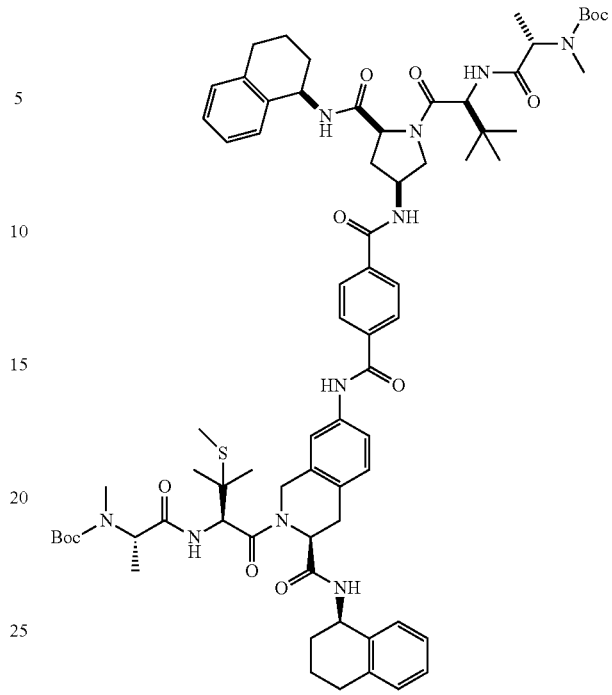

K) Intermediate I

To a solution of 4-(((S)-2-((R)-2-((S)-2-((tert-butoxycarbonyl)(methyl)amino)propanamido)-3-methyl-3-(methylthio)butanoyl)-3-4(R)-1,2,3,4-tetrahydronaphthalen-1-yl)carbamoyl)-1,2,3,4-tetrahydroisoquinolin-7-yl)carbamoyl)benzoic acid (50 mg, 0.063 mmol) in DMF (2 mL) was HATU (36 mg, 0.094 mmol). After 5 min, tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (44 mg, 0.078 mmol, Compound J in Example 1) and DIEA (0.03 mL, 0.13 mmol) were added to the reaction mixture. The reaction mixture was stirred at rt for 1.5 h. The reaction mixture was diluted with ethyl acetate and brine. The organic layer was concentrated in vacuo and the residue was purified by preparative HPLC. Fractions containing the desired product were combined, and concentrated to give the title compound as a white solid (20 mg, 24%). MS(ESI$^+$) m/z 1340.7 (M+H)$^+$.

L) $N^1$-((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-$N^4$—((S)-2-((R)-3-methyl-2-((S)-2-(methylamino)propanamido)-3-(methylthio)butanoyl)-3-(((R)-1,2,3,4-tetrahydronaphthalen-1-yl)carbamoyl)-1,2,3,4-tetrahydroisoquinolin-7-yl)terephthalamide To a solution of the above Intermediate I (20 mg, 0.015 mmol) in DCM (1.8 mL) was added TFA (0.5 mL, 6.49 mmol). The reaction mixture was stirred at rt for 1 h. The reaction mixture was concentrated in vacuo and the residue was lyophilized to give the title compound 2TFA salt as a white solid (14 mg, 94%). MS(ESI$^+$) m/z 1139.6 (M+H)$^+$.

Example 56

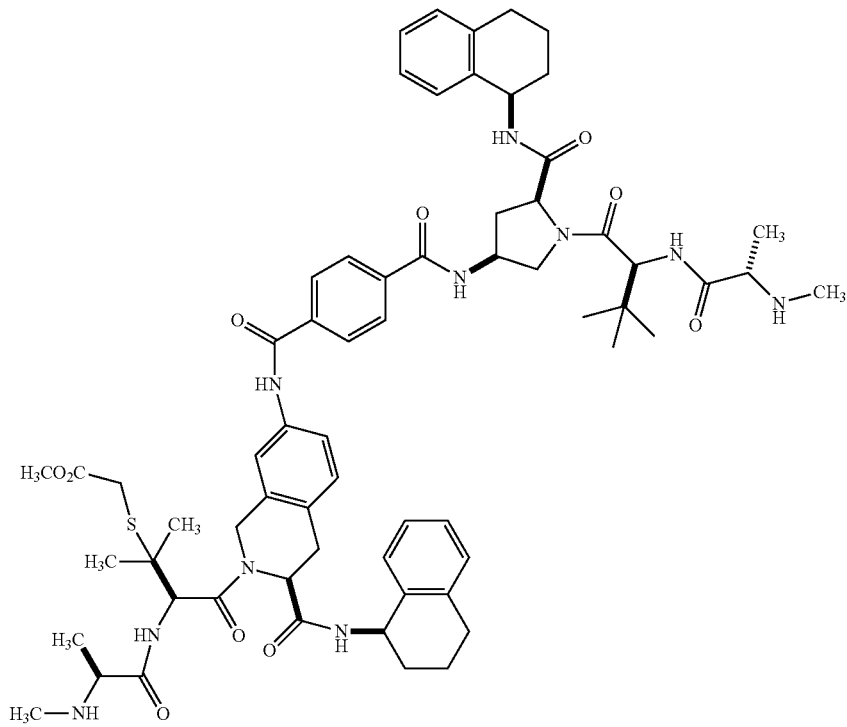

Methyl 2-(((R)-4-((S)-7-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzamido)-3-(((R)-1,2,3,4-tetrahydronaphthalen-1-yl)carbamoyl)-3,4-dihydroisoquinolin-2(1H)-yl)-2-methyl-3-((S)-2-(methylamino)propanamido)-4-oxobutan-2-yl)thio)acetate

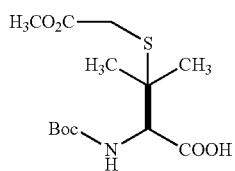

A) (R)-2-((tert-Butoxycarbonyl)amino)-3-((2-methoxy-2-oxoethyl)thio)-3-methylbutanoic acid To a solution of (R)-2-((tert-butoxycarbonyl)amino)-3-mercapto-3-methylbutanoic acid (1.00 g, 4.01 mmol) in DMF (12 mL) was added Hunig's base (1.6 mL) followed by methyl 2-bromoacetate (644 mg, 4.21 mmol) at rt. The reaction mixture was stirred at rt for 3.5 h, mixed with EtOAc and 1N HCl. The organic layer was separated, washed with water, dried over MgSO₄ and concentrated in vacuo to obtain the crude product (1.4 g). The resulting viscous material was purified by column chromatography on silica gel eluting with gradient of hexane in EtOA containing 0.5% HOAc to obtain the title compound (630 mg, 1.96 mmol, 49% yield) as a viscous material. $^1$H NMR (CDCl₃) δ 8.00 (br, 1H), 5.55 (m, 1H), 4.36 (m, 1H), 3.80 (s, 3H), 3.46 (m, 2H), 1.47 (s, 9H), 1.46 (s, 3H), 1.38 (s, 3H); MS(ESI⁺) m/z 322.2 (M+H)⁺.

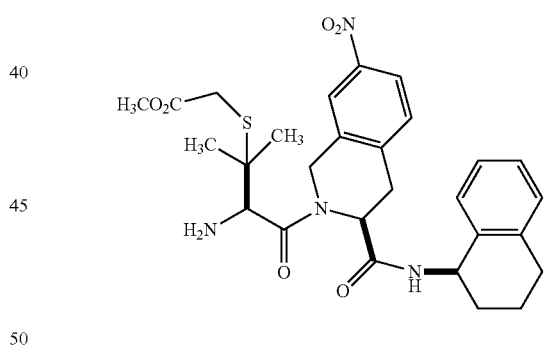

B) Methyl 2-(((R)-3-amino-2-methyl-4-((S)-7-nitro-3-(((R)-1,2,3,4-tetrahydronaphthalen-1-yl)carbamoyl)-3,4-dihydroisoquinolin-2(1H)-yl)-4-oxobutan-2-yl)thio)acetate To a solution of (R)-2-((tert-butoxycarbonyl)amino)-3-((2-methoxy-2-oxoethyl)thio)-3-methylbutanoic acid (604 mg, 1.88 mmol) in DMF (7 mL) at rt was added a solid of HATU (747 mg, 1.96 mmol). After 10 minutes, the mixture was treated with a solution of (S)-7-nitro-N—((R)-1,2,3,4-tetrahydronaphthalen-1-yl)-1,2,3,4-tetrahydroisoquinoline-3-carboxamide (Compound B in Example 1, 660 mg, 1.88 mmol) and Hunig's base (350 uL) in DMF (5 mL). The reaction mixture was stirred at rt for 4 h and diluted with EtOAc and water. The organic layer was separated, washed with 1N HCl, aq. NaHCO₃ and brine, dried over MgSO₄ and concentrated to obtain 1.4 g of crude product. The crude material was purified by column chromatography on silica gel eluting with gradient of hexane in EtOAc to obtain the title compound (866 mg, 1.32 mmol, 77% yield) as a yellow solid. $^1$H NMR (CDCl$_3$) δ 8.05-8.22 (m, 2H), 6.89-7.52 (m, 5H), 6.34 (d, J=7.5 Hz, 1H), 4.70-5.60 (m, 6H), 3.68 (s, 3H), 2.69-3.79 (m, 6H), 1.70-2.15 (m, 4H), 1.42 (s, 9H), 1.33 (s, 3H), 1.23 (s, 3H); MS(ESI$^+$) m/z 655.4 (M+H)$^+$.

The above intermediate was mixed with CH$_2$Cl$_2$ (10 mL) and TFA (3.5 mL) at rt. After 1 h it was concentrated in vacuo, and the residue was co-evaporated again with toluene to obtain the TFA salt of the title compound (880 mg, 1.32 mmol, 77% yield) as a yellow solid. $^1$H NMR (CD$_3$OD) δ 8.31 (s, 1H), 8.20 (dd, J=2.2 Hz, 8.1 Hz, 1H), 7.54 (d, J=8.4 Hz, 1H), 7.05-7.28 (m, 5H), 4.79-5.20 (m, 6H), 3.81 (s, 3H), 3.29-3.79 (m, 5H), 1.70-2.10 (m, 4H), 1.81 (s, 3H), 1.48 (s, 3H); MS(ESI$^+$) m/z 555.4 (M+H)$^+$.

at rt was added a solid of HATU (575 mg, 1.51 mmol). After 5 minutes, the mixture was treated with a solution of methyl 2-(((R)-3-amino-2-methyl-4-((S)-7-nitro-3-(((R)-1,2,3,4-tetrahydronaphthalen-1-yl)carbamoyl)-3,4-dihydroisoquinolin-2(1H)-yl)-4-oxobutan-2-yl)thio)acetate, TFA (880 mg, 1.32 mmol) and Hunig's base (575 μL, 3.29 mmol) in DMF (5 mL). The reaction mixture was stirred at rt for 1 h and diluted with EtOAc and water. The organic layer was separated, washed successively with water, 1N HCl and aq. NaHCO$_3$, dried over MgSO$_4$ and concentrated to obtain 1.3 g of crude product. The resulting viscous material was purified by column chromatography on silica gel eluting with gradient of hexane in EtOAc to obtain the title compound (840 mg, 1.14 mmol, 86% yield) as a light yellow solid. MS(ESI$^+$) m/z 740.5 (M+H)$^+$.

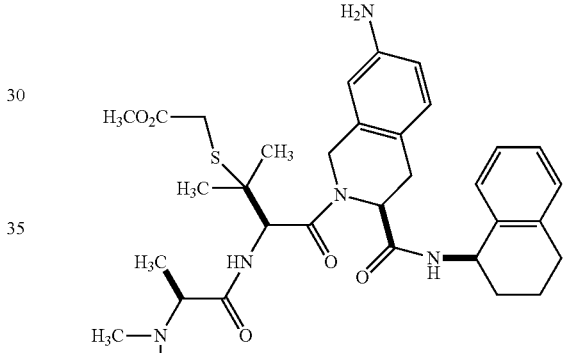

D) (6S,9R)-Methyl 9-((S)-7-amino-3-(((R)-1,2,3,4-tetrahydronaphthalen-1-yl)carbamoyl)-1,2,3,4-tetrahydroisoquinoline-2-carbonyl)-2,2,5,6,10,10-hexamethyl-4,7-dioxo-3-oxa-11-thia-5,8-diazatridecan-13-oate

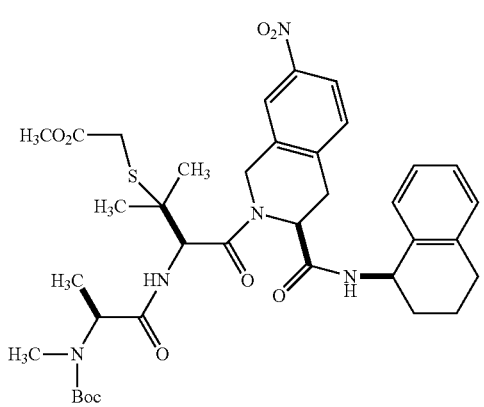

C) (6S,9R)-Methyl 2,2,5,6,10,10-hexamethyl-9-((S)-7-nitro-3-(((R)-1,2,3,4-tetrahydronaphthalen-1-yl)carbamoyl)-1,2,3,4-tetrahydroisoquinoline-2-carbonyl)-4,7-dioxo-3-oxa-11-thia-5,8-diazatridecan-13-oate To a solution of (S)-2-((tert-butoxycarbonyl)(methyl)amino)propanoic acid (294 mg, 1.45 mmol) in DMF (7 mL)

The coupled product obtained in step C was mixed with MeOH (30 mL) and 20% Pd(OH)$_2$/C (210 mg). The reaction mixture was stirred at rt for 3 h under 1 atm of H$_2$. After 3 h, a small amount of toluene was added and the reaction mixture was, stirred for 10 minutes. The solid was filtered and the filtrate was concentrated in vacuo to obtain the title compound (782 mg, 1.10 mmol, 84% yield) as a white solid. MS(ESI$^+$) m/z 710.5 (M+H)$^+$.

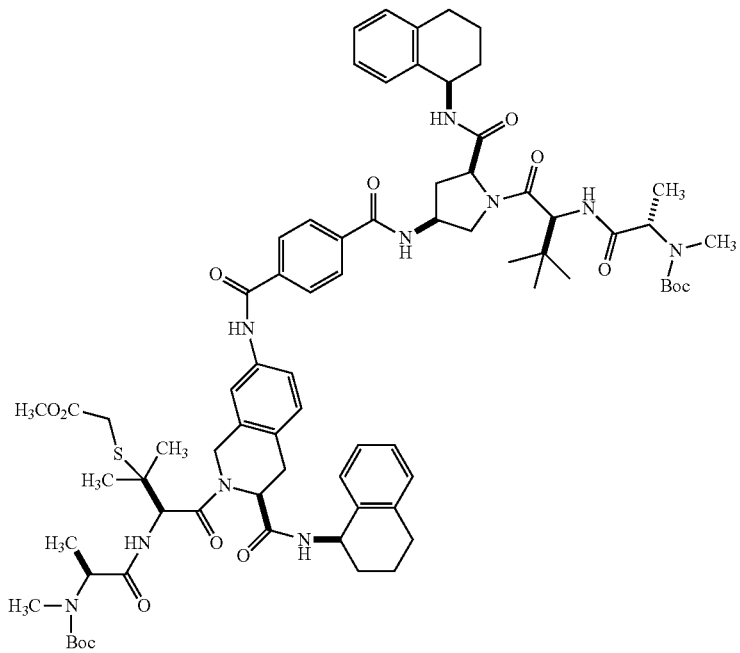

E) (6S,9R)-Methyl 9-((S)-7-(4-(((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)carbamoyl)benzamido)-3-(((R)-1,2,3,4-tetrahydronaphthalen-1-yl)carbamoyl)-1,2,3,4-tetrahydroisoquinoline-2-carbonyl)-2,2,5,6,10,10-hexamethyl-4,7-dioxo-3-oxa-11-thia-5,8-diazatridecan-13-oate To a solution of 4-(((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)carbamoyl)benzoic acid (340 mg, 0.48 mmol, Compound E in Example 2) in DMF (4 mL) at rt was added HATU (211 mg, 0.55 mmol). After 5 minutes, the mixture was treated with a solution of (6S,9R)-methyl 9-((S)-7-amino-3-(((R)-1,2,3,4-tetrahydronaphthalen-1-yl)carbamoyl)-1,2,3,4-tetrahydroisoquinoline-2-carbonyl)-2,2,5,6,10,10-hexamethyl-4,7-dioxo-3-oxa-11-thia-5,8-diazatridecan-13-oate (342 mg, 0.48 mmol) and Hunig's Base (126 µL, 0.72 mmol) in DMF (4 mL). The reaction mixture was stirred at rt for 1 h and diluted with EtOAc and water. The organic layer was separated, washed successively with water, 1N HCl and aq. NaHCO$_3$, dried over MgSO$_4$ and concentrated. The residue was purified by preparative HPLC to obtain the title compound (285 mg, 0.20 mmol, 42.3% yield) as a white solid. MS(ESI$^+$) m/z 1398.1 (M+H)$^+$.

F) Methyl 2-(((R)-4-((S)-7-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzamido)-3-(((R)-1,2,3,4-tetrahydronaphthalen-1-yl)carbamoyl)-3,4-dihydroisoquinolin-2(1H)-yl)-2-methyl-3-((S)-2-(methylamino)propanamido)-4-oxobutan-2-yl)thio) acetate A mixture of (6S,9R)-methyl 9-((S)-7-(4-(((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)carbamoyl)benzamido)-3-(((R)-1,2,3,4-tetrahydronaphthalen-1-yl)carbamoyl)-1,2,3,4-tetrahydroisoquinoline-2-carbonyl)-2,2,5,6,10,10-hexamethyl-4,7-dioxo-3-oxa-11-thia-5,8-diazatridecan-13-oate (5 mg, 3.6 µmol) in CH$_2$Cl$_2$ (1.5 mL) and 4N HCl in dioxane (0.5 mL) was stirred at rt for 1 h. The reaction mixture was concentrated in vacuo and the residue was mixed with water and lyophilized to obtain the title compound as the HCl salt (white solid, 4 mg, 3.0 µmol, 84% yield). MS(ESI$^+$) m/z 1198.8 (M+H)$^+$.

Example 57
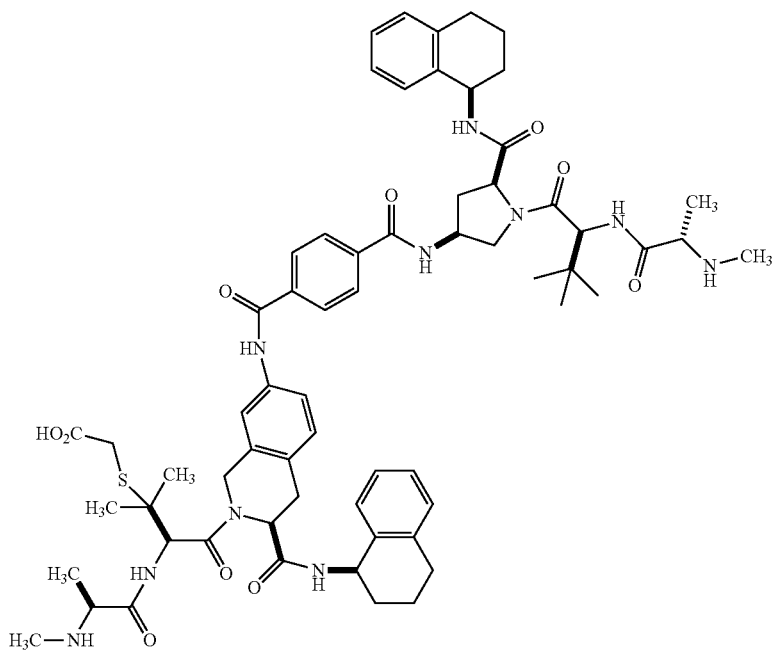
2-(((R)-4-((S)-7-(4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzamido)-3-(((R)-1,2,3,4-tetrahydronaphthalen-1-yl)carbamoyl)-3,4-dihydroisoquinolin-2(1H)-yl)-2-methyl-3-((S)-2-(methylamino)propanamido)-4-oxobutan-2-yl)thio)acetic acid
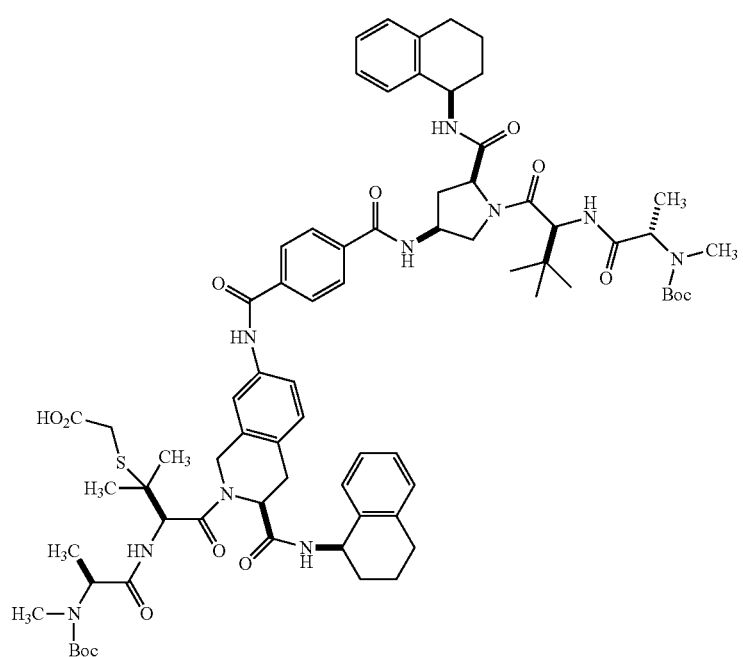

A) (6S,9R)-9-((S)-7-(4-(((3S,5S)-1-((S)-2-((S)-2-((tert-Butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)carbamoyl)benzamido)-3-(((R)-1,2,3,4-tetrahydronaphthalen-1-yl)carbamoyl)-1,2,3,4-tetrahydroisoquinoline-2-carbonyl)-2,2,5,6,10,10-hexamethyl-4,7-dioxo-3-oxa-11-thia-5,8-diazatridecan-13-oic acid Methyl 2-(((R)-4-(((S)-7-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzamido)-3-(((R)-1,2,3,4-tetrahydronaphthalen-1-yl)carbamoyl)-3,4-dihydroisoquinolin-2(1H)-yl)-2-methyl-3-((S)-2-(methylamino)propanamido)-4-oxobutan-2-yl)thio)acetate (Example 56, 0.58 g, 0.48 mmol) was mixed with MeOH (15 mL) and LiOH (450 mg) in H$_2$O (4 mL) and the reaction mixture was stirred at rt for 3 h. Most of the methanol was removed in vacuo, and the residue was mixed with EtOAc and 1N HCl. The organic layer was separated, washed with water, dried over MgSO$_4$ and concentrated in vacuo to obtain the title compound (275 mg, 0.20 mmol, 41.3% yield) as a white solid. MS(ESI$^+$) m/z 1382.7 (M+H)$^+$.

B) 2-(((R)-4-((S)-7-(4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzamido)-3-(((R)-1,2,3,4-tetrahydronaphthalen-1-yl)carbamoyl)-3,4-dihydroisoquinolin-2(1H)-yl)-2-methyl-3-((S)-2-(methylamino)propanamido)-4-oxobutan-2-yl)thio) acetic acid A mixture of the acid obtained in step A (15 mg, 10.84 μmol) in CH$_2$Cl$_2$ (1.5 mL) and 4 N HCl in dioxane (0.5 mL) was stirred at rt for 1 h. The reaction mixture was concentrated in vacuo and the residue was mixed with water and lyophilized to obtain the title compound as the HCl salt (white solid, 13 mg, 9.8 μmol, 91% yield). MS(ESI$^+$) m/z 1184.9 (M+H)$^+$.

Example 58

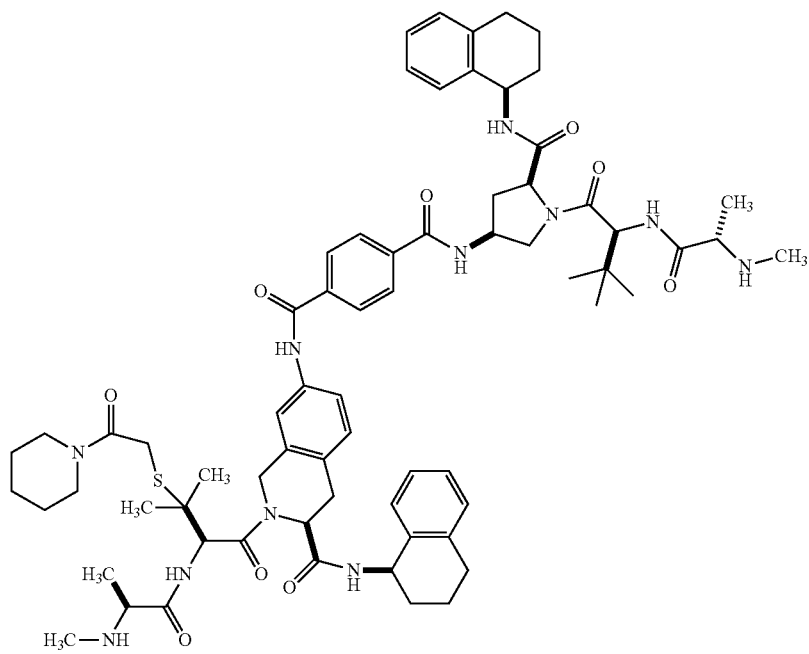

N¹-((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-N⁴—((S)-2-((R)-3-methyl-2-((S)-2-(methylamino)propanamido)-3-((2-oxo-2-(piperidin-1-yl)ethyl)thio)butanoyl)-3-(((R)-1,2,3,4-tetrahydronaphthalen-1-yl)carbamoyl)-1,2,3,4-tetrahydroisoquinolin-7-yl)terephthalamide 3,4-tetrahydroisoquinoline-2-carbonyl)-2,2,5,6,10,10-hexamethyl-4,7-dioxo-3-oxa-11-thia-5,8-diazatridecan-13-oic acid (27 mg, 0.02 mmol, Compound A of Example 57) in DMF (0.7 mL) at rt was added HATU (8.90 mg, 0.02 mmol). Piperidine was added (9.97 mg, 0.117 mmol) at rt. The resulting mixture was stirred for 30 minutes directly purified by preparative HPLC to provide the title compound. MS(ESI⁺) m/z 1451.3 (M+H)⁺.

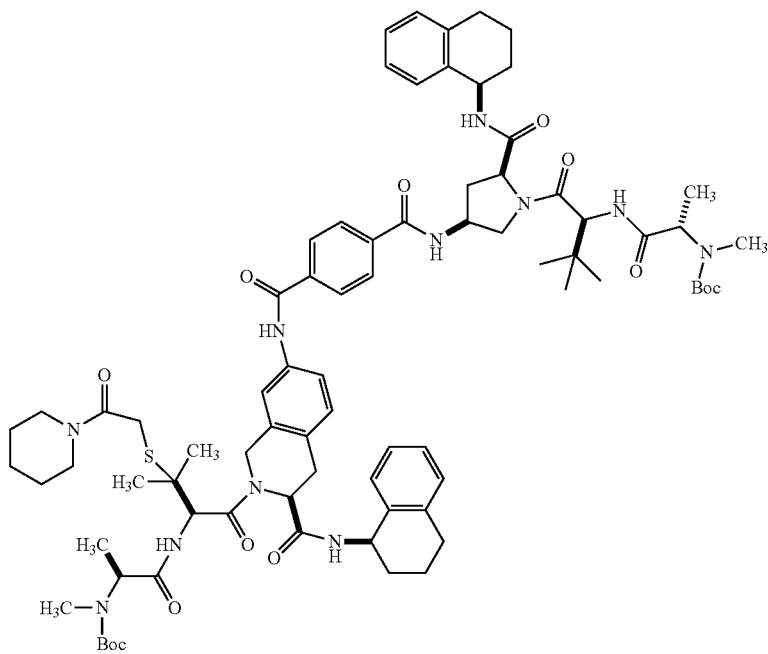

A) N¹-((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-N⁴—((S)-2-((R)-3-methyl-2-((S)-2-(methylamino)propanamido)-3-((2-oxo-2-(piperidin-1-yl)ethyl)thio)butanoyl)-3-(((R)-1,2,3,4-tetrahydronaphthalen-1-yl)carbamoyl)-1,2,3,4-tetrahydroisoquinolin-7-yl)terephthalamide, dihydrochloride salt To a solution of (6S,9R)-9-((S)-7-(4-(((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)carbamoyl)benzamido)-3-(((R)-1,2,3,4-tetrahydronaphthalen-1-yl)carbamoyl)-1,2, B) N¹-((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-N⁴—((S)-2-((R)-3-methyl-2-((S)-2-(methylamino)propanamido)-3-((2-oxo-2-(piperidin-1-yl)ethyl)thio)butanoyl)-3-(((R)-1,2,3,4-tetrahydronaphthalen-1-yl)carbamoyl)-1,2,3,4-tetrahydroisoquinolin-7-yl)terephthalamide, dihydrochloride salt The intermediate obtained in step A was mixed with CH₂Cl₂ (3 mL) and 4N HCl in dioxane (0.7 mL) at rt. The reaction mixture was stirred at rt for 1 h, concentrated in vacuo and the residue was mixed with water and lyophilized to obtain the HCl salt of the title compound (22 mg, 0.016 mmol, 81% yield) as a white solid. MS(ESI⁺) m/z 1251.1 (M+H)⁺.

Examples 59 to 66

The following Examples were prepared according to the procedure for the synthesis of Examples 58 described above.

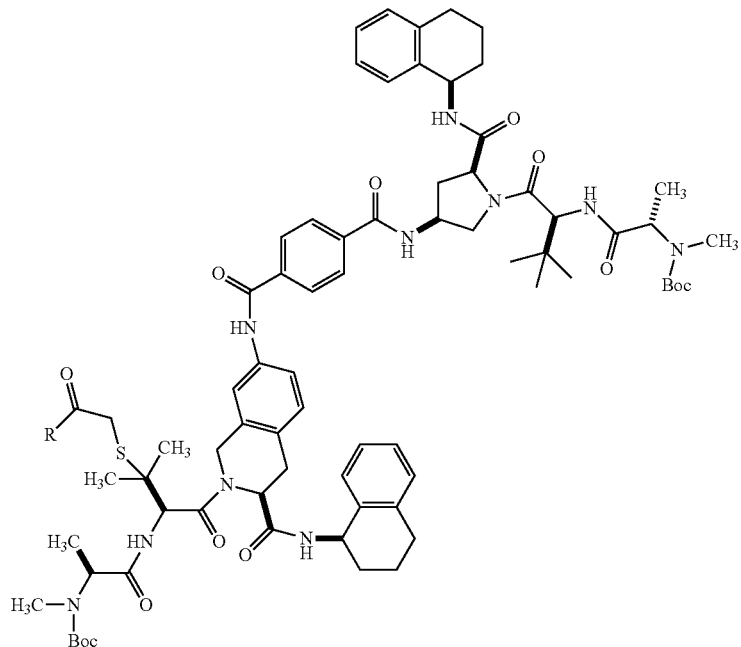

| Ex. No. | R | Name | LCMS (M + H) |
|---|---|---|---|
| 59 | HO—CH₂CH₂—N(CH₃)— | N¹-((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-N⁴-((S)-2-((R)-3-((2-((2-hydroxyethyl)(methyl)amino)-2-oxoethyl)thio)-3-methyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)terephthalamide | 1241.1 |
| 60 | thiazol-2-yl-NH— | N¹-((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-N⁴-((S)-2-((R)-3-methyl-2-((S)-2-(methylamino)propanamido)-3-((2-oxo-2-(thiazol-2-ylamino)ethyl)thio)butanoyl)-3-(((R)-1,2,3,4-tetrahydronaphthalen-1-yl)carbamoyl)-1,2,3,4-tetrahydroisoquinolin-7-yl)terephthalamide | 1266.2 |
| 61 | morpholino— | N¹-((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-N⁴-((S)-2-((R)-3-methyl-2-((S)-2-(methylamino)propanamido)-3-((2-morpholino-2-oxoethyl)thio)butanoyl)-3-(((R)-1,2,3,4-tetrahydronaphthalen-1-yl)carbamoyl)-1,2,3,4-tetrahydroisoquinolin-7-yl)terephthalamide | 1254.1 |
| 62 | 3-F-C₆H₄-CH₂-N(CH₃)— | N¹-((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-N⁴-((S)-2-((R)-3-((2-((3-fluorobenzyl)(methyl)amino)-2-oxoethyl)thio)-3-methyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)terephthalamide | 1306.0 |

-continued

| Ex. No. | R | Name | LCMS (M + H) |
|---|---|---|---|
| 63 | HO~~~N(H)~~~ | N¹-((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-N⁴-((S)-2-((R)-3-((2-((2-hydroxyethyl)amino)-2-oxoethyl)thio)-3-methyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)terephthalamide | 1227.6 |
| 64 | (CH₃)₂N~~~ | N¹-((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-N⁴-((S)-2-((R)-3-((2-(dimethylamino)-2-oxoethyl)thio)-3-methyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)terephthalamide | 1211.6 |
| 65 | HO-CH₂-CH(CH₂OH)-NH~~~ | N¹-((S)-2-((R)-3-((2-((1,3-Dihydroxypropan-2-yl)amino)-2-oxoethyl)thio)-3-methyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)-N4-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)terephthalamide | 1257.6 |
| 66 | HO-CH₂-C(CH₂OH)(CH₂OH)-NH~~~ | N¹-((S)-2-((R)-3-((2-((1,3-Dihydroxy-2-(hydroxymethyl)propan-2-yl)amino)-2-oxoethyl)thio)-3-methyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)-N⁴-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)terephthalamide | 1287.6 |

Examples 67 and 68

The following Examples were prepared according to the procedure for the synthesis of Examples 55 described above.

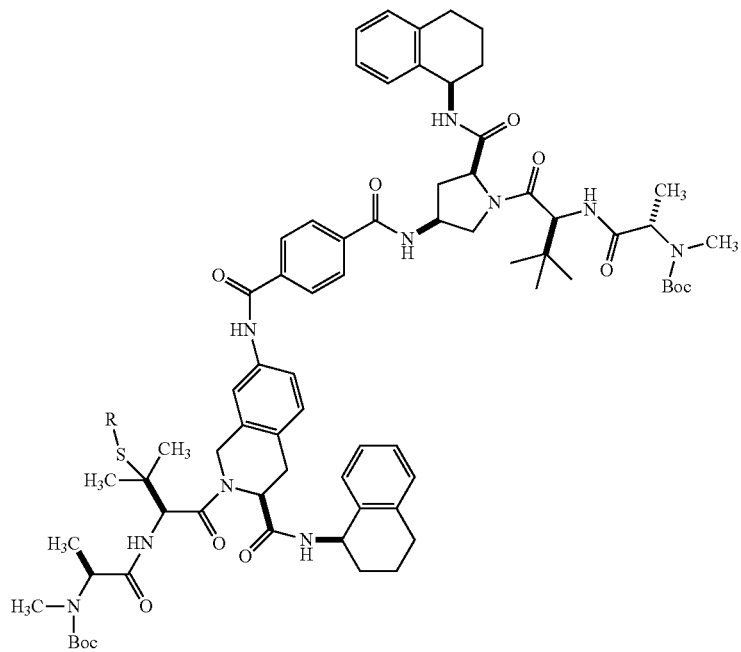

| Ex. No. | R | Name | LCMS (M + H) |
|---|---|---|---|
| 67 | HO~~~ | N¹-((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-N⁴-((S)-2-((R)-3-((2-hydroxyethyl)thio)-3-methyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)terephthalamide | 1170.5 |
| 68 | [tert-butyl oxazole CH₂ group] | N¹-((S)-2-((R)-3-(((5-(tert-Butyl)oxazol-2-yl)methyl)thio)-3-methyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)-N⁴-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)terephthalamide | 1263.6 |

Evaluation of Biological Activity

Exemplary compounds were tested for inhibition of XIAP BIR3, XIAP BIR2 and/or XIAP BIR2-3 activity. Experimental procedures and results are provided below.

A. XIAP-BIR3 SMAC Peptide Fluorescence Polarization Assay (FPA)

Assays were performed in black, flat-bottom, 384-well plates. The final assay volume was 50 µL prepared from additions of N-His-Tb-BIR3 (241-356, XIAP), fluoresceinated modified SMAC peptide, and test compounds in assay buffer consisting of 20 mM Sodium Phosphate, 1 mM EDTA, 50 mM NaCl, and 0.05% PLURONIC® F68. The reaction was incubated at room temperature for 60 minutes and fluorescence polarization of the reaction was detected on the LJL Plate Reader. Inhibition data were calculated from mP values generated by the no protein control reactions for 100% inhibition and vehicle-only reactions for 0% inhibition. The final concentration of reagents in the assay was 130 nM N-His-Tb-BIR3 (241-356, XIAP), 1.4 nM fluoresceinated modified SMAC peptide, and 1% DMSO. Dose response curves were generated to determine the concentration required for inhibiting 50% of polarization activity ($IC_{50}$). Compounds were dissolved at 10 mM in dimethylsulfoxide (DMSO) and evaluated at eleven concentrations. $IC_{50}$ values were derived by non-linear regression analysis.

B. XIAP-BIR3/SMAC Homogeneous Time Resolved Fluorescence (HTRF) Assay

Assays were performed in black, flat-bottom, 384-well plates. The final assay volume was 50 µL prepared from additions of His-BIR3 (241-356, XIAP), fluorescein labeled SMAC peptide, and test compounds in assay buffer consisting of 20 mM Sodium Phosphate, 1 mM EDTA, 50 mM NaCl, 50 µg/ml BSA, and 0.05% PLURONIC® F68. The reaction was incubated at room temperature for 60 minutes, following which 10 µl of mouse anti-6× His-terbium labeled Fab (Medarex, Cis-bio) was added to the reaction (40 µl) for an additional 30 minute incubation. The HTRF signal, ratio of fluorescence intensities at emission wavelengths for fluorescein acceptor (520 nm) and terbium donor (615 nm), the 520/615 ratio, generated by the reaction was then measured on the Envision Plate Reader Inhibition data were calculated from the 520/615 ratio generated by the no protein control reactions for 100% inhibition and vehicle-only reactions for 0% inhibition. The final concentration of reagents in the assay was 1 nM N-His-BIR3(241-356, XIAP), 5 nM fluorescein labeled SMAC peptide, 0.25 nM anti-His-Tb-Fab, and 0.1% DMSO. Dose response curves were generated to determine the concentration required for inhibiting 50% of the HTRF signal ($IC_{50}$). Compounds were dissolved at 3 mM in dimethylsulfoxide (DMSO) and evaluated at eleven serially diluted concentrations. $IC_{50}$ and $K_i$ values were derived by non-linear regression analysis.

C. XIAP-BIR2/SMAC Peptide AlphaScreen Assay

Assays were performed in white, flat-bottom, 384-well ProxiPlates (Perkin Elmer). The final assay volume was 10 µL prepared from additions of His-BIR2 (124-240/C202A/C213G), Biotinylated SMAC peptide, and test compounds in assay buffer consisting of 25 mM Hepes, 100 mM NaCl, 0.1% BSA, and 5 mM $CaCl_2$. The reaction was incubated at room temperature for 60 minutes. After 60 minutes, 2.5 µL of AlphaScreen detection reagent (Perkin Elmer) was added to the reaction mixture and incubated at room temperature in the dark for 120 minutes. The AlphaScreen signal generated by the reaction was detected on the Envision Plate Reader Inhibition data were calculated from an AlphaScreen signal generated by the no protein control reactions for 100% inhibition and vehicle-only reactions for 0% inhibition. The final concentration of reagents in the assay was 50 nM His-BIR2(124-240/C202A/C213G), 50 nM Biotinylated SMAC peptide, 4 µg/mL AlphaScreen detection reagents, and 0.5% DMSO. Dose response curves were generated to determine the concentration required for inhibiting 50% of the activity ($IC_{50}$). Compounds were dissolved at 10 mM in dimethylsulfoxide (DMSO) and evaluated at eleven concentrations. $IC_{50}$ values were derived by non-linear regression analysis.

D. XIAP-BIR2-3 Dimeric SMAC Peptide Homogeneous Time Resolved Fluorescence (HTRF) Assay Assays were performed in black, flat-bottom, 384-well plates. The final assay volume was 50 µL prepared from additions of His-BIR2-3 (125-356, C202A/C213G, XIAP), fluorescein labeled dimeric SMAC peptide, and test compounds in assay buffer consisting of 20 mM Sodium Phosphate, 1 mM EDTA, 50 mM NaCl, 50 µg/ml BSA, and 0.05% PLURONIC® F68. The reaction was incubated at room temperature for 60 minutes, following which 10 µl of mouse anti-6× His-Tb IgG (Medarex, Cis-bio) was added to the reaction (40 µl) for an additional 30 minute incubation. The HTRF signal, ratio of fluorescence intensities at emission wavelengths for fluorescein acceptor (520 nm) and terbium donor (615 nm), the 520/615 ratio, generated by the reaction was then measured on the Envision Plate Reader Inhibition data were calculated from the 520/615 ratio generated by the no protein control reactions for 100% inhibition and vehicle-only reactions for 0% inhibition. The final concentration of reagents in the assay was 0.5 nM N-His-BIR2-3(125-356, C202A/C213G, XIAP), 20 nM fluorescein labeled dimeric SMAC peptide, 0.25 nM anti-His-Tb-Fab, and 0.1% DMSO. Dose response curves were generated to determine the concentration required for inhibiting 50% of the HTRF signal ($IC_{50}$). Compounds were dissolved at 3 mM in dimethylsulfoxide (DMSO) and evaluated at eleven serially diluted concentrations. $IC_{50}$ and $K_i$ values were derived by non-linear regression analysis.

Results:

Results of the biochemical binding assays are shown in the Table below. "NT" means that the compound was not tested in the assay.

| Example No. | XIAP BIR3 FPA $IC_{50}$ (uM) | XIAP BIR3 HTRF $IC_{50}$ (uM) | XIAP-BIR2 AlphaScreen $IC_{50}$ (uM) | XIAP BIR2-3 HTRF $IC_{50}$ (uM) |
|---|---|---|---|---|
| 1 | 0.061 | | 0.096 | |
| 2 | | 0.028 | | 0.004 |
| 3 | 0.058 | | 0.072 | |
| 4 | 0.053 | | 0.15 | |
| 5 | 0.069 | | 0.10 | |
| 6 | | 0.016 | | 0.003 |
| 7 | 0.083 | | 0.12 | |
| 8 | 0.057 | | 0.099 | |
| 9 | 0.065 | | 0.26 | |
| 10 | | 0.023 | | 0.003 |
| 11 | | 0.018 | | 0.012 |
| 12 | 0.13 | | 2.0 | |
| 13 | | 0.012 | | 0.011 |
| 14 | 0.13 | | 2.00 | |
| 15 | 0.11 | | 0.22 | |
| 16 | 0.12 | | 0.32 | |
| 17 | 0.056 | | 0.11 | |
| 18 | | 0.023 | | 0.004 |
| 19 | 0.081 | | 0.18 | |
| 20 | | 0.037 | | 0.011 |
| 21 | | 0.017 | | 0.006 |
| 22 | | 0.014 | | 0.004 |
| 23 | | 0.010 | | 0.004 |
| 24 | | 0.093 | | 0.033 |
| 25 | | 0.016 | | 0.004 |
| 26 | | 0.056 | | 0.005 |
| 27 | 0.073 | | 0.12 | |
| 28 | 0.098 | | 0.90 | |
| 29 | 0.061 | | 0.18 | |
| 30 | 0.038 | | 0.11 | |
| 31 | 0.071 | | 0.52 | |
| 32 | 0.035 | | 0.11 | |
| 33 | 0.066 | | 0.79 | |
| 34 | 0.15 | | 0.41 | |
| 35 | 0.20 | | 1.4 | |
| 36 | 0.19 | | 1.9 | |
| 37 | 0.11 | | 0.29 | |
| 38 | | 0.045 | | 0.016 |
| 39 | | 0.089 | | 0.065 |
| 40 | 0.66 | | 2.1 | |
| 41 | 0.065 | | 0.29 | |
| 42 | 0.24 | | 1.3 | |
| 43 | 0.13 | | 0.70 | |
| 44 | 0.13 | | 0.74 | |
| 45 | 0.089 | | 0.96 | |
| 46 | 0.069 | | 0.19 | |
| 47 | 0.067 | | 0.13 | |
| 48 | 0.092 | | 0.50 | |
| 49 | | 0.051 | | 0.022 |
| 50 | 0.053 | | 0.61 | |
| 51 | | 0.054 | | 0.027 |
| 52 | 0.042 | | 0.36 | |
| 53 | 0.14 | | 0.25 | |
| 54 | | 0.076 | | 0.021 |
| 55 | | 0.009 | | 0.004 |
| 56 | | 0.017 | | 0.012 |
| 57 | | 0.010 | | 0.006 |
| 58 | | 0.027 | | 0.018 |
| 59 | | 0.011 | | 0.007 |
| 60 | | 0.042 | | 0.022 |
| 61 | | 0.031 | | 0.016 |
| 62 | | 0.073 | | 0.058 |
| 63 | | 0.017 | | 0.005 |
| 64 | | 0.014 | | 0.010 |
| 65 | | | | |
| 66 | | | | |
| 67 | | 0.014 | | 0.006 |
| 68 | | 0.26 | | 0.16 |

What is claimed is:

1. A compound of Formula (I)

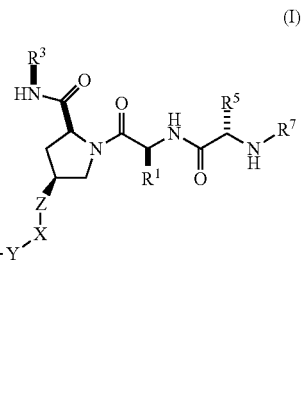

wherein

X is absent, —$(CR^{10}R^{11})_m$—, optionally substituted heteroaryl or optionally substituted heterocyclyl,

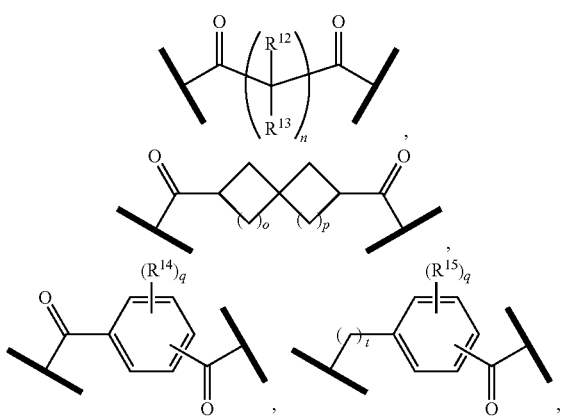

-continued

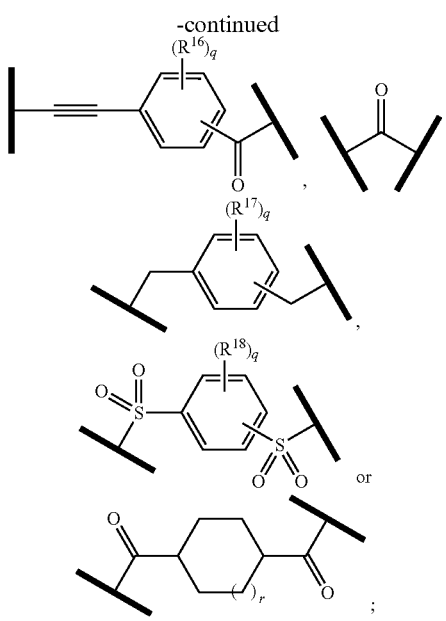

Y and Z are independently C=O, —O—, —NR$^9$—, —CONH—, —NHCO— or may be absent;
with the proviso that only one of X, Y or Z may be absent;
R$^1$ and R$^2$ are independently optionally substituted thioalkyl wherein the substituents attached to the S atom of the thioalkyl are optionally substituted alkyl, optionally substituted branched alkyl, optionally substituted heterocyclyl, —(CH$_2$)$_v$COR$^{20}$, —CH$_2$CHR$^{21}$COR$^{22}$ or —CH$_2$R$^{23}$;
wherein
v=1-3,
R$^{20}$ and R$^{22}$ are independently selected from OH, NR$^{24}$R$^{25}$ or OR$^{26}$,
R$^{21}$ is NR$^{24}$R$^{25}$,
R$^{23}$ is optionally substituted aryl or optionally substituted heterocyclyl, where the optional substituents include alkyl and halogen,
R$^{24}$ is hydrogen or optionally substituted alkyl,
R$^{25}$ is hydrogen, optionally substituted alkyl, optionally substituted branched alkyl, optionally substituted arylalkyl, optionally substituted heterocyclyl, —CH$_2$(OCH$_2$CH$_2$O)$_m$CH$_3$, or a polyamine chain,
R$^{26}$ is optionally substituted alkyl, where the optional substituents are OH, halogen or NH$_2$;
R$^3$ and R$^4$ are independently optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;
R$^5$, R$^6$, R$^7$ and R$^8$ are independently hydrogen, optionally substituted alkyl or optionally substituted cycloalkyl;
R$^9$ is hydrogen, optionally substituted alkyl, optionally substituted cycloalkyl or CO alkyl;

R$^{10}$ and R$^{11}$ are independently hydrogen, halogen or optionally substituted alkyl;
R$^{12}$ and R$^{13}$ are independently hydrogen, halogen or optionally substituted alkyl, or R$^{12}$ and R$^{13}$ can be taken together to form a carbocyclic ring;
R$^{14}$, R$^{15}$, R$^{16}$, R$^{17}$ and R$^{18}$ are independently hydrogen, halogen, optionally substituted alkyl or OR$^{19}$;
R$^{19}$ is hydrogen, optionally substituted alkyl or optionally substituted cycloalkyl;
m and n are independently 0, 1, 2, 3, or 4;
o and p are independently 0, 1, 2 or 3;
q is 0, 1, 2, 3, or 4;
r is 0 or 1;
t is 1, 2, or 3;
and/or a pharmaceutically acceptable salt, tautomer or stereoisomer thereof.

2. The compound according to claim 1 wherein:
X is absent, —(CR$^{10}$R$^{11}$)$_m$—, optionally substituted heteroaryl or optionally substituted heterocyclyl,

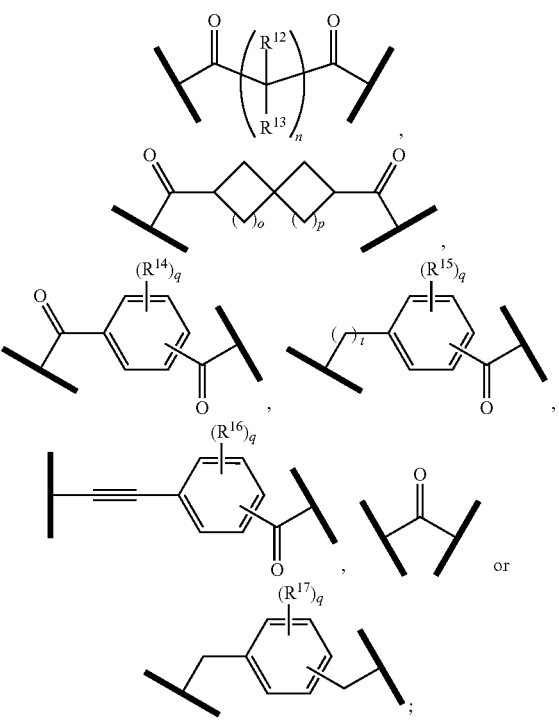

Y and Z are independently C=O, —O—, —NR$^9$—, —CONH—, —NHCO— or may be absent;
with the proviso that only one of X, Y or Z may be absent;
R$^3$ and R$^4$ are independently optionally substituted alkyl, optionally substituted cycloalkyl, optionally substituted aryl or optionally substituted arylalkyl;
R$^5$ and R$^6$ are independently hydrogen or optionally substituted alkyl;
R$^7$ and R$^8$ are independently hydrogen, optionally substituted alkyl or optionally substituted cycloalkyl;
R$^9$ is hydrogen, optionally substituted alkyl or CO alkyl;
or a pharmaceutically acceptable salt, tautomer or stereoisomer thereof.

3. A pharmaceutical composition comprising a compound of claim 1 and a pharmaceutically acceptable carrier.

* * * * *